United States Patent
Furukawa et al.

(10) Patent No.: US 8,362,474 B2
(45) Date of Patent: *Jan. 29, 2013

(54) ORGANIC FIELD EFFECT TRANSISTOR AND SEMICONDUCTOR DEVICE

(75) Inventors: Shinobu Furukawa, Atsugi (JP); Ryota Imahayashi, Atsugi (JP); Kaoru Kato, Atsugi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/280,596

(22) Filed: Oct. 25, 2011

(65) Prior Publication Data

US 2012/0032160 A1 Feb. 9, 2012

Related U.S. Application Data

(63) Continuation of application No. 11/657,718, filed on Jan. 25, 2007, now Pat. No. 8,049,206.

(30) Foreign Application Priority Data

Jan. 26, 2006 (JP) ................................. 2006-017431

(51) Int. Cl.
*H01L 51/30* (2006.01)
(52) U.S. Cl. ............ 257/40; 257/E51.005; 257/E51.051
(58) Field of Classification Search .................. 257/40
See application file for complete search history.

(56) References Cited

U.S. PATENT DOCUMENTS

| | | |
|---|---|---|
| 6,013,384 A | 1/2000 | Kido et al. |
| 7,431,997 B2 | 10/2008 | Hwang et al. |

(Continued)

FOREIGN PATENT DOCUMENTS

| | | |
|---|---|---|
| EP | 0855848 A | 7/1998 |
| EP | 1524706 A | 4/2005 |

(Continued)

OTHER PUBLICATIONS

International Search Report (Application No. PCT/JP2007/051323) Dated Apr. 17, 2007.

(Continued)

*Primary Examiner* — Jenny L Wagner
*Assistant Examiner* — Mark Tornow
(74) *Attorney, Agent, or Firm* — Eric J. Robinson; Robinson Intellectual Property Law Office, P.C.

(57) ABSTRACT

It is an object to provide an organic field effect transistor including an electrode which can reduce an energy barrier at an interface between a conductive layer and a semiconductor layer, and a semiconductor device including the organic field effect transistor. A composite layer containing an organic compound and an inorganic compound is provided in at least part of one of a source electrode and a drain electrode in an organic field effect transistor, and as the organic compound, a carbazole derivative represented by the general formula (1) is used. By providing the composite layer in at least part of one of the source electrode and the drain electrode, an energy barrier at an interface between a conductive layer and a semiconductor layer can be reduced.

(1)

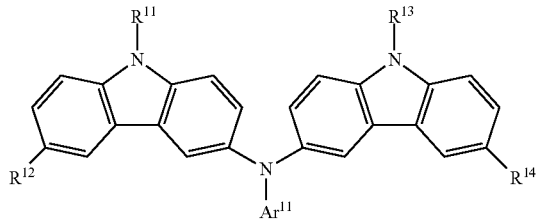

34 Claims, 60 Drawing Sheets

U.S. PATENT DOCUMENTS

| | | | |
|---|---|---|---|
| 7,560,735 | B2 | 7/2009 | Furukawa et al. |
| 7,649,197 | B2 | 1/2010 | Iwaki et al. |
| 7,737,627 | B2 | 6/2010 | Hwang et al. |
| 7,901,791 | B2 | 3/2011 | Nakashima et al. |
| 8,021,764 | B2 | 9/2011 | Hwang et al. |
| 8,021,765 | B2 | 9/2011 | Hwang et al. |
| 8,049,206 | B2 * | 11/2011 | Furukawa et al. ............. 257/40 |
| 8,188,315 | B2 | 5/2012 | Hwang et al. |
| 2003/0015698 | A1 | 1/2003 | Baldo et al. |
| 2003/0085398 | A1 | 5/2003 | Koyama et al. |
| 2003/0213952 | A1 | 11/2003 | Iechi et al. |
| 2003/0218166 | A1 | 11/2003 | Tsutsui |
| 2005/0084712 | A1 | 4/2005 | Kido et al. |
| 2005/0098207 | A1 | 5/2005 | Matsumoto et al. |
| 2005/0274946 | A1 * | 12/2005 | Yoshida et al. ................ 257/40 |
| 2006/0020136 | A1 | 1/2006 | Hwang et al. |
| 2006/0238112 | A1 | 10/2006 | Kasama et al. |
| 2006/0270066 | A1 | 11/2006 | Imahayashi et al. |
| 2006/0273303 | A1 | 12/2006 | Wu et al. |
| 2007/0007516 | A1 | 1/2007 | Seo et al. |
| 2007/0031701 | A1 | 2/2007 | Nakashima et al. |
| 2008/0048183 | A1 | 2/2008 | Ohsawa et al. |
| 2008/0254318 | A1 | 10/2008 | Nakashima et al. |
| 2009/0058267 | A1 | 3/2009 | Nakashima et al. |
| 2009/0134383 | A1 | 5/2009 | Imahayashi et al. |
| 2009/0267077 | A1 | 10/2009 | Furukawa et al. |
| 2012/0211733 | A1 | 8/2012 | Hwang et al. |

FOREIGN PATENT DOCUMENTS

| | | | |
|---|---|---|---|
| EP | 1661888 | A | 5/2006 |
| EP | 1862524 | A | 12/2007 |
| JP | 07-022670 | A | 1/1995 |
| JP | 10-270172 | A | 10/1998 |
| JP | 2003-129043 | A | 5/2003 |
| JP | 2003-298056 | | 10/2003 |
| JP | 2004-228371 | | 8/2004 |
| JP | 2005-123095 | A | 5/2005 |
| JP | 2005-290000 | A | 10/2005 |
| JP | 2006-332614 | | 12/2006 |
| JP | 2007-036188 | | 2/2007 |
| JP | 2007-063258 | | 3/2007 |
| WO | WO 2006/062217 | | 6/2006 |
| WO | WO 2007/015407 | | 2/2007 |

OTHER PUBLICATIONS

Written Opinion (Application No. PCT/JP2007/051323) Dated Apr. 17, 2007.

Y.Y. Lin, et al., *Stacked Pentacene Layer Organic Thin-Film Transistors with Improved Characteristics*, IEEE Electron Device Letter, vol. 18, No. 12, Dec. 1997, pp. 606-608.

J.T. Lin et al. *Light-emitting carbazole derivatives for electroluminescent materials*, Proc. SPIE: Organic Light-Emitting Materials and Devices, vol. 4464 (2002), pp. 307-316.

Thomas.K et al., "Light-Emitting Carbazole Derivatives: Potential Electroluminescent Materials,", J. Am. Chem. Soc. (Journal of the American Chemical Society), 2001, vol. 123, No. 38, pp. 9404-9411.

Y.Y. Lin, et al., *Stacked Pentacene Layer Organic Thin-Film Transistors with Improved Characteristics*, IEEE Electron Device Letters, vol. 18, No. 12, Dec. 1997, pp. 606-608.

\* cited by examiner

ORGANIC FIELD EFFECT TRANSISTOR AND SEMICONDUCTOR DEVICE

TECHNICAL FIELD

The present invention relates to a field effect transistor that can be used as a switching element or an amplifier element. In addition, the present invention relates to a semiconductor device including the field effect transistor.

BACKGROUND ART

In the field effect transistor, electric conductivity of a semiconductor layer which is provided between two electrodes, a source electrode and a drain electrode, is controlled by voltage that is applied to a gate electrode. The field effect transistor is basically a typical unipolar element in which a p-type or n-type carrier (a hole or an electron) transports electric charge.

Since various switching elements or amplifier elements can be formed by combination of such field effect transistors, the field effect transistor is applied in various fields. For example, a switching element of a pixel in an active matrix display or the like can be given as an application example.

So far, as a semiconductor material used for the field effect transistor, an inorganic semiconductor material typified by silicon has been widely used; however, high temperature processing is necessary to form an inorganic semiconductor material as a semiconductor layer. Therefore, it is difficult to use plastics or a film for a substrate.

On the other hand, when an organic semiconductor material is used as a semiconductor layer, the material can be formed at relatively low temperature. Therefore, it becomes theoretically possible to manufacture a field effect transistor over not only a glass substrate but also a substrate having low heat resistance, such as a plastic substrate.

As an example of a field effect transistor using an organic semiconductor material as a semiconductor layer (hereinafter referred to as an organic field effect transistor), a transistor which uses silicon dioxide ($SiO_2$) as a gate insulating layer and pentacene as a semiconductor layer is given (see Non Patent Document 1: Y. Y. Lin, D. J. Gundlach, S. F. Nelson, T. N. Jackson, IEEE Electron Device Letters, Vol. 18, 606-608 (1997)). In this repot, it has been reported that field effect mobility is 1 $cm^2/Vs$, and transistor performance that is equal to that of a transistor using amorphous silicon can be obtained even when an organic semiconductor material is used as a semiconductor layer.

In the organic field effect transistor, carriers are transported between a source and drain electrode and a semiconductor layer. When there is an energy barrier at the interface, transistor characteristics such as field effect mobility are lowered. In order to improve this situation, it has been proposed to use a lithium fluoride layer at the interface between the source electrode or the drain electrode and the semiconductor layer (see Patent Document 1: Japanese Published Patent Application No. 2003-298056). However, the lithium fluoride layer can be only applied to an n-channel organic field effect transistor, and the type of the organic semiconductor material is limited to n-type materials. In addition, it has also been proposed to dope a semiconductor layer with a conductivity imparting agent (see Patent Document 2: Japanese Published Patent Application No. 2004-228371); however, there is a problem in that a conductivity imparting agent has low chemical stability. Moreover, adhesion between these electrode materials and organic semiconductor materials is important in order to obtain a transistor having excellent durability.

As described above, a source electrode and a drain electrode which can be used for an organic field effect transistor using various organic semiconductor materials, which are chemically stable, and which have excellent adhesion with an organic semiconductor material have been expected. An organic transistor having favorable field effect mobility and excellent durability can be obtained by using such a source electrode and a drain electrode.

In addition, a source electrode and a drain electrode also serve as a wiring in an organic field effect transistor; therefore, high conductivity is required. However, a source electrode and a drain electrode with the characteristics as described above and high conductivity have not yet been reported.

DISCLOSURE OF INVENTION

It is an object of the present invention to provide, in a field effect transistor including a semiconductor layer using an organic semiconductor material (in the present invention, referred to as an organic field effect transistor), an organic field effect transistor including an electrode for an organic field effect transistor, which can reduce an energy barrier at an interface with a semiconductor layer. It is another object to provide an organic field effect transistor including an electrode for an organic field effect transistor, which can be used for various organic semiconductor materials, which is chemically stable, and which has excellent adhesion with a semiconductor layer. In addition, it is another object to provide a semiconductor device including the organic field effect transistor.

Further, it is an object to provide a conductive layer which has the above described characteristics, which is excellent in conductivity, and which can also serve as a wiring.

In addition, in an organic field effect transistor, it is necessary to consider a work function when selecting an electrode in order to inject carriers efficiently. The restriction by the work function is severe, and only the small number of conductive layers which meet requirements can be used in the actual situation. For example, gold is given as a conductive layer which is widely used as an electrode of a p-type organic field effect transistor, that is, it is necessary to fulfill a work function by using such expensive metal.

Therefore, it is an object of the present invention, in the case of using a conductive material as part of an electrode for an organic field effect transistor, to provide an electrode for an organic field effect transistor or an organic field effect transistor, which has a structure in which selection of the conductive material is not controlled by the work function.

Moreover, it is another object of the present invention to provide an organic field effect transistor having favorable field effect mobility. In addition, it is another object to provide an organic field effect transistor having excellent durability.

As a result of keen examinations, the present inventors found that, when a composite layer containing an organic compound and an inorganic compound is used as an electrode for an organic field effect transistor, that is, part of at least one of a source electrode and a drain electrode in the organic field effect transistor, an energy barrier at an interface between the electrode and a semiconductor layer is reduced and field effect mobility is improved.

Further, the present inventors found that an electrode having such a structure is chemically stable and excellent in adhesion with a semiconductor layer in the case of being used as a source electrode and/or a drain electrode of an organic field effect transistor.

One organic field effect transistor of the present invention is characterized by including a semiconductor layer containing an organic semiconductor material; and a source electrode and a drain electrode, where at least one of the source electrode and the drain electrode includes a composite layer containing an organic compound and an inorganic compound; and where the organic compound is a carbazole derivative represented by the general formula (1).

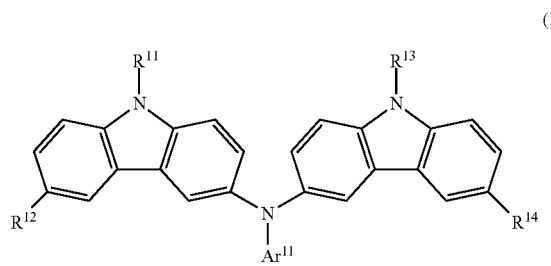

(1)

In the formula, each of $R^{11}$ and $R^{13}$ may be the same or different and represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{11}$ represents an aryl group having 6 to 25 carbon atoms or a heteroaryl group having 5 to 9 carbon atoms; $R^{12}$ represents hydrogen, an alkyl group having 1 to 6 carbon atoms, or an aryl group having 6 to 12 carbon atoms; $R^{14}$ represents hydrogen, an alkyl group having 1 to 6 carbon atoms, an aryl group having 6 to 12 carbon atoms, or a substituent represented by the general formula (2); and in the substituent represented by the general formula (2), $R^{15}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{12}$ an aryl group having 6 to 25 carbon atoms or a heteroaryl group having 5 to 9 carbon atoms; and $R^{16}$ represents hydrogen, an alkyl group having 1 to 6 carbon atoms, or an aryl group having 6 to 12 carbon atoms.

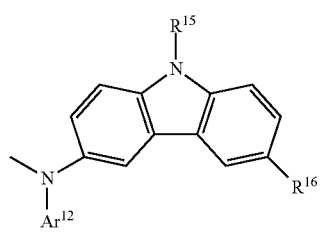

(2)

In the general formula (1), any one of $R^{11}$ and $R^{13}$ is preferably an aryl group having 6 to 25 carbon atoms or a heteroaryl group having 5 to 9 carbon atoms. Much preferably, each of $R^{11}$ and $R^{13}$ is an aryl group having 6 to 25 carbon atoms or a heteroaryl group having 5 to 9 carbon atoms. When a substituent bonded to nitrogen of the carbazole skeleton is an aryl group having 6 to 25 carbon atoms or a heteroaryl group having 5 to 9 carbon atoms, effect that a carrier transporting property is enhanced, can be obtained.

In addition, in the general formula (1), $R^{12}$ is preferably hydrogen, a tert-butyl group, a phenyl group, or a biphenyl group.

In addition, in the general formula (1), $R^{14}$ is preferably hydrogen, a tert-butyl group, a phenyl group, or a biphenyl group.

In addition, in the general formula (1), $R^{14}$ is preferably a substituent represented by the general formula (2). When $R^{14}$ is the substituent represented by the general formula (2), a carbazole derivative having much higher heat resistance can be obtained. In addition, in the general formula (2), $R^{15}$ is preferably an aryl group having 6 to 25 carbon atoms or a heteroaryl group having 5 to 9 carbon atoms. When a substituent bonded to nitrogen of the carbazole skeleton is an aryl group having 6 to 25 carbon atoms or a heteroaryl group having 5 to 9 carbon atoms, effect that a carrier transporting property is enhanced, can be obtained. In addition, in the general formula (2), $R^{16}$ is preferably hydrogen, a tert-butyl group, a phenyl group, or a biphenyl group.

In addition, among carbazole derivatives shown in the general formula (1), a carbazole derivative represented by the following general formula (3) is preferably used.

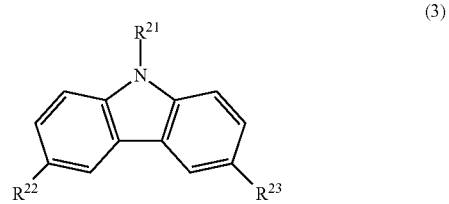

(3)

In the formula, $R^{21}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $R^{22}$ represents hydrogen, an alkyl group having 1 to 6 carbon atoms, or an aryl group having 6 to 12 carbon atoms; and $R^{23}$ represents a substituent represented by the general formula (4); and in the substituent represented by the general formula (4), $R^{24}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{21}$ represents an aryl group having 6 to 25 carbon atoms or a heteroaryl group having 5 to 9 carbon atoms; and $R^{25}$ represents hydrogen, an alkyl group having 1 to 6 carbon atoms, or an aryl group having 6 to 12 carbon atoms.

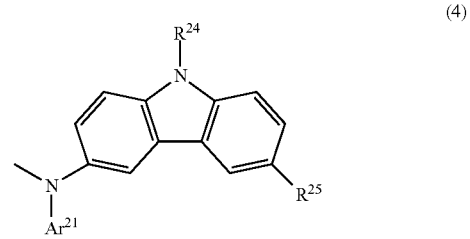

(4)

In the above structure, $R^{22}$ is preferably hydrogen, a tert-butyl group, a phenyl group, or a biphenyl group.

Much preferably, a carbazole derivative represented by the general formula (5) is used.

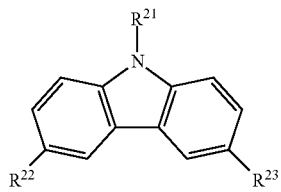

(5)

In the formula, $R^{21}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; each of $R^{22}$ and $R^{23}$ represents a substituent represented by the general formula (6); and in the substituent represented by the general formula (6), $R^{24}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{21}$ represents an aryl group having 6 to 25 carbon atoms or a heteroaryl group having 5 to 9 carbon atoms; and $R^{25}$ represents hydrogen, an alkyl group having 1 to 6 carbon atoms, or an aryl group having 6 to 12 carbon atoms.

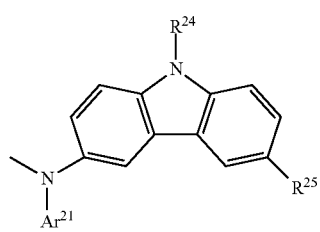

(6)

In the above structure, $R^{25}$ is preferably hydrogen, a tert-butyl group, a phenyl group, or a biphenyl group.

In addition, in the above structure, $R^{21}$ is preferably an aryl group having 6 to 25 carbon atoms or a heteroaryl group having 5 to 9 carbon atoms.

When a substituent bonded to nitrogen of the carbazole skeleton is an aryl group having 6 to 25 carbon atoms or a heteroaryl group having 5 to 9 carbon atoms, effect that a carrier transporting property is enhanced, can be obtained.

In addition, a carbazole derivative represented by the general formula (7) is preferably used.

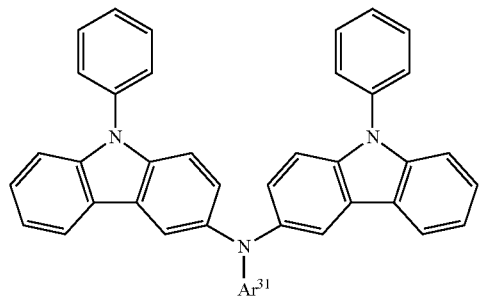

(7)

In the formula, $Ar^{31}$ represents a phenyl group or a naphthyl group.

In addition, a carbazole derivative represented by the general formula (8) is preferably used.

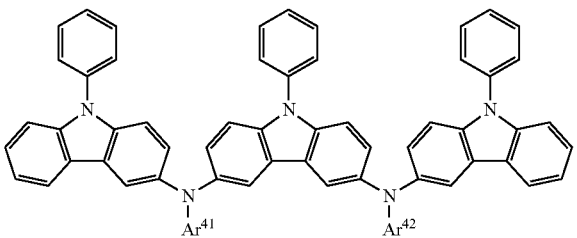

(8)

In the formula, each of $Ar^{41}$ and $Ar^{42}$ may be the same or different and represents a phenyl group or a naphthyl group.

In the above structure, as the inorganic compound, transition metal oxide is preferable. In particular, titanium oxide, zirconium oxide, hafnium oxide, vanadium oxide, niobium oxide, tantalum oxide, chromium oxide, molybdenum oxide, tungsten oxide, rhenium oxide, ruthenium oxide, or the like is preferably used.

The above structure has a feature that the organic semiconductor material is the same material as the organic compound.

The above structure has a feature that the composite layer is provided so as to be in contact with the semiconductor layer.

The above structure has a feature that at least one of the source electrode and the drain electrode further includes a second layer containing alkali metal, alkaline earth metal, an alkali metal compound, or an alkaline earth metal compound. Further, it is also a feature that the second layer is provided between the semiconductor layer and the composite layer.

In the above structure, preferably, at least one of the source electrode and the drain electrode further includes a conductive layer. Accordingly, a source electrode and a drain electrode which are excellent in conductivity and which can also serve as a wiring can be obtained.

The above structure has a feature that, in the organic field effect transistor further including the above conductive layer, the side edge of the conductive layer is covered with the composite layer containing an organic compound and an inorganic compound.

In the composite layer, a mixing ratio of the organic compound to the inorganic compound is preferably organic compound/inorganic compound=0.1 to 10, much preferably 0.5 to 2 in molar ratio.

In addition, a semiconductor device of the present invention includes the above organic field effect transistor.

By implementing the present invention, it is possible to obtain a source electrode and a drain electrode which can reduce an energy barrier at an interface with a semiconductor layer in a field effect transistor including a semiconductor layer using an organic semiconductor material. In addition, it is possible to obtain a source electrode and a drain electrode which can be used for various organic semiconductor materials, which are chemically stable, and which have excellent adhesion with a semiconductor layer.

In addition, as for an electrode for an organic field effect transistor of the present invention having, in part thereof, a composite layer containing an organic compound and an inorganic compound, it is possible to select a conductive material without considering restriction by a work function. Therefore, the range of choice is expanded, and its structure is advantageous in terms of the cost. In addition, resistance can be reduced through the use of a conductive material, and the electrode can also be preferably used as a wiring.

In addition, a carbazole derivative, which is an organic compound that is used for an electrode for an organic field effect transistor of the present invention, is excellent in heat resistance. Therefore, an electrode for an organic field effect transistor of the present invention is excellent in heat resistance.

Further, by implementing the present invention, an organic field effect transistor with favorable field effect mobility can be provided. In addition, an organic field effect transistor with excellent durability can be provided.

Further, by implementing the present invention, a semiconductor device with favorable operation characteristics and high reliability can be provided.

BEST MODE FOR CARRYING OUT THE INVENTION

Figure 1A:
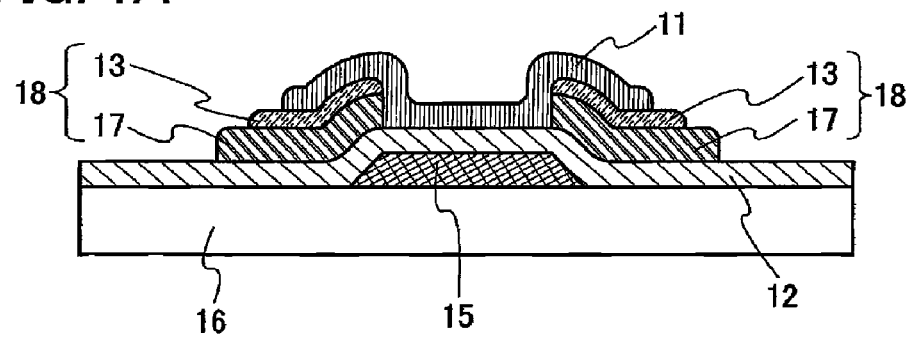
FIGS. 1A to 1D are schematic views each showing a structural example of an organic field effect transistor of the present invention.

As for an organic field effect transistor of the present invention, in order to obtain excellent field effect transistor characteristics, it is necessary that: carrier density of an organic semiconductor layer is efficiently controlled by electric field effect; carriers are efficiently supplied from a source electrode to the organic semiconductor layer; and carriers are efficiently discharged from the organic semiconductor layer to a drain electrode. Therefore, it is desirable that there is no energy barrier between the source electrode and the organic semiconductor layer, and between the drain electrode and the organic semiconductor layer. However, in the case of a p-type organic field effect transistor, since there is generally an energy difference between a Fermi level of electrode metal and a HOMO level of an organic semiconductor material, there is an energy barrier. Further, in the case of an n-type organic field effect transistor, since there is an energy difference between a Fermi level of electrode metal and a LUMO level of an organic semiconductor material, there is an energy barrier. These are factors in restriction of the characteristics of the organic field effect transistor, and are reasons why a work function is required to be considered when selecting an electrode material.

The present inventors found that: through the use of a composite layer containing an organic compound and an inorganic compound as parts of a source electrode and a drain electrode, an energy barrier between the source electrode and an organic semiconductor layer and between the drain electrode and the organic semiconductor layer is reduced, and further, carriers are efficiently supplied from the source electrode to the organic semiconductor layer and discharged from the organic semiconductor layer to the drain electrode, and field effect transistor characteristics are improved.

It is considered that the phenomenon as described above occurs because, in the composite layer in which an organic compound and an inorganic compound are mixed, a charge-transfer complex is formed between the organic compound and the inorganic compound and carrier density is improved in the composite layer.

In this specification, a semiconductor device means all devices which can function by utilizing semiconductor characteristics, such as a liquid crystal display device, a light emitting device, a semiconductor circuit, and an electronic device.

Embodiment Mode 1

FIGS. 1A to 1D each show a structural example of an organic field effect transistor of the present invention. In the drawings, reference numeral 11 denotes a semiconductor layer containing an organic semiconductor material; 12, an insulating layer; 13, a composite layer; 15, a gate electrode; and 16, a substrate. A source electrode and a drain electrode 18 each include the composite layer 13 and a conductive layer 17. Arrangement of each layer or each electrode can be appropriately selected depending on the usage of an element. In addition, in the drawings, the composite layer 13 is provided so as to be in contact with the semiconductor layer 11; however, the present invention is not limited thereto. The composite layer 13 may be included in part of the source electrode and/or the drain electrode. It is to be noted that arrangement of each layer or each electrode can be appropriately selected from FIGS. 1A to 1D depending on the usage of the element.

As the substrate 16, a glass substrate, a quartz substrate, an insulating substrate formed of crystalline glass or the like, a ceramic substrate, a stainless steel substrate, a metal substrate (such as tantalum, tungsten, or molybdenum), a semiconductor substrate, a plastic substrate (such as polyimide, acrylic, polyethylene terephthalate, polycarbonate, polyalylate, or polyether sulfone), or the like can be used. Further, these substrates may be used after being polished by a CMP method or the like, if necessary.

The insulating layer 12 can be formed using an inorganic insulating material such as silicon oxide, silicon nitride, silicon oxide containing nitrogen, or silicon nitride containing oxygen; an organic insulating material such as acrylic or polyimide; or a siloxane based material. In siloxane, a skeleton structure is formed of a bond of silicon and oxygen, and a compound at least containing hydrogen (such as an alkyl group or aromatic hydrocarbon) is used as a substituent. Fluorine may also be used as a substituent. Alternatively, fluorine and a compound at least containing hydrogen may be used as a substituent. In addition, the insulating layer 12 may be formed using a single layer or a plurality of layers. When the insulating layer includes two layers, an inorganic insulating material as a first insulating layer and an organic insulating material as a second insulating layer are preferably stacked.

It is to be noted that these insulating layers can be deposited by a known method such as a dipping method; a coating method such as a spin coating method or a droplet-discharging method; a CVD method; or a sputtering method. An organic material or a siloxane based material can be deposited by a coating method, and concavity and convexity of the lower layer can be reduced.

Any of a low molecular material, a middle molecular material, and a high molecular material can be used for an organic semiconductor material used in the present invention as long as it is an organic material which has a carrier transporting property and in which carrier density can be changed by electric field effect. The types of the material are not particularly limited, and a polycyclic aromatic compound, a conjugated double bond compound, a macroring compound, a metallophthalocyanine complex, a charge transfer complex, condensed ring tetracarboxylic diimide, oligothiophene, fullerene, carbon nanotube, and the like can be given. For example, polypyrrole, polythiophene, poly(3-alkylthiophene), polyisothianaphthene, polythienylenevinylene, poly(p-phenylenevinylene), polyaniline, polyacetylene, polyazulene, polypyrene, polycarbazole, polyselenophene, polyfuran, poly(p-phenylene), polyindole, polypyridazine, naphthacene, tetracene, pentacene, hexacene, heptacene, pyrene, chrysene, perylene, coronene, hexacene-6,15-quinone, polyvinylcarbazole, polyphenylenesulfide, polyvinylenesulfide, polyvinylpyridine, naphthalenetetracarboxylic diimide, anthracenetetracarboxylic diimide, C60, C70, C76, C78, C84, and a derivative thereof can be used. In addition, as a specific example thereof, there is pentacene, tetracene, sexythiophene (6T), α,ω-dihexylsexythiophene, copper phthalocyanine, 2,2'-bi(dithieno[3,2-b:2',3'-d]thiophene), bis-(1,2,5-thiadiazolo)-p-quinobis(1,3-dithiol), 2,5-di(4-biphenylyl)thiophene, 5,5'-di(4-biphenylyl)-2,2-bithiophene, di(4-biphenyl)-α-terthiophene, 2,8-dihexylanthra[2,3-b:6,7-b']dithiophene, rubrene, 5,5'''-di(4-biphenylyl)-α-quaterthiophene, 5,5''''-dihexyl-α-quinquethiophene, poly(2,5-thienylenevinylene) (abbreviation: PTV), poly(3-hexylthiophene-2,5-diyl) (abbreviation: P3HT), or poly(9,9-dioctylfluorene-co-bithiophene) (abbreviation: F8T2), which is generally referred to as a p-type semiconductor; or 7,7,8,8,-tetracyanoquinodimethane (abbreviation: TCNQ), 3,4,9,10-perylenetetracarboxylicdianhydride (abbreviation: PTCDA), 1,4,5,8-naphthalenetetracarboxylicdianhydride (abbreviation: NTCDA), 9,9,10,10-tetracyano-2,6-naphthoquinodimethane (abbreviation: TCNNQ), N,N'-dioctyl-3,4,9,10-perylenetetracarboxylicdiimide (abbreviation: PTCDI-C8H), copperhexadecafluorophthalocyanine (abbreviation: $F_{16}CuPc$), N,N'-di(terfluorohexyl)-1,4,5,8-naphthalenetetracarboxylicdiimide (abbreviation: NTCDI-C8F), α,ω-bis(perfluorohexyl)sexythiophene (abbreviation: DFH-6T), or 3',4'-dibutyl-5,5''-bis(dicyanomethylene)-5,5''-dihydro-2,2':5',2''-terthiophen) (abbreviation DCMT), which is generally referred to as an n-type semiconductor; or the like. It is to be noted that characteristics of p-type or n-type in an organic semiconductor are not peculiar to the substance but depend on a relation with an electrode which injects carriers or intensity of an electric field when carriers are injected. Therefore, the semiconductor material can be p-type, n-type, or bipolar type, while it has a tendency to easily become either p-type or n-type.

It is to be noted that the same organic compound as that for the composite layer, which will be described later, may also be used as the organic semiconductor material.

These organic semiconductor materials can be formed by various methods such as an evaporation method, a spin coating method, and a droplet-discharging method.

The gate electrode 15 and the conductive layer 17 which is used for the source electrode and the drain electrode 18 used in the present invention are not particularly limited. Preferably, the following material can be used: metal such as platinum, gold, aluminum, chromium, nickel, cobalt, copper, titanium, magnesium, calcium, barium, or sodium; alloy containing these metal; a conductive high molecular compound such as polyaniline, polypyrrole, polythiophene, polyacetylene, or polydiacetylene; an inorganic semiconductor such as silicon, germanium, or gallium arsenic; a carbon material such as carbon black, fullerene, carbon nanotube, or graphite; the conductive high molecular compound, the inorganic semiconductor, and the carbon material doped with acid (including Lewis acid), a halogen atom, or a metal atom of alkali metal, alkaline earth metal, or the like; and the like. In general, metal is used as a conductive material used for the source electrode and the drain electrode.

These electrode materials may be formed by a known method such as etching after being deposited by a sputtering method, an evaporation method, or the like.

As an organic compound contained in the composite layer 13 used in the present invention, a carbazole derivative represented by the following general formula (1) is preferable.

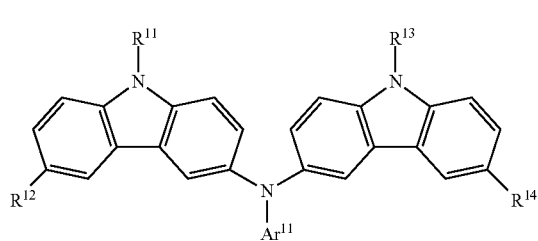

(1)

In the formula, each of $R^{11}$ and $R^{13}$ may be the same or different and represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{11}$ represents an aryl group having 6 to 25 carbon atoms or a heteroaryl group having 5 to 9 carbon atoms; $R^{12}$ represents hydrogen, an alkyl group having 1 to 6 carbon atoms, or an aryl group having 6 to 12 carbon atoms; $R^{14}$ represents hydrogen, an alkyl group having 1 to 6 carbon atoms, an aryl group having 6 to 12 carbon atoms, or a substituent represented by the general formula (2); and in the substituent represented by the general formula (2), $R^{15}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{12}$ represents an aryl group having 6 to 25 carbon atoms or a heteroaryl group having 5 to 9 carbon atoms; and $R^{16}$ represents hydrogen, an alkyl group having 1 to 6 carbon atoms, or an aryl group having 6 to 12 carbon atoms.

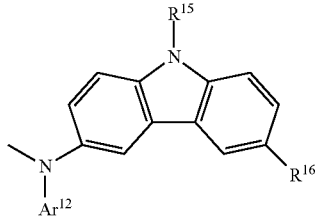

(2)

As an alkyl group having 1 to 6 carbon atoms, specifically, a methyl group, an ethyl group, an n-propyl group, an n-butyl group, an n-hexyl group, or the like is given. In addition, an alkyl group having a branch such as an iso-propyl group or a tert-butyl group may also be used.

As an aryl group having 6 to 25 carbon atoms, specifically, a phenyl group, a 4-biphenylyl group, a 1-naphthyl group, a 2-naphthyl group, a 9-anthryl group, a 9-phenanthryl group, a 1-pyrenyl group, a 9,9'-dimethyl-2-fluorenyl group, a spiro-9,9'-bifluoren-2-yl group, or the like is given. In addition, an aryl group having a substituent such as an m-tolyl group, a p-tolyl group, a 2-fluorophenyl group, a 3-fluorophenyl group, or a 4-fluorophenyl group may also be used.

As a heteroaryl group having 5 to 9 carbon atoms, specifically, a 2-pyridyl group, a 8-quinolyl group, a 3-quinolyl group, or the like is given.

As an arylalkyl group, specifically, a benzyl group or the like is given.

As an acyl group having 1 to 7 carbon atoms, specifically, an acetyl group, a benzoyl group, a propionyl group, or the like is given.

In the above general formula (1), any one of $R^{11}$ and $R^{13}$ is preferably an aryl group having 6 to 25 carbon atoms or a heteroaryl group having 5 to 9 carbon atoms. Much preferably, each of $R^{11}$ and $R^{13}$ is an aryl group having 6 to 25 carbon atoms or a heteroaryl group having 5 to 9 carbon atoms. When a substituent bonded to nitrogen of the carbazole skeleton is an aryl group having 6 to 25 carbon atoms or a heteroaryl group having 5 to 9 carbon atoms, effect that a carrier transporting property is enhanced, can be obtained.

In addition, in the above general formula (1), $R^{12}$ is preferably hydrogen, a tert-butyl group, a phenyl group, or a biphenyl group.

In addition, in the above general formula (1), $R^{14}$ is preferably hydrogen, a tert-butyl group, a phenyl group, or a biphenyl group.

In the above general formula (1), $R^{14}$ is preferably a substituent represented by the general formula (2). When $R^{14}$ is the substituent represented by the general formula (2), a carbazole derivative having higher heat resistance can be obtained. In the general formula (2), $R^{15}$ is preferably an aryl group having 6 to 25 carbon atoms or a heteroaryl group having 5 to 9 carbon atoms. When the substituent bonded to nitrogen of the carbazole skeleton is an aryl group having 6 to 25 carbon atoms or a heteroaryl group having 5 to 9 carbon atoms, effect that a carrier transporting property is enhanced, can be obtained. In addition, in the general formula (2), $R^{16}$ is preferably hydrogen, a tert-butyl group, a phenyl group, or a biphenyl group.

In addition, among carbazole derivatives having the structure shown in the above general formula (1), a carbazole derivative having a structure represented by the following general formula (3) is preferable because synthesis thereof is easy.

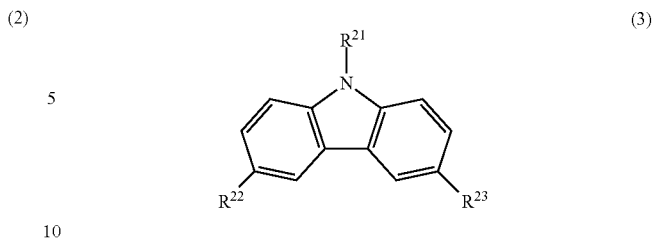

(3)

In the formula, $R^{21}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $R^{22}$ represents hydrogen, an alkyl group having 1 to 6 carbon atoms, or an aryl group having 6 to 12 carbon atoms; $R^{23}$ represents a substituent represented by the general formula (4); and in the substituent represented by the general formula (4), $R^{24}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{21}$ represents an aryl group having 6 to 25 carbon atoms or a heteroaryl group having 5 to 9 carbon atoms; and $R^{25}$ represents hydrogen, an alkyl group having 1 to 6 carbon atoms, or an aryl group having 6 to 12 carbon atoms.

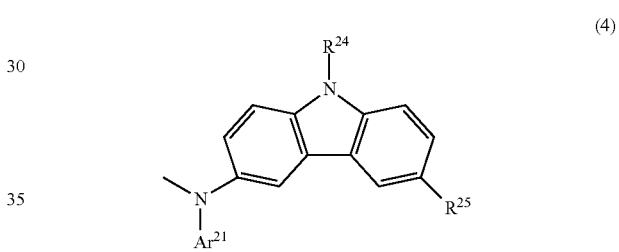

(4)

In the above structure, $R^{22}$ is preferably hydrogen, a tert-butyl group, a phenyl group, or a biphenyl group.

In addition, a carbozole derivative having a structure represented by the following general formula (5) is preferable.

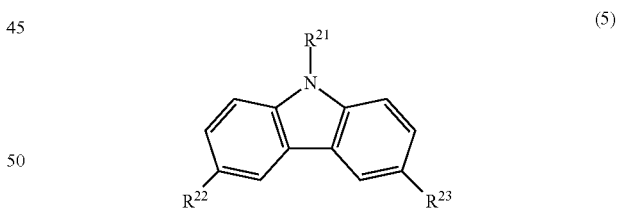

(5)

In the formula, $R^{21}$ represents hydrogen, an alkyl group having 1 to 6 carbon atoms, an aryl; group having 6 to 25 carbon atoms, a heteroaryl group having 5 to 9 carbon atoms, an arylalkyl group, or an acyl group having 1 to 7 carbon atoms; each of $R^{22}$ and $R^{23}$ represents a substituent represented by the general formula (6); and in the substituent represented by the general formula (6), $R^{24}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{21}$ represents an aryl group having 6 to 25 carbon atoms or a heteroaryl group having 5 to 9 carbon atoms; and $R^{25}$ represents hydrogen, an alkyl group having 1 to 6 carbon atoms, or an aryl group having 6 to 12 carbon atoms.

(6)

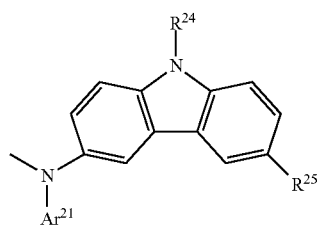

In the above structure, $R^{25}$ is preferably hydrogen, a tert-butyl group, a phenyl group, or a biphenyl group.

In the above structure, $R^{24}$ is preferably an aryl group having 6 to 25 carbon atoms or a heteroaryl group having 5 to 9 carbon atoms.

In the above structure, $R^{21}$ is preferably an aryl group having 6 to 25 carbon atoms or a heteroaryl group having 5 to 9 carbon atoms.

In addition, a carbazole derivative having a structure represented by the following general formula (7) is preferable.

(7)

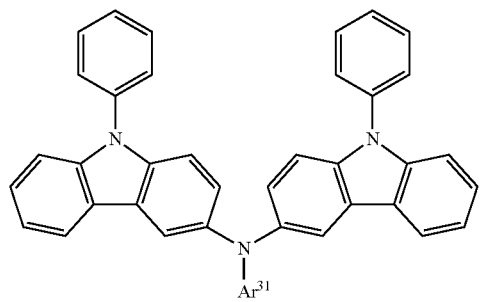

In the formula, $Ar^{31}$ represents a phenyl group or a naphthyl group.

In addition, a carbazole derivative having a structure represented by the following general formula (8) is preferable.

(8)

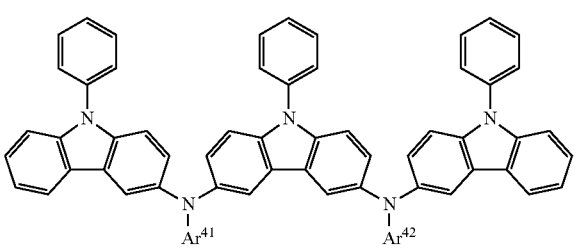

In the formula, each of $Ar^{41}$ and $Ar^{42}$ may be the same or different and represents a phenyl group or a naphthyl group.

In addition, as a specific example of a carbazole derivative used in the present invention, carbazole derivatives represented by the following structural formulas (9) to (71) can be given. However, the present invention is not limited thereto.

(9)

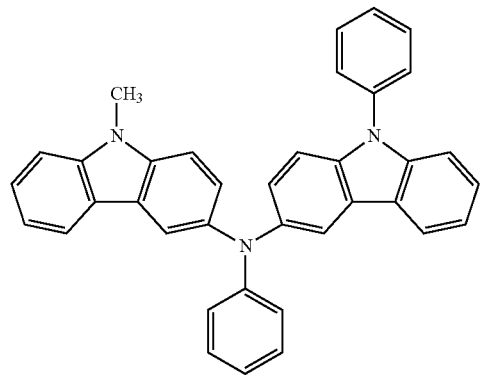

(10)

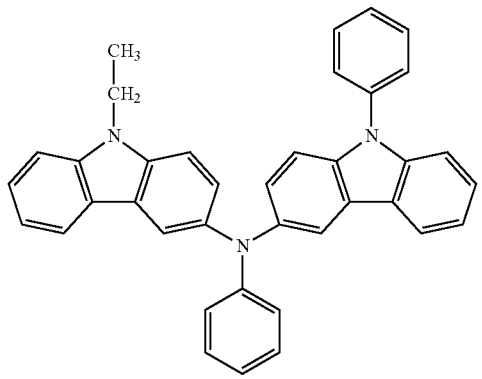

(11)

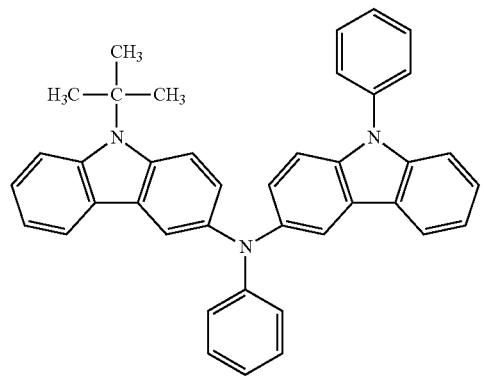

(12)

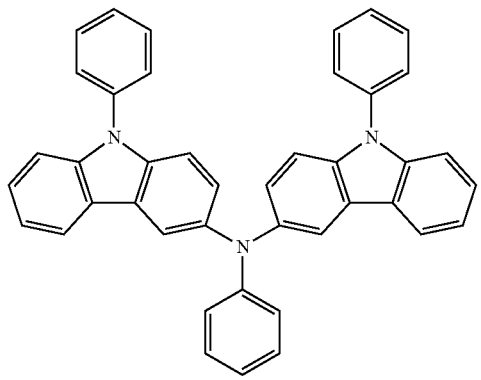

(13)
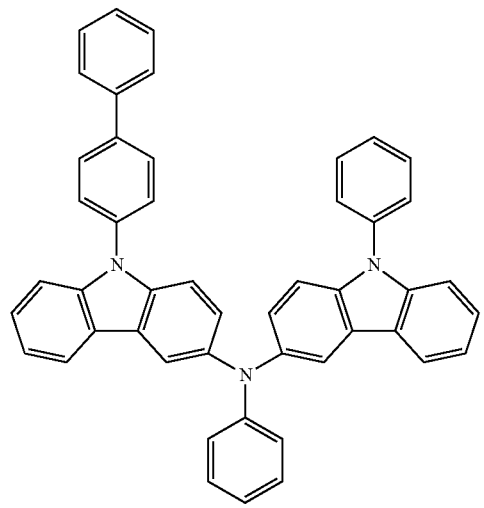
(14)
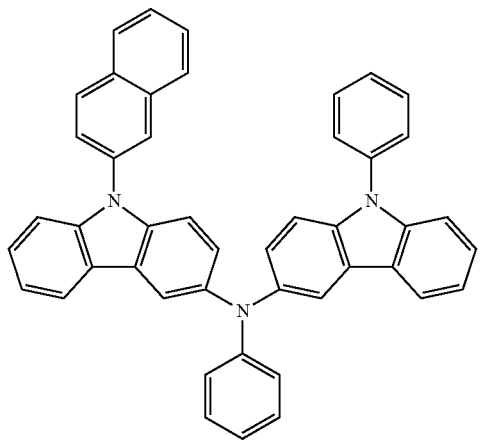
(15)
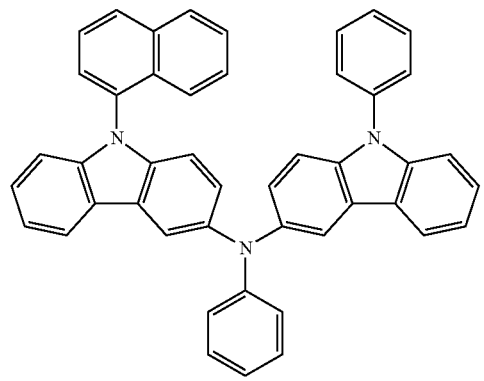
(16)
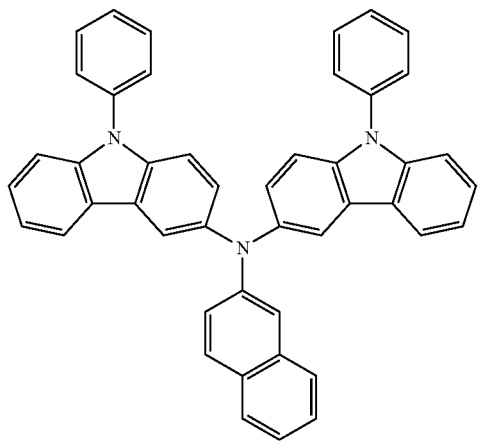
(17)
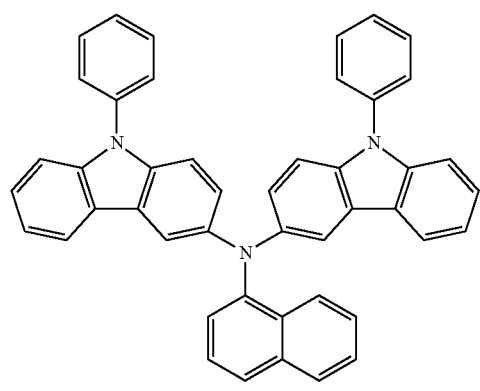
(18)
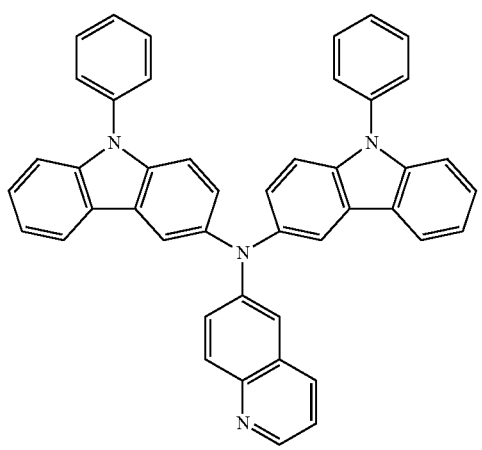

-continued
(19)
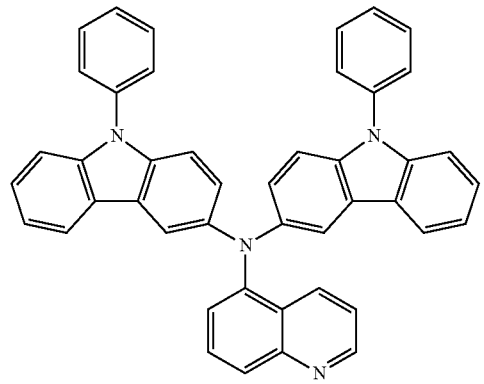
(20)
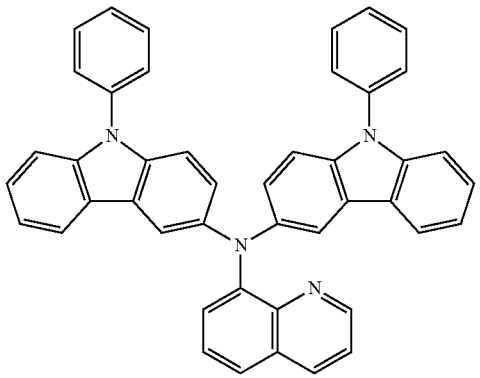
(21)
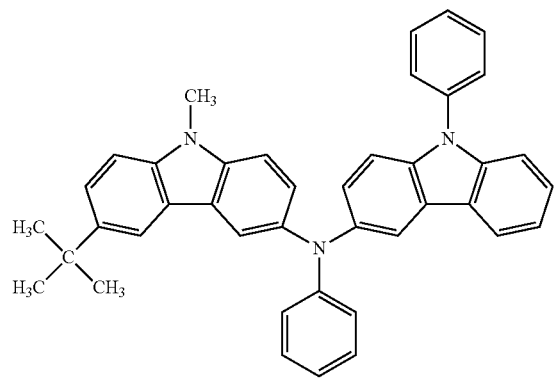
(22)
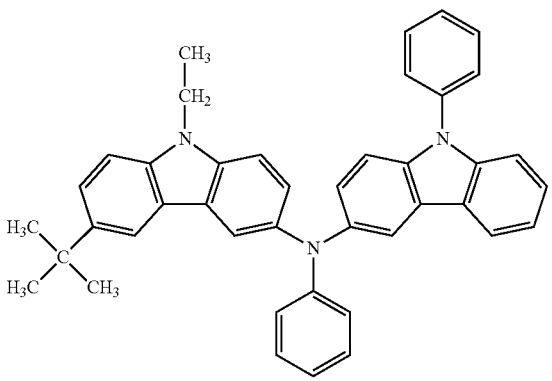
(23)
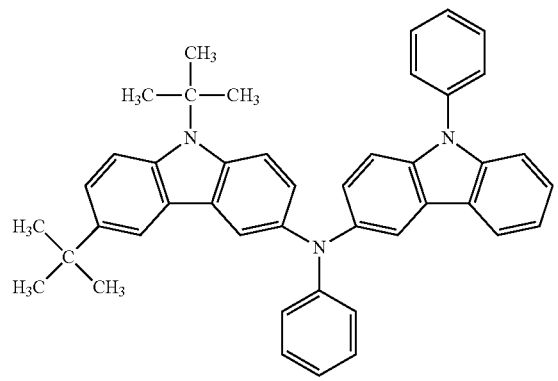
(24)
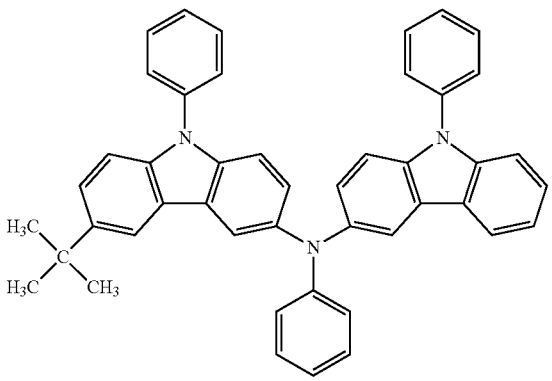
(25)
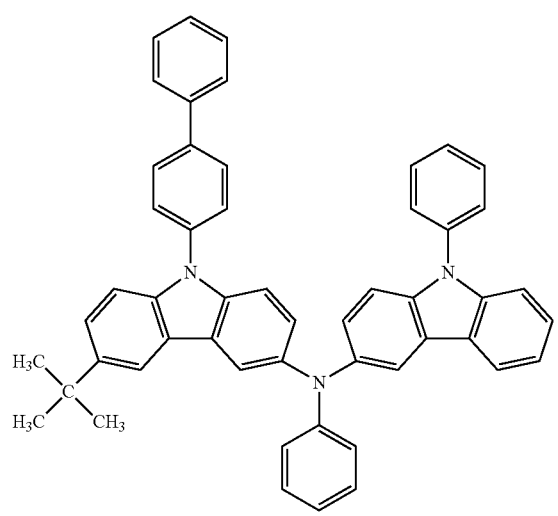
(26)
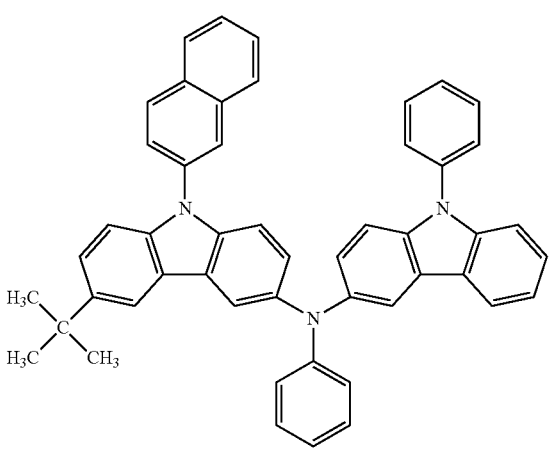

(27)
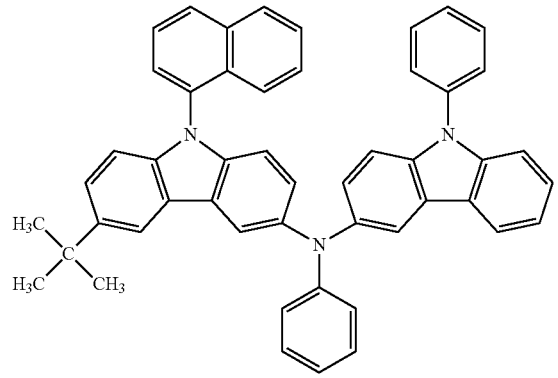
(28)
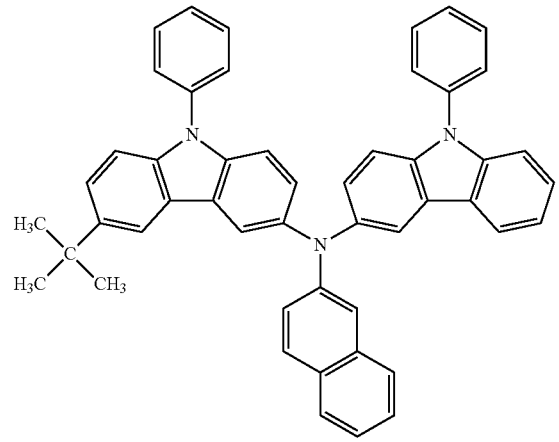
(29)
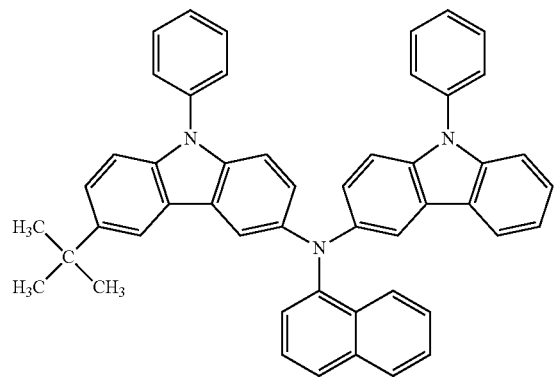
(30)
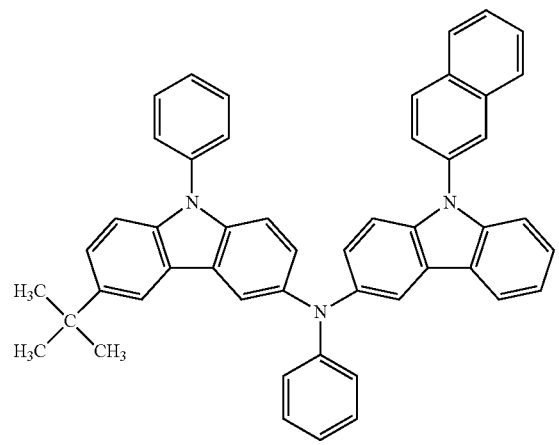
(31)
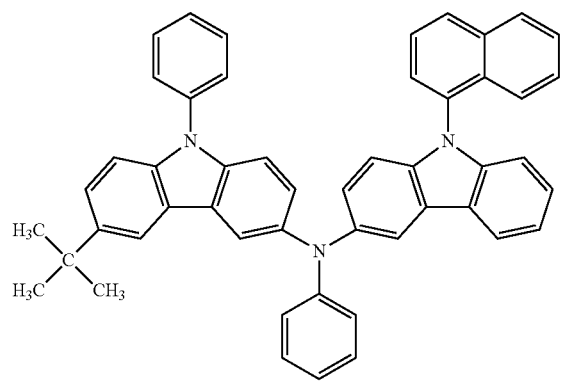
(32)
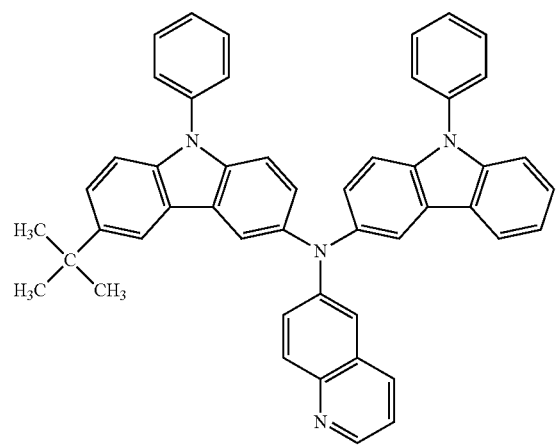

-continued
(33)
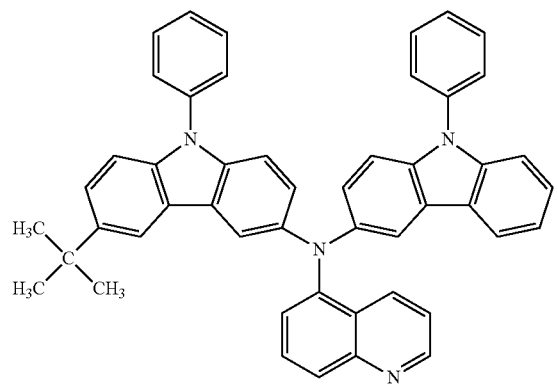
(34)
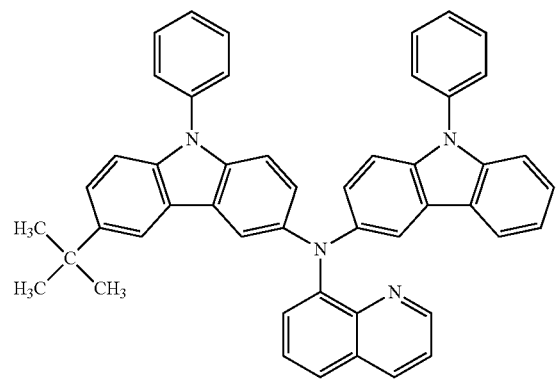
(35)
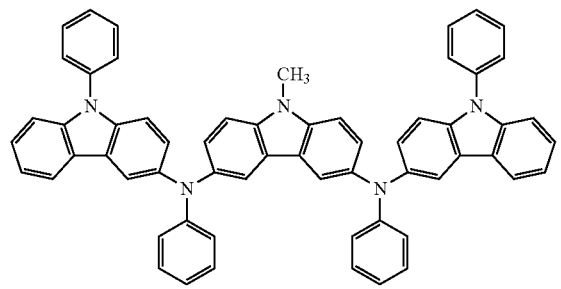
(36)
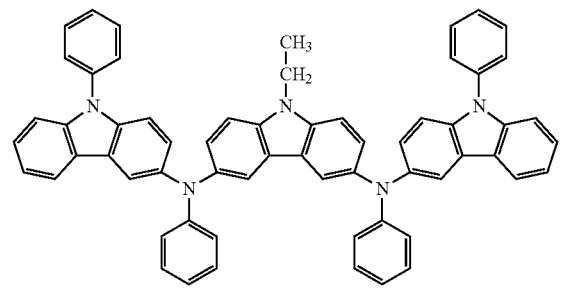
(37)
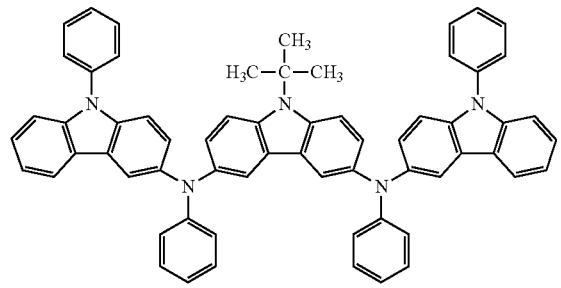
(38)
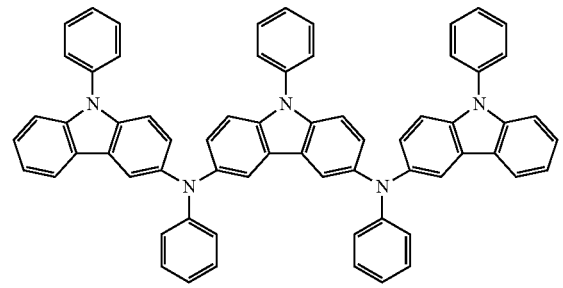
(39)
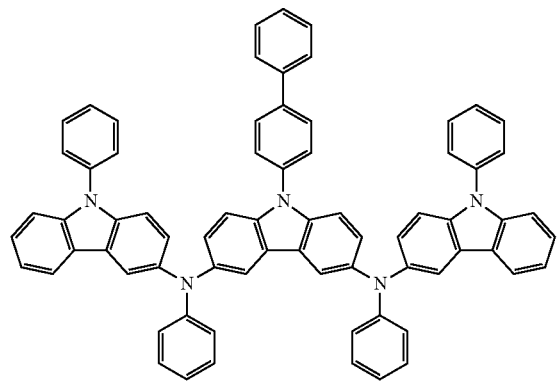
(40)
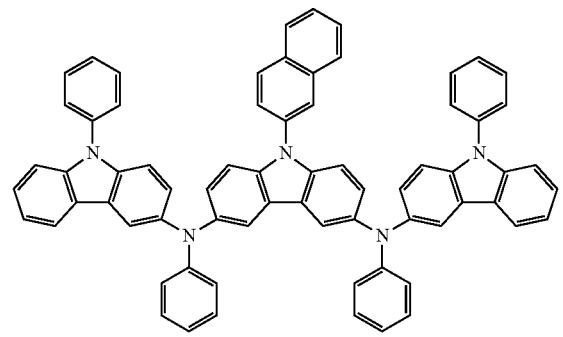

-continued
(41)
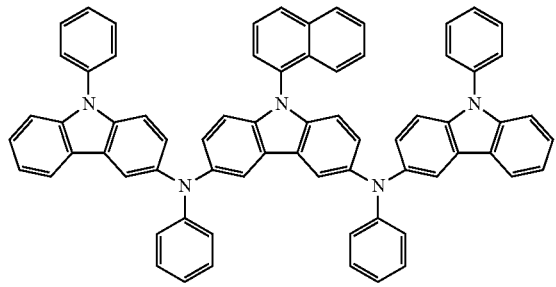
(42)
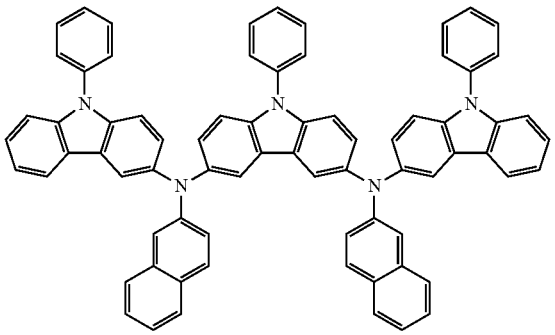
(43)
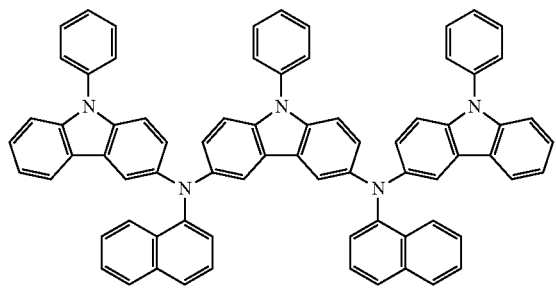
(44)
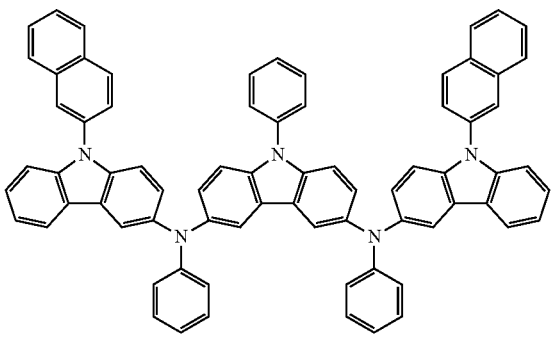
(45)
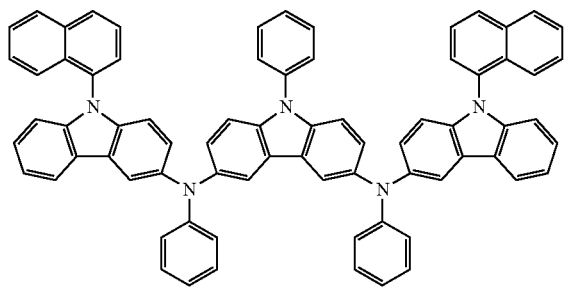
(46)
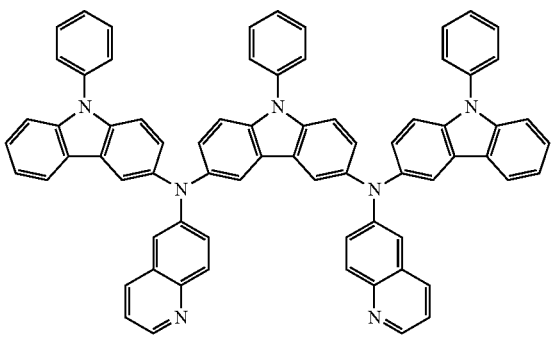
(47)
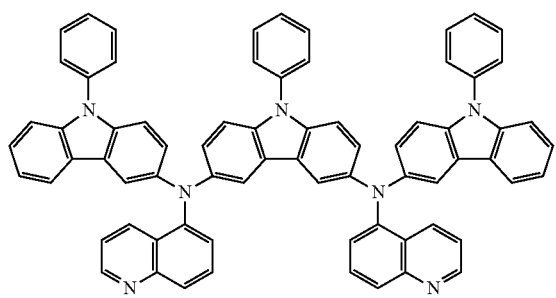
(48)
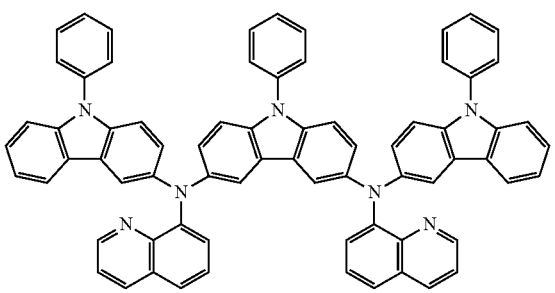

-continued
(49)
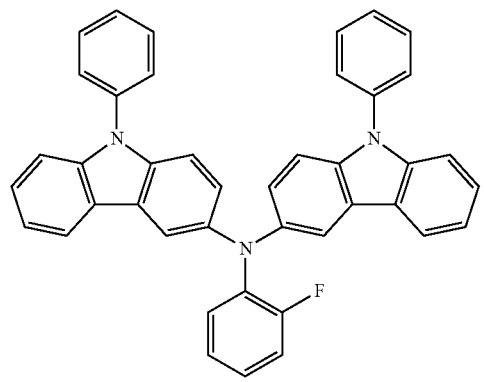
(50)
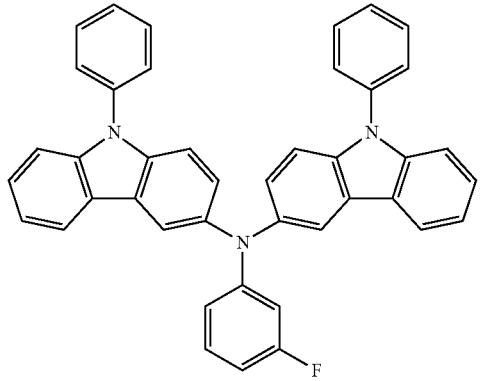
(51)
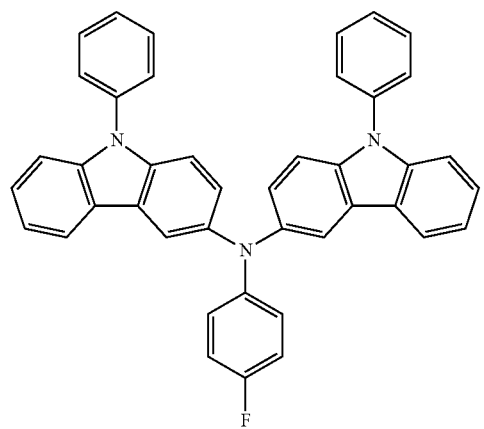
(52)
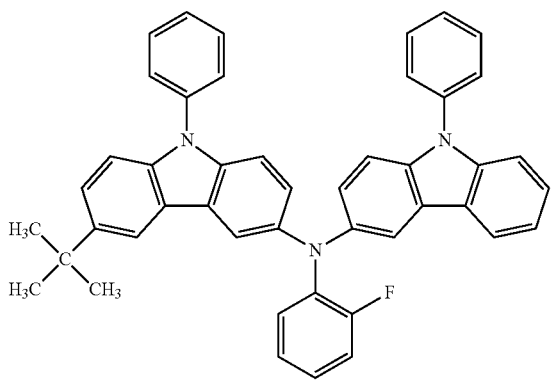
(53)
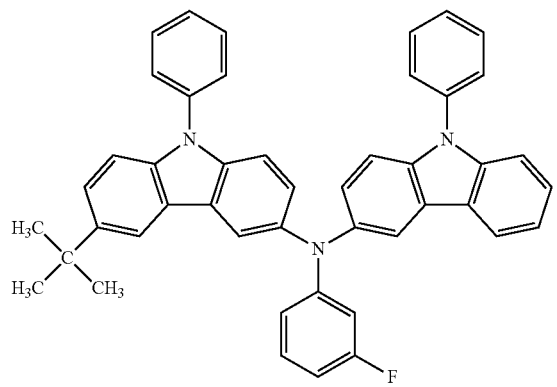
(54)
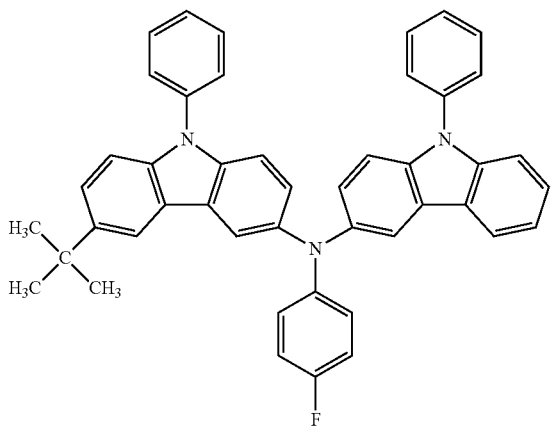
(55)
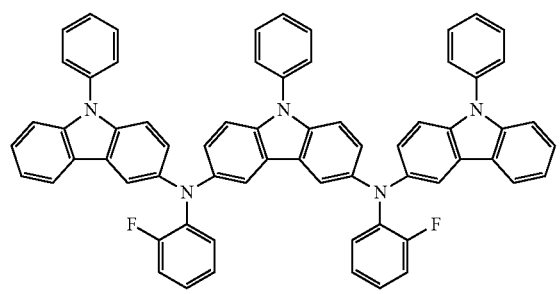
(56)
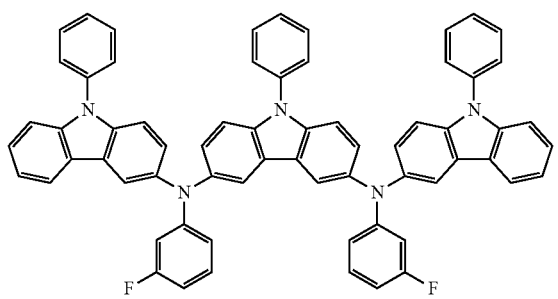

-continued
(57)
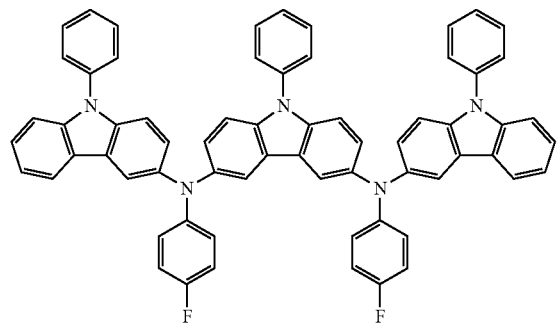
(58)
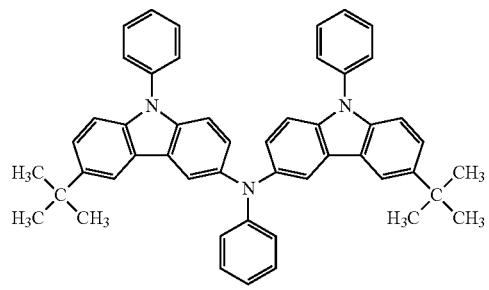
(59)
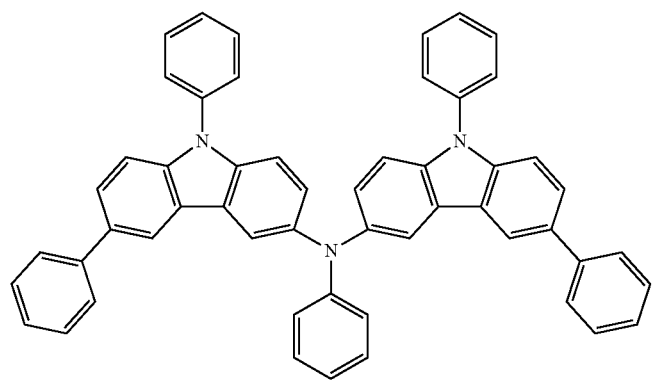
(60)
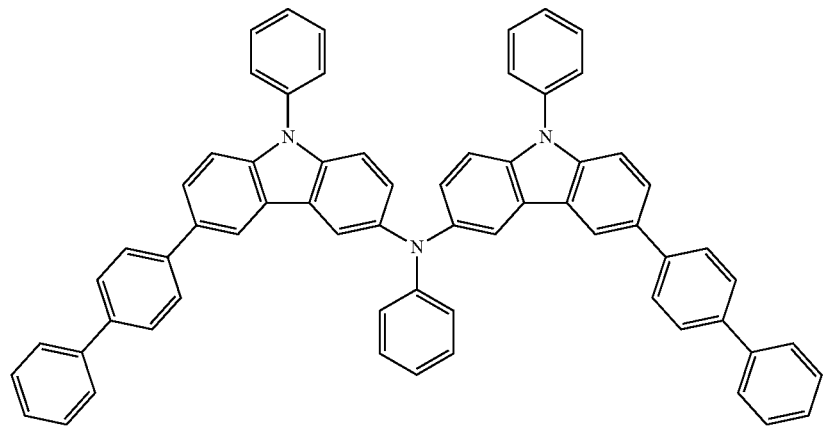
(61)
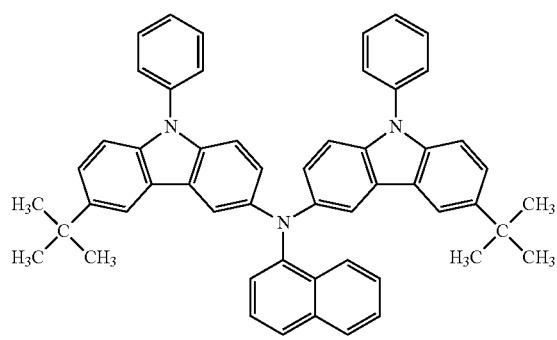
(62)
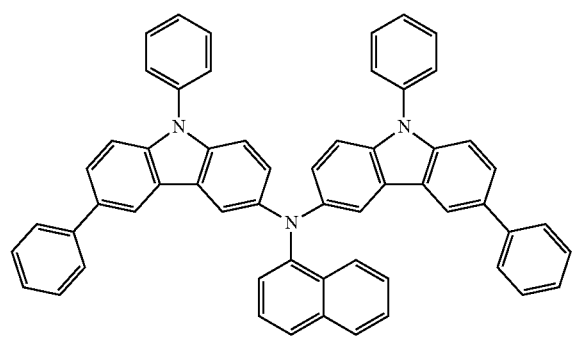

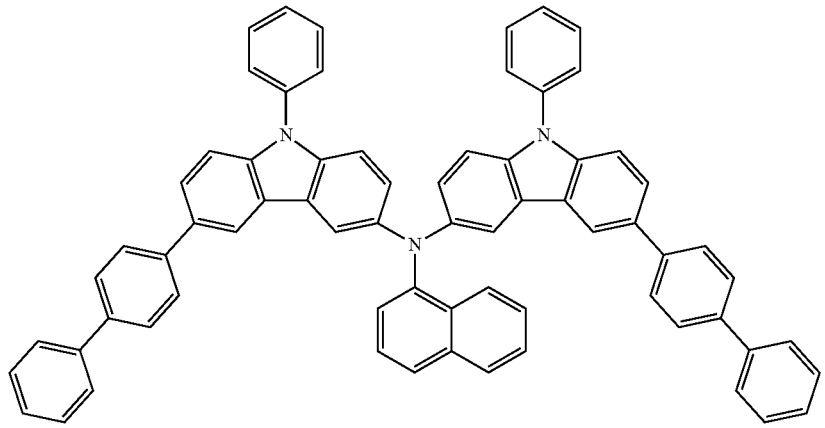
(63)
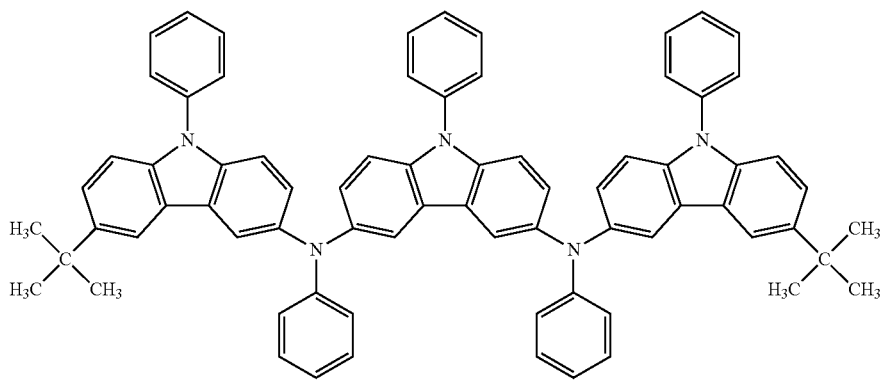
(64)
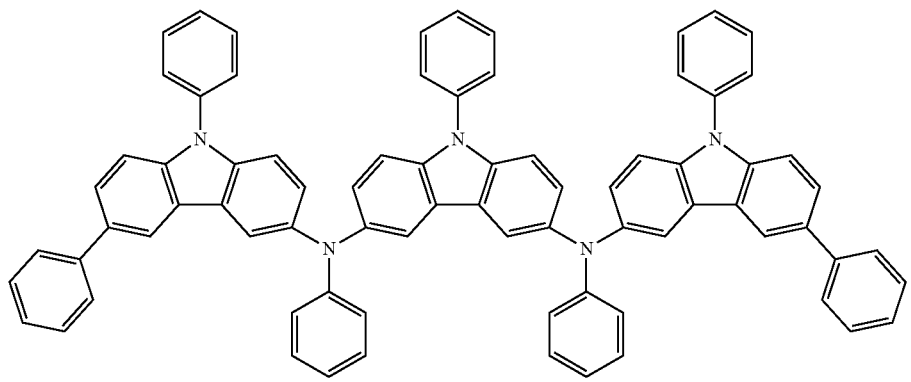
(65)
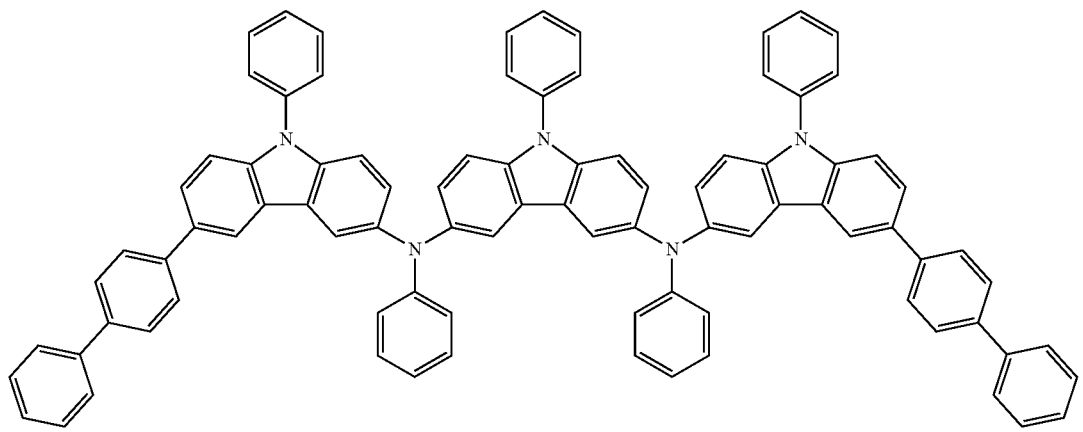
(66)

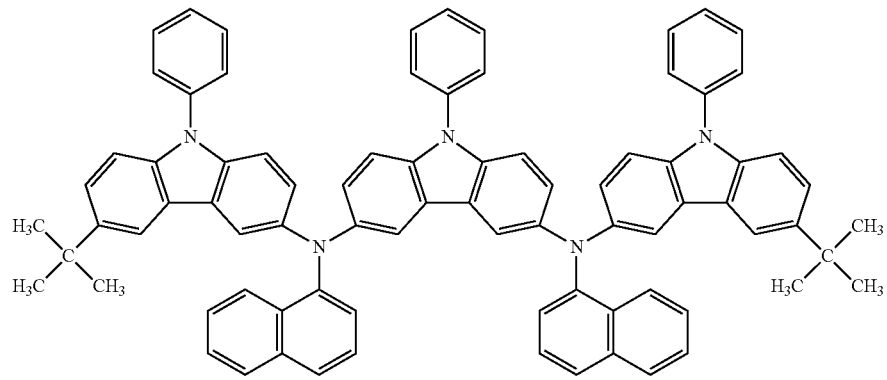
(67)
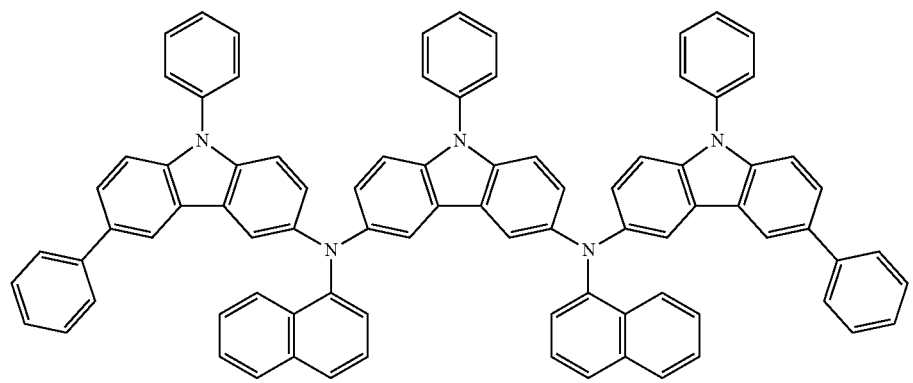
(68)
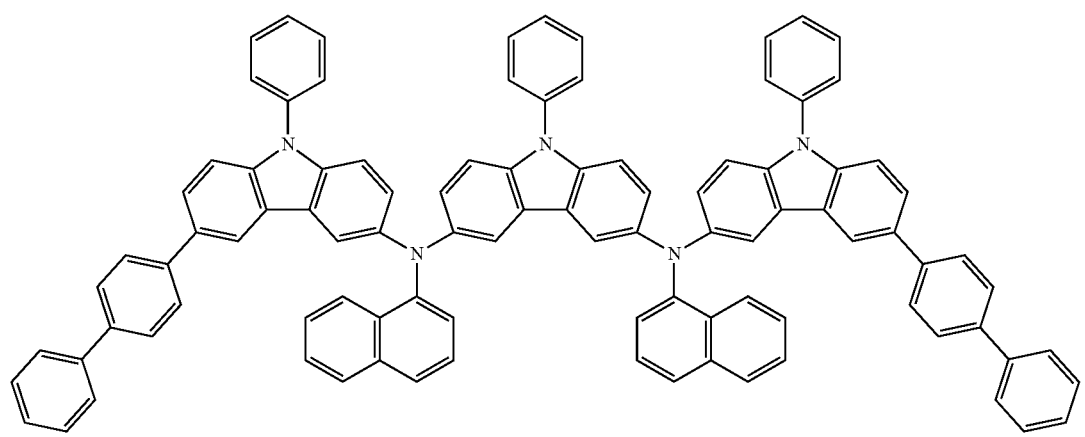
(69)

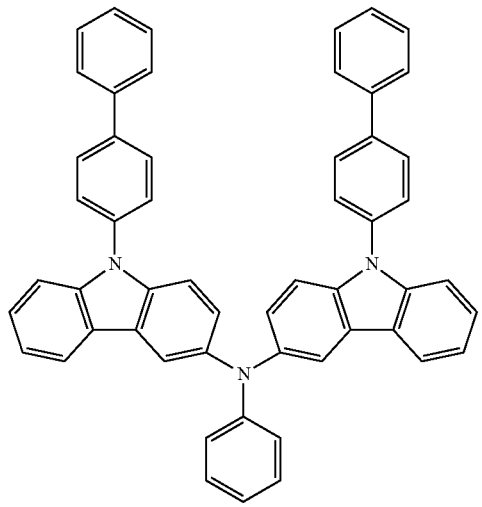

(70)

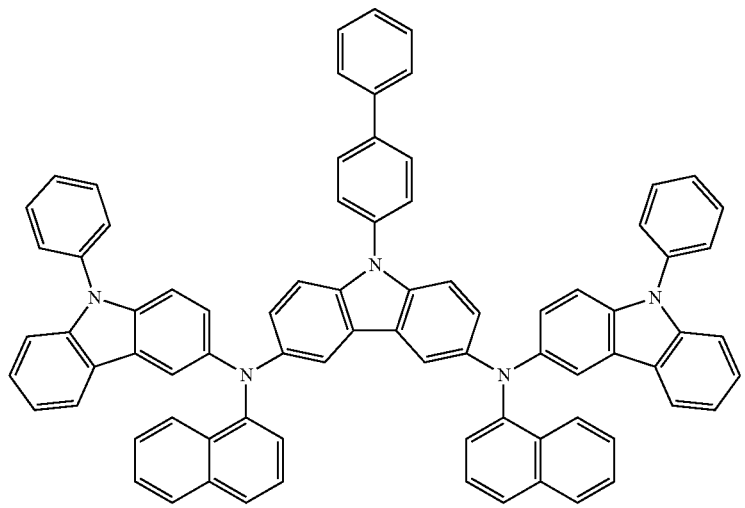

(71)

In the carbazole derivatives represented by the structural formulas (9) to (20), $R^{14}$ in the general formula (1) is hydrogen. In the carbazole derivatives represented by the structural formulas (21) to (34), $R^{14}$ in the general formula (1) is an alkyl group.

The carbazole derivatives represented by the structural formulas (35) to (48) each have a structure in which the same substituents are bonded to the carbazole skeleton, and are easier to be synthesized than the carbazole derivative having a structure in which different substituents are bonded. In other words, when, in the general formula (3), $R^{22}$ and $R^{23}$ have the same structure represented by the general formula (4), the same substituents may be bonded to the carbazole skeleton; therefore, synthesis thereof gets easier.

In addition, the carbazole derivative used in the present invention may have fluorine as represented in the structural formulas (49) to (57).

In addition, as represented in the structural formulas (58) to (69), an alkyl group having 1 to 6 carbon atoms or an aryl group having 6 to 12 carbon atoms is preferably bonded to 6 position of the carbazole skeleton. When 6 position of the carbazole skeleton has a substituent of an alkyl group having 1 to 6 carbon atoms or an aryl group having 6 to 12 carbon atoms, the carbazole skeleton can be chemically stabilized and the side reaction can be suppressed.

Various reactions can be applied to a synthesis method of the carbazole derivative used in the present invention. For example, a method shown in the following reaction scheme (A-1) or the reaction scheme (A-2) can be given. It is to be noted that a synthesis method of the carbazole derivative used in the present invention is not limited thereto.

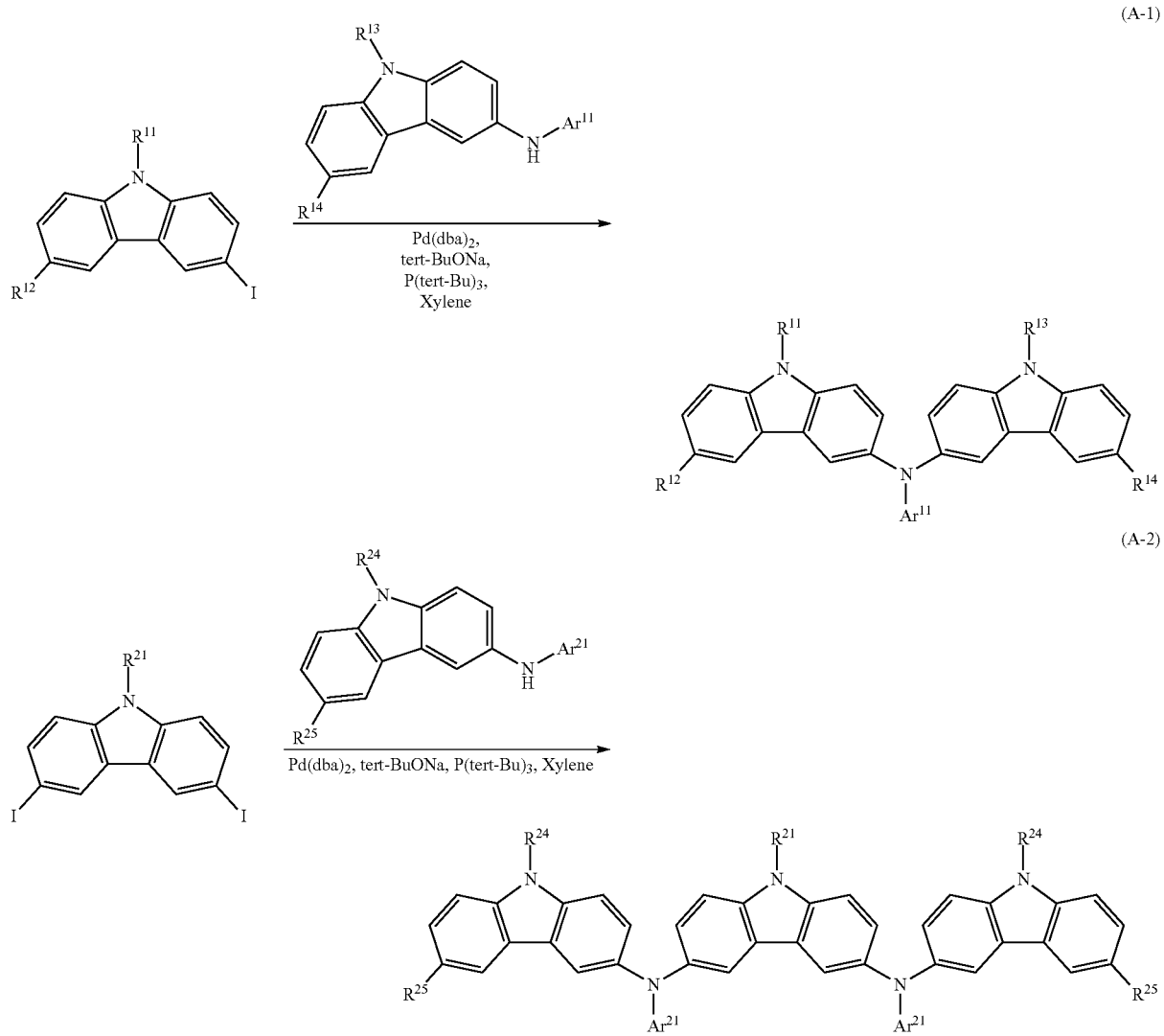

An inorganic compound used for the composite layer 13 of the present invention is not particularly limited; however, oxide of titanium, vanadium, chromium, zirconium, niobium, molybdenum, hafnium, tantalum, tungsten, or rhenium is preferable.

Any method can be used for forming the composite layer 13, regardless of a wet method or a dry method. For example, the composite layer 13 may be formed by co-evaporation using resistance heating, co-evaporation using resistance heating evaporation and electron beam evaporation (EB evaporation), concurrent deposition using sputtering and resistance heating, or the like with the use of the organic compound and the inorganic compound as described above. In addition, a wet method such as a sol-gel method may be used. It is to be noted that, when the composite layer 13 is formed by an evaporation method, molybdenum oxide is preferable from an aspect of the manufacturing process since molybdenum oxide is easily evaporated in vacuum.

The electric conductivity of the composite layer 13 is as high as about $10^{-5}$ [S/cm], and change in resistance of a transistor is small even when the film thickness is changed from several nm to several hundred nm; therefore, the film thickness of the composite layer can be controlled appropriately from several nm to greater than or equal to several hundred nm depending on the usage or shape of an element which is manufactured.

The structure of FIG. 1A is used as an example in order to explain the present invention more in detail. This structure is suitable for a p-type organic field effect transistor in which a hole is a carrier. As shown in FIG. 1A, the gate electrode 15 is formed over the substrate 16, the insulating layer 12 is formed over the gate electrode 15, and the source electrode and the drain electrode 18 are formed over the insulating layer 12. In FIG. 1A, the gate electrode 15 has a tapered shape; however, the present invention is not limited thereto. As each of the source electrode and the drain electrode, the conductive layer 17 is formed, and the composite layer 13 is stacked over the conductive layer 17. At this time, the conductive layer 17 and the composite layer 13 may be formed using the same mask so that edges of the conductive layer 17 and the composite layer 13 are in alignment. Finally, the semiconductor layer 11 is formed at least between the source electrode and the drain electrode, whereby an organic filed effect transistor is obtained. In FIG. 1A, the semiconductor layer 11 is formed so as to partially overlap with the source electrode and the drain electrode 18. The composite layer 13 is provided so as to be in contact with the semiconductor layer 11. In the structure of FIG. 1A, surface oxidation or stabilization of a surface level of the conductive layer 17 are generated after the conductive layer 17 is formed. Accordingly, when the conductive layer 17 is directly used as each of the source electrode and the drain electrode, an energy barrier is easily generated between the source and drain electrode 18 and the semiconductor layer 11; thus, transistor performance is easily lowered. However, by employing the source electrode and the drain electrode with the structure having the composite layer 13, effect that an energy barrier between the semiconductor layer 11 and the conductive layer 17 is reduced, is obtained.

Figure 1B:
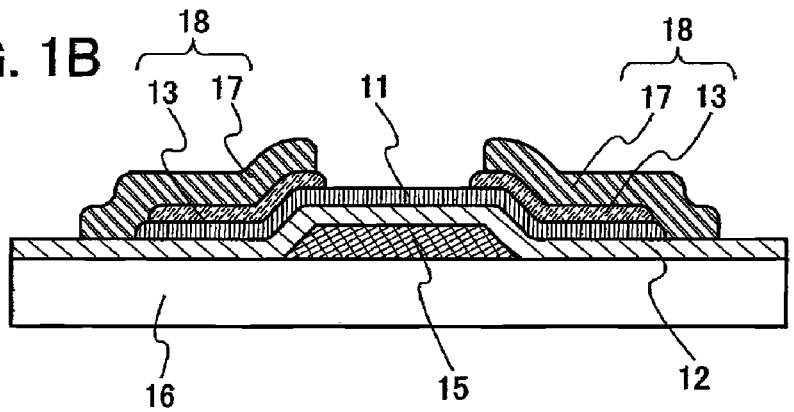
Figure 1C:
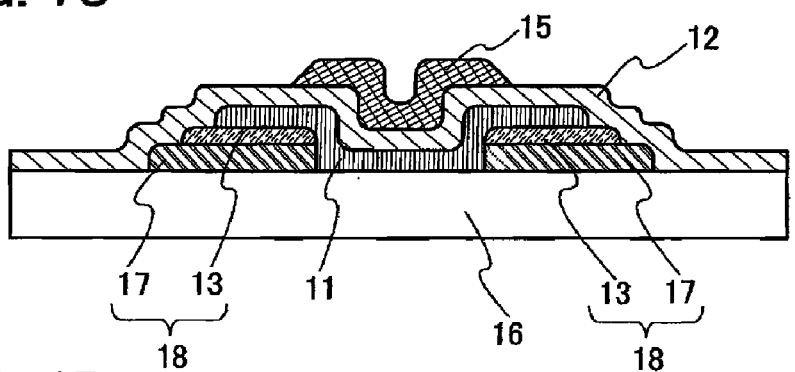
Figure 1D:
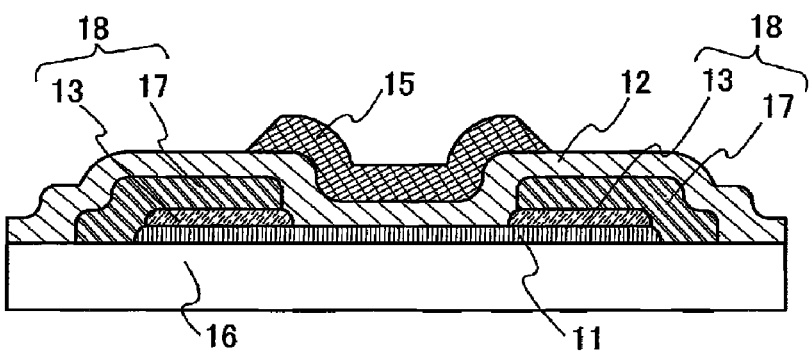

FIG. 1A shows an organic field effect transistor which is a bottom gate type and a bottom contact type. The bottom contact type has a structure in which a source electrode and a drain electrode are provided below an organic semiconductor layer. FIG. 1B shows an organic field effect transistor which is a bottom gate type and a top contact type. The top contact type has a structure in which a source electrode and a drain electrode are in contact with an upper surface of a semiconductor layer. FIG. 1C shows an organic field effect transistor which is a top gate type and a bottom contact type, and FIG. 1D shows an organic field effect transistor which is a top gate type and a top contact type.

In the case of a top contact organic transistor, a source electrode and a drain electrode should be formed over the semiconductor layer 11. Therefore, when the electrode is formed by a sputtering method or the like, the semiconductor layer 11 is damaged, whereby transistor characteristics are lowered in some cases. Accordingly, the electrode has been formed by an evaporation method which causes less damage, but an electrode material which can be formed by an evaporation method and which can satisfy restriction by a work function has been only a few materials such as gold. However, when the composite layer 13 that can be formed by an evaporation method is formed over the semiconductor layer 11 as in the present invention, an organic transistor having favorable transistor characteristics can be easily obtained without damaging the semiconductor layer 11 also in the case of a top contact organic transistor. It is to be noted that, by forming the composite layer 13 previously, the semiconductor layer 11 can also be prevented from being damaged when the conductive layer 17 is formed over the composite layer 13 by a sputtering method or the like.

In such a manner, when the source electrode and the drain electrode 18 each having a structure in which the composite layer 13 is interposed between the semiconductor layer 11 and the conductive layer 17 are employed, an energy barrier between the semiconductor layer 11 and the source and drain electrode is reduced; thus, carrier injection from the source electrode to the semiconductor layer and carrier discharge from the semiconductor layer to the drain electrode are smoothly performed. Accordingly, it becomes possible to select the conductive layer 17 without restriction by the work function. The edge of the composite layer 13 may be in alignment with the edge of the conductive layer 17 as shown in FIGS. 1A and 1C, or the edge of the composite layer 13 may extend beyond the side surface of the conductive layer 17 over the semiconductor layer 11 as shown in FIGS. 1B and 1D.

In addition, the composite layer 13 is chemically stable, and adhesion with the semiconductor layer 11 is favorable compared to the conductive layer 17. Further, when the composite layer 13 is combined with the conductive layer 17 as in this structure, the source electrode and the drain electrode 18 which are favorable in conductivity and which can also be used as a wiring can be provided.

As described above, by employing the source electrode and the drain electrode of this structure, an organic field effect transistor with favorable field effect mobility can be provided. In addition, an organic field effect transistor with excellent durability can be provided.

It is to be noted that, through the use of the composite layer 13, an energy barrier between the source and drain electrode 18 and the semiconductor layer 11 is reduced; thus, it is not necessary to select a material with a low energy barrier with the semiconductor layer 11 as a material for the source electrode and the drain electrode (that is, there is no restriction by the work function), which is also one of the advantages of the present invention.

Further, when a composite layer contains the carbazole derivative represented by the above general formula (1) and an inorganic compound, a composite material without an absorption peak in a visible light region can be obtained. Therefore, it is possible to obtain a composite layer having high transmittance of visible light and an organic filed effect transistor having high transmittance of visible light.

In addition, since the carbazole derivative represented by the general formula (1) has high glass transition temperature, the composite layer used in the present invention is excellent in heat resistance.

Embodiment Mode 2

Subsequently, an example of a structure which is suitable for an n-channel organic field effect transistor and in which an electron is a carrier will be explained. This structure further includes a second layer 14 containing alkali metal, alkaline earth metal, or a compound containing alkali metal or alkaline earth metal (oxide, nitride, or salt) in addition to the structure of Embodiment Mode 1 including the composite layer 13 in part of the source electrode or the drain electrode.

An organic semiconductor material used in the present invention is not particularly limited. However, in particular, as an organic semiconductor material having characteristics as an n-channel field effect transistor, the following material is preferable: perylene tetra carboxylic anhydride and a derivative thereof, a perylene tetra carboxylic diimide derivative, naphthalene tetra carboxylic anhydride and a derivative thereof, a naphthalene tetra carboxylic diimide derivative, a metallophthalocyanine derivative, or fullerene.

The type of alkali metal or alkaline earth metal, or oxide, nitride, or salt containing alkali metal or alkaline earth metal used for the second layer 14 of the present invention is not particularly limited; however, the following material is preferable: lithium, sodium, potassium, cesium, magnesium, calcium, strontium, barium, lithium oxide, magnesium nitride, or calcium nitride. In addition, the second layer 14 may be formed using a mixed material of these materials and an organic compound having an electron transporting property. As the organic compound having an electron transporting property, the following material can be used: a material which is composed of metal complex having a quinoline skeleton or a benzoquinoline skeleton such as tris(8-quinolinolato)aluminum (abbreviation: $Alq_3$), tris(4-methyl-8-quinolinolato) aluminum (abbreviation: $Almq_3$), bis(10-hydroxybenzo)[h]-quinolinato)beryllium (abbreviation: $BeBq_2$), or bis(2-methyl-8-quinolinolato)-4-phenylphenolato-aluminum (abbreviation: BAlq) in addition to perylene tetra carboxylic anhydride and a derivative thereof, a perylene tetra carboxylic diimide derivative, naphthalene tetra carboxylic anhydride and a derivative thereof, a naphthalene tetra carboxylic diimide derivative, a metallophthalocyanine derivative, or fullerene used for the semiconductor layer. In addition, a material such as metal complex having an oxazole based or thiazole based ligand such as bis[2-(2-hydroxyphenyl)benzoxazolato]zinc (abbreviation: $Zn(BOX)_2$) or bis[2-(2-hydroxyphenyl)benzothiazolato]zinc (abbreviation: $Zn(BTZ)_2$) can be used. In addition to such metal complex, 2-(4-biphenylyl)-5-(4-tert-butylphenyl)-1,3,4-oxadiazole (abbreviation: PBD), 1,3-bis[5-(p-tent-butylphenyl)-1,3,4-oxadiazol-2-yl]benzene (abbreviation: OXD-7), 3-(4-tent-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), or the like can be used.

FIGS. 2A to 2D each show a structural example of an organic field effect transistor of the present invention. In the drawings, reference numeral 11 denotes a semiconductor layer containing an organic semiconductor material; 12, an insulating layer; 15, a gate electrode; and 16, a substrate. A source electrode and a drain electrode 18 each include a composite layer 13, a second layer 14, and a conductive layer 17. In addition, the second layer 14 is provided between the composite layer 13 and the semiconductor layer 11. Arrangement of each layer or each electrode can be appropriately selected from FIGS. 2A to 2D depending on the usage of an element. FIGS. 2A to 2D correspond to FIGS. 1A to 1D, respectively, in which the second layer is further provided. Therefore, detailed explanation on the element structure will be omitted here. In addition, in the drawings, the second layer 14 is provided so as to be in contact with the composite layer 13 and the semiconductor layer 11; however, the present invention is not limited thereto. The second layer 14 may be included in part of the source electrode and/or the drain electrode.

Figure 2A:
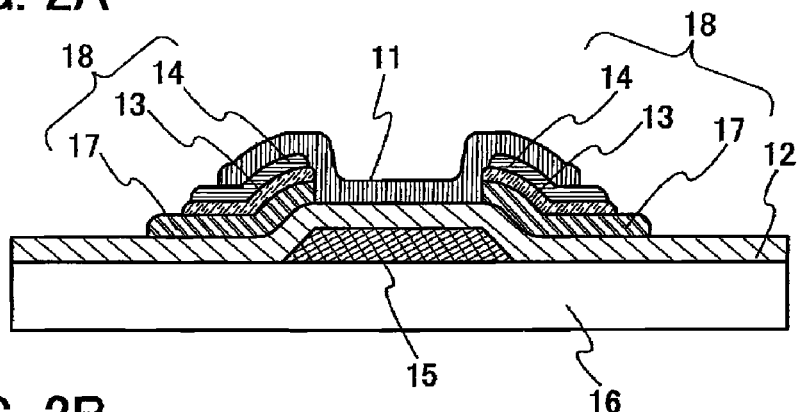
FIGS. 2A to 2D are schematic views each showing a structural example of an organic field effect transistor of the present invention.

The structure of FIG. 2A is used as an example in order to explain the present invention. As described above, this structure is suitable for an n-type organic field effect transistor in which an electron is a carrier. As shown in FIG. 2A, the source electrode and the drain electrode 18 are formed over the substrate 16, over which the gate electrode 15 and the insulating layer 12 are formed. As each of the source electrode and the drain electrode, the conductive layer 17 is formed, and the composite layer 13 and the second layer 14 are sequentially stacked over the conductive layer 17. At this time, the conductive layer 17 and the composite layer 13 may be formed using the same mask so that edges of the conductive layer 17 and the composite layer 13 are in alignment. Finally, the organic semiconductor layer is formed at least between the source electrode and the drain electrode, whereby an organic filed effect transistor is obtained. In FIG. 2A, the semiconductor layer 11 is formed so as to partially overlap with the source electrode and the drain electrode 18. The second layer 14 is provided so as to be in contact with the semiconductor layer 11. Further, the composite layer 13 is provided between the conductive layer 17 and the second layer 14.

When voltage is applied to the source electrode having the structure in which the composite layer 13 and the second layer 14 are stacked as described above, a hole and an electron are generated from an interface between the composite layer 13 and the second layer 14 due to carrier separation. Among generated carriers, the electron is supplied from the second layer 14 to the semiconductor layer 11, and the hole is discharged to the conductive layer 17. The electron discharged from the semiconductor layer 11 to the drain electrode and the hole supplied from a conductive material in the drain electrode are annihilated at the interface between the second layer 14 and the composite layer 13 in the drain electrode. Accordingly, current in which an electron is a carrier flows in the semiconductor layer 11.

In such a manner, the structure in which the composite layer 13 and the second layer 14 are stacked is interposed between the semiconductor layer 11 and the conductive layer 17; thus, an energy barrier between the semiconductor layer 11 and the source and drain electrode 18 is reduced, whereby electron supply from the source electrode to the semiconductor layer and electron discharge from the semiconductor layer to the drain electrode are smoothly performed.

In addition, the composite layer 13 is chemically stable, and adhesion of the second layer 14 with the semiconductor layer 11 is favorable compared to the conductive layer 17. Further, when the composite layer 13 and the second layer 14 are combined with the conductive layer 17 as in this structure, the source electrode and the drain electrode 18 which are favorable in conductivity and which can also be used as a wiring can be provided.

As described above, by employing the source electrode and the drain electrode of this structure, an organic field effect transistor with favorable field effect mobility can be provided. In addition, an organic field effect transistor with excellent durability can be provided.

It is to be noted that, through the use of this structure, an energy barrier between the source and drain electrode 18 and the semiconductor layer 11 is reduced; thus, it is not necessary to select a material with a low energy barrier with the semiconductor layer 11 for a material of the conductive layer 17. That is, the conductive layer 17 can be selected regardless of the work function, which is also one of the advantages of the present invention.

It is to be noted that the matter which has not been clarified in this embodiment mode is based on Embodiment Mode 1.

Further, when the composite layer contains the carbazole derivative represented by the above general formula (1) and an inorganic compound, a composite layer without an absorption peak in a visible light region can be obtained. Therefore, it is possible to obtain a composite layer having high transmittance of visible light and an organic filed effect transistor having high transmittance of visible light.

In addition, since the carbazole derivative represented by the general formula (1) has high glass transition temperature, the composite layer used in the present invention is excellent in heat resistance.

Embodiment Mode 3

Subsequently, a structure in which an organic compound used for a composite layer is also used for a semiconductor layer will be explained. In this structure, the same organic compound is used for the composite layer and the semiconductor layer; thus, the manufacturing process is simplified and is advantageous in terms of the cost. Further, since adhesion between the semiconductor layer and a source and drain electrode, and chemical stability at the interface are improved, further improvement in transistor characteristics can be expected. In addition, improvement in durability of an organic filed effect transistor can be expected.

A semiconductor material used in the present invention is not particularly limited; however, in this embodiment mode, since the same organic compound as that used for the composite layer is used, the carbazole derivative represented by the above general formula (1) is preferable.

The structure of FIG. 1A is used as an example in order to explain the present invention more in detail. As shown in FIG. 1A, a source electrode and a drain electrode 18 are formed over a substrate 16, over which a gate electrode 15 and an insulating layer 12 are formed. As each of the source electrode and the drain electrode, a conductive layer 17 is formed, and a composite layer 13 is stacked over the conductive layer 17. At this time, the conductive layer 17 and the composite layer 13 may be formed using the same mask so that edges of the conductive layer 17 and the composite layer 13 are in alignment, or edges of the conductive layer 17 and the composite layer 13 on one side are in alignment as shown in FIG. 1A. It is to be noted that an organic compound used for the composite layer 13 is the same as an organic semiconductor material used for a semiconductor layer 11 that is subsequently formed. Finally, the semiconductor layer 11 is formed at least between the source electrode and the drain electrode, whereby an organic filed effect transistor is obtained. In this case, the composite layer 13 is provided so as to be in contact with the semiconductor layer 11.

In such a manner, the source electrode and the drain electrode 18 each having the structure in which the composite layer 13 is interposed between the semiconductor layer 11 and conductive layer 17 are employed; thus, an energy barrier between the semiconductor layer 11 and the source and drain electrode is reduced as described in Embodiment Mode 1, whereby carrier injection from the source electrode to the organic semiconductor layer and carrier discharge from the semiconductor layer to the drain electrode are smoothly performed. In addition, when the organic compound used for the composite layer 13 and the organic semiconductor material used for the semiconductor layer 11 are the same, adhesion between the semiconductor layer 11 and the source and drain electrode 18 and chemical stability at the interface are improved; thus, effect that an energy barrier between the semiconductor layer 11 and the conductive layer 17 is reduced by the composite layer 13, gets higher. In addition, durability of the organic field effect transistor is also improved.

It is to be noted that, when the structure of this embodiment mode is applied to the structure of Embodiment Mode 2, the material used for the organic semiconductor layer may be used as an organic compound for the second layer. Other structures are the same as those of Embodiment Mode 2.

Embodiment Mode 4

This embodiment mode will explain a structure with reference to FIGS. 3A to 3D, in which an edge surface of a conductive layer 17 or a semiconductor layer 11 of an organic field effect transistor is covered with a composite layer, and the conductive layer 17 and the semiconductor layer 11 are not directly in contact with each other. In other words, the edge surfaces of the conductive layers 17 which face each other are covered with composite layers 13. In the structures of FIGS. 3A to 3D, only the above described portion is different from Embodiment Mode 1, and portions in the structures of FIGS. 3A to 3D, which will not be explained in this embodiment mode, are to be based on Embodiment Mode 1. It is to be noted that FIGS. 3A to 3D correspond to FIGS. 1A to 1D, respectively. Therefore, detailed explanation on the element structure will be omitted here.

In an organic field effect transistor, depending on an organic material used for a semiconductor layer, an orientation direction of the semiconductor layer highly influences current flow in some cases. Therefore, normally, consideration is given to the orientation of the semiconductor layer so that current easily flows in a carrier flow direction in a portion where a channel is formed.

In the structure of this embodiment mode, the conductive layer 17 and the semiconductor layer 11 of the organic field effect transistor shown in Embodiment Mode 1 are not directly in contact with each other as described above. By such a structure, a carrier can be injected more smoothly in the current flow direction, whereby characteristics of the organic field effect transistor can be improved. In particular, as shown in FIGS. 3A to 3D, it is preferable to cover the edge surface of the conductive layer 17 or the semiconductor layer 11 provided in a carrier flow direction with the composite layer 13.

It is to be noted that the structure as described above is suitable for a p-channel organic field effect transistor. As a structure suitable for an n-channel organic field effect transistor, FIGS. 4A to 4D are given. FIGS. 4A to 4D correspond to FIGS. 2A to 2D, respectively, and portions which will not be explained in this embodiment mode in the structures of FIGS. 4A to 4D are to be based on Embodiment Mode 2.

In the structures of FIGS. 4A to 4D, a conductive layer 17 and a semiconductor layer 11 of an organic field effect transistor shown in Embodiment Mode 2 are not directly in contact with each other, a composite layer 13 and a second layer 14 are provided between the conductive layer 17 and the semiconductor layer 11, and the composite layer 13 and the semiconductor layer 11 are not directly in contact with each other. By such a structure, a carrier can be injected more smoothly into the current flow direction, whereby characteristics of the organic field effect transistor can be improved. In particular, as shown in FIGS. 4A to 4D, it is preferable to cover the edge surface of the conductive layer 17 provided in a carrier flow direction with the composite layer 13, and to cover the edge surface of the composite layer 13 provided in a carrier flow direction with the second layer 14. Alternatively, it is preferable to cover the edge surface of the semiconductor layer 11 provided in a carrier flow direction with the second layer 14, and to cover the edge surface of the second layer 14 provided in a carrier flow direction with the composite layer 13.

Embodiment Mode 5

A manufacturing method of the organic field effect transistor of the present invention shown in FIG. 1A will be hereinafter explained with reference to FIGS. 5A to 5E. First, an example of a p-channel organic field effect transistor will be explained.

A gate electrode 15 is feinted using tungsten to be 100 nm thick over a substrate 16, an insulating layer 12 is formed using silicon dioxide ($SiO_2$) to be 100 nm thick as a gate insulating film over the gate electrode, and a conductive layer 17 is formed using tungsten to be 100 nm thick over the insulating layer 12. The gate electrode 15 may be formed through the steps of: forming tungsten over the entire surface of the substrate by a sputtering method or the like, forming a mask by photolithography, and etching tungsten into a desired shape. Either wet etching or dry etching may be used as the etching. The insulating layer 12 is formed by a CVD method. In addition, the conductive layer 17 may be formed in a manner similar to that of the gate electrode. Over the conductive layer 17, as a composite layer 13, molybdenum oxide (VI) and the carbazole derivative represented by the general formula (1) are co-evaporated to be 10 nm thick using a mask by vacuum evaporation using resistance heating so that a molar ratio becomes 1 to 1, and a source electrode and a drain electrode 18 each including the conductive layer 17 and the composite layer 13 are formed. Thereafter, as a semiconductor layer 11, pentacene is formed at least between the source electrode and the drain electrode 18 by evaporation;

accordingly, an organic transistor is manufactured. The semiconductor layer 11 may be evaporated by using a mask.

Pentacene can be purified by in-situ by being formed by an evaporation method; thus, purity of a material can be improved.

In addition, a conductive material can be selected without restriction by a work function in the present invention; therefore, if the gate electrode 15 and the conductive layer 17 are formed by selecting aluminum as a material and by evaporation, formation of all of the layers other than the insulating layer 12 can be performed by an evaporation method.

As for a manufacturing method of FIGS. 1B to 1D, there is no big difference basically except that the manufacturing order is changed; thus, the organic field effect transistors shown in FIGS. 1B to 1D can be manufactured similarly.

When drain current is measured in the case where gate voltage is applied to a manufactured organic field effect transistor to obtain field effect mobility, p-channel transistor characteristics can be obtained. More excellent transistor characteristics can be obtained compared to a transistor in which a composite layer is not used for parts of a source electrode and a drain electrode.

It is to be noted that an organic field effect transistor, in which an edge surface of a conductive layer or a semiconductor layer is covered with a composite layer, can be manufactured by changing a shape of a mask which forms the composite layer.

Embodiment Mode 6

A manufacturing method of an n-channel organic field effect transistor as shown in FIG. 2A will be explained with reference to FIGS. 6A to 6F as an example.

A gate electrode 15 is formed using tungsten to be 100 nm thick over a substrate 16, an insulating layer 12 is formed using silicon dioxide to be 100 nm thick as a gate insulating film over the gate electrode, and a conductive layer 17 is formed using tungsten to be 100 nm thick over the insulating layer 12. The gate electrode 15 and the conductive layer 17 are formed through the steps of: forming a tungsten film by a sputtering method, forming a mask by photolithography, and etching the tungsten film into a desired shape. Either wet etching or dry etching may be used as the etching. The insulating layer 12 may be formed by a CVD method or the like. Over the conductive layer 17, as a composite layer 13, molybdenum oxide (VI) and the carbazole derivative represented by the general formula (1) are co-evaporated to be 10 nm thick using a mask by vacuum evaporation using resistance heating so that a molar ratio becomes 1 to 1. Further, as a second layer 14, lithium metal and BCP that is an organic compound are co-evaporated to be 10 nm thick in a similar manner so that a molar ratio becomes 1 to 1; accordingly, a source electrode and a drain electrode 18 each including the conductive layer 17, the composite layer 13, and the second layer 14 are formed. Thereafter, as a semiconductor layer 11, perylenetetracarboxylic diimide is formed between the source electrode and the drain electrode by vacuum evaporation using resistance heating using a mask; accordingly, an organic field effect transistor is manufactured.

Figure 2B:
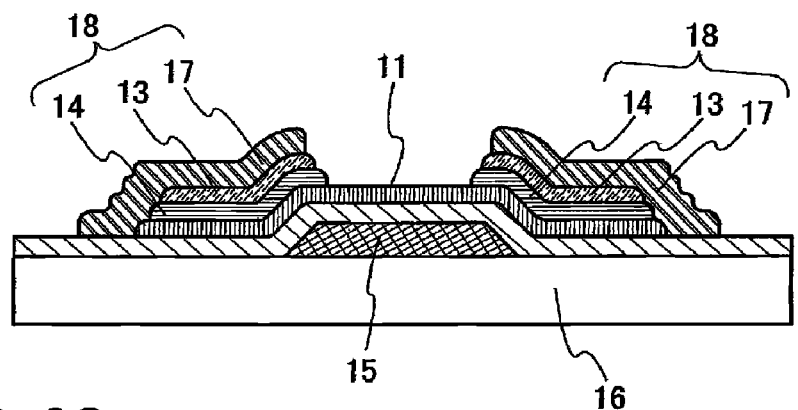
Figure 2C:
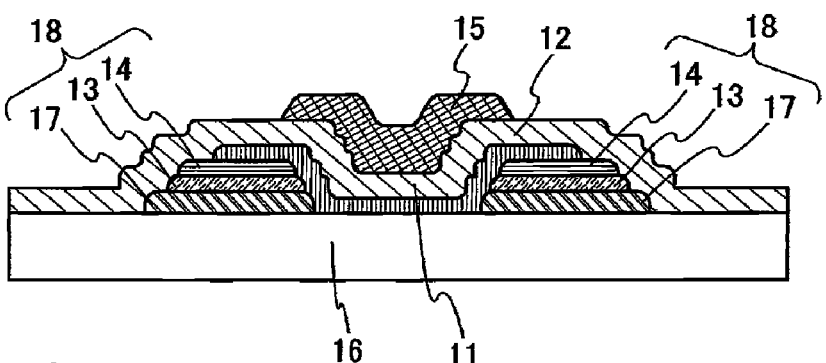
Figure 2D:
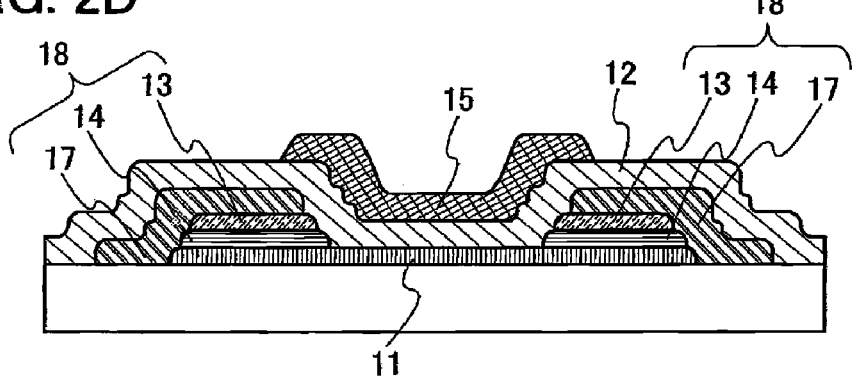
Figure 3A:
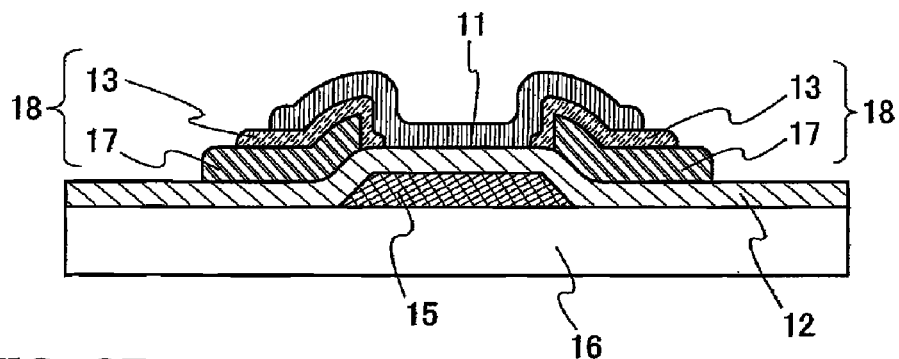
FIGS. 3A to 3D are schematic views each showing a structural example of an organic field effect transistor of the present invention.
Figure 3B:
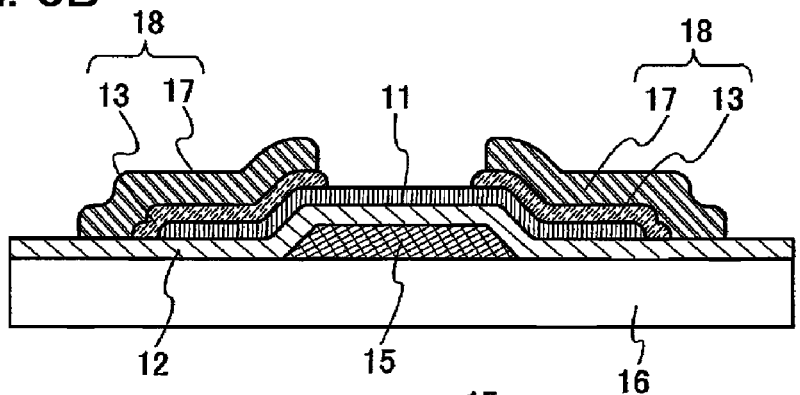
Figure 3C:
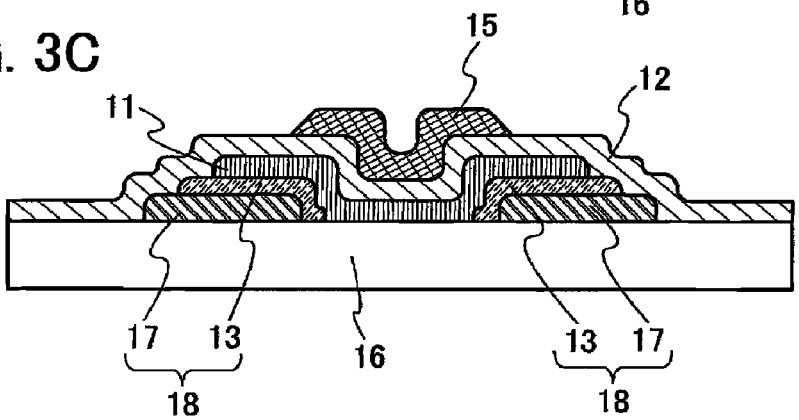
Figure 3D:
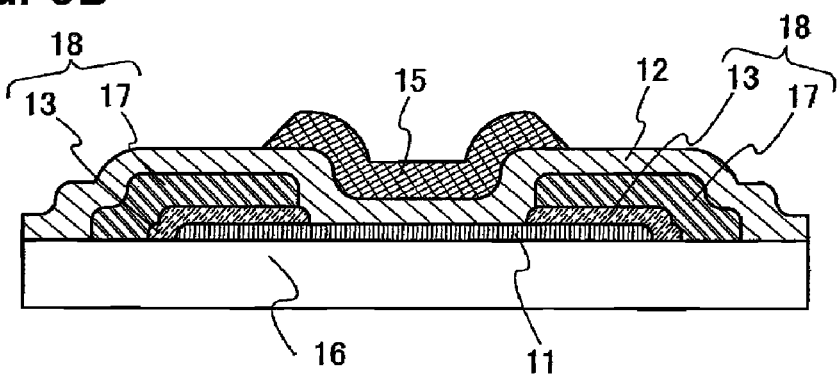
Figure 4A:
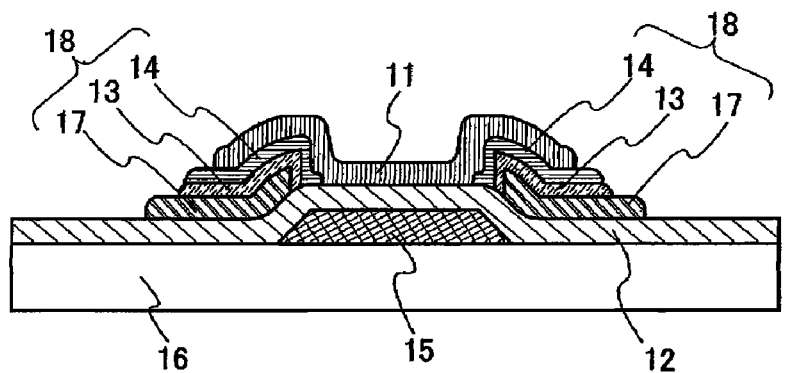
FIGS. 4A to 4D are schematic views each showing a structural example of an organic field effect transistor of the present invention.
Figure 4B:
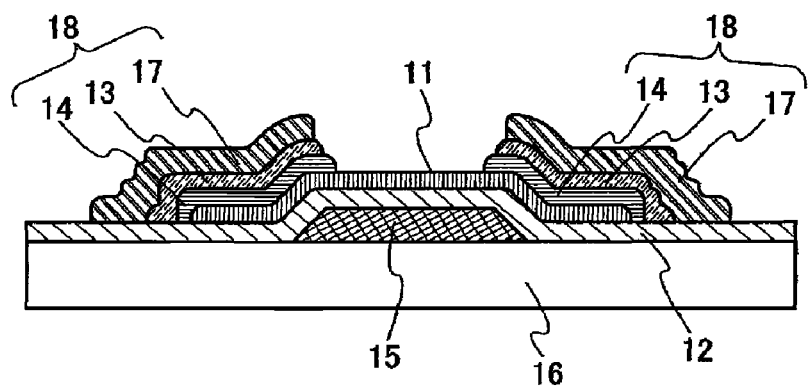
Figure 4C:
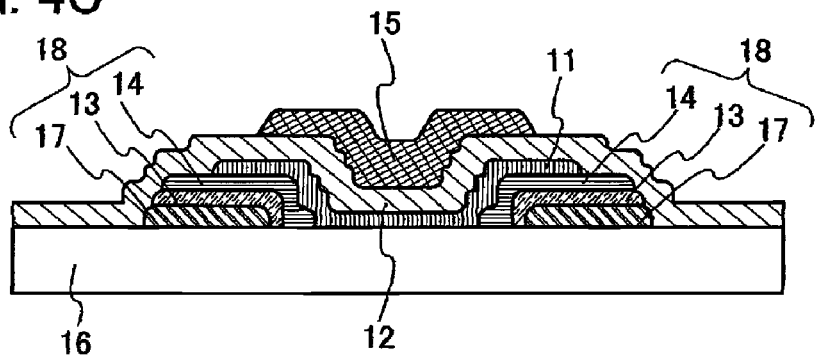
Figure 4D:
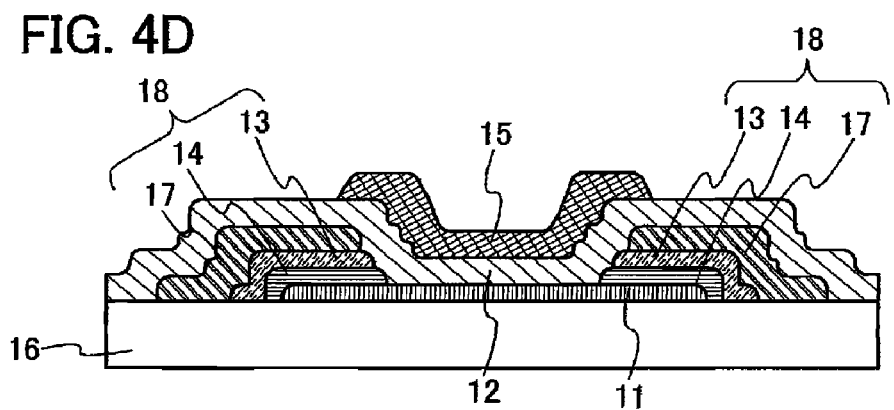
Figure 5A:
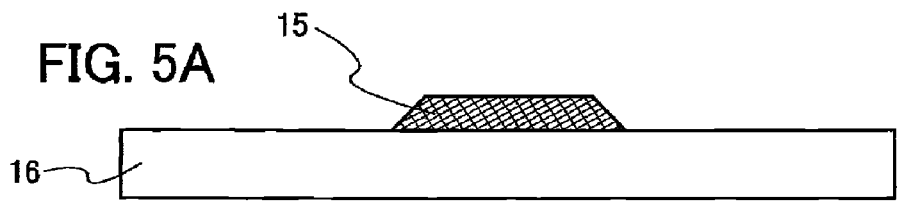
FIGS. 5A to 5E are views each explaining a manufacturing method of an organic field effect transistor of the present invention.
Figure 5B:
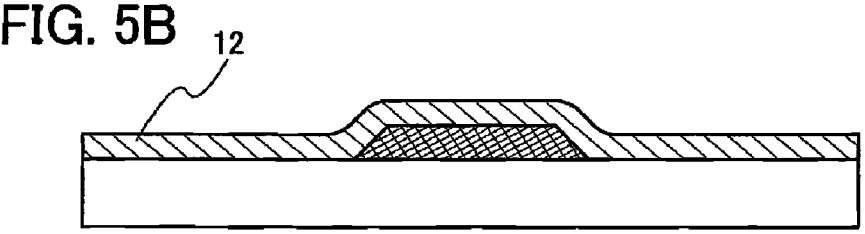
Figure 5C:
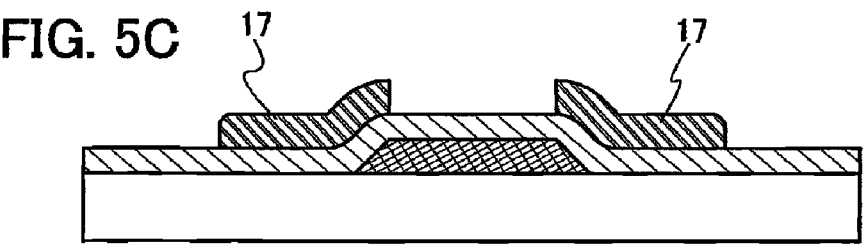
Figure 5D:
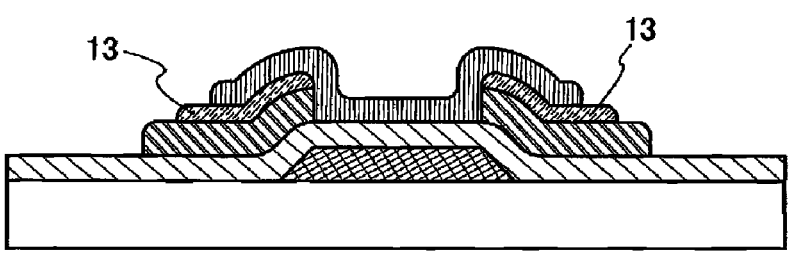
Figure 5E:
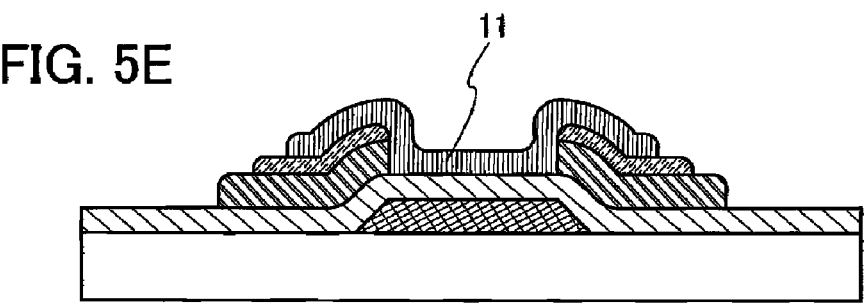
Figure 6A:
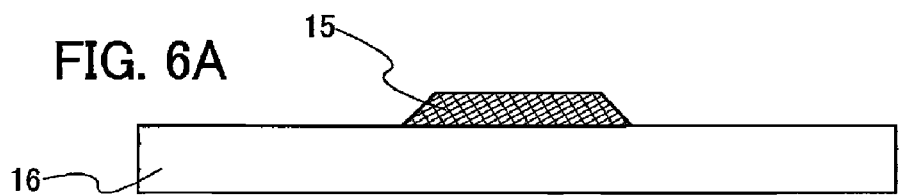
FIGS. 6A to 6F are views each explaining a manufacturing method of an organic field effect transistor of the present invention.
Figure 6B:
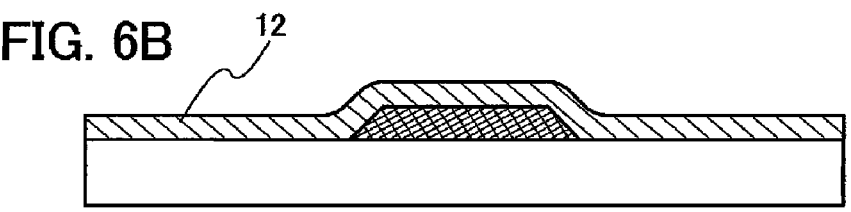
Figure 6C:
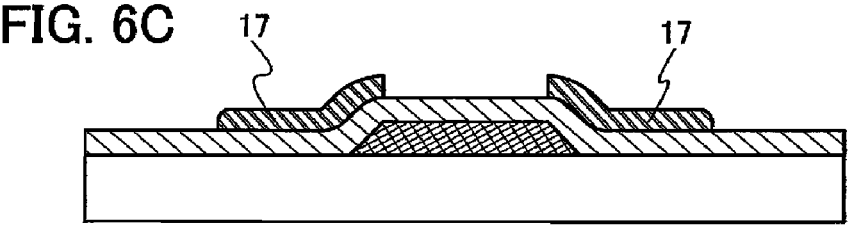
Figure 6D:
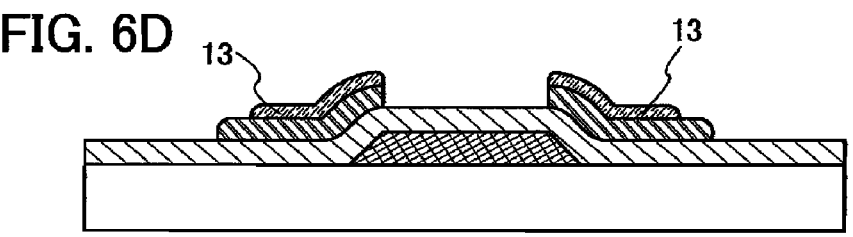
Figure 6E:
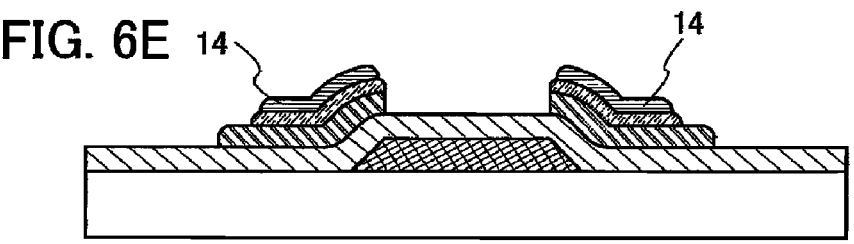
Figure 6F:
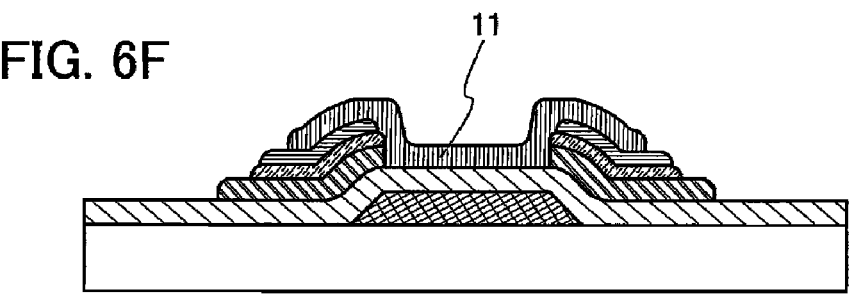

As for a manufacturing method of FIGS. 2B to 2D, there is no big difference basically except that the manufacturing order is changed, and the organic field effect transistors shown in FIGS. 2B to 2D can be manufactured in the similar manner. When the conductive layer 17 is formed in FIGS. 2B and 2D, an electrode is to be formed over a semiconductor layer 11; therefore, gold may be formed by vacuum evaporation using a mask.

When drain current is measured in the case where gate voltage is applied to a manufactured organic field effect transistor to obtain field effect mobility, n-channel transistor characteristics can be obtained. More excellent transistor characteristics can be obtained compared to a transistor in which a composite layer and a second layer are not used for parts of a source electrode and a drain electrode.

It is to be noted that an organic field effect transistor, in which an edge surface of a conductive layer or a semiconductor layer is covered with a composite layer and a second layer, can be manufactured by changing a shape of a mask which forms the composite layer and the second layer.

Embodiment Mode 7

A manufacturing method of an organic field effect transistor in which an organic compound used for a composite layer and an organic semiconductor material used for a semiconductor layer are the same will be hereinafter explained with reference to FIGS. 5A to 5E.

A gate electrode 15 is formed using tungsten to be 100 nm thick over a substrate 16, an insulating layer 12 is formed using silicon dioxide ($SiO_2$) to be 100 nm thick as a gate insulating film over the gate electrode, and a conductive layer 17 is formed using tungsten to be 100 nm thick over the insulating layer 12. Over the conductive layer 17, as a composite layer 13, molybdenum oxide (VI) and the carbazole derivative represented by the general formula (1) are co-evaporated to be 10 nm thick so that a molar ratio becomes 1 to 1, whereby a source electrode and a drain electrode 18 each including the conductive layer 17 and the composite layer 13 are formed. Thereafter, as a semiconductor layer 11, the carbazole derivative represented by the general formula (1) is formed between the source electrode and the drain electrode 18 by evaporation; accordingly, an organic field effect transistor is manufactured.

In the organic field effect transistor having such a structure of this embodiment mode, since a material for the semiconductor layer 11 and the organic compound used for the composite layer 13 are the same, adhesion between the composite layer 13 and the semiconductor layer 11 can be improved, and a defect generated due to peeling of the semiconductor layer from the source electrode or the drain electrode can be effectively reduced.

It is to be noted that a manufacturing method is the same as that of Embodiment Mode 1, and explanation thereof will thus be omitted.

When drain current is measured in the case where gate voltage is applied to a manufactured organic field effect transistor to obtain field effect mobility, excellent p-channel transistor characteristics can be obtained. More excellent transistor characteristics can be obtained compared to a transistor in which a composite layer is not used for parts of a source electrode and a drain electrode.

It is to be noted that an organic field effect transistor, in which an edge surface of a conductive layer or a semiconductor layer is covered with a composite layer, can be manufactured by changing a shape of a mask which forms the composite layer.

Embodiment Mode 8

This embodiment mode will explain an organic transistor of the present invention having another structure with reference to FIGS. 12A to 12D.

In the structures of this embodiment mode, a buffer layer 19 is provided between a source and drain electrode 18 and a semiconductor layer 11. The buffer layer 19 may be formed using 4,4'-bis{N-[4-(N,N-di-m-tolylamino)phenyl]-N-phenylamino}biphenyl (abbreviation: DNTPD), 4,4',4"-tris[N-(3-methylphenyl)-N-phenylamino]triphenylamine (abbreviation: MTDATA), or vanadium oxide.

By the buffer layer, characteristics of the organic transistor can be improved.

In addition, by the buffer layer, reliability of the organic transistor is also improved.

This is because a depletion layer is formed and junction of a junction type can be formed through formation of the buffer layer.

It is to be noted that FIGS. 12A to 12D show the structures in which the buffer layer is further provided in the structures shown in FIGS. 3A to 3D, but the structure with the buffer layer can also be applied to other structures.

Embodiment Mode 9

A liquid crystal device using the organic field effect transistor of the present invention will be explained with reference to FIGS. 7, and 8A and 8B.

Figure 7:
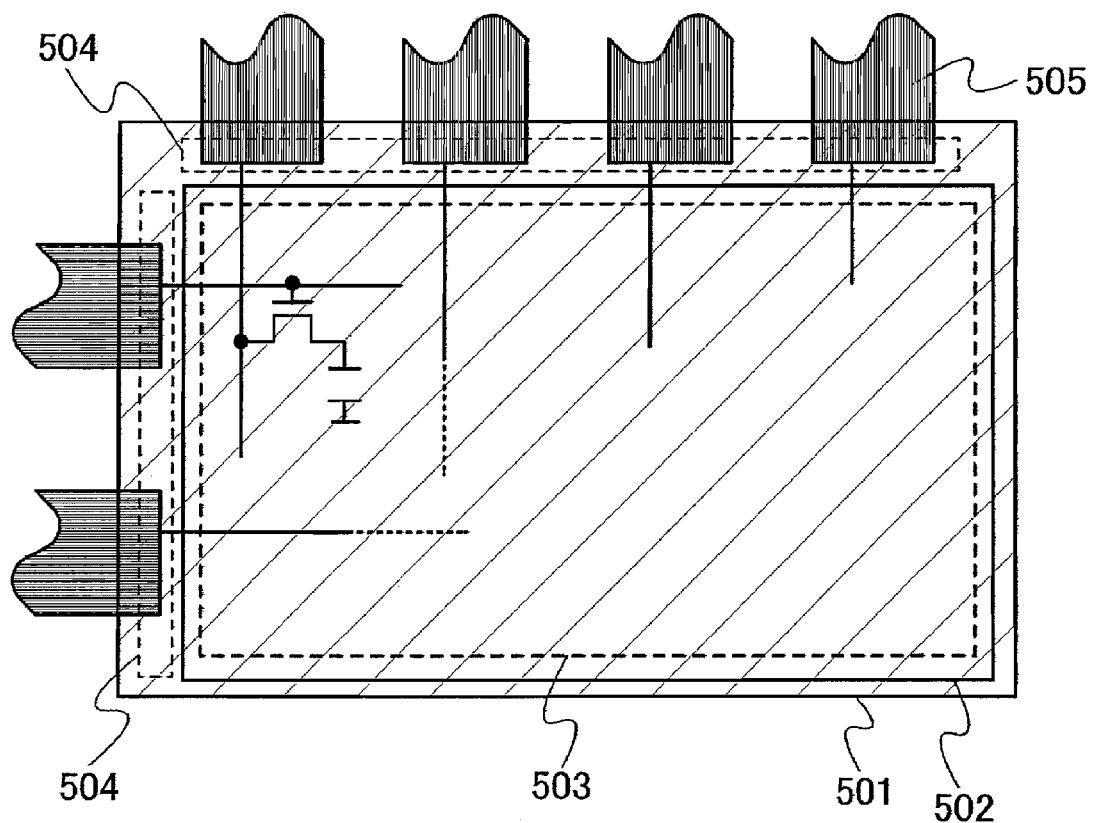
FIG. 7 is a top schematic view of a liquid crystal display device using the present invention.

FIG. 7 is a top schematic view of a liquid crystal device. In a liquid crystal device in this embodiment mode, an element substrate 501 and a counter substrate 502 are attached to each other, and a pixel portion 503 formed over the element substrate 501 is sealed with the counter substrate and a sealing material. A flexible printed circuit (FPC) 505 is connected to an external connection portion 504 which is provided at the periphery of the pixel portion 503; thus, a signal from outside is input. It is to be noted that a driver circuit and a flexible printed circuit may be independently provided as in this embodiment mode, or a driver circuit may be provided by being combined, like a TCP where an IC chip is mounted on an FPC having a wiring pattern, or the like.

The pixel portion 503 is not particularly limited. For example, the pixel portion includes a liquid crystal element and a transistor for driving the liquid crystal element as shown in cross-sectional views of FIGS. 8A and 8B.

Figure 8A:
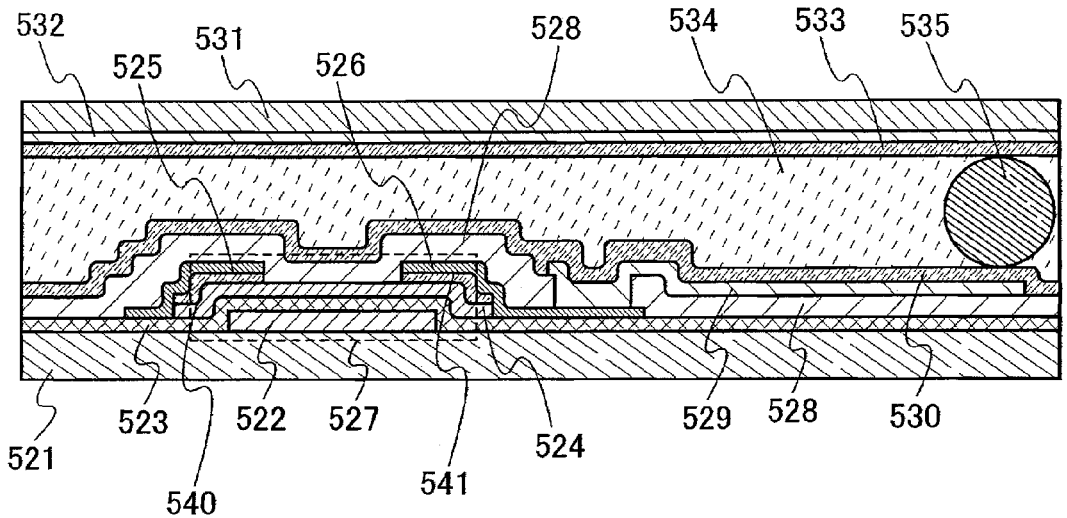
FIGS. 8A and 8B are cross-sectional schematic views each showing a liquid crystal display device using the present invention.

A liquid crystal device shown in the cross-sectional view of FIG. 8A includes a transistor 527 having a gate electrode 522 over a substrate 521, a gate insulating layer 523 over the gate electrode 522, a semiconductor layer 524 over the gate insulating layer 523, composite layers 540 and 541 and conductive layers 525 and 526 each serving as a source or a drain over the semiconductor layer 524. Here, since the composite layers 540 and 541 are provided in the source electrode or the drain electrode, carriers are transported smoothly between the semiconductor layer 524 and the source electrode or the drain electrode. Also, the conductive layers 525 and 526 can be selected without being restricted by a work function; therefore, the range of material choice is expanded.

A liquid crystal element includes a liquid crystal layer 534 interposed between a pixel electrode 529 and a counter electrode 532. A surface of the pixel electrode 529 on the liquid crystal layer 534 side is provided with an alignment film 530, and a surface of the counter electrode 532 on the liquid crystal layer 534 side is provided with an alignment film 533. A spacer 535 is dispersed in the liquid crystal layer 534 to keep a cell gap. The transistor 527 is covered with an insulating layer 528 provided with a contact hole, and an electrode formed using the conductive layer 526 and the pixel electrode 529 are electrically connected to each other. Here, the counter electrode 532 is supported by a counter substrate 531. In addition, in the transistor 527, the semiconductor layer 524 and the gate electrode 522 partially overlap with each other with the gate insulating layer 523 interposed therebetween.

Figure 8B:
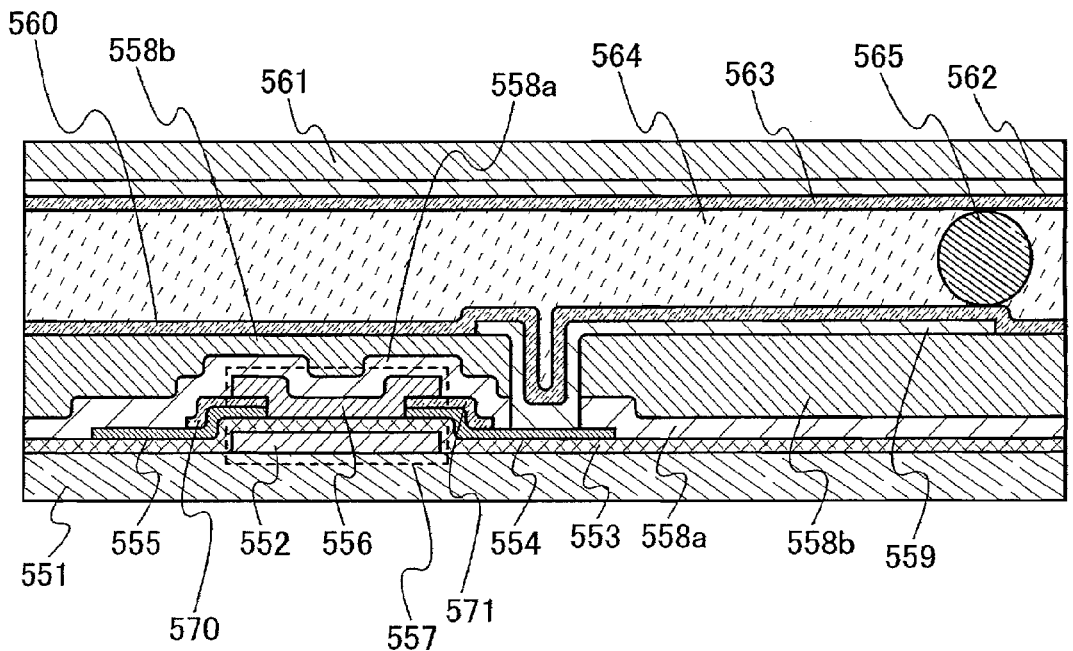

In addition, a liquid crystal device shown in the cross-sectional view of FIG. 8B has an element substrate 551 including a transistor 557 with a structure in which at least parts of electrodes (including conductive layers 555 and 554 and composite layers 570 and 571) serving as a source or a drain are covered with a semiconductor layer 556.

Here, since the composite layers 570 and 571 are provided in the source electrode or the drain electrode, carriers are transported smoothly between the semiconductor layer 556 and the source electrode or the drain electrode. In addition, the conductive layers 554 and 555 can be selected without being restricted by a work function; therefore, the range of material choice is expanded.

In addition, a liquid crystal element includes a liquid crystal layer 564 interposed between a pixel electrode 559 and a counter electrode 562. A surface of the pixel electrode 559 on the liquid crystal layer 564 side is provided with an alignment film 560, and a surface of the counter electrode 562 on the liquid crystal layer 564 side is provided with an alignment film 563. A spacer 565 is dispersed in the liquid crystal layer 564 to keep a cell gap. The transistor 557 over the substrate 551 is covered with insulating layers 558a and 558b provided with a contact hole, and an electrode formed using the conductive layer 554 and the pixel electrode 559 are electrically connected to each other. It is to be noted that the insulating layer which covers the transistor may be a multilayer including the insulating layers 558a and 558b as shown in FIG. 8B, or a single layer including the insulating layer 528 as shown in FIG. 8A. In addition, the insulating layer which covers the transistor may be a layer having a planarized surface like the insulating layer 558b as shown in FIG. 8B. Here, the counter electrode 562 is supported by a counter substrate 561. In addition, in the transistor 557, the semiconductor layer 556 and a gate electrode 552 partially overlap with each other with a gate insulating layer 553 interposed therebetween.

It is to be noted that the structure of the liquid crystal device is not particularly limited. In addition to the mode shown in this embodiment mode, for example, a driver circuit may be provided over an element substrate.

Figure 9A:
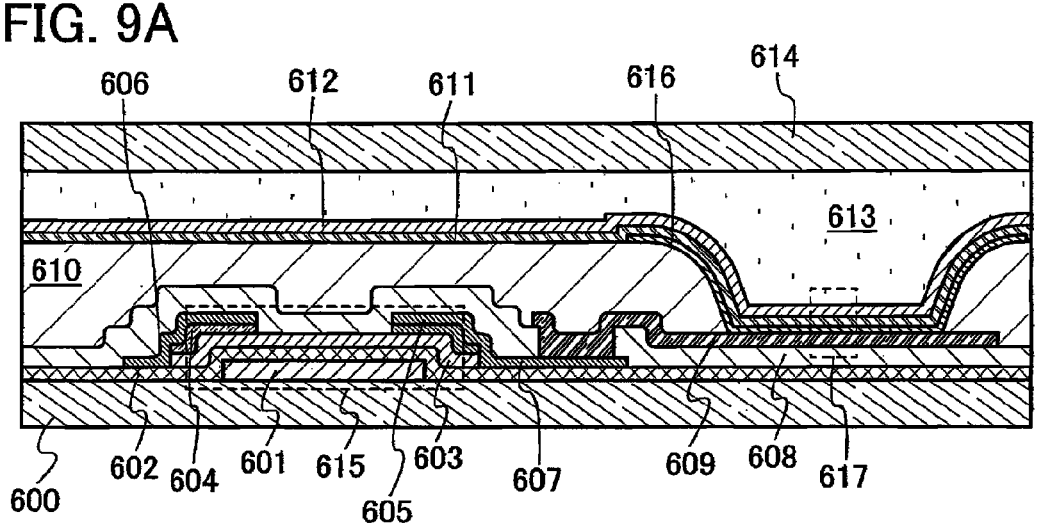
FIGS. 9A and 9B are cross-sectional schematic views each showing a light emitting display device using the present invention.

Subsequently, a light emitting device using the organic field effect transistor of the present invention will be explained with reference to FIGS. 9A and 9B. A light emitting element 617 which forms a pixel portion of the light emitting device includes a light emitting layer 616 interposed between a pixel electrode 609 and a common electrode 611 as shown in FIG. 9A. The pixel electrode 609 is electrically connected to a conductive layer 607 which is part of an electrode of an organic field effect transistor 615 through a contact hole which is provided in an interlayer insulating film 608 formed to cover the organic field effect transistor 615. The electrodes of the organic field effect transistor are formed using stacked layers of composite layers 604 and 605 and conductive layers 606 and 607. A semiconductor layer 603 is provided by using the materials given in Embodiment Mode 1 such as pentacene, and part thereof overlaps with a gate electrode 601 with a gate insulating film 602 interposed therebetween. The gate electrode 601 is formed over a substrate 600, and the gate electrode 601 and a source electrode and a drain electrode of the organic field effect transistor 615 partially overlap with each other with the gate insulating film 602 and the semiconductor layer 603 interposed therebetween. The edge of the pixel electrode 609 is covered with an insulating layer 610, and the light emitting layer 616 is formed so as to cover a portion exposed from the insulating layer 610. It is to be noted that, although a passivation film 612 is formed to cover the common electrode 611, the passivation film 612 may not be formed. The substrate 600 over which these elements are formed is sealed with a counter substrate 614 and a sealing material outside the pixel portion which is not shown, and the light emitting element 617 is insulated from the outside air. A space 613 between the counter substrate 614 and the substrate 600 may be filled with an inert gas such as dried nitrogen, or the substrate 600 may be sealed by filling the space 613 with a resin or the like instead of the sealing material.

Figure 9B:
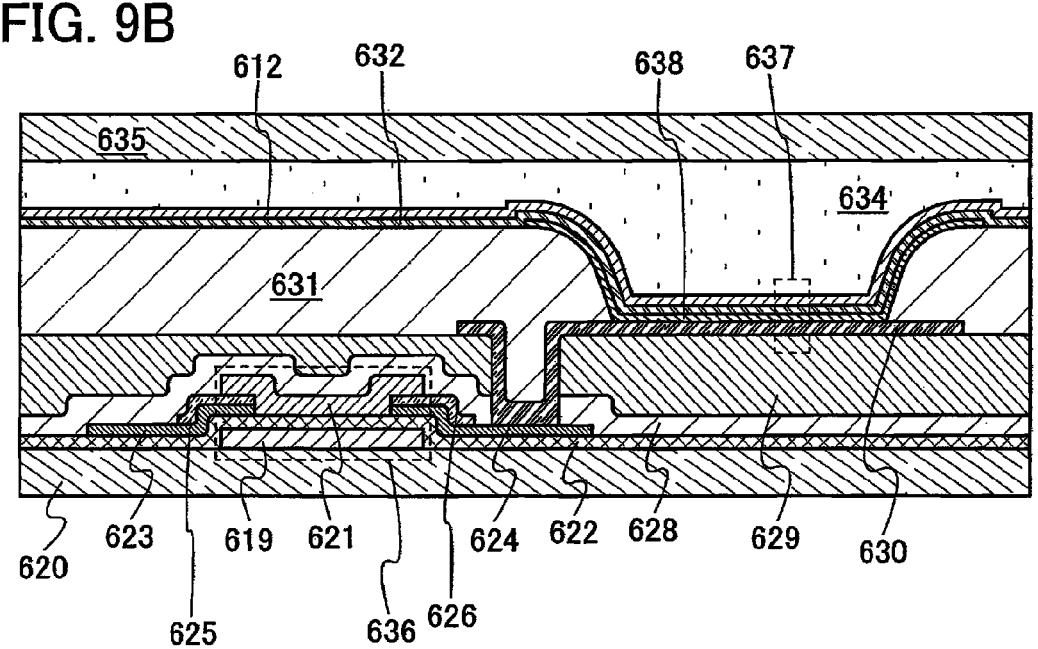

FIG. 9B is a structure of a light emitting device which is different from FIG. 9A. Similarly to FIG. 9A, a light emitting element 637 which forms a pixel portion of the light emitting device includes a light emitting layer 638 interposed between a pixel electrode 630 and a common electrode 632. The pixel electrode 630 is electrically connected to a conductive layer 624 which is part of an electrode of an organic field effect transistor 636 through a contact hole which is provided in a first interlayer insulating film 628 and a second interlayer insulating film 629, which are formed to cover the organic field effect transistor 636. The electrodes of the organic field effect transistor 636 are formed using stacked layers of composite layers 625 and 626 and conductive layers 623 and 624. A semiconductor layer 621 is provided by using the materials given in Embodiment Mode 1 such as pentacene, and part thereof overlaps with a gate electrode 619 with a gate insulating film 622 interposed therebetween. The gate electrode 619 is formed over a substrate 620, and the gate electrode 619 and a source electrode and a drain electrode of the organic field effect transistor 636 partially overlap with each other with the gate insulating film 622 interposed therebetween. The edge of the pixel electrode 630 is covered with an insulating layer 631, and the light emitting layer 638 is formed so as to cover a portion exposed from the insulating layer 631. It is to be noted that, although a passivation film 612 is formed to cover the common electrode 632, the passivation film 612 may not be formed. The substrate 620 over which these elements are formed is sealed with a counter substrate 635 and a sealing material outside the pixel portion which is not shown, and the light emitting element 637 is insulated from the outside air. A space 634 between the counter substrate 635 and the substrate 620 may be filled with an inert gas such as dried nitrogen, or the substrate 620 may be sealed by filling the space 634 with a resin or the like instead of the sealing material.

Figure 10A:
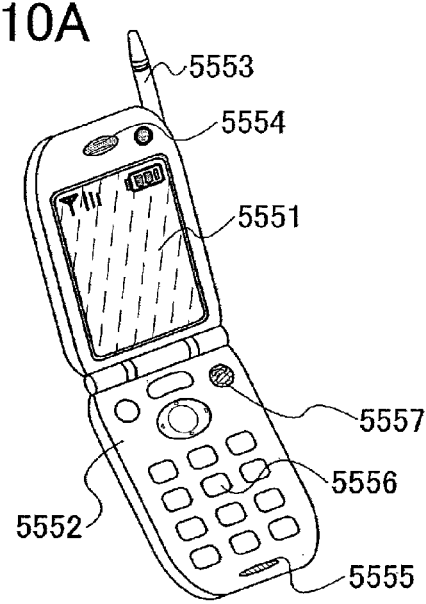
FIGS. 10A to 10C are views showing electronic devices using the present invention.
Figure 10B:
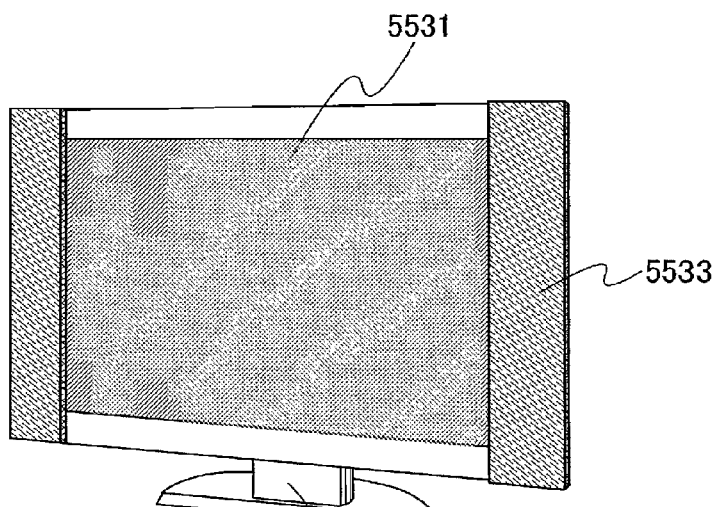
Figure 10C:
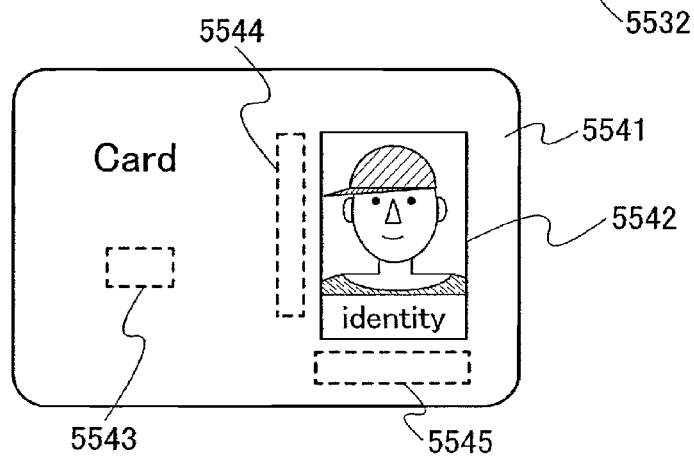

The display device as described above can be used as a display device that is mounted on a telephone set, a television set, or the like as shown in FIGS. 10A to 10C. In addition, the display device may also be mounted on a card having a function of controlling personal information such as an ID card or the like.

FIG. 10A shows a telephone set, which includes a main body 5552 having a display portion 5551, an audio output portion 5554, an audio input portion 5555, operation switches 5556 and 5557, an antenna 5553, and the like. The telephone set has favorable operation characteristics and high reliability. Such a telephone set can be completed by incorporating a semiconductor device including the organic field effect transistor of the present invention into the display portion.

FIG. 10B shows a television set manufactured by employing the present invention, which includes a display portion 5531, a housing 5532, a speaker 5533, and the like. The television set has favorable operation characteristics and high reliability. Such a television set can be completed by incorporating the light emitting device of the present invention into the display portion.

FIG. 10C shows an ID card manufactured by employing the present invention, which includes a supporting body 5541, a display portion 5542, an integrated circuit chip 5543 which is incorporated into the supporting body 5541, and the like. Further, integrated circuits 5544 and 5545 for driving the display portion 5542 are also incorporated into the supporting body 5541. The ID card has high reliability. In addition, for example, information which is input into or output to/from the integrated circuit chip 5543 can be displayed on the display portion 5542. Thus, it can be confirmed what kind of information is input or output.

Embodiment Mode 10

As another embodiment mode of the present invention, an example in which the organic transistor described in Embodiment Modes 1 to 3 is applied to a display device having flexibility will be described with reference to FIG. 11.

Figure 11:
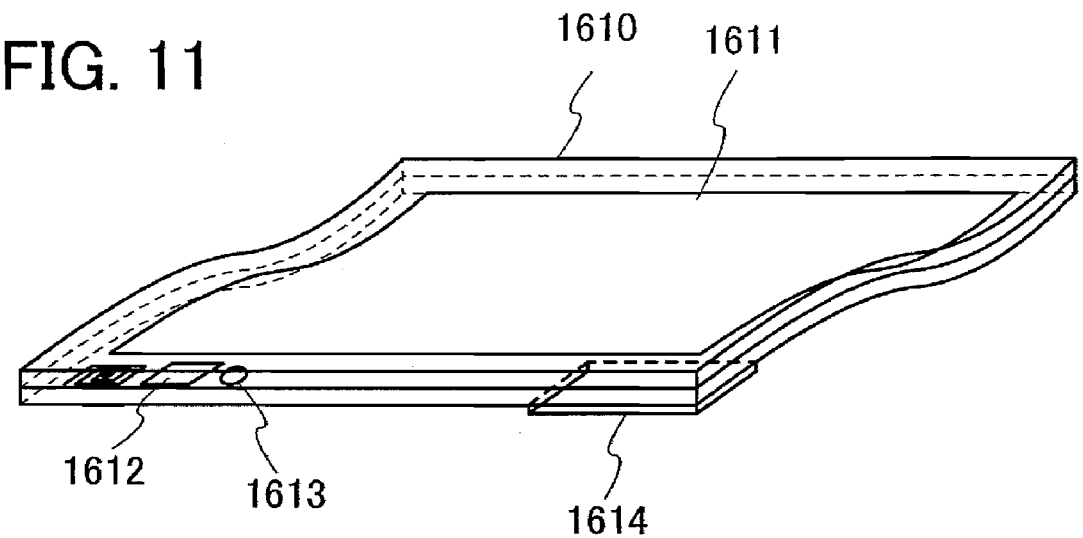
FIG. 11 is a view showing an electronic device using the present invention.
Figure 12A:
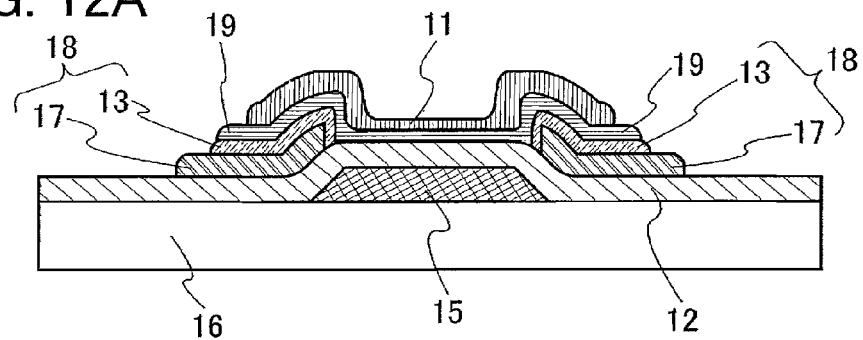
FIGS. 12A to 12D are schematic views each showing a structural example of an organic transistor of the present invention.
Figure 12B:
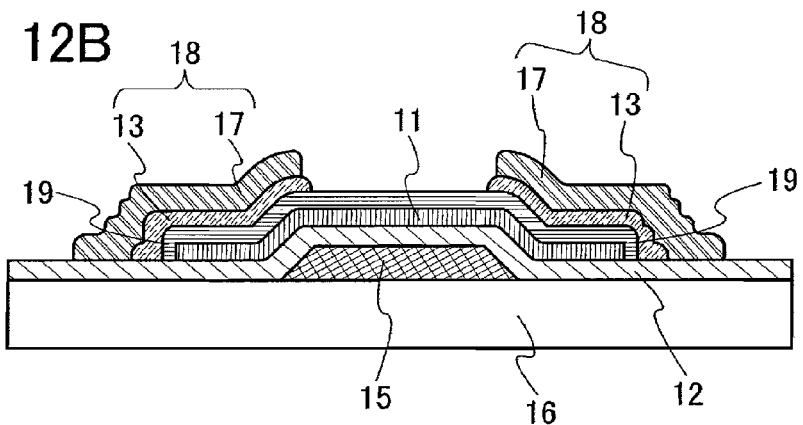
Figure 12C:
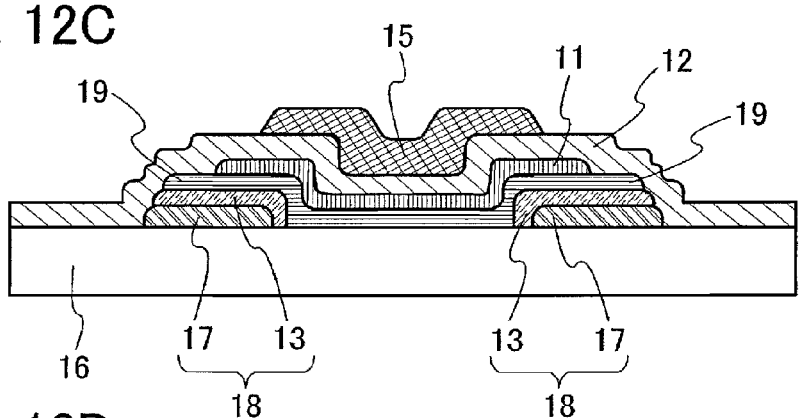
Figure 12D:
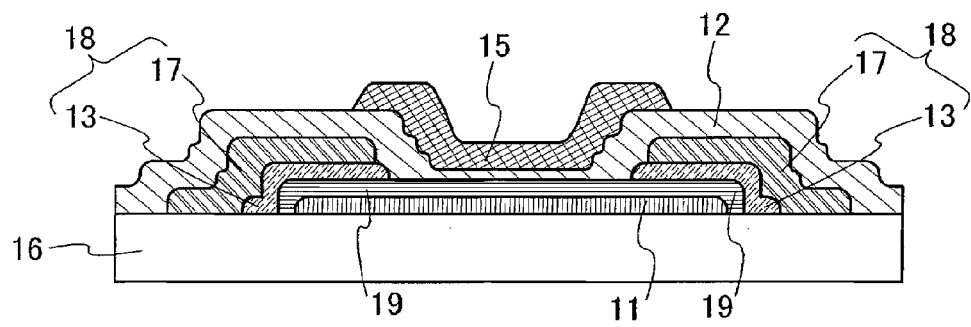

A display device of the present invention shown in FIG. 11 may be included in a housing, and the display device includes a main body 1610, a pixel portion 1611 which displays an image, a driver IC 1612, a receiver device 1613, a film battery 1614, and the like. The driver IC 1612, the receiver device 1613, and the like may be mounted by using a semiconductor part. The main body 1610 of the display device of the present invention is formed using a material having flexibility such as plastics or a film. Such a material is usually thermally fragile; however, by forming a transistor in a pixel portion using the organic transistor described in Embodiment Modes 1 to 3, it becomes possible to form a display device by using such a material which is thermally fragile.

Such a display device is extremely light and flexible; therefore, the display device can be rolled into a cylinder shape, and the display device is extremely advantageous to be carried. By the display device of the present invention, a display medium having a large screen can be freely carried.

Besides, the display device can be used as a display means of a navigation system, a sound reproduction device (such as a car audio or an audio component), a computer, a game machine, and a portable information terminal (such as a mobile computer, a cell phone, a portable game machine, or an electronic book). Moreover, the display device can be used as a means for mainly displaying a still image for electrical home appliances such as a refrigerator, a washing machine, a rice cooker, a fixed telephone, a vacuum cleaner, or a clinical thermometer, railroad wall banners, and a large-sized information display such as an arrival and departure guide plate in a railroad station and an airport.

As described above, preferable embodiment modes of the present invention are particularly described; however, it is easily understood by those skilled in the art that modes and details thereof can be modified in various ways without departing from the purpose and the scope of the present invention.

Embodiment 1

As an example of the carbazole derivative used in the present invention, a synthesis method of 3-[N-(9-phenylcarbazol-3-yl)-N-phenylamino]-9-phenylcarbazole (abbreviation: PCzPCA1) represented by the structural formula (12) will be explained.

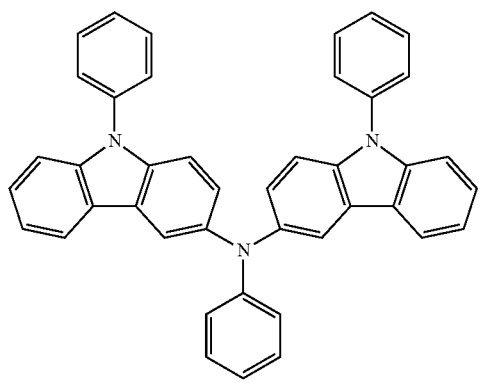

(12)

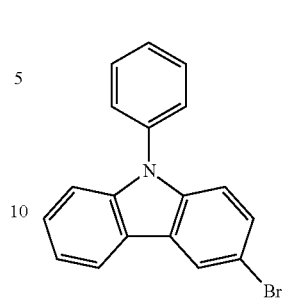

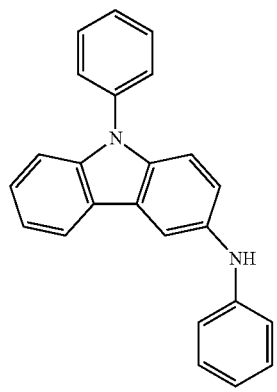

(A-4)

[Step 1]

First, a synthesis method of 3-bromo-9-phenylcarbazole will be explained. (A-3) shows a synthesis scheme of 3-bromo-9-phenylcarbazole.

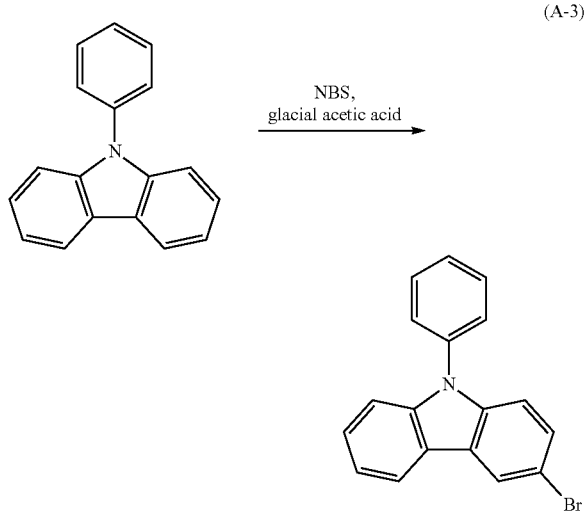

(A-3)

First, 24.3 g (100 mmol) of 9-phenylcarbazole was dissolved in 600 mL of glacial acetic acid, 17.8 g (100 mmol) of N-bromosuccinimide was slowly added therein, and the mixture was stirred at room temperature for approximately 12 hours. This glacial acetic acid solution was dripped to 1 L of ice water while being stirred, and a white solid which was precipitated was washed with water three times. This solid was dissolved in 150 mL of diethyl ether and washed with a saturated sodium hydrogen-carbonate aqueous solution and water. Then, an organic layer was dried with magnesium sulfate. After filtration, the obtained filtrate was concentrated. Thereafter, approximately 50 mL of methanol was added to the obtained residue, and the residue was uniformly dissolved. This solution was left at rest, and a white solid was precipitated. This solid was collected and dried; thus, 28.4 g of a white powder of 3-bromo-9-phenylcarbazole was obtained (yield: 88%).

[Step 2]

Next, a synthesis method of 3-(N-phenylamino)-9-phenyl-carbazole (abbreviation: PCA) will be explained. (A-4) shows a synthesis scheme of PCA.

Figure 13:
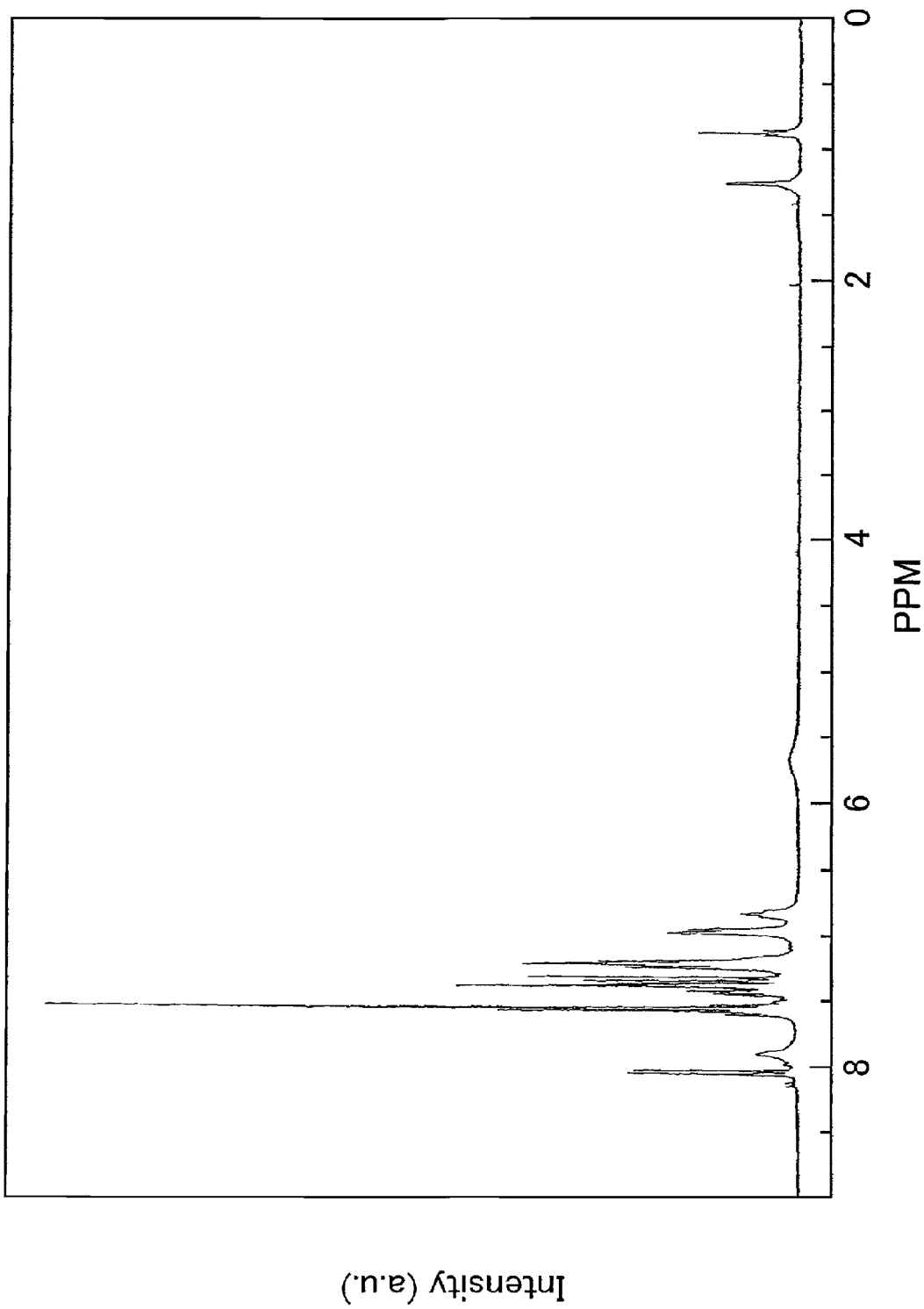
FIG. 13 is a diagram showing an $^1$H-NMR chart of 3-(N-phenylamino)-9-phenylcarbazole.
Figure 14:
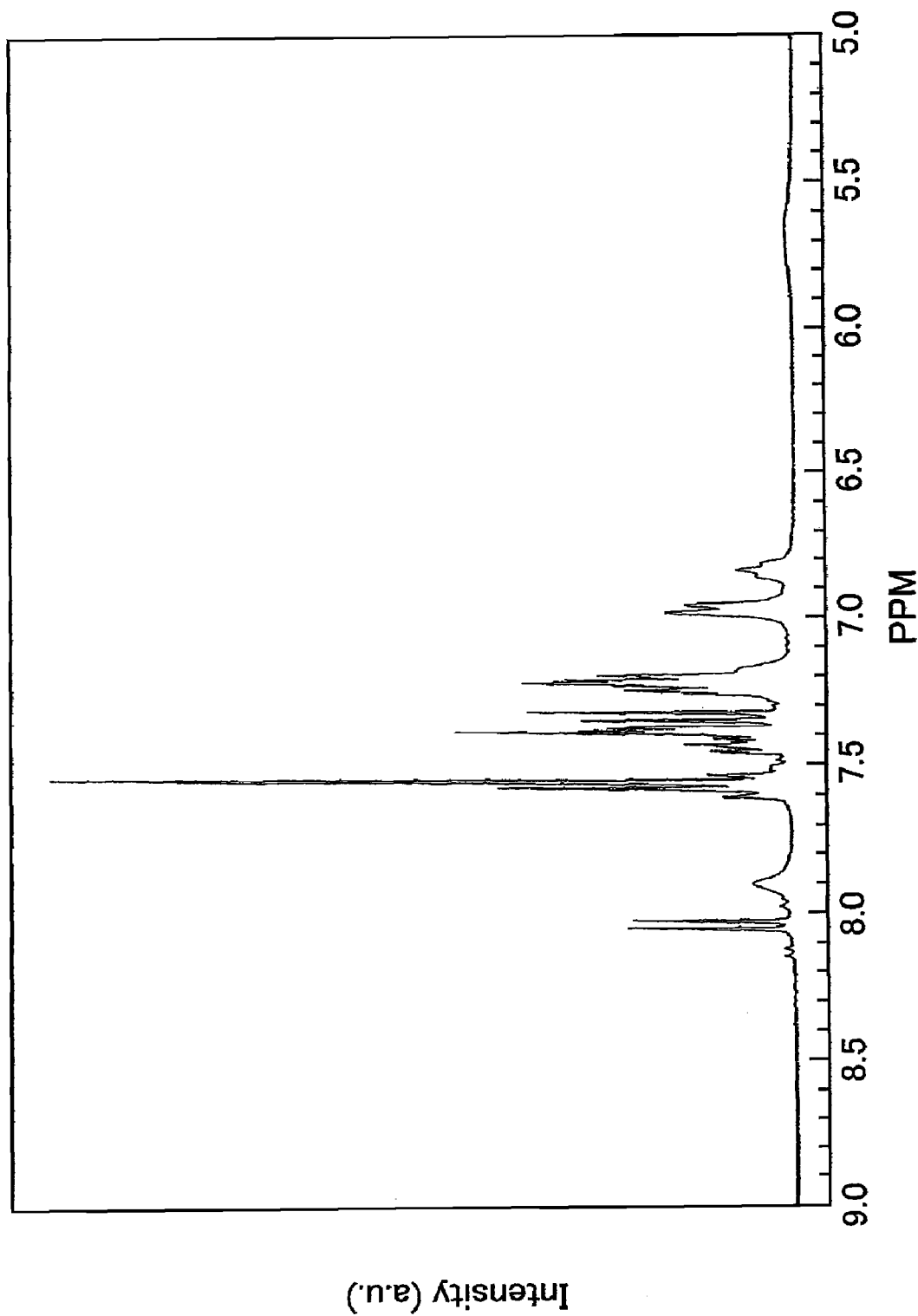
FIG. 14 is a diagram showing an $^1$H-NMR chart of 3-(N-phenylamino)-9-phenylcarbazole.

In a nitrogen atmosphere, 110 mL of dehydrated xylene and 7.0 g (75 mmol) of aniline were added to a mixture of 19 g (60 mmol) of 3-bromo-9-phenylcarbazole, 340 mg (0.6 mmol) of bis(dibenzylideneacetone)palladium(0), 1.6 g (3.0 mmol) of 1,1-bis(diphenylphosphino)ferrocene, and 13 g (180 mmol) of sodium-tert-butoxide. This mixture was heated and stirred at 90° C. for 7.5 hours in a nitrogen atmosphere. After the reaction was terminated, approximately 500 mL of warm toluene was added to the suspension, and this suspension was filtered through Florisil, alumina, and Celite. The thus obtained filtrate was concentrated, and hexane-ethyl acetate was added to the residue and irradiation with ultrasonic waves was performed. The thus obtained suspension was filtered and the residue was dried; thus, 15 g of a cream-colored powder of 3-(N-phenylamino)-9-phenylcarbazole was obtained (yield: 75%). The following shows NMR data. $^1$H-NMR (300 MHz, CDCl$_3$): δ=6.84 (t, J=6.9, 1H), 6.97 (d, J=7.8, 2H), 7.20-7.61 (m, 13H), 7.90 (s, 1H), 8.04 (d, J=7.8, 1H). In addition, FIG. 13 shows an $^1$H-NMR chart, and a portion of 5.0 to 9.0 ppm in FIG. 13 is enlarged and shown in FIG. 14.

[Step 3]

A synthesis method of 3-iodo-9-phenylcarbazole will be explained. (A-5) shows a synthesis scheme of 3-iodo-9-phenylcarbazole.

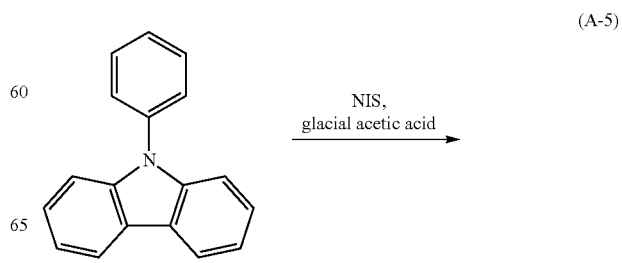

(A-5)

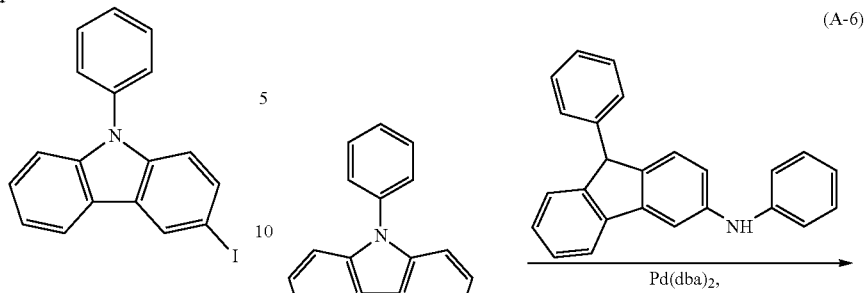

24.3 g (100 mmol) of 9-phenylcarbazole was dissolved in 600 mL of glacial acetic acid, 22.5 g (100 mmol) of N-iodosuccinimide was slowly added therein, and the mixture was stirred at room temperature for approximately 20 hours. The generated precipitate was filtered. Further, the residue was washed with a saturated sodium hydrogen-carbonate aqueous solution, water, and methanol and dried. Thus, 24.7 g of a white powder of 3-iodo-9-phenylcarbazole was obtained (yield: 67%).

It is to be noted that 3-iodo-9-phenylcarbazole can also be synthesized by using the following method. (A-5b) shows a synthesis scheme of 3-iodo-9-phenylcarbazole.

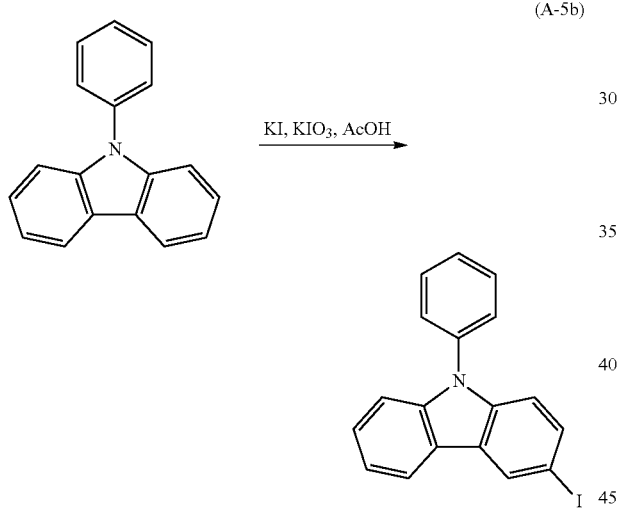

(A-5b)

10 g (10.0 mmol) of 9-phenylcarbazole, 838 mg (5.0 mmol) of potassium iodide, 1.1 g (5.0 mmol) of potassium iodate, and 30 mL of glacial acetic acid were put in a three-neck flask, and the mixture was refluxed at 120° C. for one hour. After the reaction, the reaction solution was sufficiently cooled. Then, water was added therein, extraction with toluene was performed, and an organic layer was washed with a saturated saline solution once and dried with magnesium sulfate. After the solution was filtered naturally, the obtained filtrate was concentrated and recrystallized with acetone and methanol; thus, 8.0 g of an objected white solid was obtained (yield: 50%).

Through the used of the synthesis method shown in the synthesis scheme (A-5b), 3-iodo-9-phenylcarbazole can be synthesized using a less expensive material, whereby the cost can be reduced.

[Step 4]

A synthesis method of 3-[N-(9-phenylcarbazol-3-yl)-N-phenylamino]-9-phenylcarbazole (abbreviation: PCzPCA1) will be explained. (A-6) shows a synthesis scheme of PCzPCA1.

Figure 15:
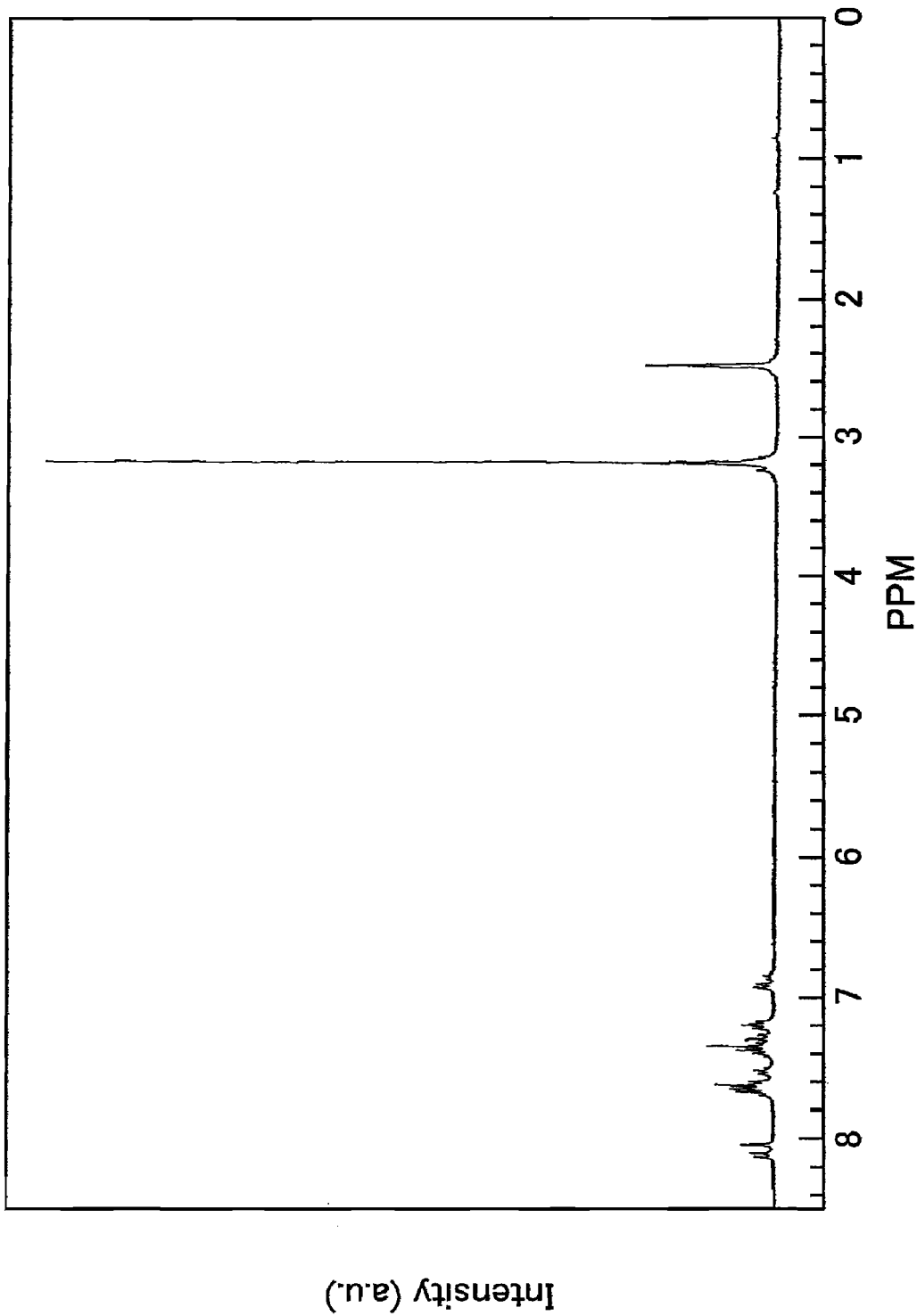
FIG. 15 is a diagram showing an $^1$H-NMR chart of 3-[N-(9-phenylcarbazol-3-yl)-N-phenylamino]-9-phenylcarbazole.
Figure 16:
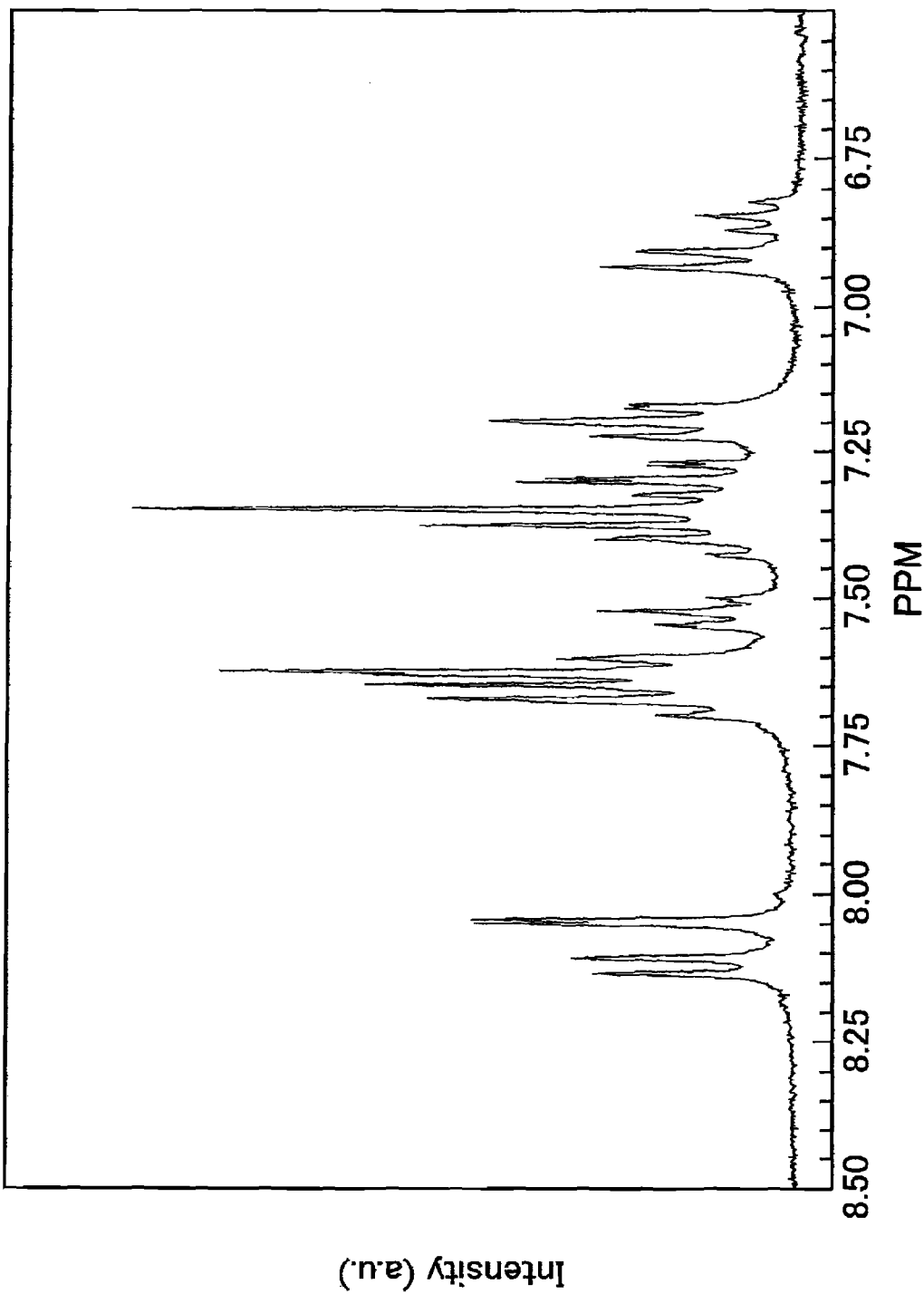
FIG. 16 is a diagram showing an $^1$H-NMR chart of 3-[N-(9-phenylcarbazol-3-yl)-N-phenylamino]-9-phenylcarbazole.

In a nitrogen atmosphere, 40 mL of dehydrated xylene was added to a mixture of 3.7 g (10.0 mmol) of 3-iodo-9-phenylcarbazole, 3.4 g (10.0 mmol) of PCA, 57 mg (0.1 mmol) of bis(dibenzylideneacetone)palladium(0), 200 mL (0.5 mmol) of a 49 wt % hexane solution of tri-tert-butylphosphine, and 3.0 g (30 mmol) of sodium-tert-butoxide. This mixture was heated and stirred at 90° C. for 6.5 hours in a nitrogen atmosphere. After the reaction was terminated, approximately 500 mL of warm toluene was added to the suspension, and the suspension was filtered through Florisil, alumina, and Celite. The obtained filtrate was concentrated, and the residue was sorted by silica gel column chromatography (toluene:hexane=1:1). Sorted solvent was concentrated and recrystallized by adding ethyl acetate-hexane; thus, 3.2 g of a cream colored powder of 3-[N-(9-phenylcarbazol-3-yl)-N-phenylamino]-9-phenylcarbazole was obtained (yield: 56%). The following shows NMR data. $^1$H-NMR (300 MHz, DMSO-d): δ=6.85 (t, J=7.5, 1H), 6.92 (d, J=7.8, 2H), 7.17-7.70 (m, 22H), 8.05 (d, J=2.1, 2H), 8.12 (d, J=7.8, 2H). In addition, FIG. 15 shows an $^1$H-NMR chart, and a portion of 6.50 to 8.50 ppm in FIG. 15 is enlarged and shown in FIG. 16.

Figure 17:
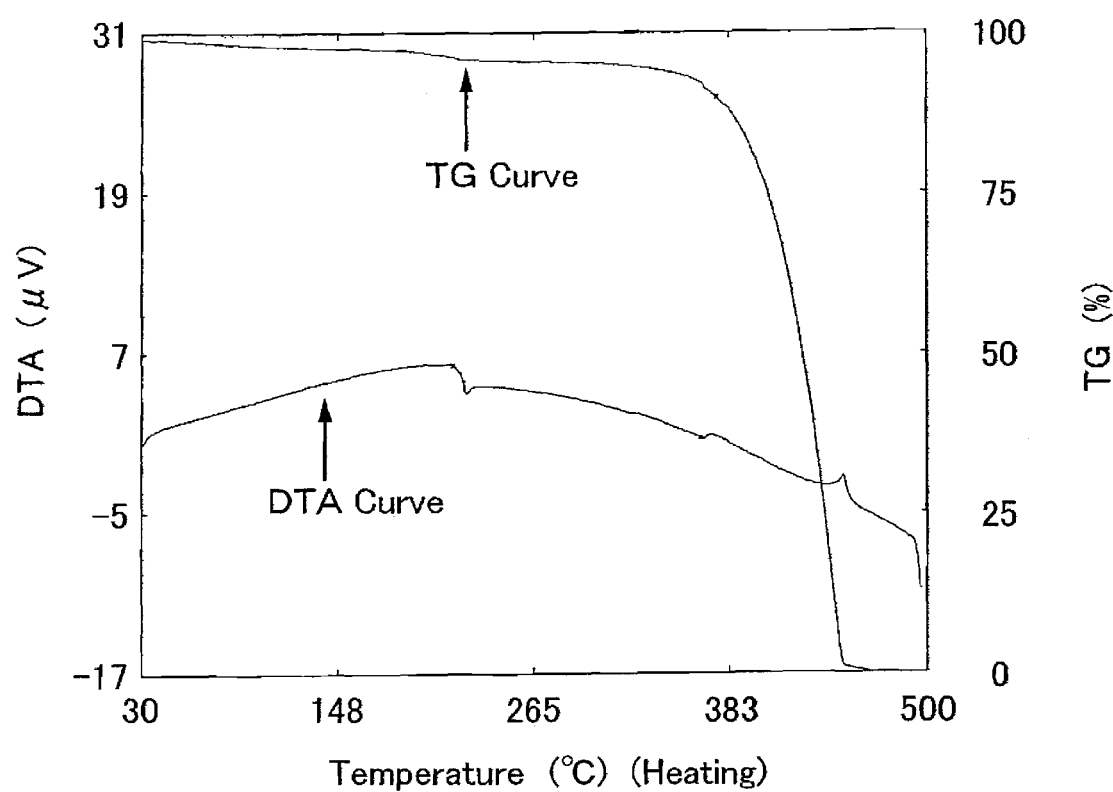
FIG. 17 is a diagram showing a result of Thermogravimetry-Differential Thermal Analysis of 3-[N-(9-phenylcarbazol-3-yl)-N-phenylamino]-9-phenylcarbazole.

Thermogravimetry-Differential Thermal Analysis (TG-DTA) of the obtained PCzPCA1 was performed. FIG. 17 shows the result. In FIG. 17, the left-hand vertical axis indicates differential heat in differential thermal analysis (DTA) (electric motive force of a thermocouple (μV)), whereas the right-hand vertical axis indicates weight in thermogravimetry (TG mesurement) (%; weight represented on the basis that the weight at onset of measurement is to be 100%). Further, the lower horizontal axis indicates temperature (° C.). A thermogravimetric/differential thermal analyzer (TG/DTA-320, by Seiko Instruments Inc.) was used for the measurement, which evaluated thermophysical properties in a nitrogen atmosphere at heating rate of 10° C./min. As a result, from the relationship between the weight and the temperature (thermogravimetry), the temperature at which the weight is less than or equal to 95% with respect to the weight at the onset of measurement at normal pressure was 375° C.

Figure 18:
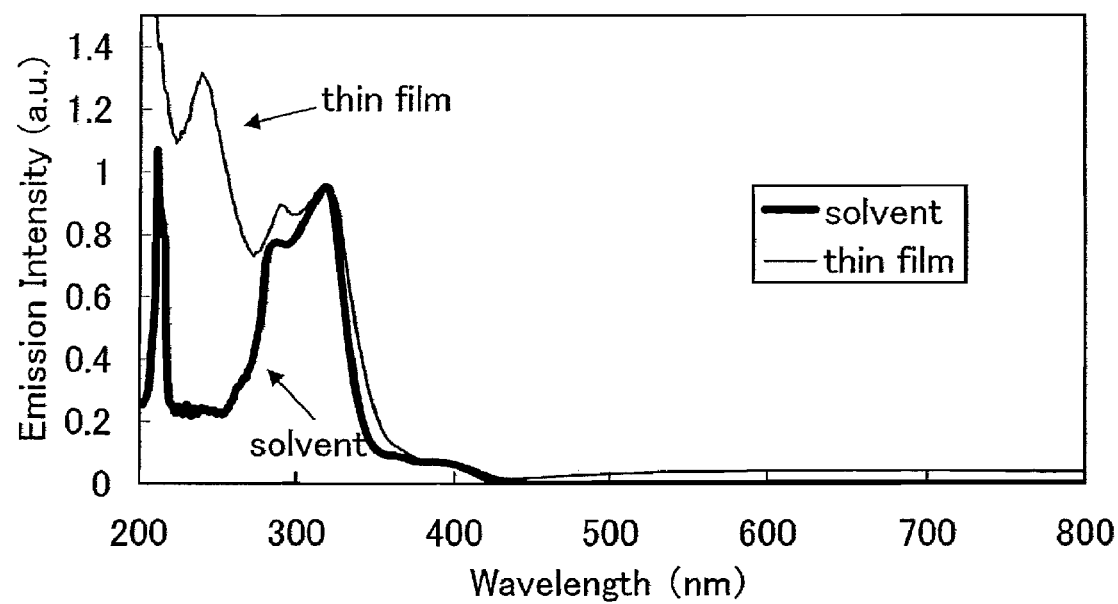
FIG. 18 is a diagram showing the absorption spectra of 3-[N-(9-phenylcarbazol-3-yl)-N-phenylamino]-9-phenylcarbazole.
Figure 19:
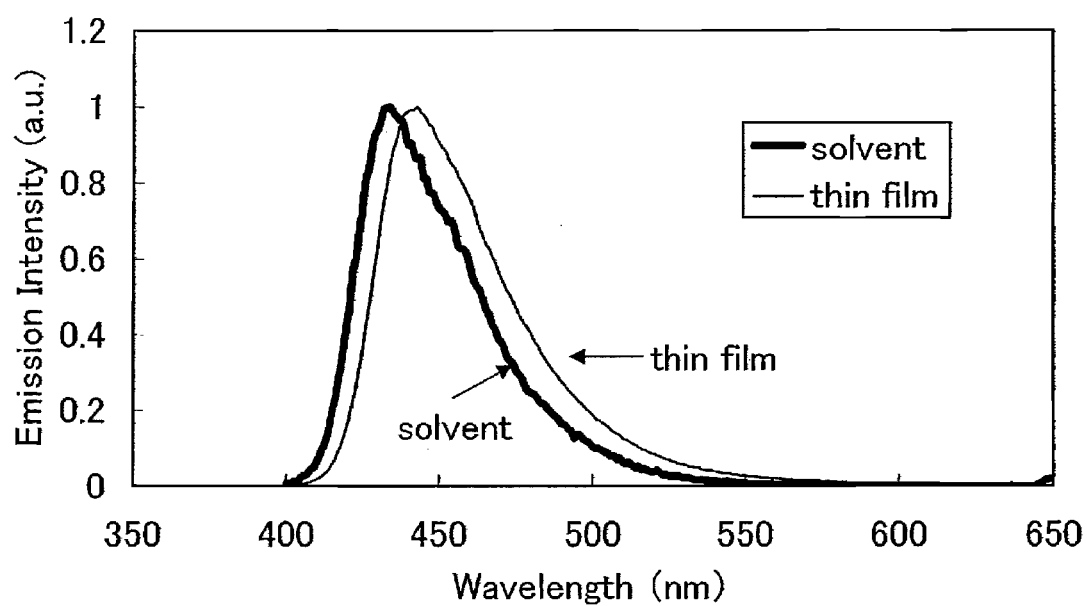
FIG. 19 is a diagram showing the emission spectra of 3-[N-(9-phenylcarbazol-3-yl)-N-phenylamino]-9-phenylcarbazole.

FIG. 18 shows the absorption spectra for a toluene solution of PCzPCA1 and a thin film of PCzPCA1. An ultraviolet-visible spectrophotometer (V-550, by JASCO Corporation) was used for the measurement. The solution was put in a quartz cell and the thin film was evaporated over a quartz substrate as samples, and the absorption spectra thereof, from each of which the absorption spectrum of quartz was subtracted, are shown in FIG. 18. In FIG. 18, the horizontal axis indicates the wavelength (nm) and the vertical axis indicates the absorption intensity (arbitrary unit). The maximum absorption wavelength was 320 nm in the case of the toluene solution, and 321 nm in the case of the thin film. FIG. 19 shows the emission spectra for the toluene solution of PCzPCA1 and the thin film of PCzPCA1. In FIG. 19, the horizontal axis indicates the wavelength (nm) and the vertical axis indicates the emission intensity (arbitrary unit). The maximum emission wavelength was 435 nm (the excitation wavelength: 325 nm) in the case of the toluene solution and 443 nm (the excitation wavelength: 380 nm) in the case of the thin film.

The HOMO level and the LUMO level of PCzPCA1 in a thin-film state were measured. The value of the HOMO level was obtained by converting the ionization potential measured by using a photoelectron spectrometer (AC-2, by Riken Keiki Co., Ltd.) to a negative value. Furthermore, the value of the LUMO level was obtained by setting the absorption edge of the thin film in FIG. 18 as an energy gap and adding the value of the absorption edge to the value of the HOMO level. As a result, the HOMO level was −5.17 eV, and the LUMO level was −1.82 eV.

Subsequently, an oxidation reaction property of PCzPCA1 was examined by cyclic voltammetry (CV). An electrochemical analyzer (ALS model 600A, by BAS Inc.) was used for the measurement.

The solution for the CV measurement was prepared by using dehydrated dimethylformamide (DMF) as a solvent, dissolving a supporting electrolyte of tetra-n-butylammonium perchlorate (n-Bu$_4$NClO$_4$) to the concentration of 100 mmol/L, and dissolving PCzPCA1, the object of measurement, to the concentration of 1 mmo/L. A platinum electrode (PTE platinum electrode, by BAS Inc.) was used as a working electrode, another platinum electrode (Pt counter electrode (5 cm) for VC-3, by BAS Inc.) was used as an auxiliary electrode, and an Ag/Ag$^+$ electrode (RE5 non-aqueous solvent reference electrode, by BAS Inc.) was used as a reference electrode.

The oxidation reaction property was measured as follows. After potential of the working electrode with respect to the reference electrode was changed from −0.16 to 0.5 V, scanning from 0.5 to −0.16 V was set to be one cycle, and 100 cycles were measured. The scanning speed of the CV measurement was set to be 0.1 V/s.

Figure 20:
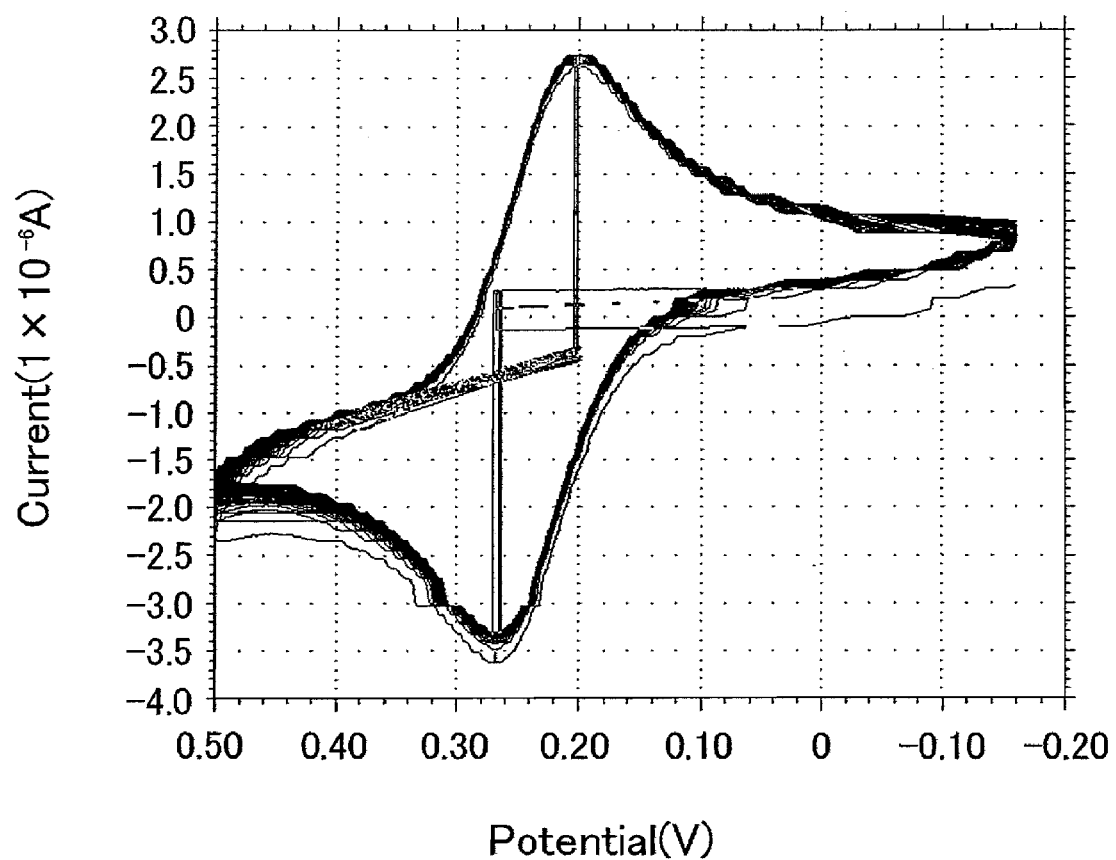
FIG. 20 is a diagram showing CV characteristics of 3-[N-(9-phenylcarbazol-3-yl)-N-phenylamino]-9-phenylcarbazole.

FIG. 20 shows a result of examining the oxidation reaction property of PCzPCA1. In FIG. 20, the horizontal axis indicates potential (V) of the working electrode with respect to the reference electrode, and the vertical axis indicates a value of current which flows between the working electrode and the auxiliary electrode (1×10$^{-6}$ A).

According to FIG. 20, it was found that the oxidation potential was 0.27 V (vs. Ag/Ag$^+$ electrode). In addition, although the scanning was repeated for 100 cycles, changes in the peak position and the peak intensity of a CV curve were scarcely observed in the oxidation reaction. Accordingly, it was found that the carbazole derivative used in the present invention is significantly stable in the oxidation reaction.

Figure 21:
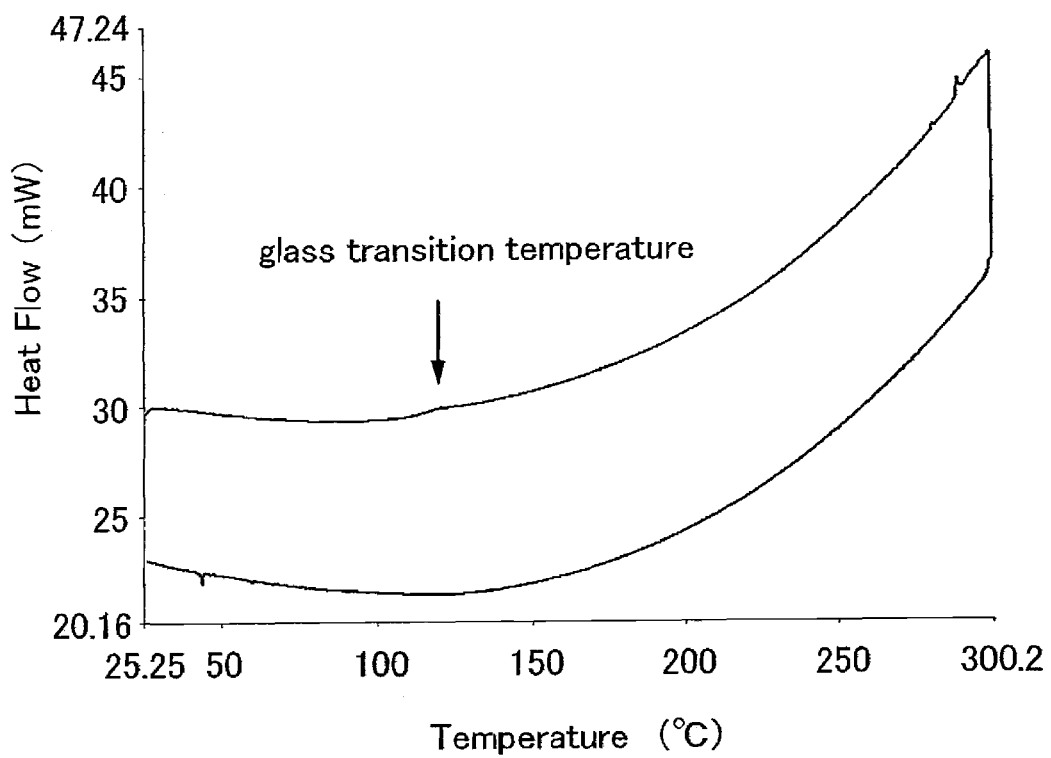
FIG. 21 is a diagram showing a result of analyzing 3-[N-(9-phenylcarbazol-3-yl)-N-phenylamino]-9-phenylcarbazole using a differential scanning calorimeter.

Furthermore, the glass transition temperature of the obtained compound PCzPCA1 was measured using a differential scanning calorimeter (Pyris 1 DSC, by PerkinElmer, Inc.). FIG. 21 shows a measurement result by DSC. A temperature is shown in an X axis and a heat flow is shown in a Y axis, respectively. An upwardness in the heat flow shows endotherm. According to the measurement result, it was found that the glass transition temperature of the obtained compound is 112° C. Thus, the obtained compound has a high glass transition temperature of 112° C. and favorable heat resistance. FIG. 21 has no peak showing crystallization of the obtained compound, and it was found that the obtained compound is a substance that is difficult to be crystallized.

Embodiment 2

As an example of the carbazole derivative used in the present invention, a synthesis method of 3,6-bis[N-(9-phenylcarbazol-3-yl)-N-phenylamino]-9-phenylcarbazole (abbreviation: PCzPCA2) represented by the structural formula (38) will be explained.

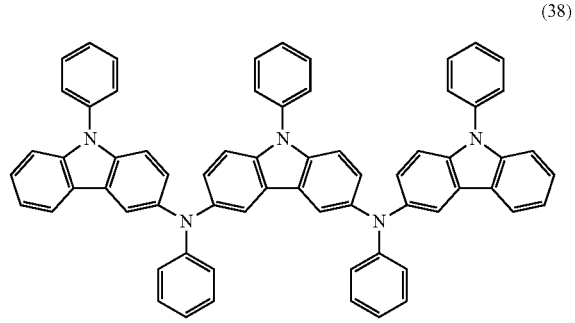 [SMILES: c1ccc(N(c2ccc3c(c2)c2ccccc2n3-c2ccccc2)c2ccc3c(c2)c2cc(N(c4ccccc4)c4ccc5c(c4)c4ccccc4n5-c4ccccc4)ccc2n3-c2ccccc2)cc1]

(38)

[Step 1]

A synthesis method of 3,6-diiodo-9-phenylcarbazole will be explained. (A-7) shows a synthesis scheme of 3,6-diiodo-9-phenylcarbazole.

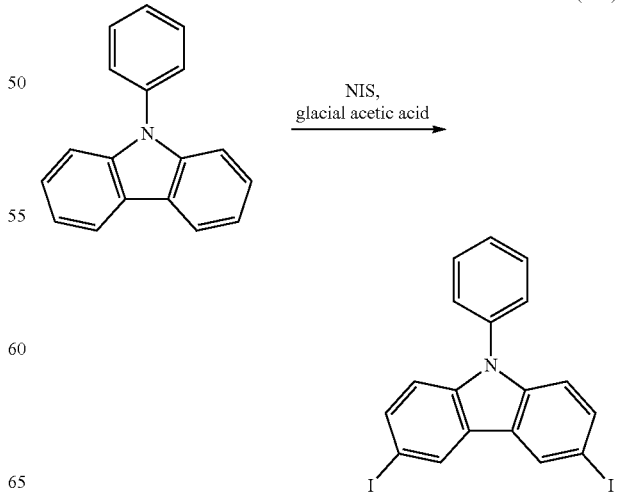

(A-7)

24.3 g (100 mmol) of 9-phenylcarbazole was dissolved in 700 mL of glacial acetic acid, 44.9 g (200 mmol) of N-iodosuccinimide was slowly added therein, and the mixture was stirred at room temperature for approximately 20 hours. The generated precipitate was filtered, and the residue was washed with a saturated sodium hydrogen-carbonate aqueous solution, water, and methanol and dried. Thus, 47.0 g of a white powder of 3,6-diiodo-9-phenylcarbazole was obtained (yield: 95%).

[Step 2]

A synthesis method of 3,6-bis[N-(9-phenylcarbazol-3-yl)-N-phenylamino]-9-phenylcarbazole (abbreviation: PCzPCA2) will be explained. (A-8) shows a synthesis scheme of PCzPCA2.

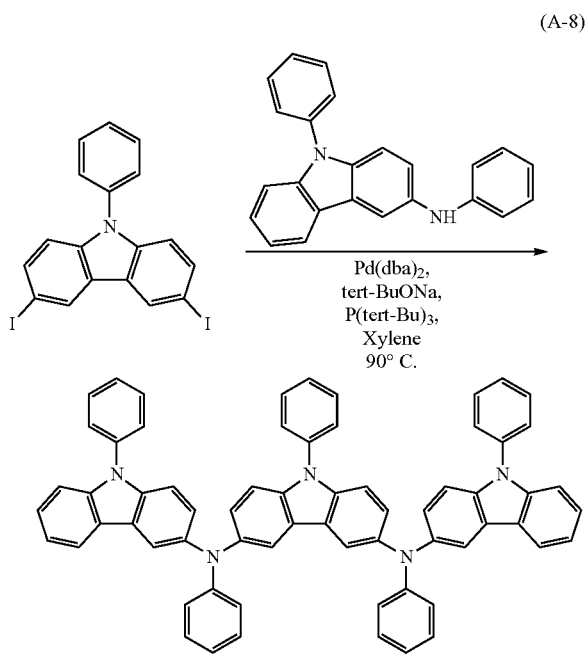

(A-8)

Figure 22:
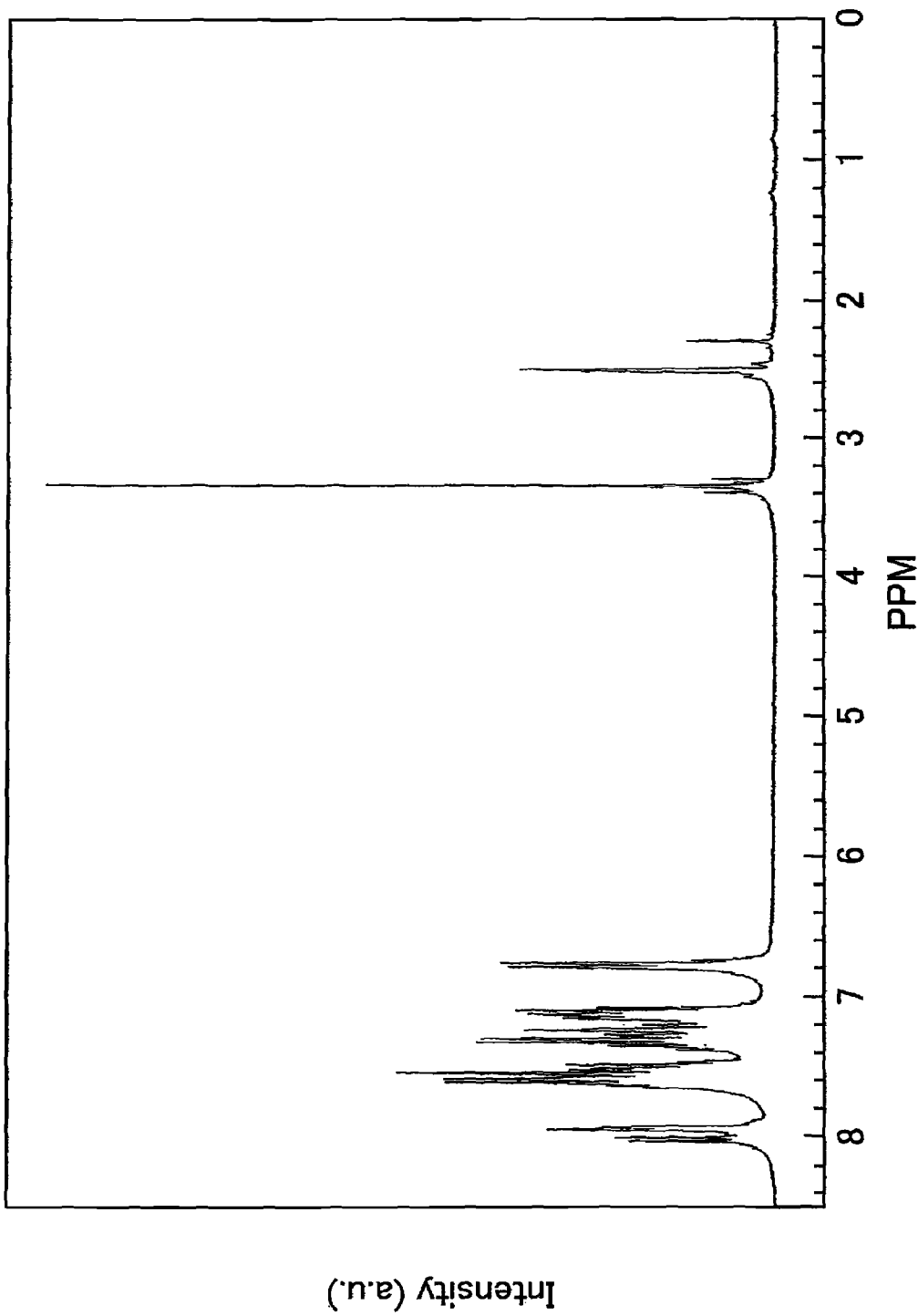
FIG. 22 is a diagram showing an $^1$H-NMR chart of 3,6-bis[N-(9-phenylcarbazol-3-yl)-N-phenylamino]-9-phenylcarbazole.
Figure 23:
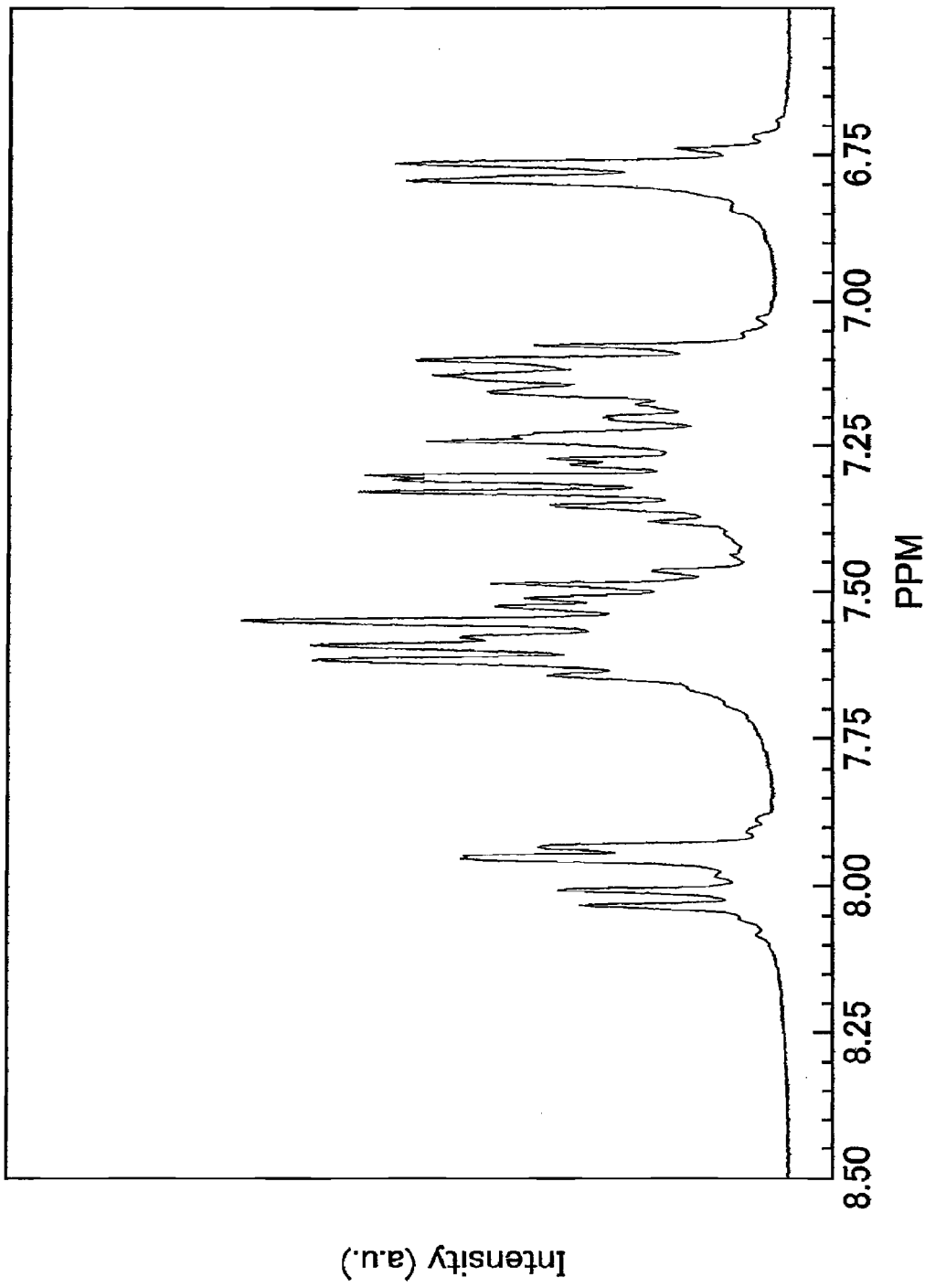
FIG. 23 is a diagram showing an $^1$H-NMR chart of 3,6-bis[N-(9-phenylcarbazol-3-yl)-N-phenylamino]-9-phenylcarbazole.

In a nitrogen atmosphere, 30 mL of dehydrated xylene was added to a mixture of 2.5 g (5 mmol) of 3,6-diiodo-9-phenylcarbazole, 3.4 g (10 mmol) of PCA, 30 mg (0.05 mmol) of bis(dibenzylideneacetone)palladium(0), 0.2 mL (0.5 mmol) of a 49 wt % hexane solution of tri-tert-butylphosphine, and 3.0 g (30 mmol) of sodium-tert-butoxide. This mixture was heated and stirred at 90° C. for 6.5 hours in a nitrogen atmosphere. After the reaction was terminated, approximately 500 mL of warm toluene was added to the suspension, and the suspension was filtered through Florisil, alumina, and Celite. The obtained filtrate was concentrated, and the concentrate was sorted by silica gel column chromatography (toluene: hexane=1:1). The purified concentrate was obtained from sorted solvent was concentrated and recrystallized by adding ethyl acetate-hexane; thus, 2.5 g of a cream colored powder of 3,6-bis[N-(9-phenylcarbazol-3-yl)-N-phenylamino]-9-phenylcarbazole was obtained (yield: 55%). The following shows NMR data. $^1$H-NMR (300 MHz, DMSO-d): δ=6.74-6.80 (m, 6H), 7.08-7.64 (m, 33H), 7.94-8.04 (m, 6H). In addition, FIG. 22 shows an $^1$H-NMR chart, and a portion of 6.50 to 8.50 ppm in FIG. 22 is enlarged and shown in FIG. 23.

Figure 24:
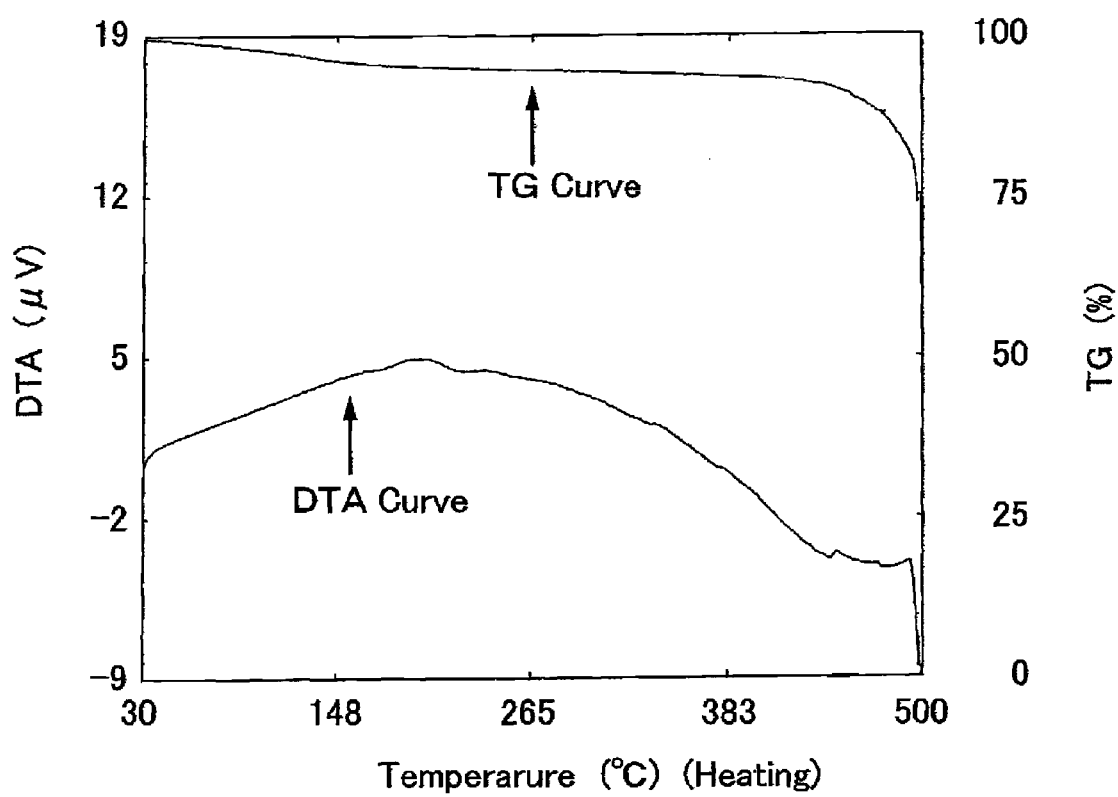
FIG. 24 is a diagram showing a result of Thermogravimetry-Differential Thermal Analysis of 3,6-bis[N-(9-phenylcarbazol-3-yl)-N-phenylamino]-9-phenylcarbazole.

Thermogravimetry-Differential Thermal Analysis (TG-DTA) of the obtained PCzPCA2 was performed. FIG. 24 shows the result. In FIG. 24, the left-hand vertical axis indicates differential heat in differential thermal analysis (DTA) (electric motive force of a thermocouple (μV)), whereas the right-hand vertical axis indicates weight in thermogravimetry (TG mesurement) (%; weight represented on the basis that the weight at onset of measurement is to be 100%). Further, the lower horizontal axis indicates temperature (° C.). A thermogravimetric/differential thermal analyzer (TG/DTA-320, by Seiko Instruments Inc.) was used for the measurement, which evaluated thermophysical properties in a nitrogen atmosphere at heating rate of 10° C./min. As a result, from the relationship between the weight and the temperature (thermogravimetry), the temperature at which the weight is less than or equal to 95% with respect to the weight at the onset of measurement at normal pressure was 476° C.

Figure 25:
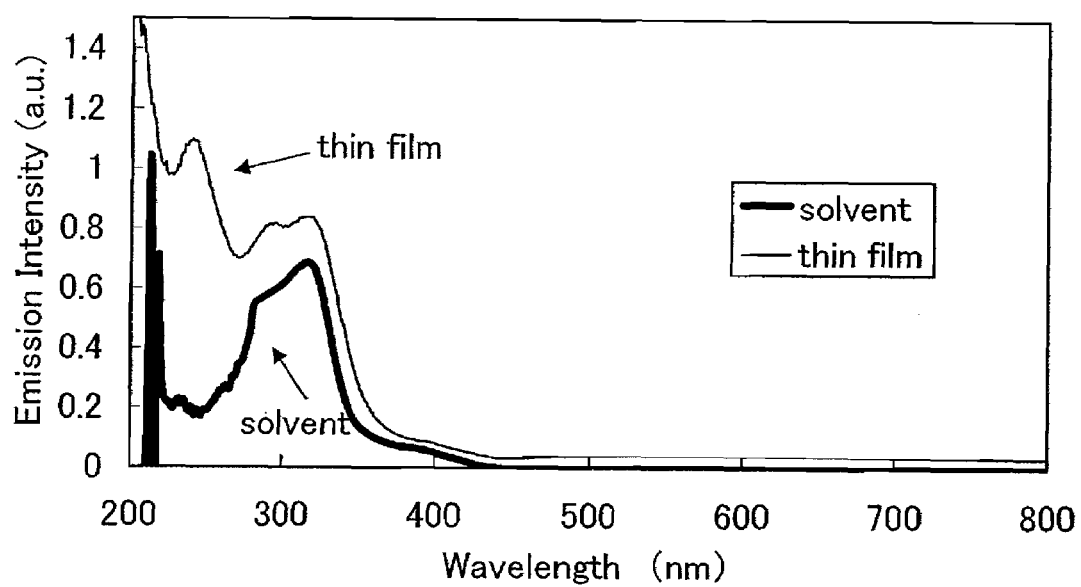
FIG. 25 is a diagram showing the absorption spectra of 3,6-bis[N-(9-phenylcarbazol-3-yl)-N-phenylamino]-9-phenylcarbazole.
Figure 26:
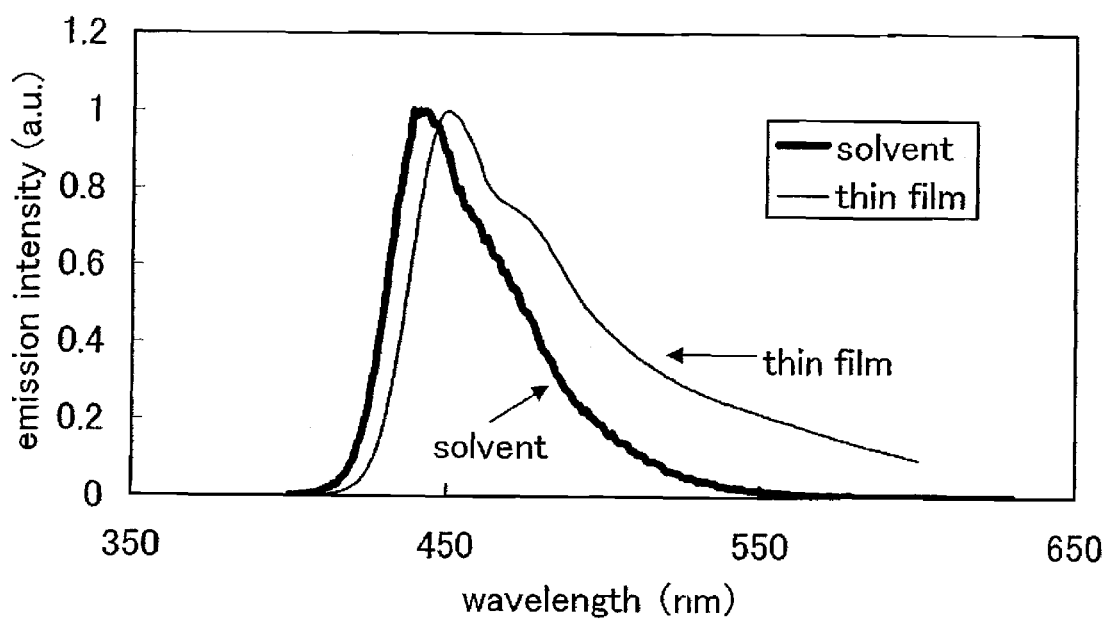
FIG. 26 is a diagram showing the emission spectra of 3,6-bis[N-(9-phenylcarbazol-3-yl)-N-phenylamino]-9-phenylcarbazole.

FIG. 25 shows the absorption spectra for a toluene solution of PCzPCA2 and a thin film of PCzPCA2. An ultraviolet-visible spectrophotometer (V-550, by JASCO Corporation) was used for the measurement. The solution was put in a quartz cell and the thin film was evaporated over a quartz substrate as samples, and the absorption spectra thereof, from each of which the absorption spectrum of quartz was subtracted, are shown in FIG. 25. In FIG. 25, the horizontal axis indicates the wavelength (nm) and the vertical axis indicates the absorption intensity (arbitrary unit). The maximum absorption wavelength was 320 nm in the case of the toluene solution, and 320 nm in the case of the thin film. FIG. 26 shows the emission spectra for the toluene solution of PCzPCA2 and the thin film of PCzPCA2. In FIG. 26, the horizontal axis indicates the wavelength (nm) and the vertical axis indicates the emission intensity (arbitrary unit). The maximum emission wavelength was 442 nm (the excitation wavelength: 325 nm) in the case of the toluene solution and 449 nm (the excitation wavelength: 320 nm) in the case of the thin film.

The HOMO level and the LUMO level of PCzPCA2 in a thin-film state were measured. The value of the HOMO level was obtained by converting the ionization potential measured by using a photoelectron spectrometer (AC-2, by Riken Keiki Co., Ltd.) to a negative value. Furthermore, the value of the LUMO level was obtained by setting the absorption edge of the thin film in FIG. 25 as an energy gap and adding the value of the absorption edge to the value of the HOMO level. As a result, the HOMO level was −5.10 eV, and the LUMO level was −1.75 eV.

Subsequently, an oxidation reaction property of PCzPCA2 was examined by cyclic voltammetry (CV). An electrochemical analyzer (ALS model 600A, by BAS Inc.) was used for the measurement.

The solution for the CV measurement was prepared by using dehydrated dimethylformamide (DMF) as a solvent, dissolving a supporting electrolyte of tetra-n-butylammonium perchlorate (n-Bu$_4$NClO$_4$) to the concentration of 100 mmol/L, and dissolving PCzPCA2, the object of measurement, to the concentration of 1 mmo/L. A platinum electrode (PTE platinum electrode, by BAS Inc.) was used as a working electrode, another platinum electrode (Pt counter electrode (5 cm) for VC-3, by BAS Inc.) was used as an auxiliary electrode, and an Ag/Ag+ electrode (RE5 non-aqueous solvent reference electrode, by BAS Inc.) was used as a reference electrode.

The oxidation reaction property was measured as follows. After potential of the working electrode with respect to the reference electrode was changed from −0.01 to 0.33 V, scanning from 0.33 to −0.01 V was set to be one cycle, and 100 cycles were measured. The scanning speed of the CV measurement was set to be 0.1 V/s.

Figure 27:
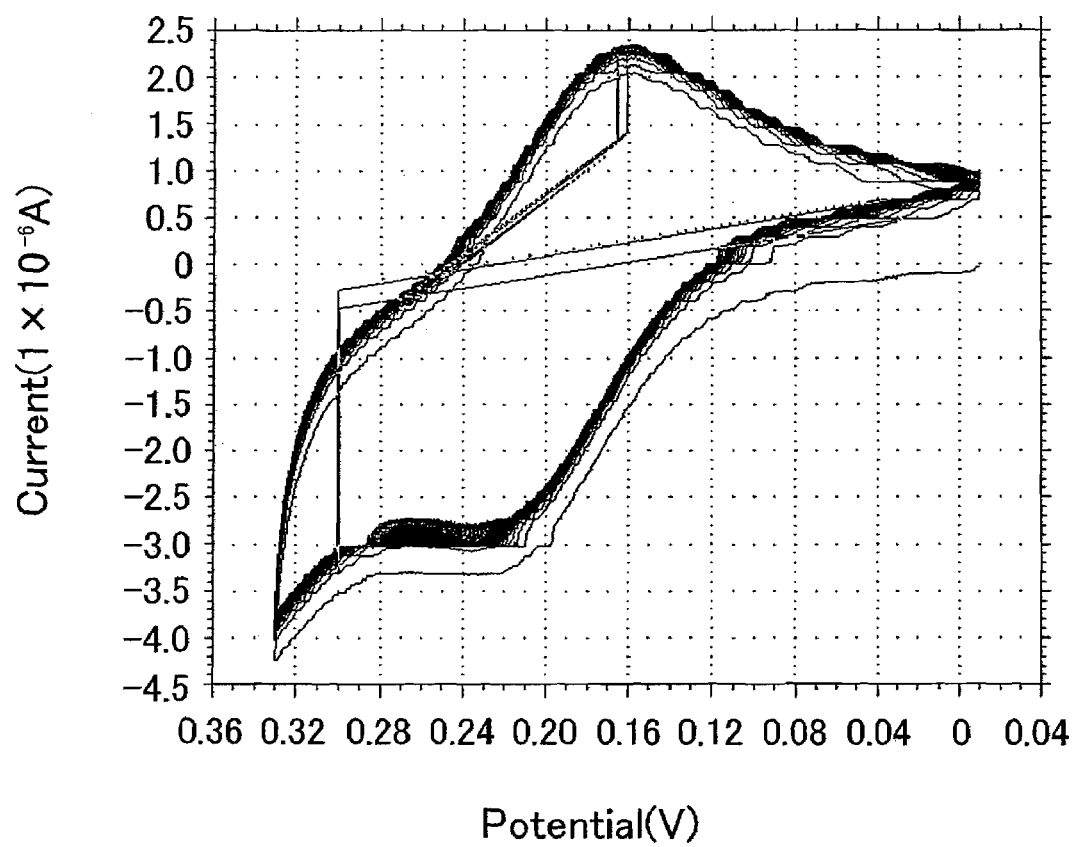
FIG. 27 is a diagram showing CV characteristics of 3,6-bis[N-(9-phenylcarbazol-3-yl)-N-phenylamino]-9-phenylcarbazole.

FIG. 27 shows a result of examining the oxidation reaction property of PCzPCA2. In FIG. 27, the horizontal axis indicates potential (V) of the working electrode with respect to the reference electrode, and the vertical axis indicates a value of current which flows between the working electrode and the auxiliary electrode (1×10$^{-6}$ A).

According to FIG. 27, it was found that the oxidation potential was 0.22 V (vs. Ag/Ag+ electrode). In addition, although the scanning was repeated for 100 cycles, changes in the peak position and the peak intensity of a CV curve were scarcely observed in the oxidation reaction. Accordingly, it was found that the carbazole derivative used in the present invention is significantly stable in the oxidation reaction.

Figure 28:
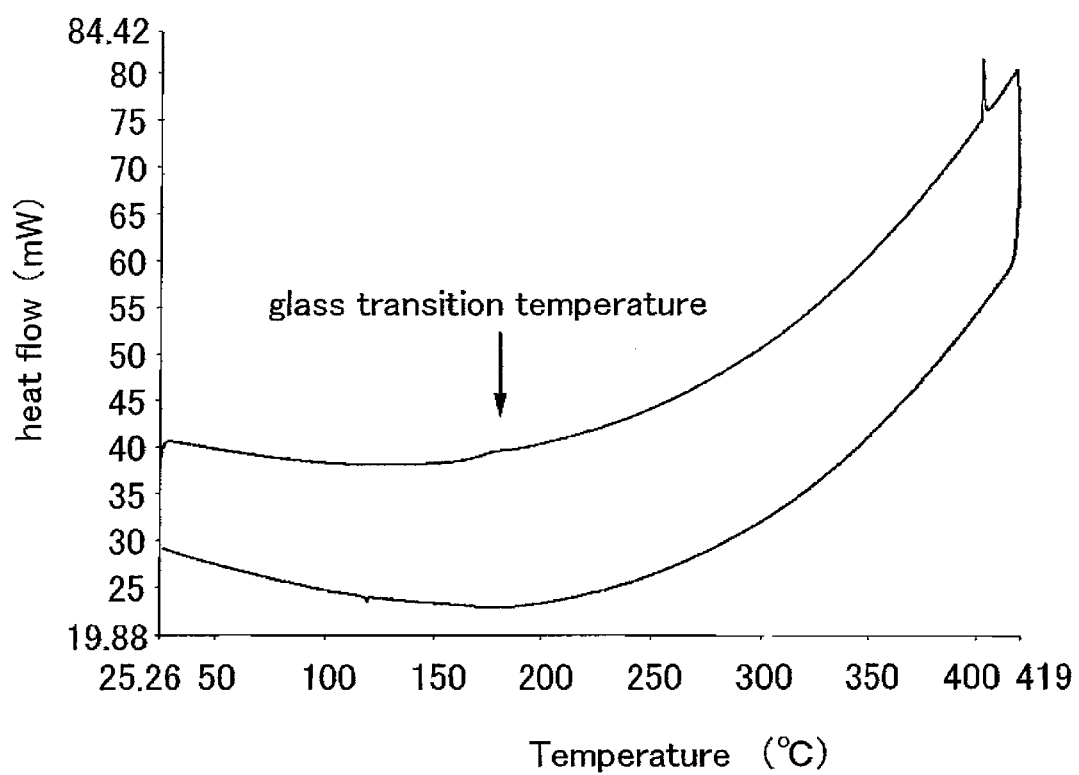
FIG. 28 is a diagram showing a result of analyzing 3,6-bis[N-(9-phenylcarbazol-3-yl)-N-phenylamino]-9-phenylcarbazole using a differential scanning calorimeter.

Furthermore, the glass transition temperature of the obtained compound PCzPCA2 was measured using a differential scanning calorimeter (Pyris 1 DSC, by PerkinElmer, Inc.). FIG. 28 shows a measurement result by DSC. A temperature is shown in an X axis and a heat flow is shown in a Y axis, respectively. An upwardness in the heat flow shows endotherm. According to the measurement result, it was found that the glass transition temperature of the obtained compound is 168° C. Thus, the obtained compound has a high glass transition temperature of 168° C. and favorable heat resistance. FIG. 28 has no peak showing crystallization of the obtained compound and it was found that the obtained compound is a substance that is difficult to be crystallized.

Embodiment 3

As an example of the carbazole derivative used in the present invention, a synthesis method of 3-[N-(1-naphthyl)-N-(9-phenylcarbazol-3-yl)amino]-9-phenylcarbazole (abbreviation: PCzPCN1) represented by the structural formula (17) will be explained.

(17)

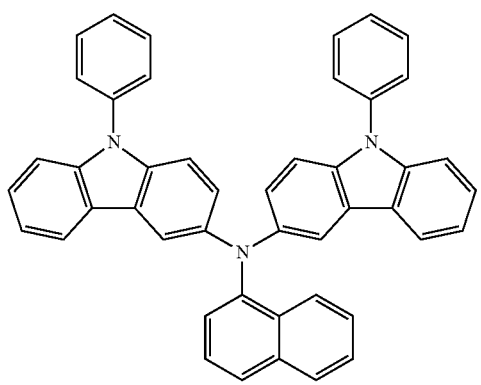

[Step 1]

First, a synthesis method of 3-[N-(1-naphthyl)amino]-9-phenylcarbazole (abbreviation: PCN) will be explained. (A-9) shows a synthesis scheme of PCN.

(A-9)

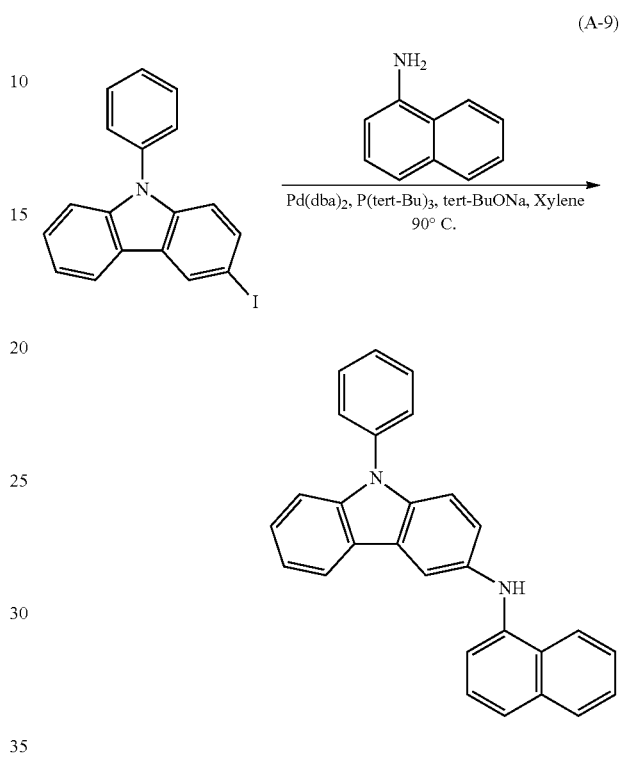

Figure 29:
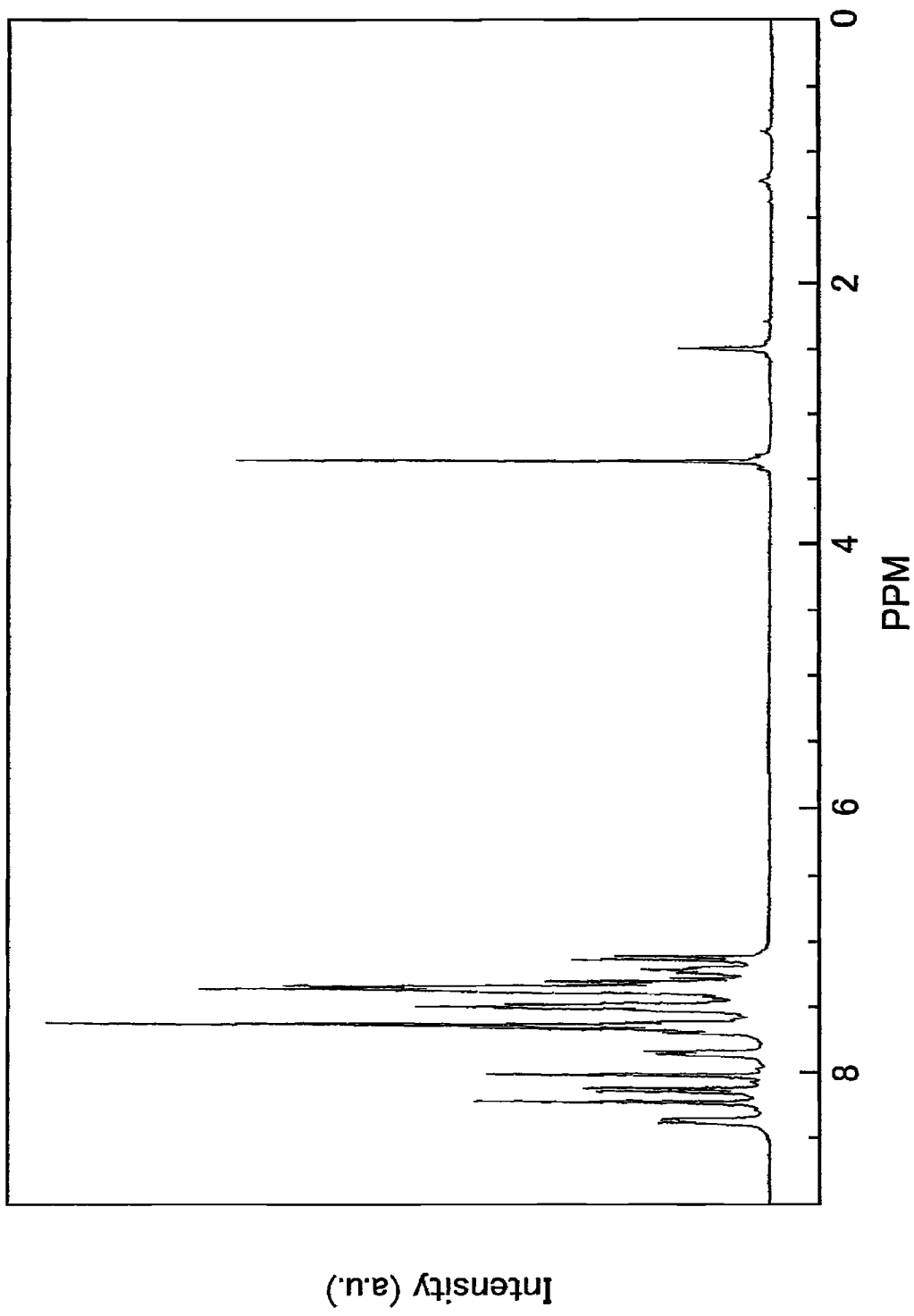
FIG. 29 is a diagram showing an $^1$H-NMR chart of 3-[N-(1-naphthyl)amino]-9-phenylcarbazole.
Figure 30:
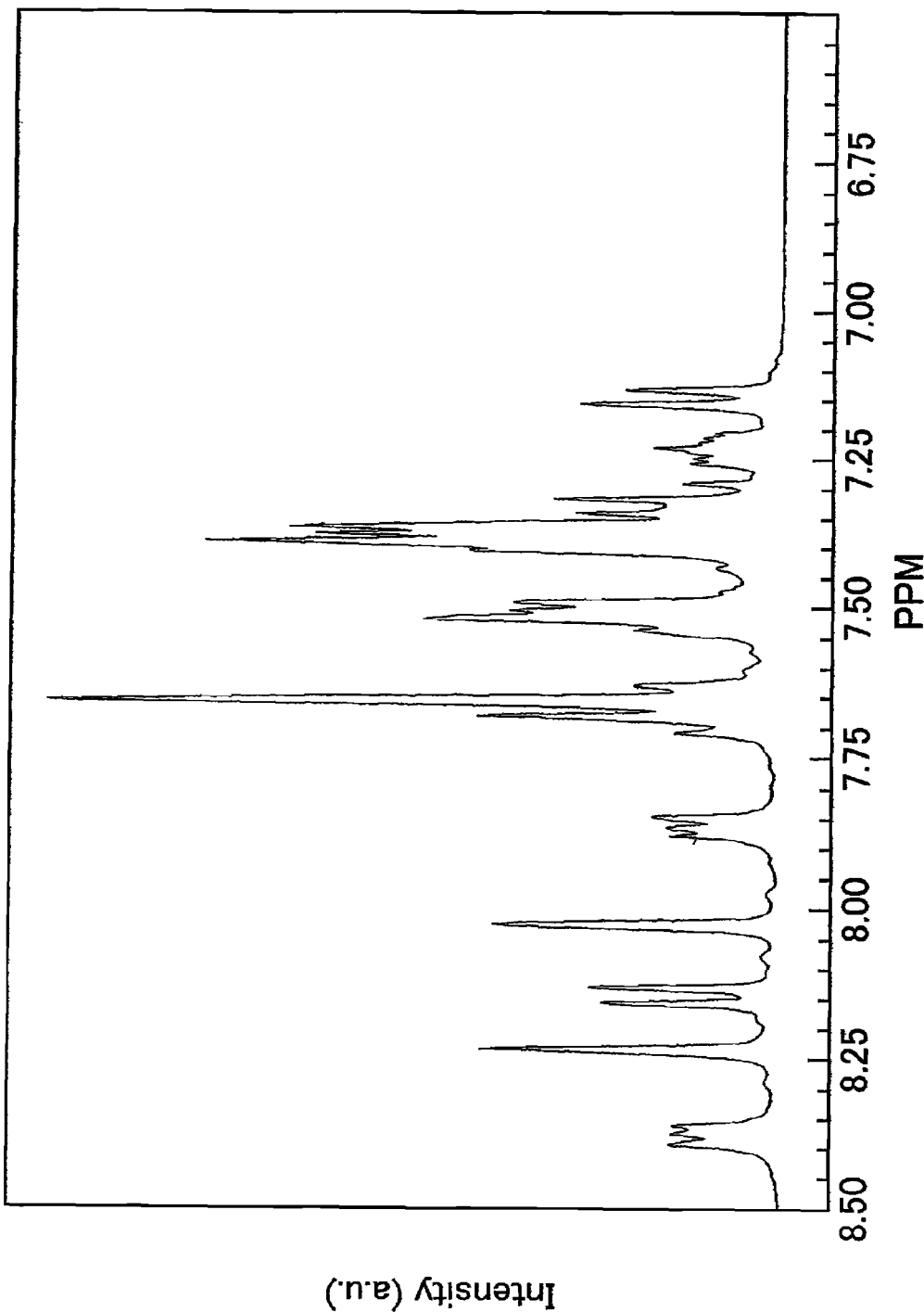
FIG. 30 is a diagram showing an $^1$H-NMR chart of 3-[N-(1-naphthyl)amino]-9-phenylcarbazole.

In a nitrogen atmosphere, 12 mL of dehydrated xylene was added to a mixture of 3.7 g (10 mmol) of 3-iodo-9-phenylcarbazole, 1.6 g (5 mmol) of 1-aminonaphthalene, 60 mg (0.1 mmol) of bis(dibenzylideneacetone)palladium(0), 0.2 mL (0.5 mmol) of a 49 wt % hexane solution of tri-tert-butylphosphine, and 3 g (30 mmol) of sodium-tert-butoxide. This mixture was heated and stirred at 90° C. for 7 hours in a nitrogen atmosphere. After the reaction was terminated, approximately 200 mL of warm toluene was added to the suspension, and the suspension was filtered through Florisil, alumina, and Celite. The obtained filtrate was concentrated, and the obtained concentrate was sorted by silica gel column chromatography (toluene:hexane=1:1). Sorted solvent was concentrated, and the concentrate was recrystallized with ethyl acetate-hexane; thus, 1.5 g of a cream colored powder of 3-[N-(1-naphthyl)amino]-9-phenylcarbazole was obtained (yield: 79%). The following shows NMR data. $^1$H-NMR (300 MHz, DMSO-d): δ=7.13-7.71 (m, 15H), 7.85-7.88 (m, 1H), 8.03 (s, 1H), 8.15 (d, J=7.8, 1H), 8.24 (s, 1H), 8.36-8.39 (m, 1H). In addition, FIG. 29 shows an $^1$H-NMR chart, and a portion of 6.50 to 8.50 ppm in FIG. 29 is enlarged and shown in FIG. 30.

[Step 2]

Next, a synthesis method of 3-[N-(1-naphthyl)-N-(9-phenylcarbazol-3-yl)amino]-9-phenylcarbazole (abbreviation: PCzPCN1) will be explained. (A-10) shows a synthesis scheme of PCzPCN1.

(A-10)

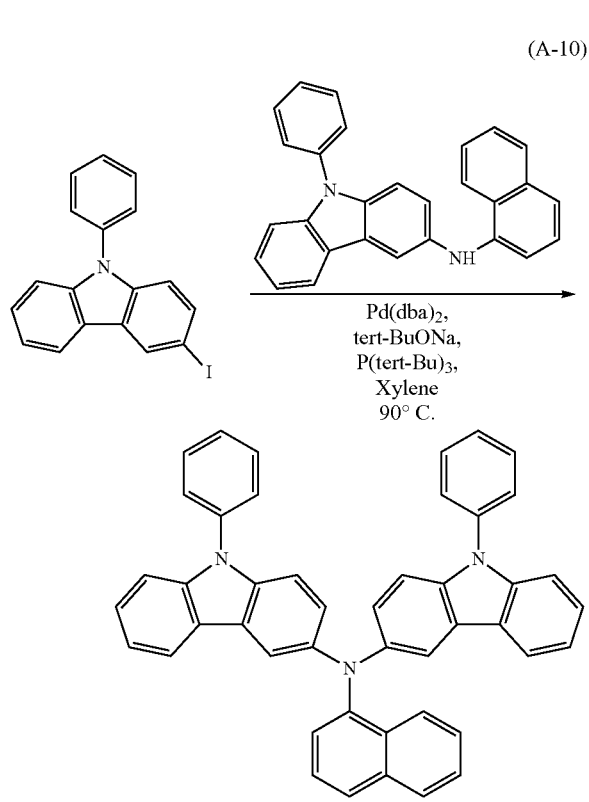

Figure 31:
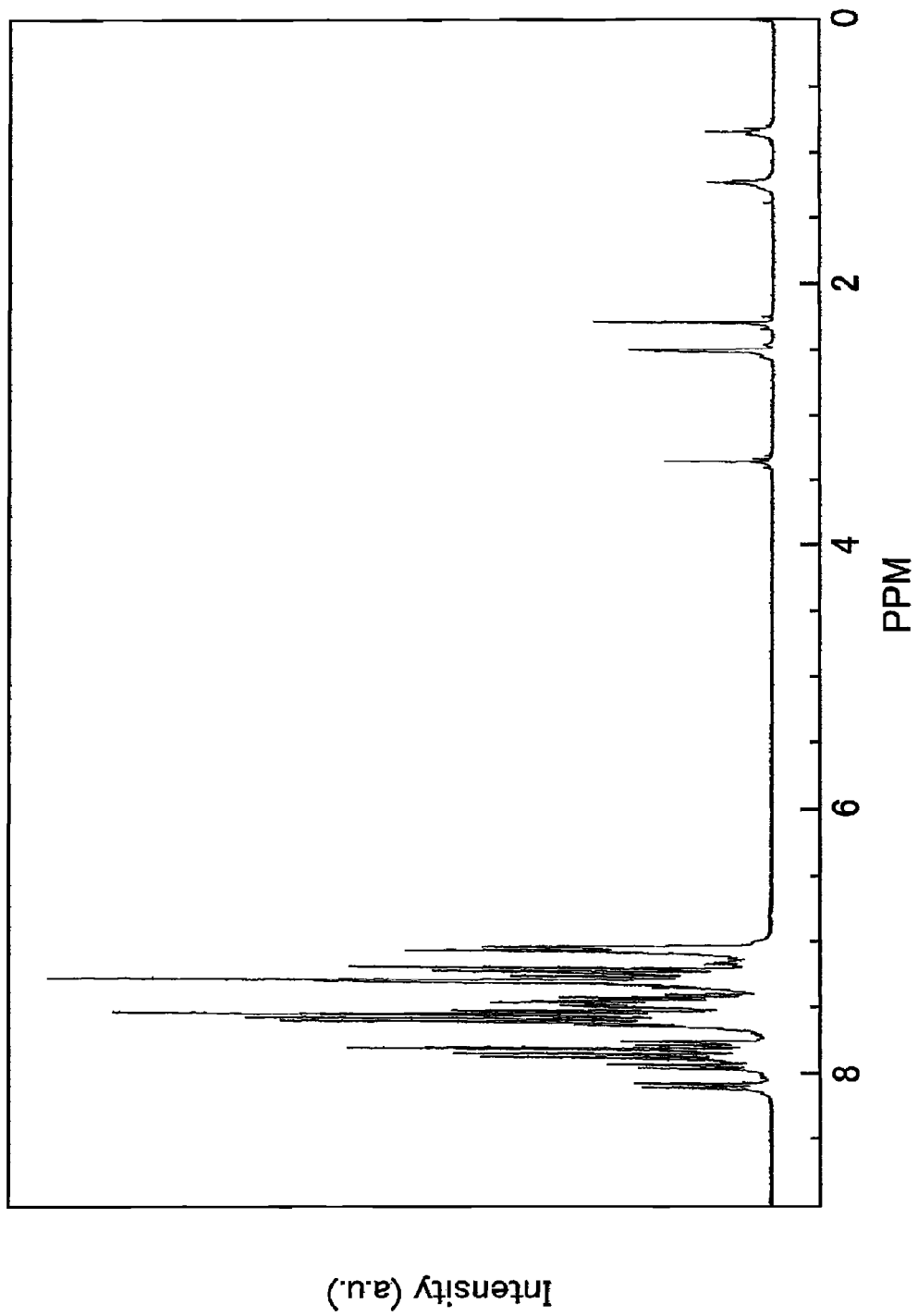
FIG. 31 is a diagram showing an $^1$H-NMR chart of 3-[N-(1-naphthyl)-N-(9-phenylcarbazol-3-yl)amino]-9-phenylcarbazole.
Figure 32:
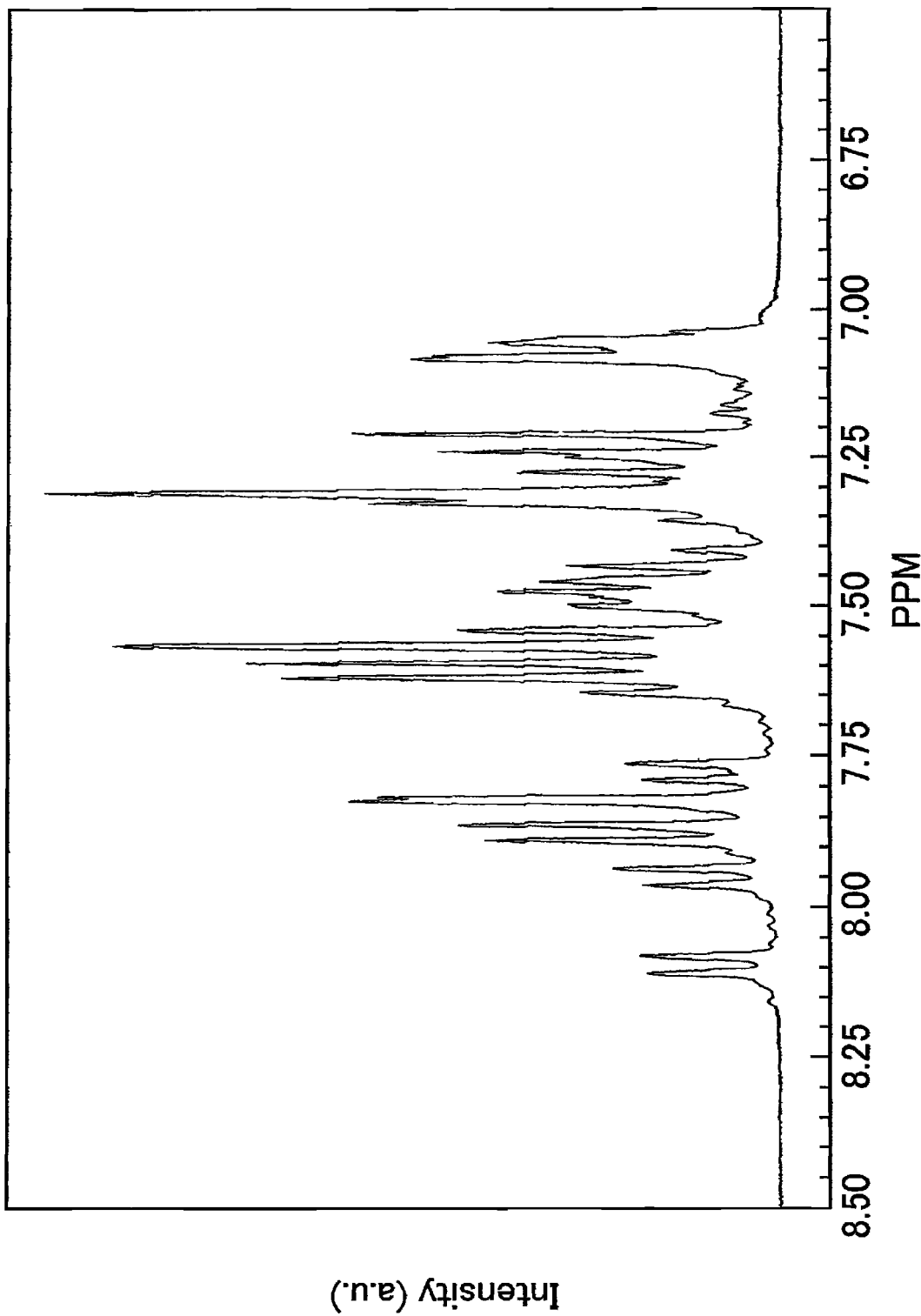
FIG. 32 is a diagram showing an $^1$H-NMR chart of 3-[N-(1-naphthyl)-N-(9-phenylcarbazol-3-yl)amino]-9-phenylcarbazole.

In a nitrogen atmosphere, 7 mL of dehydrated xylene was added to a mixture of 1.8 g (5 mmol) of 3-iodo-9-phenylcarbazole, 2.5 g (6.6 mmol) of PCN, 30 mg (0.05 mmol) of bis(dibenzylideneacetone)palladium(0), 0.2 mL (0.5 mmol) of a 49 wt % hexane solution of tri-tert-butylphosphine, and 700 mg (7 mmol) of sodium-tert-butoxide. This mixture was heated and stirred at 90° C. for 4.5 hours in a nitrogen atmosphere. After the reaction was terminated, approximately 500 mL of warm toluene was added to the suspension, and the suspension was filtered through Florisil, alumina, and Celite. The obtained filtrate was concentrated, and the concentrate was sorted by silica gel column chromatography (toluene: hexane=1:1). Sorted solvent was concentrated and recrystalized with ethyl acetate-hexane; thus, 2.1 g of a yellow powder of PCzPCN1 was obtained (yield: 62%). The following shows NMR data. $^1$H-NMR (300 MHz, DMSO-d): δ=7.04-7.65 (m, 24H), 7.78 (d, J=8.4, 1H), 7.82 (d, J=2.1, 2H), 7.88 (d, J=7.8, 2H), 7.95 (d, J=8.4, 1H), 8.10 (d, J=9.0, 1H). In addition, FIG. 31 shows an $^1$H-NMR chart, and a portion of 6.50 to 8.50 ppm in FIG. 31 is enlarged and shown in FIG. 32.

Figure 33:
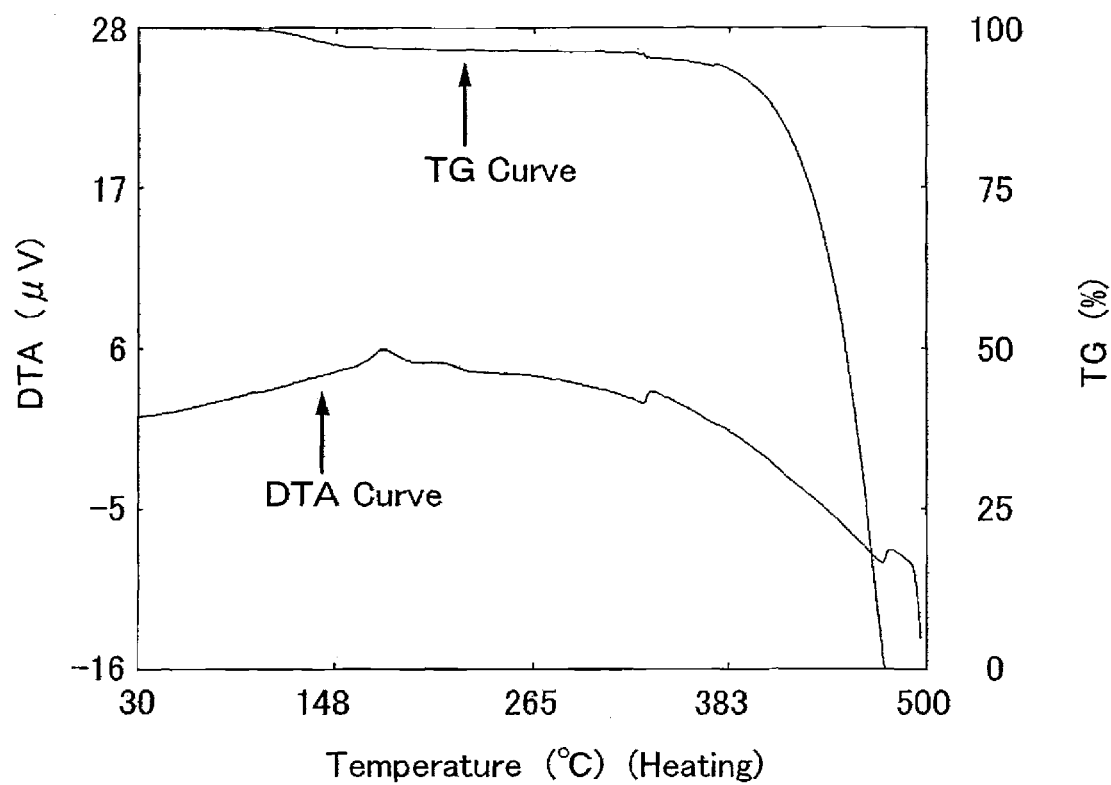
FIG. 33 is a diagram showing a result of Thermogravimetry-Differential Thermal Analysis of 3-[N-(1-naphthyl)-N-(9-phenylcarbazol-3-yl)amino]-9-phenylcarbazole.

Thermogravimetry-Differential Thermal Analysis (TG-DTA) of the obtained PCzPCN1 was performed similarly to Embodiments 1 and 2. FIG. 33 shows the result. In FIG. 33, the left-hand vertical axis indicates differential heat in differential thermal analysis (DTA) (electric motive force of a thermocouple (μV)), whereas the right-hand vertical axis indicates weight in thermogravimetry (TG mesurement) (%; weight represented on the basis that the weight at onset of measurement is to be 100%). Further, the lower horizontal axis indicates temperature (° C.). A thermo-gravimetric/differential thermal analyzer (TG/DTA-320, by Seiko Instruments Inc.) was used for the measurement, which evaluated thermophysical properties in a nitrogen atmosphere at heating rate of 10° C./min. As a result, from the relationship between the weight and the temperature (thermogravimetry), the temperature at which the weight is less than or equal to 95% with respect to the weight at the onset of measurement at normal pressure was 400° C.

Figure 34:
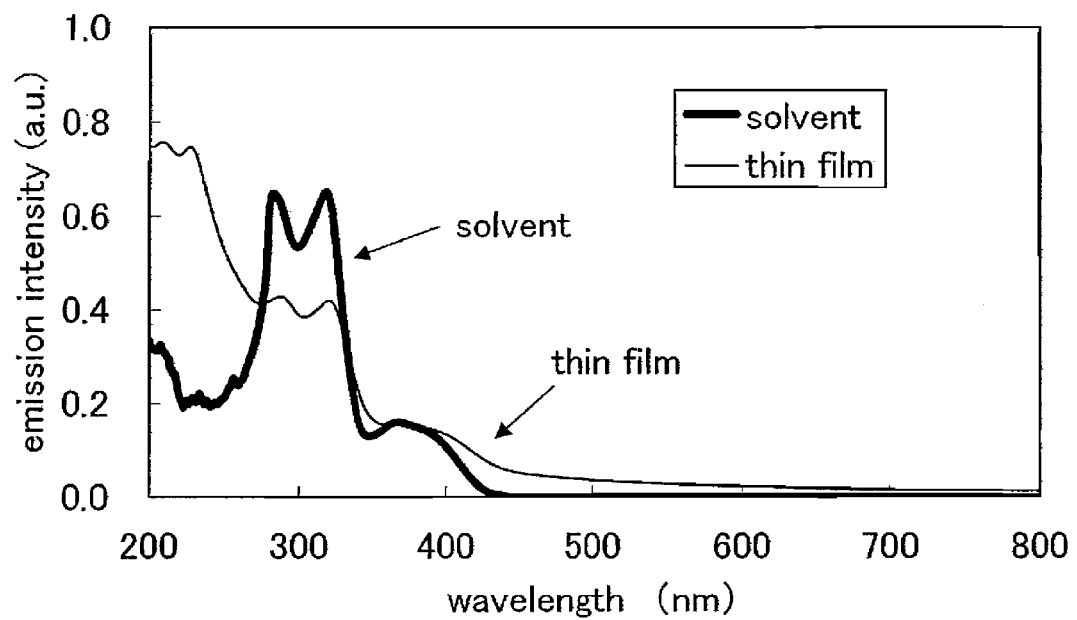
FIG. 34 is a diagram showing the absorption spectra of 3-[N-(1-naphthyl)-N-(9-phenylcarbazol-3-yl)amino]-9-phenylcarbazole.
Figure 35:
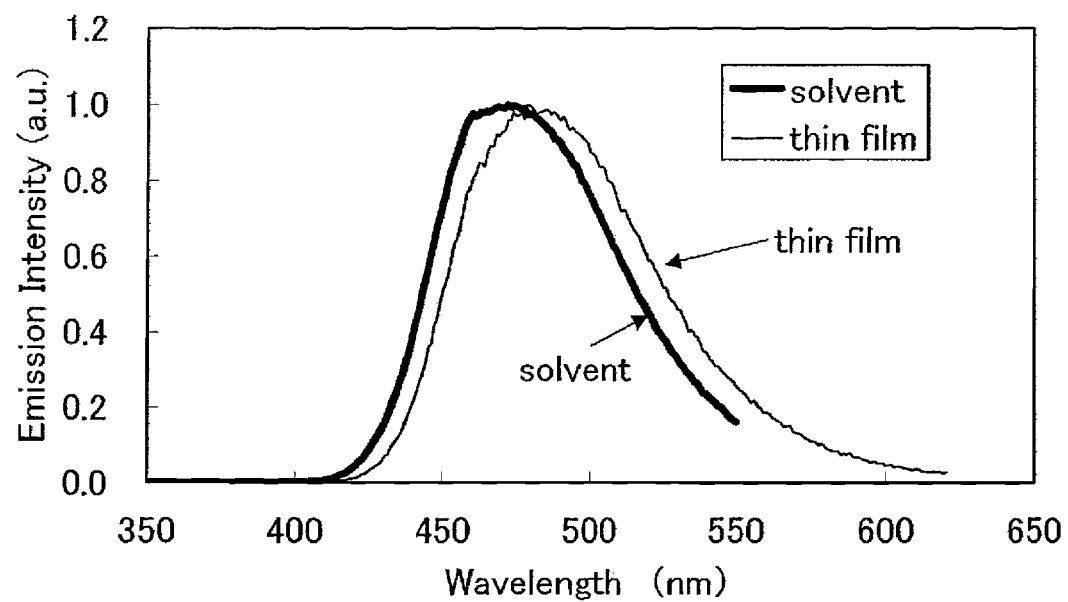
FIG. 35 is a diagram showing the emission spectra of 3-[N-(1-naphthyl)-N-(9-phenylcarbazol-3-yl)amino]-9-phenylcarbazole.

FIG. 34 shows the absorption spectra for a toluene solution of PCzPCN1 and a thin film of PCzPCN1. An ultraviolet-visible spectrophotometer (V-550, by JASCO Corporation) was used for the measurement. The solution was put in a quartz cell and the thin film was evaporated over a quartz substrate as samples, and the absorption spectra thereof, from each of which the absorption spectrum of quartz was subtracted, are shown in FIG. 34. In FIG. 34, the horizontal axis indicates the wavelength (mu) and the vertical axis indicates the absorption intensity (arbitrary unit). The maximum absorption wavelength was 314 nm in the case of the toluene solution, and 320 nm in the case of the thin film. FIG. 35 shows the emission spectra for the toluene solution of PCzPCN1 and the thin film of PCzPCN1. In FIG. 35, the horizontal axis indicates the wavelength (nm) and the vertical axis indicates the emission intensity (arbitrary unit). The maximum emission wavelength was 475 nm (the excitation wavelength: 320 nm) in the case of the toluene solution and 485 nm (the excitation wavelength: 320 nm) in the case of the thin film.

The HOMO level and the LUMO level of PCzPCN1 in a thin-film state were measured. The value of the HOMO level was obtained by converting the ionization potential measured by using a photoelectron spectrometer (AC-2, by Riken Keiki Co., Ltd.) to a negative value. Furthermore, the value of the LUMO level was obtained by setting the absorption edge of the thin film in FIG. 34 as an energy gap and adding the value of the absorption edge to the value of the HOMO level. As a result, the HOMO level was −5.15 eV, and the LUMO level was −2.82 eV.

Subsequently, an oxidation property of PCzPCN1 was examined by cyclic voltammetry (CV). An electrochemical analyzer (ALS model 600A, by BAS Inc.) was used for the measurement.

The solution for the CV measurement was prepared by using dehydrated dimethylformamide (DMF) as a solvent, dissolving a supporting electrolyte of tetra-n-butylammonium perchlorate (n-Bu$_4$NClO$_4$) to the concentration of 100 mmol/L, and dissolving PCzPCN1, the object of measurement, to the concentration of 1 mmo/L. A platinum electrode (PTE platinum electrode, by BAS Inc.) was used as a working electrode, another platinum electrode (Pt counter electrode (5 cm) for VC-3, by BAS Inc.) was used as an auxiliary electrode, and an Ag/Ag$^+$ electrode (RE5 non-aqueous solvent reference electrode, by BAS Inc.) was used as a reference electrode.

The oxidation reaction property was measured as follows. After potential of the working electrode with respect to the reference electrode was changed from −0.20 to 0.50 V, scanning from 0.50 to −0.20 V was set to be one cycle, and 100 cycles were measured. The scanning speed of the CV measurement was set to be 0.1 V/s.

Figure 36:
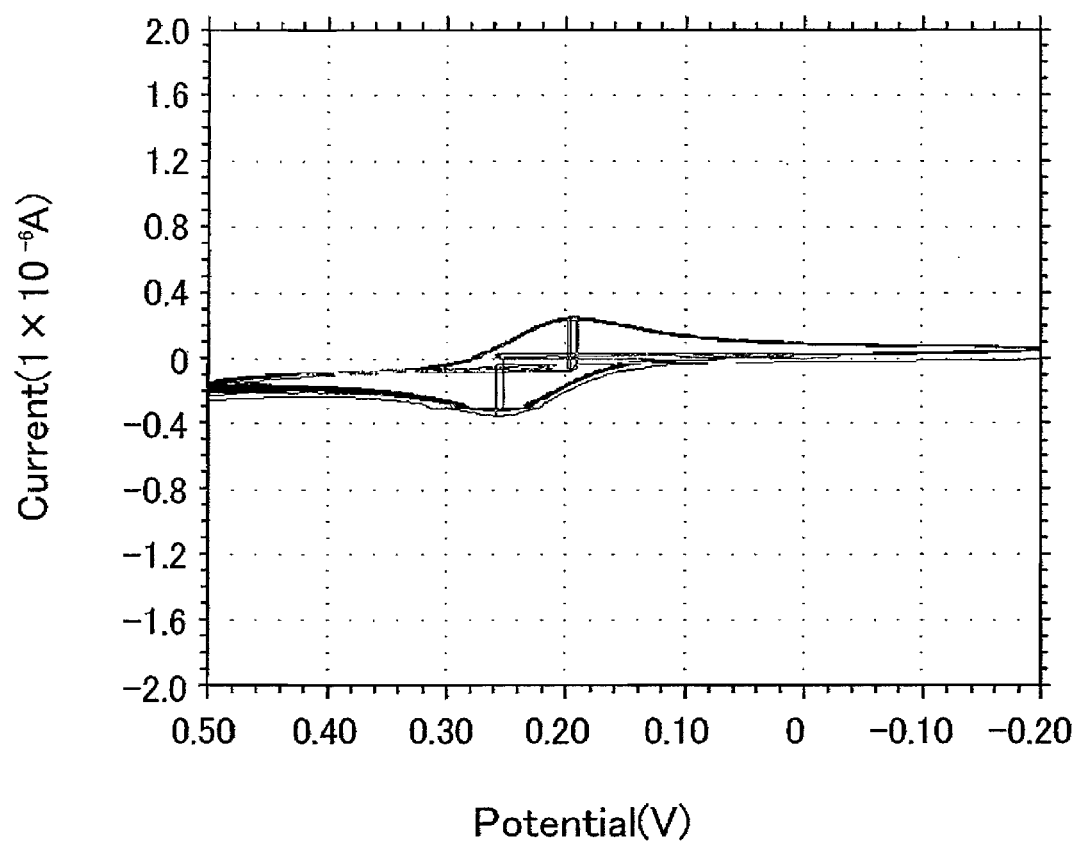
FIG. 36 is a diagram showing CV characteristics of 3-[N-(1-naphthyl)-N-(9-phenylcarbazol-3-yl)amino]-9-phenylcarbazole.

FIG. 36 shows a result of examining the oxidation reaction property of PCzPCN1. In FIG. 36, the horizontal axis indicates potential (V) of the working electrode with respect to the reference electrode, and the vertical axis indicates a value of current which flows between the working electrode and the auxiliary electrode (1×10$^{-6}$ A). According to FIG. 36, it was found that the oxidation potential was 0.25 V (vs. Ag/Ag$^+$ electrode). In addition, although the scanning was repeated for 100 cycles, changes in the peak position and the peak intensity of a CV curve were scarcely observed in the oxidation reaction. Accordingly; it was found that the carbazole derivative used in the present invention is significantly stable in the oxidation reaction.

Figure 37:
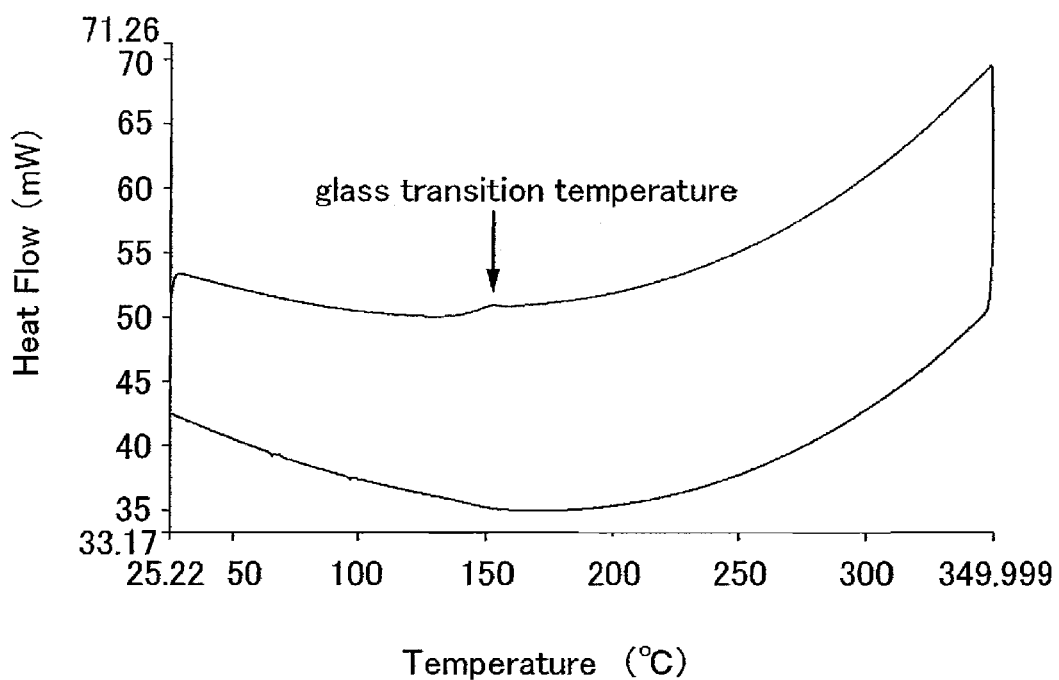
FIG. 37 is a diagram showing a result of analyzing 3-[N-(1-naphthyl)-N-(9-phenylcarbazol-3-yl)amino]-9-phenylcarbazole using a differential scanning calorimeter.

Furthermore, the glass transition temperature of the obtained compound PCzPCN1 was measured using a differential scanning calorimeter (Pyris 1 DSC, by PerkinElmer, Inc.). FIG. 37 shows a measurement result by DSC. A temperature is shown in an X axis and a heat flow is shown in a Y axis, respectively. An upwardness in the heat flow shows endotherm. According to the measurement result, it was found that the glass transition temperature of the obtained compound is 142° C. Thus, the obtained compound has a high glass transition temperature of 142° C. and favorable heat resistance. FIG. 37 has no peak showing crystallization of the obtained compound and it was found that the obtained compound is a substance that is difficult to be crystallized.

Embodiment 4

This embodiment will show a specific example of a composite layer containing the carbazole derivative represented by the general formula (1) and an inorganic compound. As the carbazole derivative, 3-[N-(9-phenylcarbazol-3-yl)-N-phenylamino]-9-phenylcarbazole (abbreviation: PCzPCA1) represented by the structural formula (10) synthesized in Embodiment 1 was used, and as the inorganic compound, molybdenum oxide was used.

First, a glass substrate was fixed to a substrate holder in a vacuum evaporation apparatus. Next, PCzPCA1 and molybdenum oxide (VI) were separately put in different resistance-heating evaporation sources, and a composite layer containing PCzPCA1 and molybdenum oxide was formed in vacuum by a co-evaporation method. At this time, the co-evaporation was performed so that a weight ratio of PCzPCA1 to molybdenum oxide was 4:1. Therefore, a molar ratio of PCzPCA1 to molybdenum oxide was 1.0:1.0. It is to be noted that a film thickness thereof was 90 nm.

Figure 38:
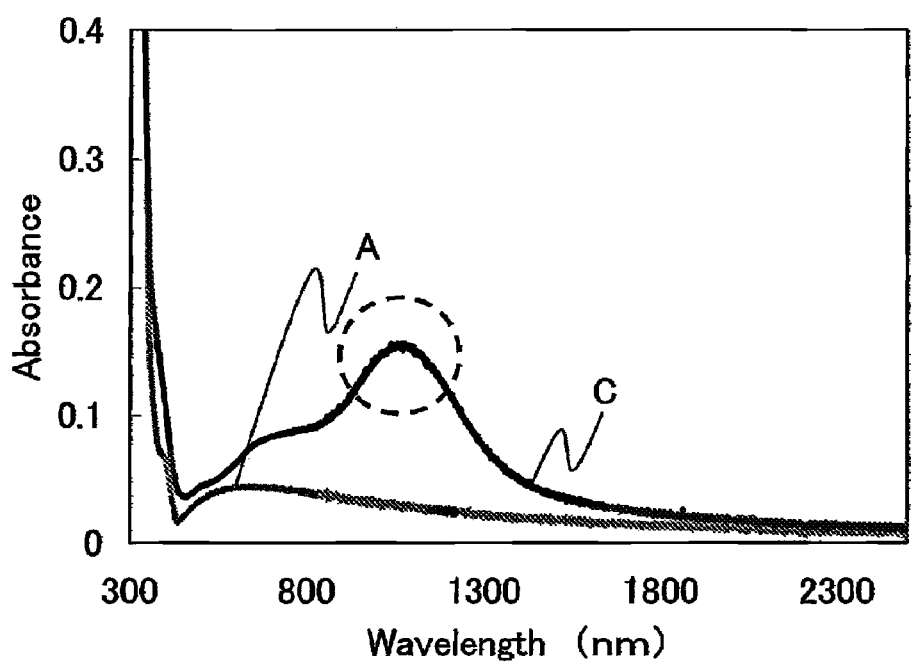
FIG. 38 is a diagram showing the absorption spectrum of a composite layer.

A measurement result of the absorption spectrum of the PCzPCA1-molybdenum oxide composite layer which was formed in this manner is indicated by C in FIG. 38. For comparison, the absorption spectrum of a layer containing only PCzPCA1 (A in the diagram) is also shown.

As shown in FIG. 38, new absorption, which was not observed in the layer containing only PCzPCA1, was observed in the composite layer of C (a portion surrounded by a dashed line in the diagram, and there is a peak around 1070 nm). It is thought that this is because electrons are transported between molybdenum oxide and PCzPCA1, and that molybdenum oxide receives electrons from PCzPCA1 and holes are generated in PCzPCA1.

Consequently, the PCzPCA1-molybdenum oxide composite layer formed in this embodiment, in which carriers are generated internally, can reduce drive voltage of a light emitting element.

In addition, as shown in FIG. 38, notable absorption was not observed in a visible light region (400 to 700 nm) as for the PCzPCA1-molybdenum oxide composite layer.

Embodiment 5

This embodiment will show a specific example of a composite layer containing the carbazole derivative represented by the general formula (1) and an inorganic compound. As the carbazole derivative, 3,6-bis[N-(9-phenylcarbazol-3-yl)-N-phenylamino]-9-phenylcarbazole (abbreviation: PCzPCA2) represented by the structural formula (36) synthesized in Embodiment 2 was used, and as the inorganic compound, molybdenum oxide was used.

First, a glass substrate was fixed to a substrate holder in a vacuum evaporation apparatus. Next, PCzPCA2 and molybdenum oxide (VI) were separately put in different resistance-heating evaporation sources, and a composite layer containing PCzPCA2 and molybdenum oxide was formed in vacuum by a co-evaporation method. At this time, the co-evaporation was performed so that a weight ratio of PCzPCA2 to molybdenum oxide was 4:1. Therefore, a molar ratio of PCzPCA2 to molybdenum oxide was 1.0:1.6. It is to be noted that a film thickness thereof was 90 nm.

Figure 39:
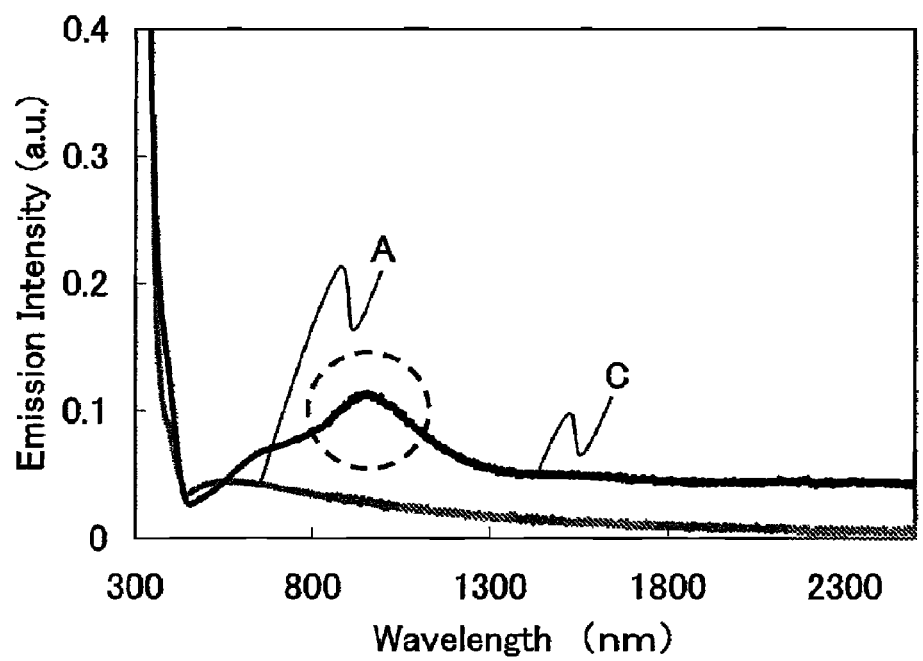
FIG. 39 is a diagram showing the absorption spectrum of a composite layer.

A measurement result of the absorption spectrum of the PCzPCA2-molybdenum oxide composite layer which was formed in this manner is indicated by C in FIG. 39. For comparison, the absorption spectrum of a layer containing only PCzPCA2 (A in the diagram) is also shown.

As shown in FIG. 39, new absorption, which was not observed in the layer containing only PCzPCA2, was observed in the composite layer of C (a portion surrounded by a dashed line in the diagram, and there is a peak around 960 nm). It is thought that this is because electrons are transported between molybdenum oxide and PCzPCA2, and that molybdenum oxide receives electrons from PCzPCA2 and holes are generated in PCzPCA2.

Consequently, the PCzPCA2-molybdenum oxide composite layer formed in this embodiment, in which carriers are generated internally, can reduce drive voltage of a light emitting element.

In addition, as shown in FIG. 39, notable absorption was not observed in a visible light region (400 to 700 nm) as for the PCzPCA2-molybdenum oxide composite layer.

Embodiment 6

Figure 40:
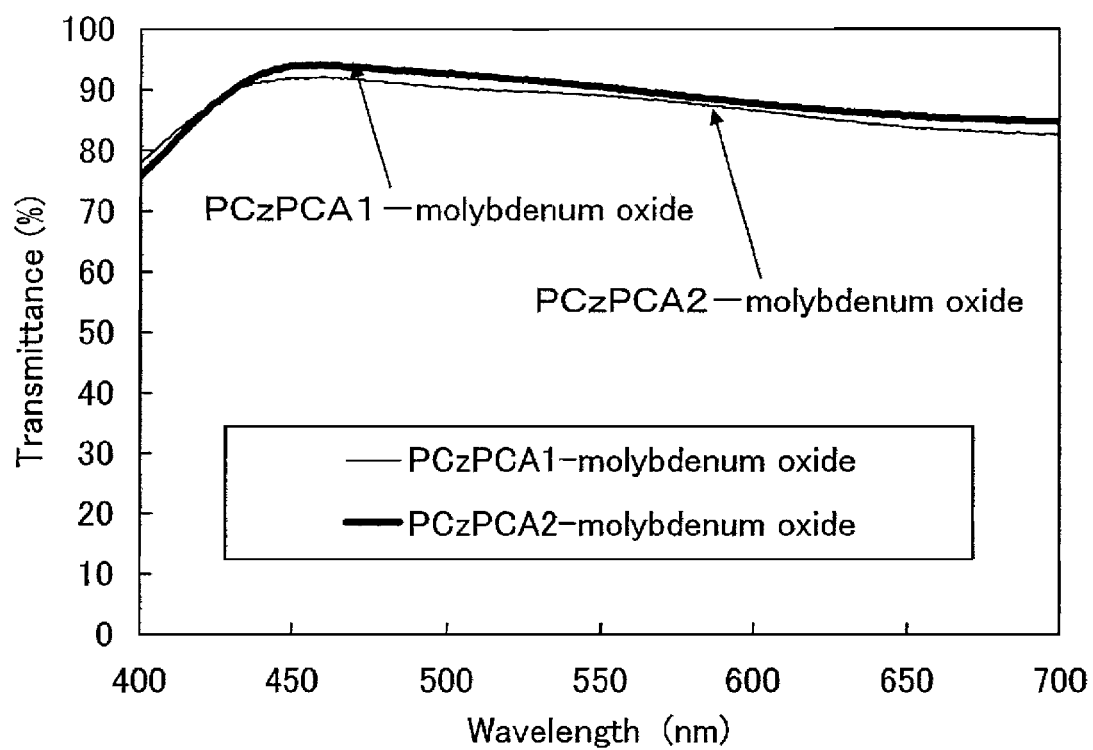
FIG. 40 is a diagram showing transmittance of a composite layer.

Next, visible light transmittances of the composite layers manufactured in Embodiments 4 and 5 are shown in FIG. 40.

FIG. 40 shows a diagram where the vertical axes of FIGS. 38 and 39 are each converted from absorbance to transmittance and compared on the same graph. It is to be noted that the wavelength of the horizontal axis is limited to a visible light region (400 to 700 nm) in FIG. 40. As shown in FIG. 40, transmittances in the visible light region of the PCzPCA1-molybdenum oxide composite layer manufactured in Embodiment 4 and the PCzPCA2-molybdenum oxide composite layer manufactured in Embodiment 5 are approximately 90% or greater than or equal to 90%.

Figure 41:
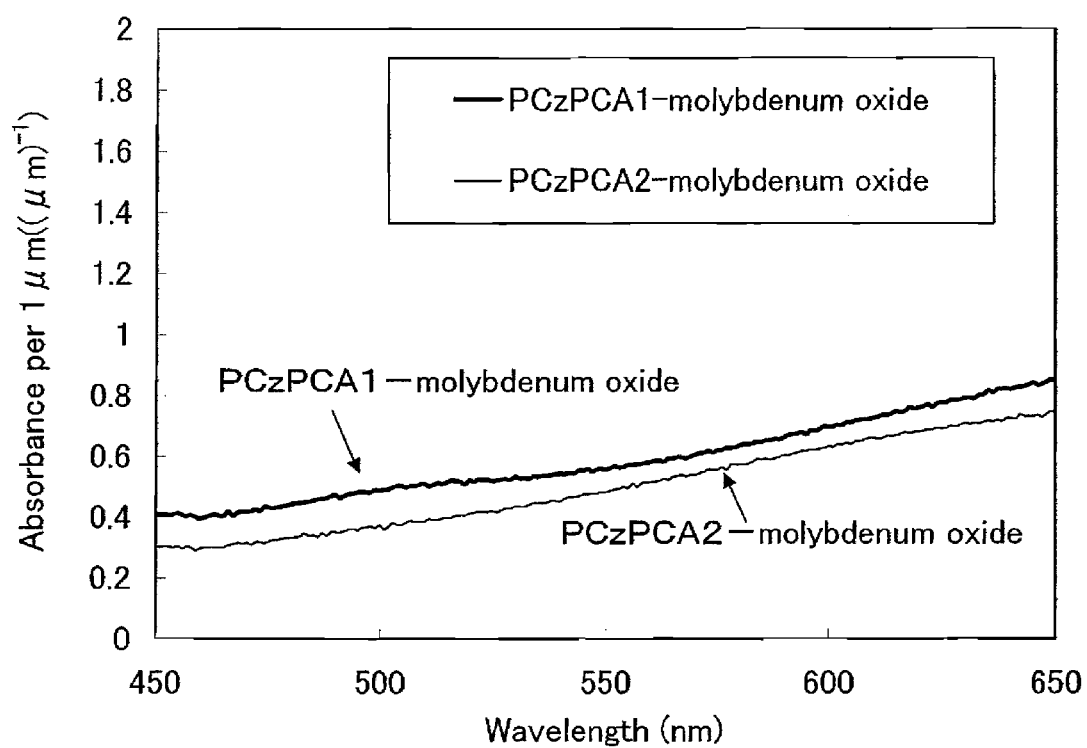
FIG. 41 is a diagram showing absorbance per 1 μm of a composite layer.

In addition, absorbances per 1 μm in the range of blue (450 nm) to red (650 nm) of the PCzPCA1-molybdenum oxide composite layer manufactured in Embodiment 4 and the PCzPCA2-molybdenum oxide composite layer manufactured in Embodiment 5 are shown in FIG. 41. As shown in FIG. 41, absorbance per 1 μm of each composite layer is less than or equal to $2(\mu m)^{-1}$.

As described above, it was found that the composite layer used in the present invention has an excellent transmitting property of visible light. Therefore, by using the composite layer, an organic field effect transistor with an excellent transmitting property of visible light can be manufactured. In addition, by using the organic field effect transistor of the present invention, a semiconductor device with an excellent transmitting property of visible light can be manufactured.

Embodiment 7

This embodiment will show a specific example of a composite layer containing the carbazole derivative represented by the general formula (1) and an inorganic compound. As the carbazole derivative, PCzPCN1 was used, and as the inorganic compound, molybdenum oxide was used.

First, a glass substrate was fixed to a substrate holder in a vacuum evaporation apparatus. Next, PCzPCN1 and molybdenum oxide (VI) were separately put in different resistance-heating evaporation sources, and a composite layer containing PCzPCN1 and molybdenum oxide was formed under reduced pressure by a co-evaporation method. At this time, the co-evaporation was performed so that a weight ratio of PCzPCN1 to molybdenum oxide was 4:2. It is to be noted that a film thickness thereof was 100 nm.

Figure 42:
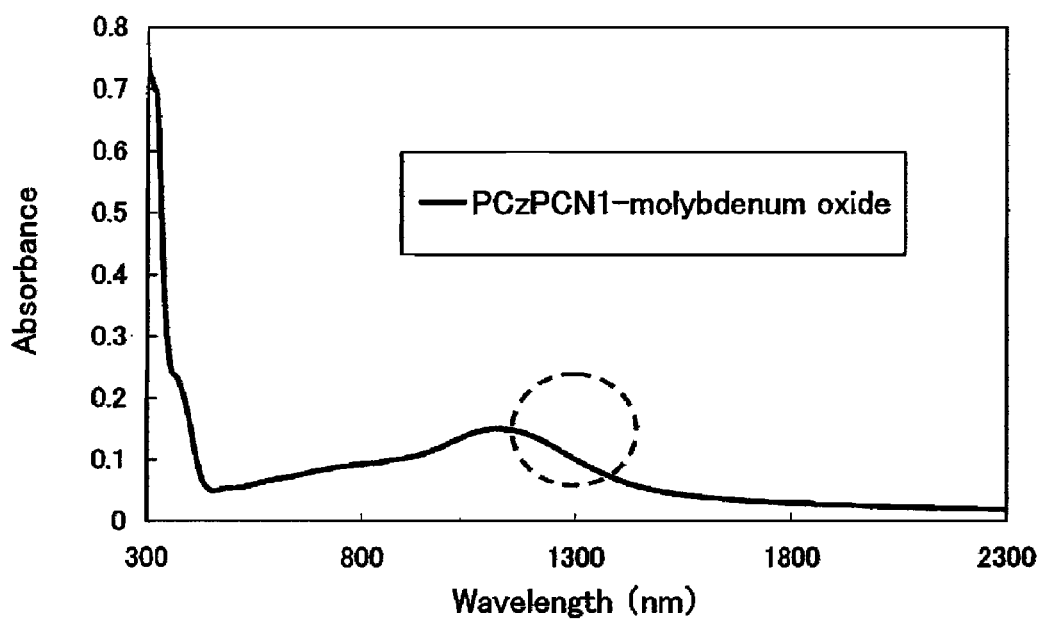
FIG. 42 is a diagram showing the absorption spectrum of a composite layer.

A measurement result of the absorption spectrum of the PCzPCN1-molybdenum oxide composite layer which was formed in this manner is indicated in FIG. 42.

As shown in FIG. 42, new absorption, which was not observed in a layer containing only PCzPCN1, was observed in the PCzPCN1-molybdenum oxide composite layer (a portion surrounded by a dashed line in the diagram, and there is a peak around 1120 nm). It is thought that this is because electrons are transported between molybdenum oxide and PCzPCN1, and that molybdenum oxide receives electrons from PCzPCN1 and holes are generated in PCzPCN1.

Consequently, the PCzPCN1-molybdenum oxide composite layer formed in this embodiment, in which carriers are generated internally, can reduce drive voltage of a light emitting element.

In addition, as shown in FIG. 42, notable absorption was not observed in a visible light region (400 to 700 nm) as for the PCzPCN1-molybdenum oxide composite layer.

Embodiment 8

Figure 43:
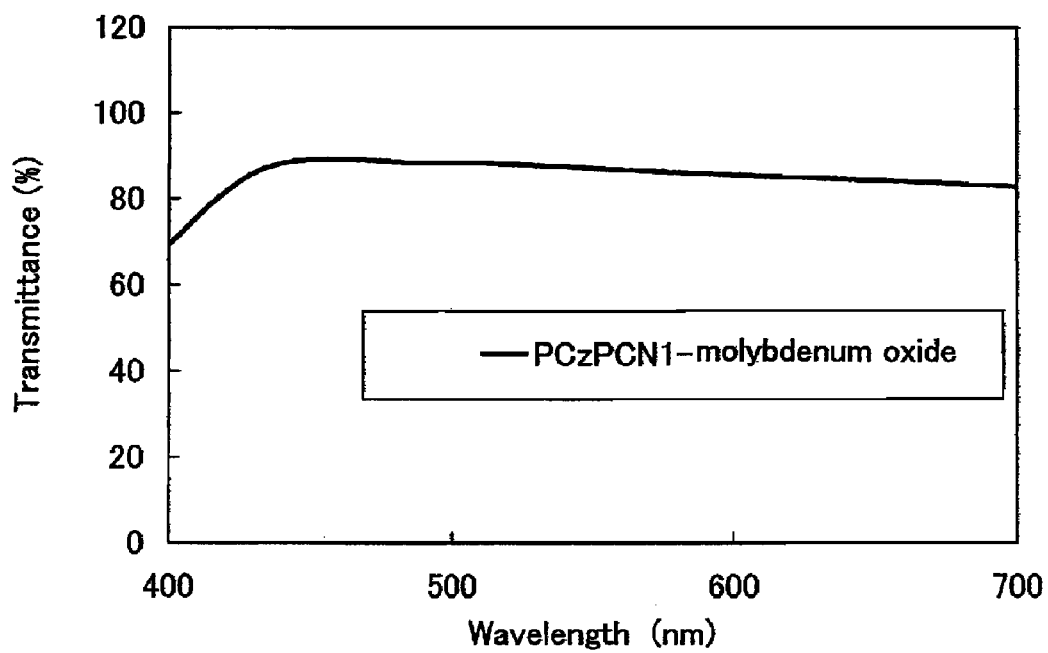
FIG. 43 is a diagram showing transmittance of a composite layer.

Next, visible light transmittance of the composite layer manufactured in Embodiment 7 is shown in FIG. 43.

FIG. 43 shows a diagram where the vertical axis of FIG. 42 is converted from absorbance to transmittance. It is to be noted that the wavelength of the horizontal axis is limited to a visible light region (400 to 700 nm) in FIG. 43. As shown in FIG. 43, transmittance in the visible light region of the PCzPCN1-molybdenum oxide composite layer manufactured in Embodiment 7 is approximately 90%.

Figure 44:
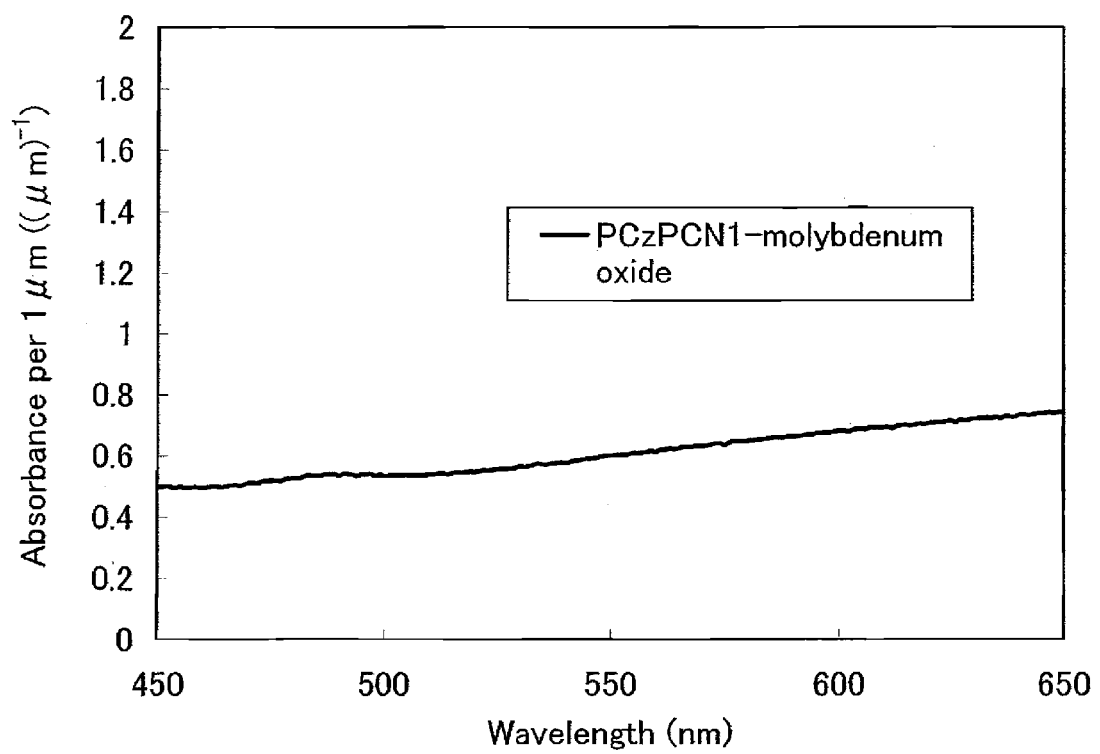
FIG. 44 is a diagram showing absorbance per 1 μm of a composite layer.

In addition, absorbance per 1 μm in the range of blue (450 nm) to red (650 nm) of the PCzPCN1-molybdenum oxide composite layer manufactured in Embodiment 7 is shown in FIG. 44. As shown in FIG. 44, absorbance per 1 μm of each composite layer used in the present invention is less than or equal to $2(\mu m)^{-1}$.

As described above, it was found that the composite layer used in the present invention has an excellent transmitting property of visible light. Therefore, by using the composite layer, an organic field effect transistor with an excellent transmitting property of visible light can be manufactured. In addition, by using the organic field effect transistor of the present invention, a semiconductor device with an excellent transmitting property of visible light can be manufactured.

Embodiment 9

In this embodiment, current-voltage characteristics of a composite layer used in the present invention were measured.

First, indium tin oxide containing silicon oxide (ITSO) was formed over a glass substrate by a sputtering method, whereby a first electrode was formed. The size of the electrode was set to be 2 mm×2 mm.

Next, the substrate, over which the first electrode was formed, was fixed to a substrate holder in a vacuum evaporation apparatus so that the side, on which the first electrode was formed, faced downward.

Subsequently, after air was exhausted from the vacuum evaporation apparatus to reduce pressure, PCzPCN1 and molybdenum oxide (VI) were co-evaporated on the first electrode, whereby a composite layer was formed. The film thickness thereof was set to be 200 nm. It is to be noted that a co-evaporation method is a method to perform evaporation concurrently from a plurality of evaporation sources in one treatment chamber. The ratio of PCzPCN1 to molybdenum oxide (VI) was adjusted to be 4:2 in weight ratio.

On the composite layer, aluminum (Al) was formed by an evaporation method using resistance heating to form a second electrode, whereby an element was manufactured.

Current-voltage characteristics were measured by a two terminal method, in which the case where voltage is applied when ITSO is an anode and Al is a cathode is to be a forward direction, and the case where voltage is applied when ITSO is a cathode and Al is an anode is to be a reverse direction.

Figure 45:
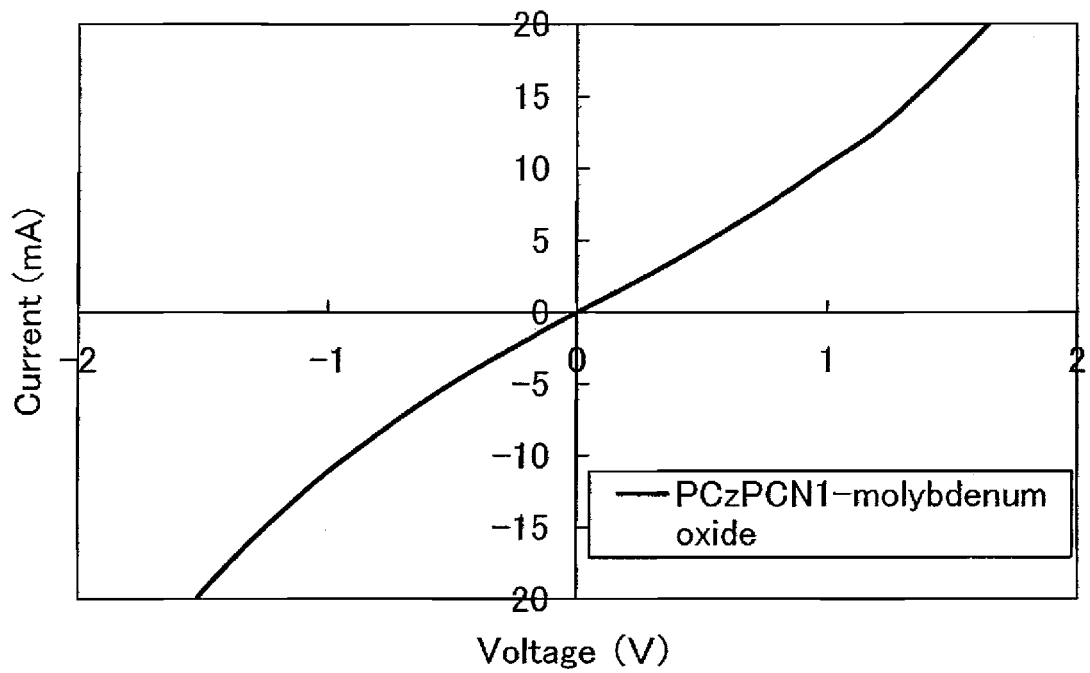
FIG. 45 is a diagram showing current-voltage characteristics of a composite layer.

FIG. 45 shows a result of measuring current-voltage characteristics at room temperature (25° C.). In the element manufactured in this embodiment, current flows both in a forward direction and a reverse direction, and the current-voltage characteristics in both directions are symmetrical with the origin point as a center. Although the electrodes use different materials such as ITSO and AL, the characteristics are symmetrical; therefore, it is considered that the interface between the electrode and the composite layer is not Schottky contact.

Embodiment 10

In this embodiment, an electron state of a composite layer was measured.

Figure 46:
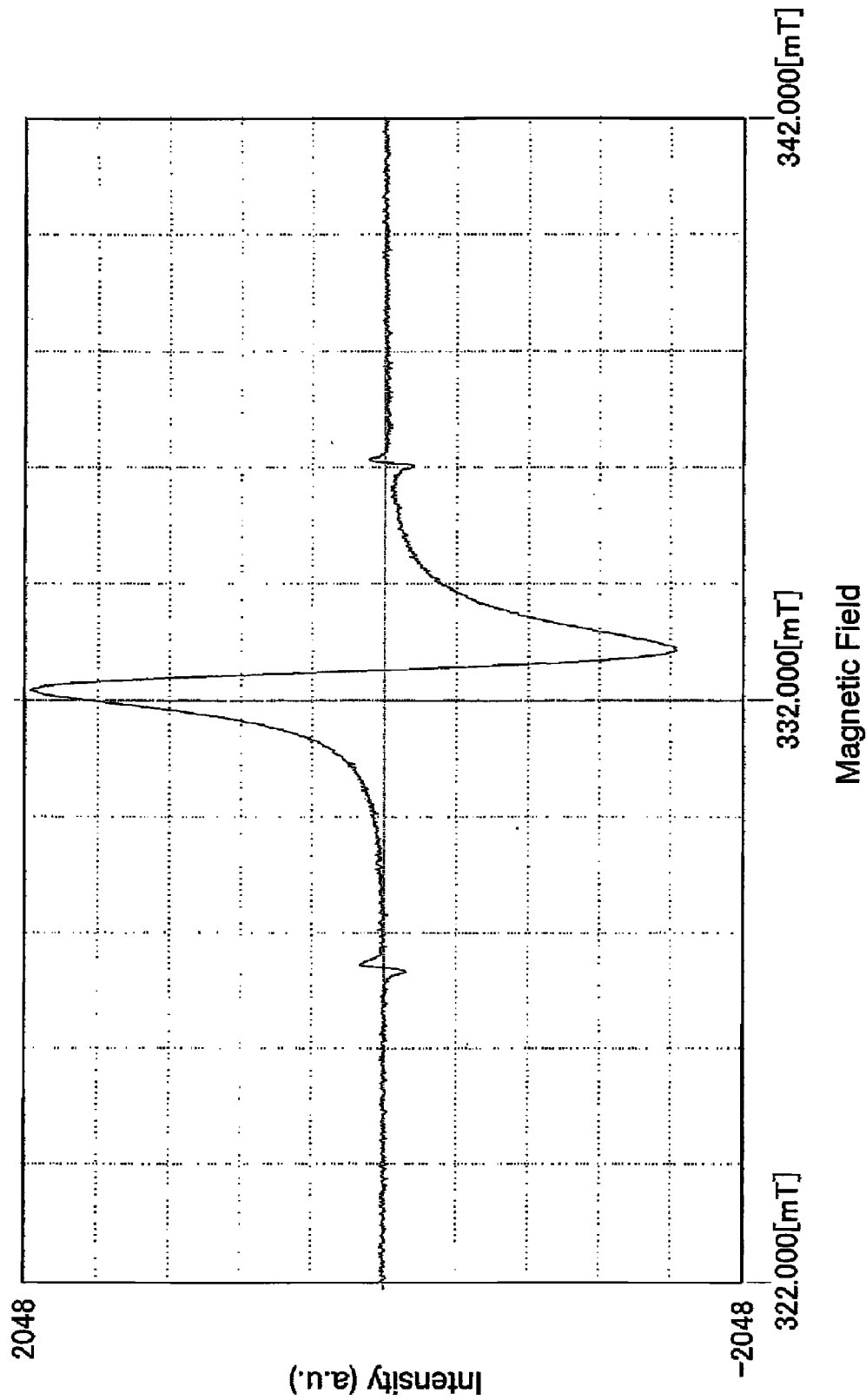
FIG. 46 is a diagram showing an ESR measurement result of a layer containing PCzPCA1 and molybdenum oxide.
Figure 47:
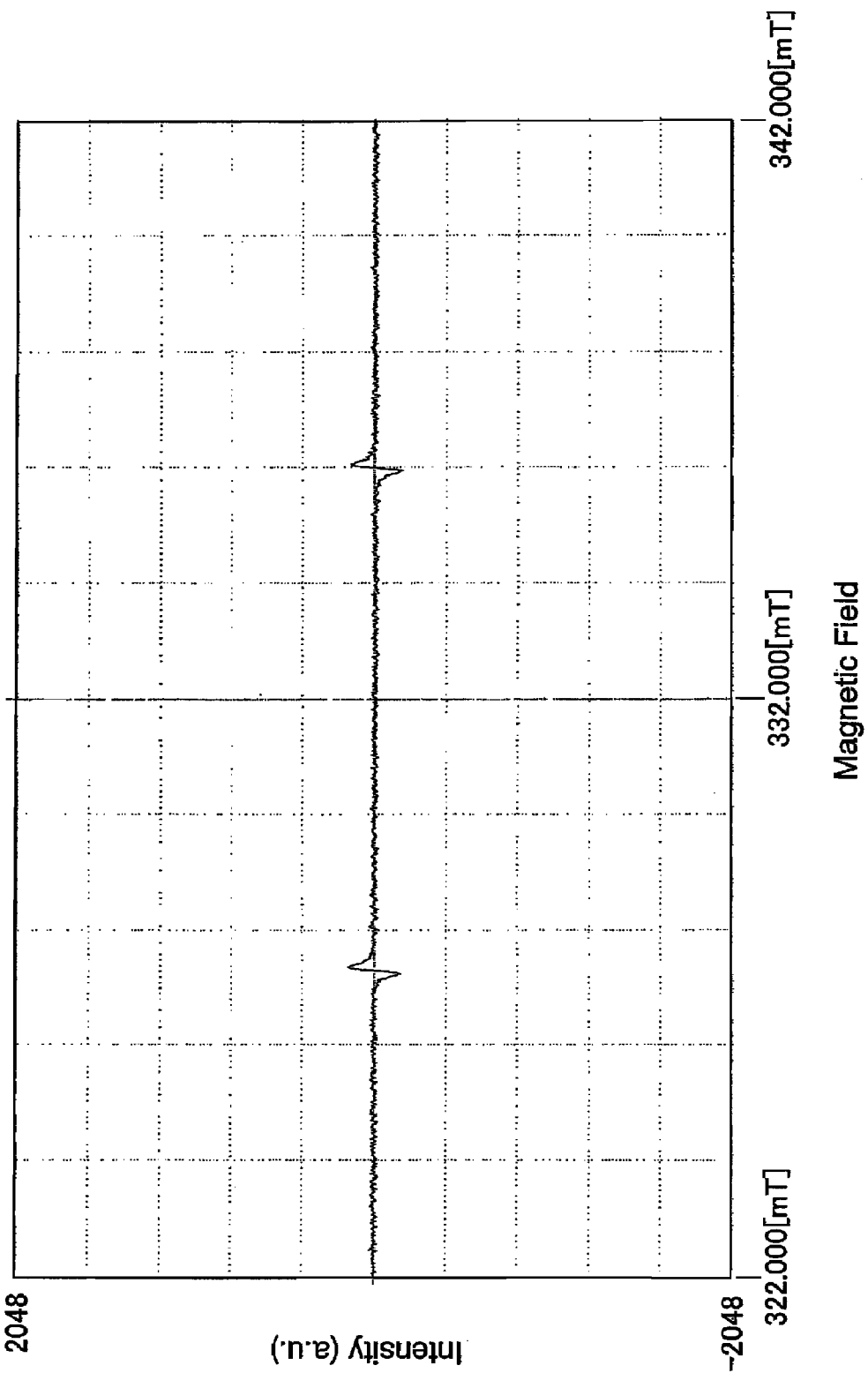
FIG. 47 is a diagram showing an ESR measurement result of a single layer of PCzPCA1.

A composite layer containing PCzPCA1 and molybdenum oxide was formed over a quartz substrate by co-evaporation to have a film thickness of 200 nm. In this case, the co-evaporation was performed so that a weight ratio of PCzPCA1 to molybdenum oxide was 1:0.5. An ESR (electron spin resonance) measurement of the layer containing PCzPCA1 and molybdenum oxide was performed. The ESR measurement is a measurement method in which, by applying strong magnetic field to a sample having unpaired electrons, energy levels of unpaired electrons cause Zeeman splitting, and a measurement is performed by utilizing resonance absorption transition of a microwave, which is a difference in energy between the energy levels. In the ESR measurement, by measuring frequency at the time of absorption and the intensity of the magnetic field, presence of unpaired electrons and a spin condition can be known. In addition, from the absorption intensity, the concentration of electron spin can be obtained. The measurement was performed by using electron spin resonance analysis equipment (JES-TE200, by JEOL Ltd.) under a condition where the resonance frequency was 9.3 GHz; modulation frequency, 100 kHz; the modulation width, 0.63 mT; amplification degree, 50; time constant, 0.1 sec; microwave input, 1 mW; sweep time, 4 min; and measurement temperature, room temperature. As a sample for correcting magnetic field, manganese supported by magnesium oxide was used. FIG. 46 shows the ESR measurement result. In addition, as a comparative example, an ESR measurement was also performed to a single layer of PCzPCA1 (with a film thickness of 200 nm) and a single layer of molybdenum oxide (with a film thickness of 200 nm). FIG. 47 shows the ESR measurement result of the single layer of PCzPCA1, and FIG. 48 shows the ESR measurement result of the single layer of molybdenum oxide.

Figure 48:
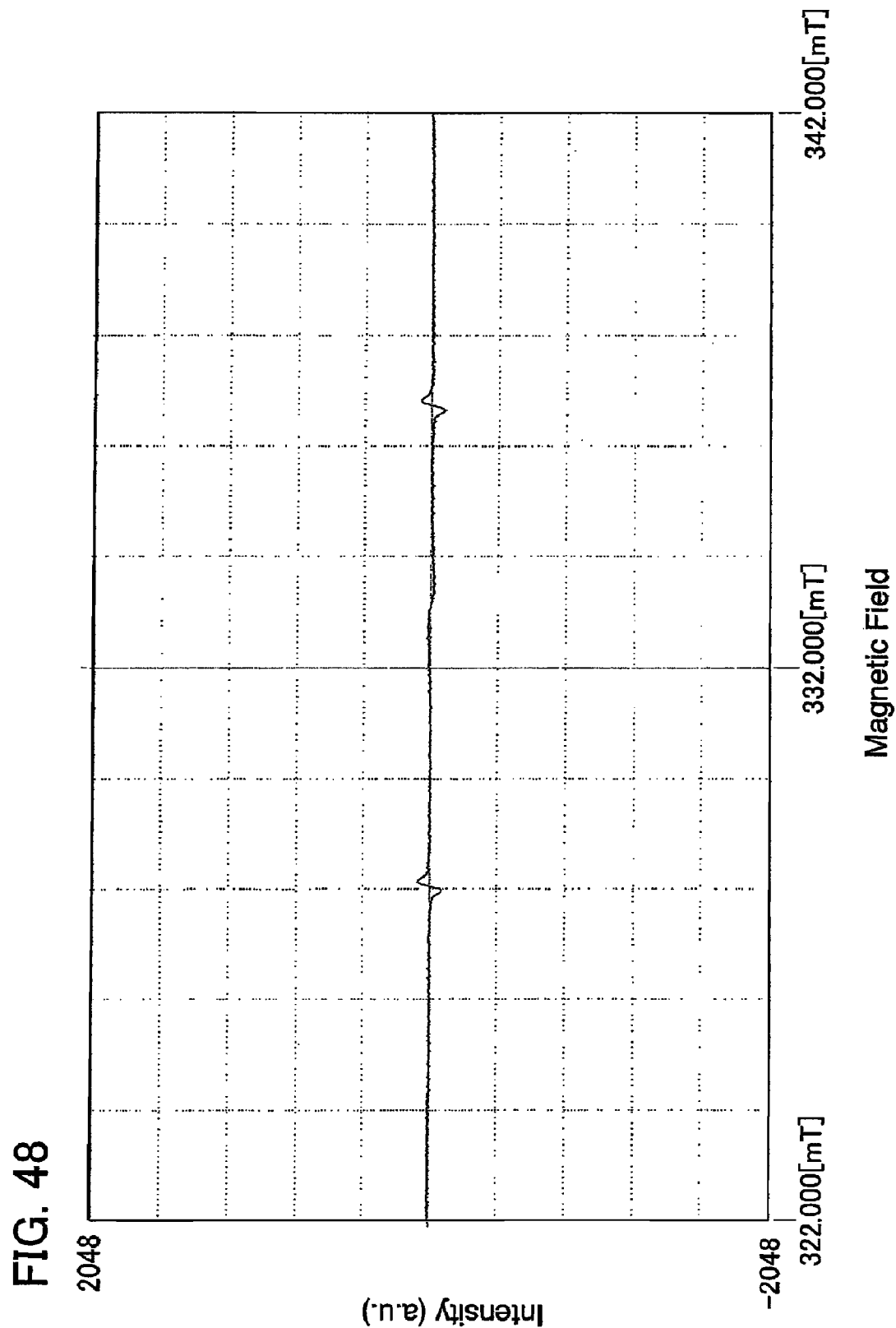
FIG. 48 is a diagram showing an ESR measurement result of a single layer of molybdenum oxide.

In FIGS. 46 to 48, an ESR signal was not detected in the single layer of PCzPCA1 and the single layer of molybdenum oxide. However, an ESR signal was detected in the composite layer containing PCzPCA1 and molybdenum oxide. Accordingly, it was found that the composite layer containing PCzPCA1 and molybdenum oxide has unpaired electrons and is in a different electron state from those of the single layer of PCzPCA1 and the single layer of molybdenum oxide which have no unpaired electrons. Further, according to FIG. 46, the value of "g" of the composite layer containing PCzPCA1 and molybdenum oxide is determined to be 2.0024, and it was found that this value is extremely close to 2.0023, which is the value of "g" of a free electron. On the other hand, it was found that the line width was as narrow as 0.67 mT, and the spin concentration was $3.4 \times 10^{20}$ spin/cm$^3$.

Embodiment 11

This embodiment will explain a method for synthesizing 3-[N-(9-phenylcarbazol-3-yl)-N-phenylamino]-9-phenylcarbazole (abbreviation: PCzPCA1) represented by the structural formula (10) by a synthesis method different from that in Embodiment 1. (D-1) shows a synthesis scheme.

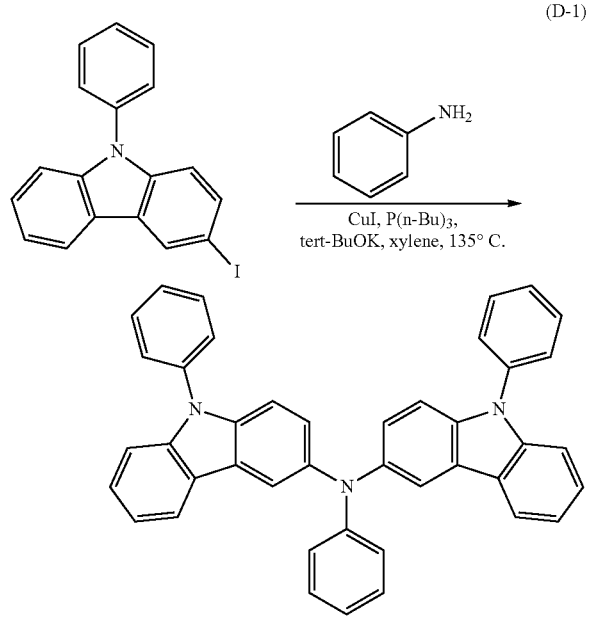

1.60 mg (4.33 mmol) of 3-iodo-9-phenylcarbazole, 19.0 mg (0.1 mmol) of copper (I) iodide, 1.10 g (10 mmol) of tert-butoxy potassium, and 1.0 ml of tri-n-butylphosphine (a 0.2 mol/L dehydrated hexane solution) were put in a 200-mL three-neck flask, and nitrogen was substituted for air in the flask. 10 ml of xylene and 0.2 ml (2.1 mmol, 195.6 mg) of aniline were added therein, and the mixture was refluxed at 135° C. for 6 hours. The reaction solution was cooled to room temperature and then filtered through Florisil and Celite by adding 100 mL of toluene. The obtained filtrate was washed with water twice, and a water layer was extracted with toluene twice. The extraction solution as well as an organic layer was washed with a saturated saline solution and dried with magnesium sulfate. The solution was filtered naturally, and a compound obtained by concentrating the filtrate was subjected to silica gel column chromatography (a mixed solution of toluene and hexane); thus, 140 mg of a light yellow solid that was an object was obtained (yield: 21%).

By using the synthesis method shown in this embodiment, the carbazole derivative used in the present invention can be obtained in one-step reaction.

Embodiment 12

This embodiment will explain a method for synthesizing 3-[N-(1-naphthyl)-N-(9-phenylcarbazol-3-yl)amino]-9-phenylcarbazole (abbreviation: PCzPCN1) represented by the structural formula (15) by a synthesis method different from that in Embodiment 3. (D-2) shows a synthesis scheme.

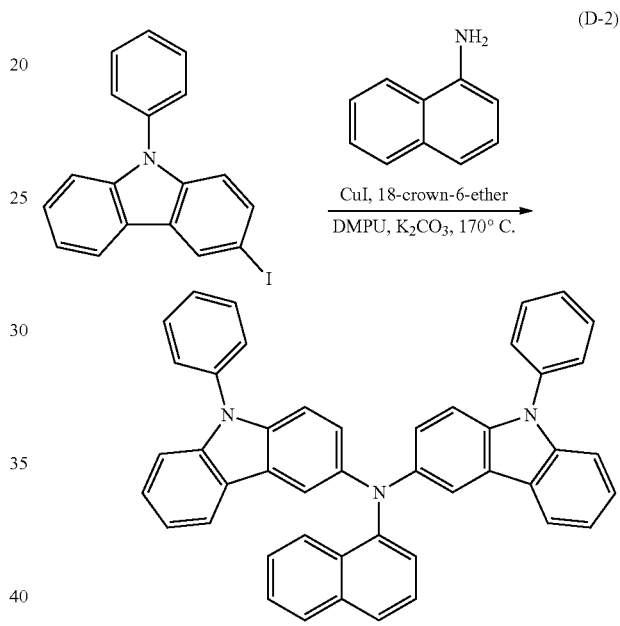

3.69 g (0.01 mol) of 3-iodo-9-phenylcarbazole, 716 mg (5 mmol) of 1-naphthylamine, 385 mg (2 mmol) of copper iodide, 2.74 g (0.02 mol) of potassium carbonate, and 771 mg (0.02 mol) of 18-crown-6-ether were put in a 200-mL three-neck flask, and nitrogen was substituted for air in the flask. 8 ml of DMPU was added therein, and the mixture was stirred at 170° C. for 24 hours. The reaction solution was cooled to room temperature, and washed with water twice. A water layer was extracted with toluene twice. Then, the extraction solution as well as an organic layer that was previously washed was washed with a saturated saline solution and dried with magnesium sulfate. The solution was filtered naturally, and a compound obtained by concentrating the filtrate was subjected to silica gel column chromatography (toluene:hexane=7:3) to be purified; thus, 1.52 g of a light yellow solid that was an object was obtained (yield: 48%).

By using the synthesis method shown in this embodiment, the carbazole derivative used in the present invention can be obtained in one-step reaction.

Embodiment 13

As an example of the carbazole derivative used in the present invention, a synthesis method of 3-{N-[9-(4-biphenylyl)carbazol-3-yl]-N-phenylamino}-9-(4-biphenylyl)carbazole (abbreviation: BCzBCA1) represented by the structural formula (70) will be explained.

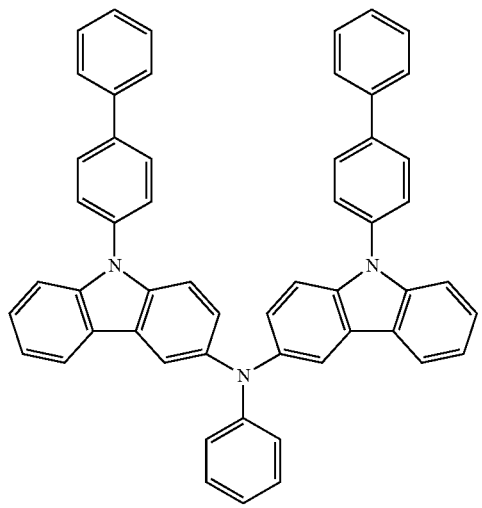
(70)

[Step 1]
First, a synthesis method of 9-(4-biphenylyl)carbazole will be explained. (B-1) shows a synthesis scheme of 9-(4-biphenylyl)carbazole.

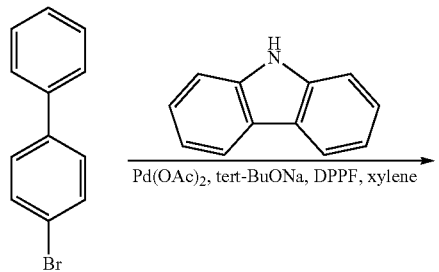
(B-1)

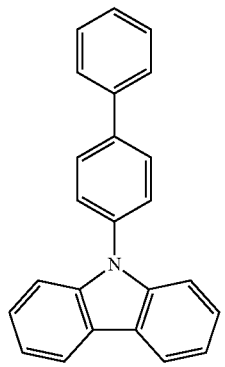

12 g (50 mmol) of 4-bromobiphenyl, 8.4 g (50 mmol) of carbazole, 230 mg (1 mmol) of palladium acetate, 1.8 g (3.0 mmol) of 1,1-bis(diphenylphosphino)ferrocene, and 13 g (180 mmol) of sodium-tert-butoxide were put in a three-neck flask, and nitrogen was substituted for air in the flask. Thereafter, 80 mL of dehydrated xylene was added therein, and the flask was deaerated. In a nitrogen atmosphere, the mixture was heated and stirred at 120° C. for 7.5 hours. After the reaction was terminated, approximately 600 mL of warm toluene was added to the suspension, and the suspension was filtered through Florisil, alumina, and Celite twice. The obtained filtrate was concentrated and recrystallized by adding hexane. Then, filtration was performed, and the residue was collected and dried; thus, 14 g of a cream-colored powder of 9-(4-biphenylyl)carbazole was obtained (yield: 87%).

[Step 2]
Next, a synthesis method of 3-bromo-9-(4-biphenylyl)carbazole will be explained. (B-2) shows a synthesis scheme of 3-bromo-9-(4-biphenylyl)carbazole.

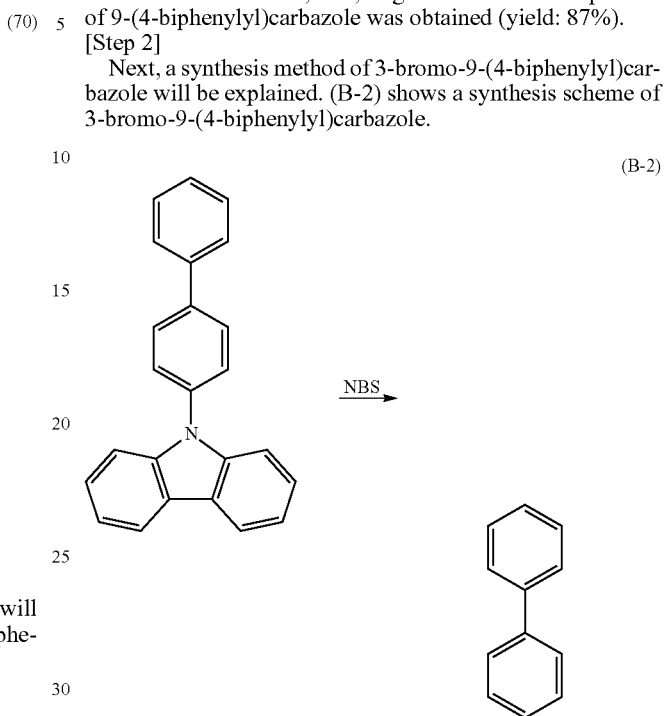
(B-2)

3.1 g (10 mmol) of 9-(4-biphenylyl)carbazole was dissolved in 100 mL of chloroform, and 1.8 g (10 mmol) of N-bromosuccinimide was slowly added therein. The mixture was stirred for approximately 24 hours and washed with water. Magnesium sulfate was added therein to remove moisture, and filtration was performed to obtain the filtrate. This filtrate was concentrated, collected, and dried. Thus, 3.7 g of a beige powder of 3-bromo-9-(4-biphenylyl)carbazole was obtained (yield: 95%).

[Step 3]
Next, a synthesis method of 3-iodo-9-(4-biphenylyl)carbazole will be explained. (B-3) shows a synthesis scheme of 3-iodo-9-(4-biphenylyl)carbazole.

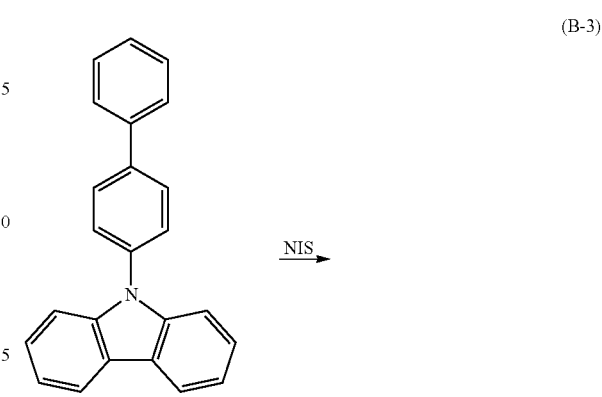
(B-3)

-continued

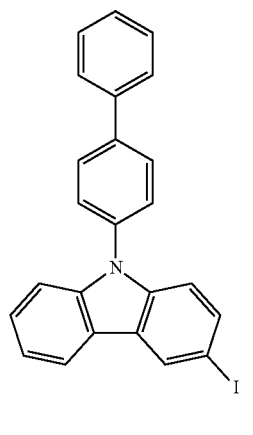

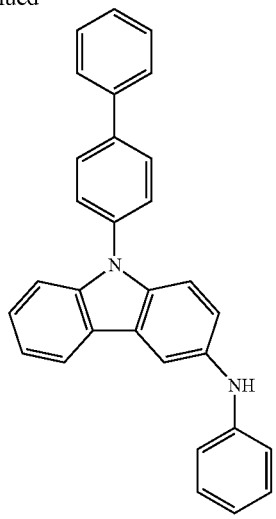

3.2 g (10 mmol) of 9-(4-biphenylyl)carbazole was dissolved in a mixed solution of 200 mL of glacial acetic acid, 200 mL of toluene, and 50 mL of ethyl acetate, and 2.3 g (10 mmol) of N-iodosuccinimide was slowly added therein. The mixture was stirred for approximately 24 hours, and then washed with water, a sodium thiosulfate aqueous solution, and a saturated saline solution. Magnesium sulfate was added therein to remove moisture, and filtration was performed to obtain the filtrate. The filtrate was concentrated and recrystallized by adding acetone and hexane and by irradiation with ultrasonic waves. Then, filtration was performed, and the residue was collected and dried; thus, 4.4 g of a beige powder of 3-iodo-9-(4-biphenylyl)carbazole was obtained (yield: 98%).

[Step 4]

Next, a synthesis method of N-[(4-biphenylyl)carbazol-3-yl]-N-phenylamine (abbreviation: BCA) will be explained. (B-4) shows a synthesis scheme of BCA.

3.7 g (9.2 mmol) of 3-bromo-9-(4-biphenylyl)carbazole, 63 mg (0.3 mmol) of palladium acetate, 330 mg (0.6 mmol) of 1,1-bis(diphenylphosphino)ferrocene, and 1.5 g (15 mmol) of sodium-tent-butoxide were put in a three-neck flask, and nitrogen was substituted for air in the flask. 20 mL of dehydrated xylene was added therein, and the flask was deaerated. Thereafter, 9.3 g (10 mmol) of aniline was added therein. In a nitrogen atmosphere, the mixture was heated and stirred at 130° C. for 4 hours. After the reaction was terminated, approximately 300 mL of warm toluene was added to the suspension, and the suspension was filtered through Florisil, alumina, and Celite. The obtained filtrate was concentrated and precipitated by adding hexane and by irradiation with ultrasonic waves. Then, filtration was performed, and the residue was dried; thus, 3.5 g of a cream-colored powder of N-[(4-biphenylyl)carbazol-3-yl]-N-phenylamine (abbreviation: BCA) was obtained (yield: 93%).

[Step 5]

Subsequently, a synthesis method of 3-{N-[9-(4-biphenylyl)carbazol-3-yl]-N-phenylamino}-9-(4-biphenylyl)carbazole (abbreviation: BCzBCA1) will be explained. (B-5) shows a synthesis scheme of BCzBCA1.

(B-5)

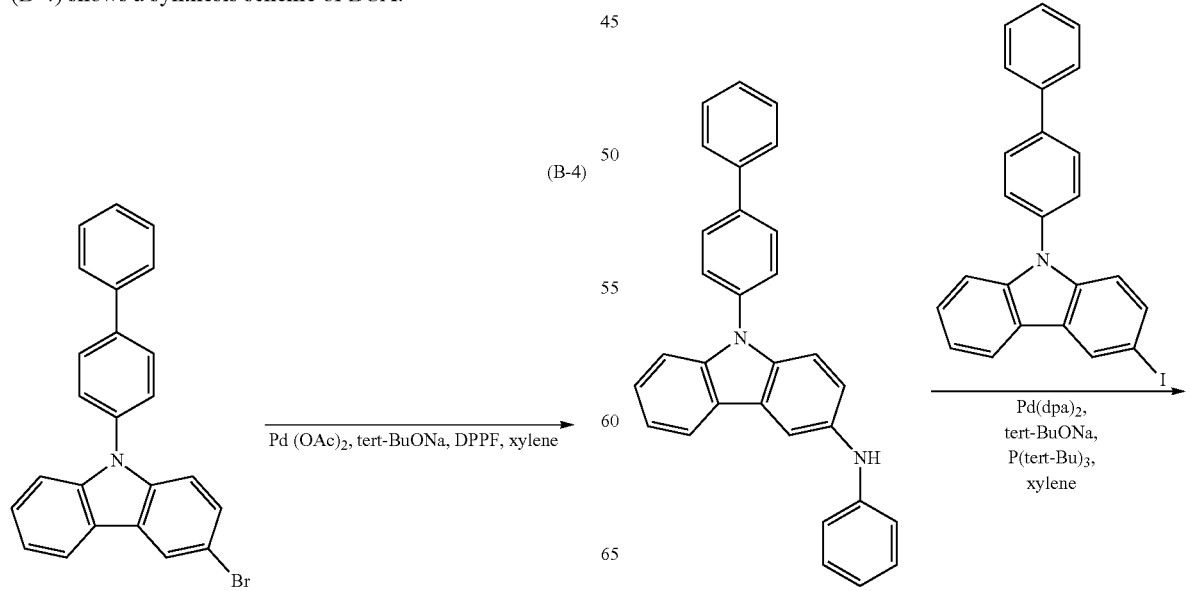

(B-4)

-continued

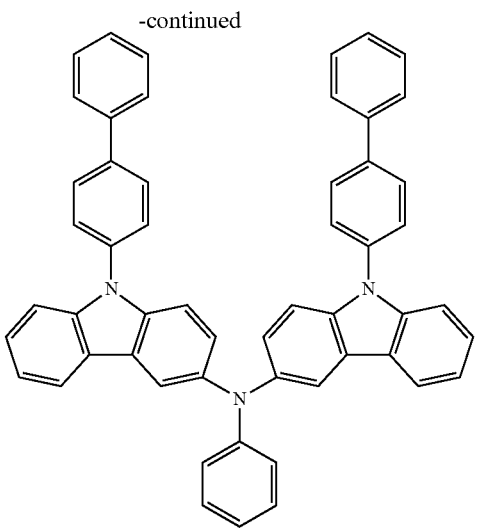

Figure 49A:
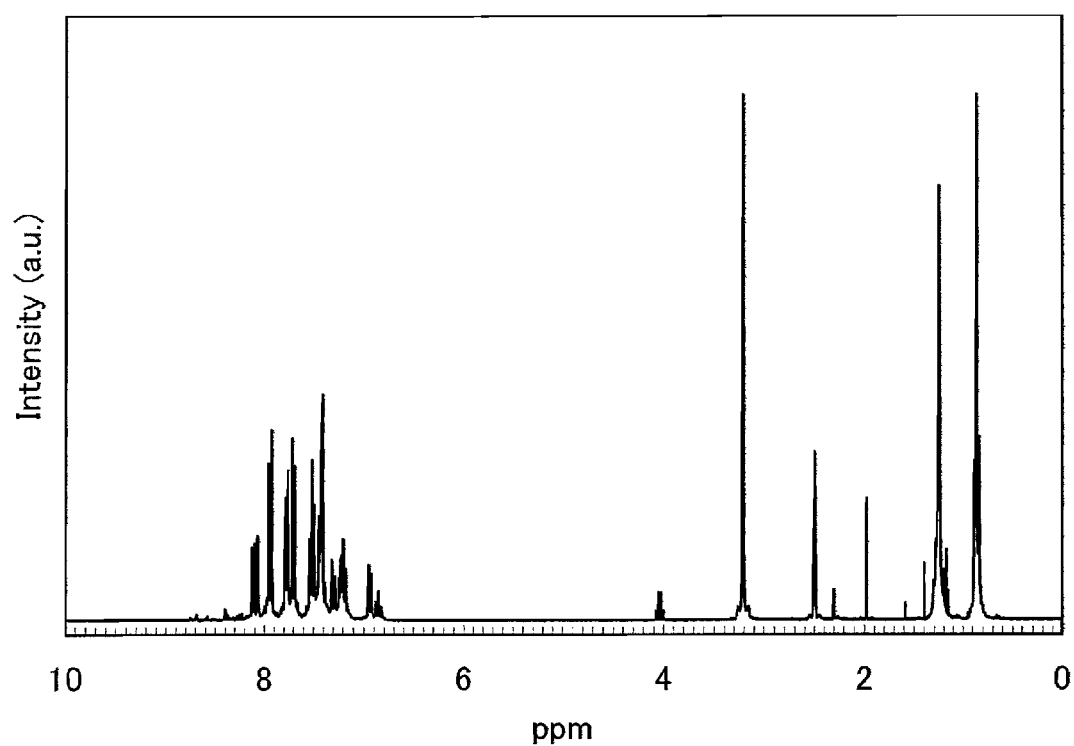
FIGS. 49A and 49B are diagrams each showing an $^1$H-NMR chart of 3-{N-[9-(4-biphenylyl)carbazol-3-yl]-N-phenylamino}-9-(4-biphenylyl)carbazole.
Figure 49B:
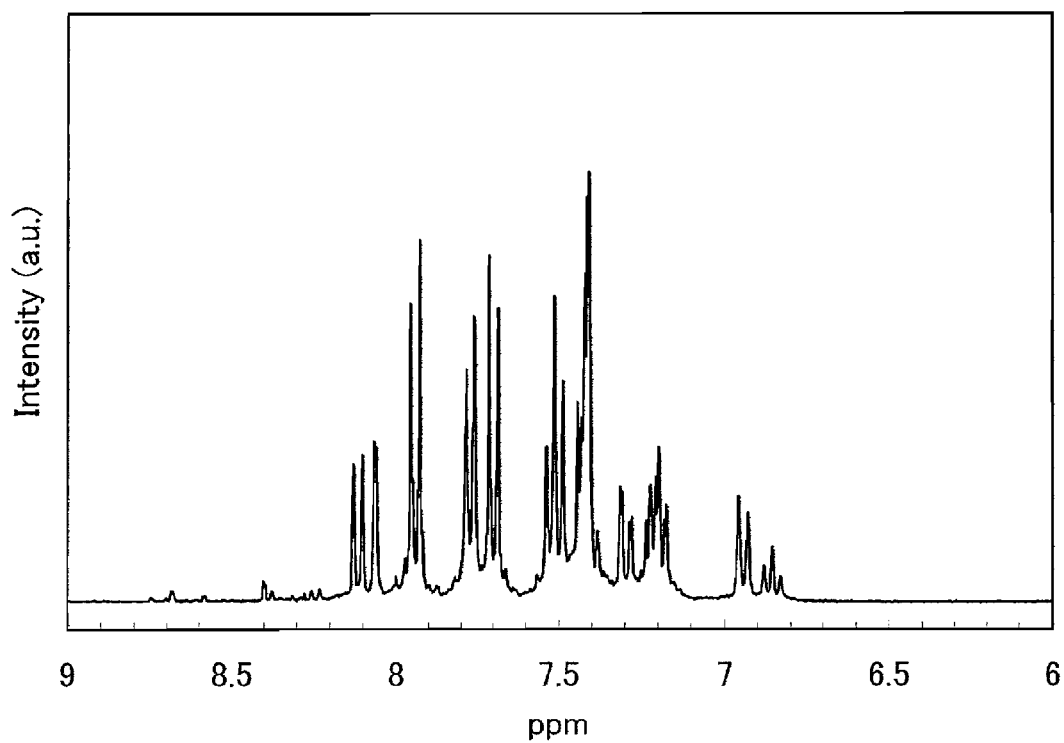
Figure 50A:
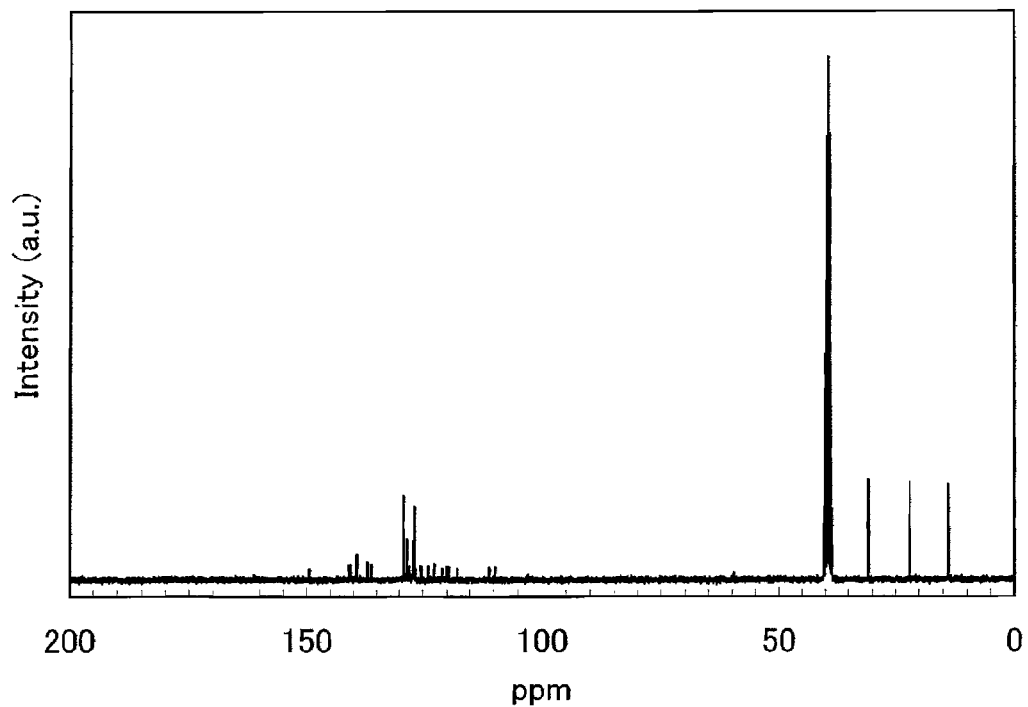
FIGS. 50A and 50B are diagrams each showing a $^{13}$C-NMR chart of 3-{N-[9-(4-biphenylyl)carbazol-3-yl]-N-phenylamino}-9-(4-biphenylyl)carbazole.
Figure 50B:
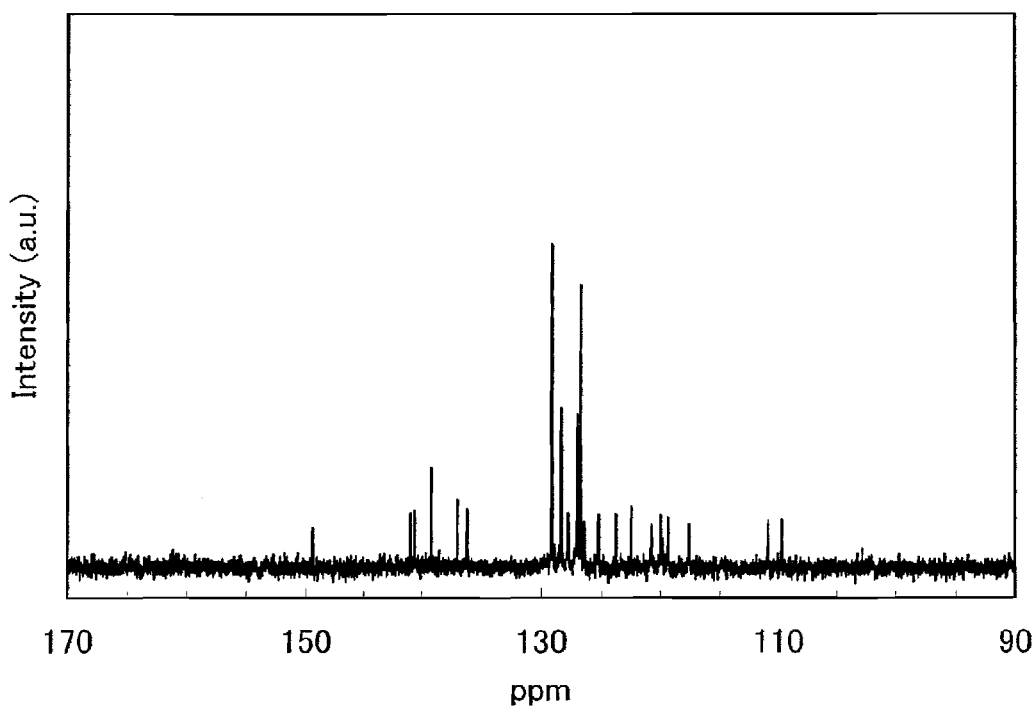

3.5 g (7.9 mmol) of 3-iodo-9-(4-biphenylyl)carbazole, 3.3 g (8.0 mmol) of N-[(4-biphenylyl)carbazol-3-yl]-N-phenylamine, 230 mg (0.4 mmol) of bis(dibenzylideneacetone) palladium(0), and 1.2 g (12 mmol) of sodium-tert-butoxide were put in a three-neck flask, and nitrogen was substituted for air in the flask. 30 mL of dehydrated xylene was added therein, and the flask was deaerated. Thereafter, 1.4 mL (1.2 mmol) of a 10 wt % hexane solution of tri-tert-butylphosphine was added therein. In a nitrogen atmosphere, the mixture was heated and stirred at 110° C. for 3 hours. After the reaction was terminated, approximately 500 mL of warm toluene was added to the suspension, and the suspension was filtered through Florisil, alumina, and Celite. The obtained filtrate was concentrated and sorted by silica gel column chromatography (toluene:hexane=1:1). Sorted solvent was concentrated and precipitated by adding hexane and by irradiation with ultrasonic waves; thus, 1.1 g of a cream-colored powder of 3-{N-[9-(4-biphenylyl)carbazol-3-yl]-N-phenylamino}-9-(4-biphenylyl)carbazole (abbreviation: BCzBCA1) was obtained (yield: 19%). The following shows $^1$H-NMR data. $^1$H-NMR (300 MHz, DMSO-d): δ=6.86 (t, J=7.2, 1H), 6.94 (d, J=7.8, 2H), 7.18-7.24 (m, 4H), 7.30 (dd, J=8.9, 1.8, 2H), 7.41-7.54 (m, 12H), 7.70 (d, J=8.4, 4H), 7.77 (d, J=7.2, 4H), 7.94 (d, J=8.4, 4H), 8.06 (d, J=2.1, 2H), 8.12 (d, J=7.8, 2H). In addition, FIGS. 49A and 49B each show an $^1$H-NMR chart, and a portion of 6.0 to 9.0 ppm in FIG. 49A is enlarged and shown in FIG. 49B. Further, the following shows $^{13}$C-NMR data: (75.5 MHz, DMSO-d): δ=109.6, 110.7, 117.4, 119.4, 119.7, 119.8, 120.5, 120.5, 122.4, 123.7, 125.0, 126.2, 126.5, 126.8, 127.5, 128.1, 128.8, 136.0, 136.9, 139.1, 139.1, 140.6, 140.8, 149.3. In addition, FIGS. 50A and 50B each show a $^{13}$C-NMR chart, and a portion of 6.0 to 9.0 ppm in FIG. 50A is enlarged and shown in FIG. 50B.

Thermogravimetry-Differential Thermal Analysis (TG-DTA) of the obtained BCzBCA1 was performed similarly to Embodiments 1 to 3. A thermogravimetric/differential thermal analyzer (TG/DTA-320, by Seiko Instruments Inc.) was used for the measurement, which evaluated thermophysical properties in a nitrogen atmosphere at heating rate of 10° C./min. As a result, from the relationship between the weight and the temperature (thermogravimetry), the temperature at which the weight is less than or equal to 95% with respect to the weight at the onset of measurement at normal pressure was 425° C.

Figure 51:
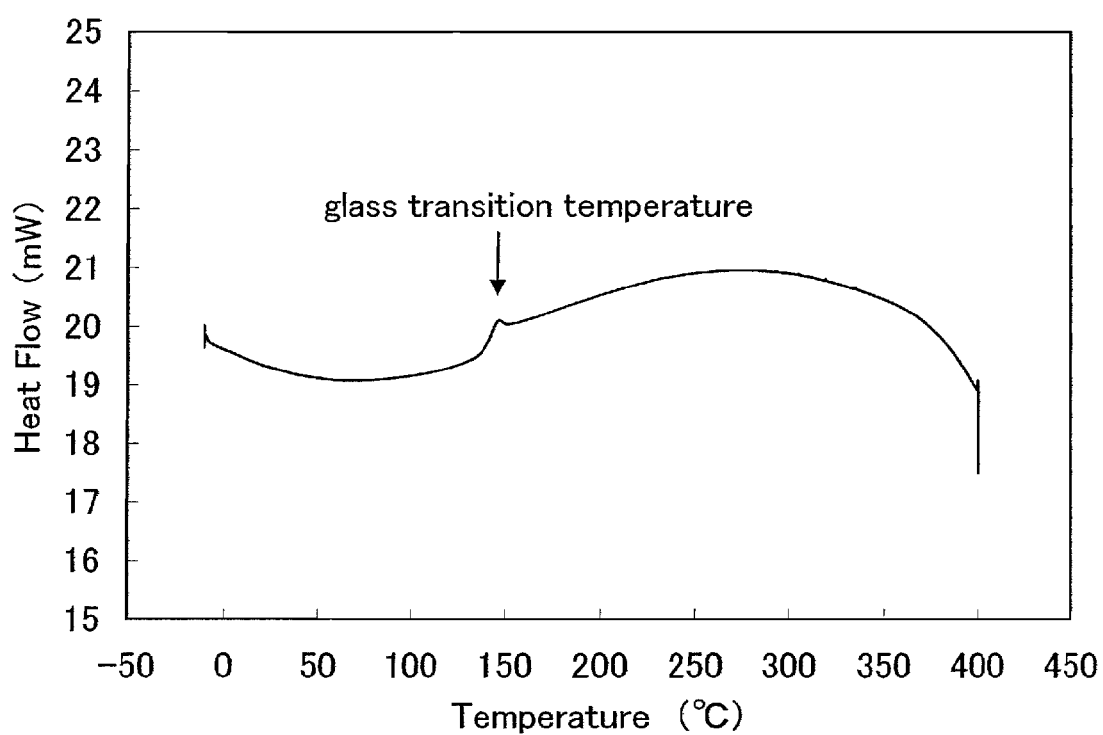
FIG. 51 is a diagram showing a result of Thermogravimetry-Differential Thermal Analysis of 3-{N-[9-(4-biphenylyl)carbazol-3-yl]-N-phenylamino}-9-(4-biphenylyl)carbazole.

Furthermore, the glass transition temperature (Tg) was measured using a differential scanning calorimeter (Pyris 1 DSC, by PerkinElmer, Inc.). First, the sample was heated from −10° C. to 400° C. at 40° C./min, and then cooled to −10° C. at 40° C./min. Thereafter, the sample was heated to 400° C. at 10° C./min, whereby a DSC chart of FIG. 51 was obtained. A temperature is shown in an X axis and a heat flow is shown in a Y axis, respectively. An upwardness in the heat flow shows endotherm. According to this chart, it was found that the glass transition temperature (Tg) of BCzBCA1 is 137° C. Thus, it was found that BCzBCA1 has a high glass transition temperature. It is to be noted that an endothermic peak showing a melting point was not observed in this measurement.

Figure 52:
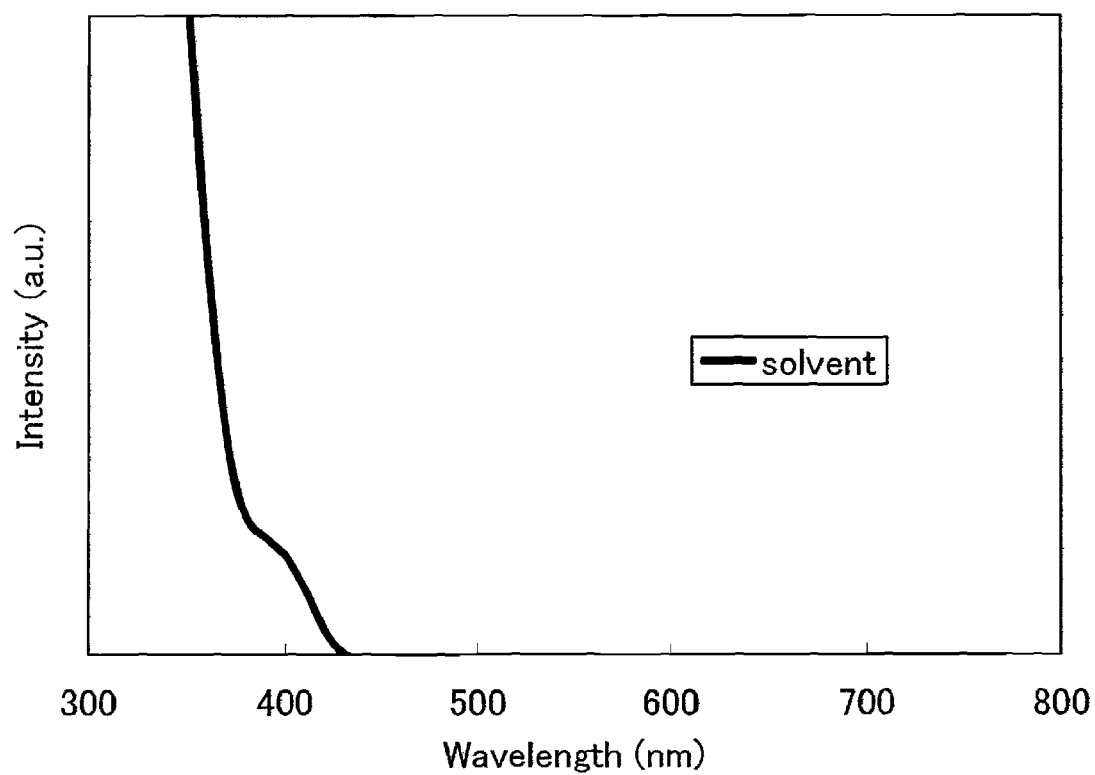
FIG. 52 is a diagram showing the absorption spectrum for a toluene solution of 3-{N-[9-(4-biphenylyl)carbazol-3-yl]-N-phenylamino}-9-(4-biphenylyl)carbazole.
Figure 53:
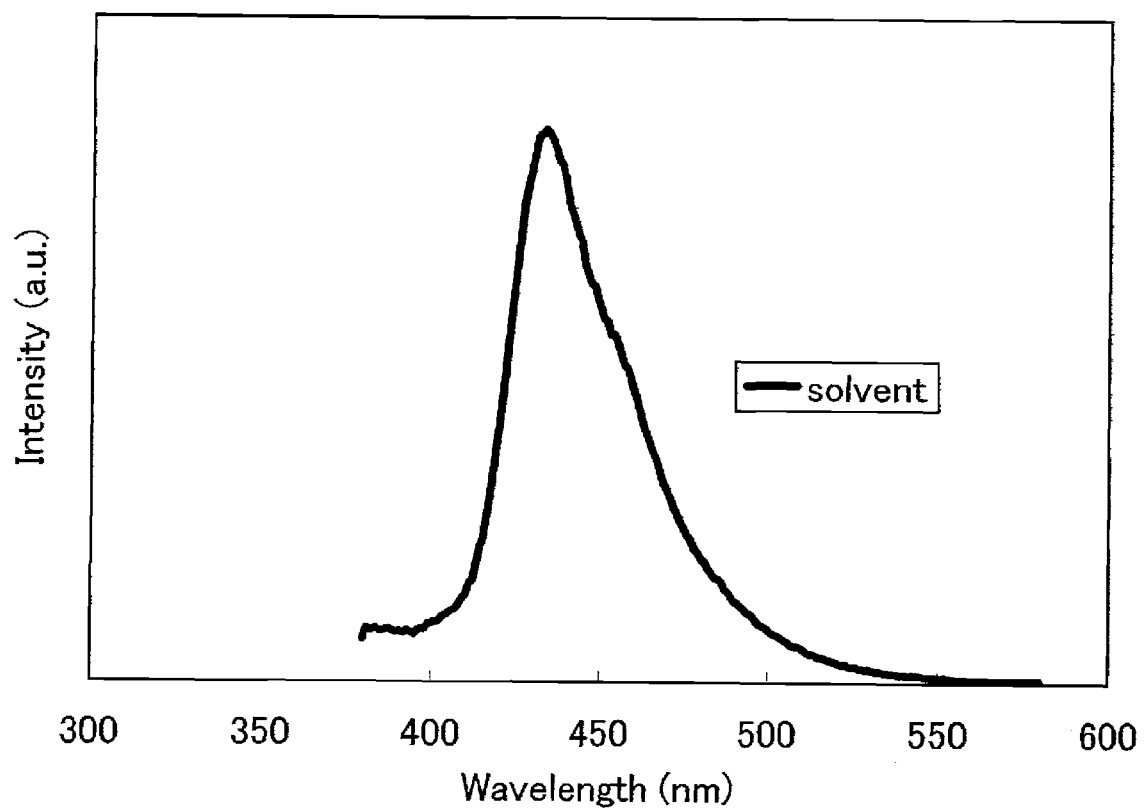
FIG. 53 is a diagram showing the emission spectrum for a toluene solution of 3-{N-[9-(4-biphenylyl)carbazol-3-yl]-N-phenylamino}-9-(4-biphenylyl)carbazole.

FIG. 52 shows the absorption spectrum for a toluene solution of BCzBCA1. An ultraviolet-visible spectrophotometer (V-550, by JASCO Corporation) was used for the measurement. The solution was put in a quartz cell as a sample, and the absorption spectrum thereof, from which the absorption spectrum of quartz was subtracted, is shown in FIG. 52. In FIG. 52, the horizontal axis indicates the wavelength (nm) and the vertical axis indicates the absorption intensity (arbitrary unit). The maximum absorption wavelength was 395 nm in the case of the toluene solution. FIG. 53 shows the emission spectrum for the toluene solution of BCzBCA1. In FIG. 53, the horizontal axis indicates the wavelength (nm) and the vertical axis indicates the emission intensity (arbitrary unit). The maximum emission wavelength was 434 nm (the excitation wavelength: 323 nm) in the case of the toluene solution.

Figure 54:
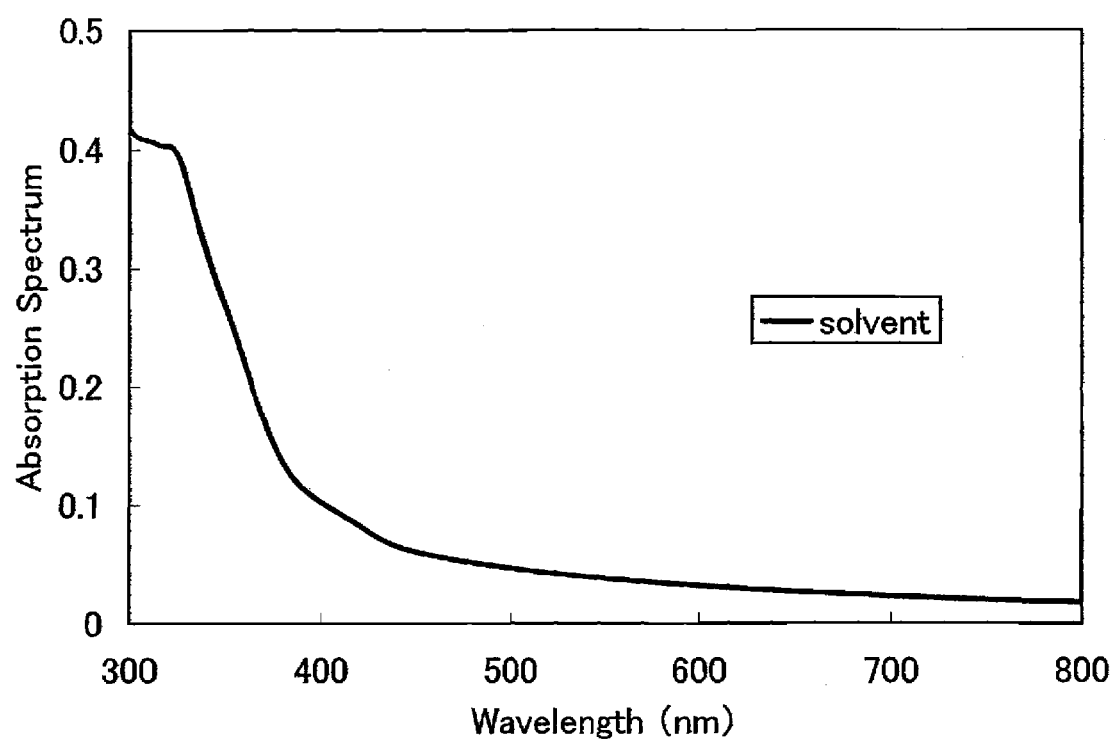
FIG. 54 is a diagram showing the absorption spectrum for a thin film of 3-{N-[9-(4-biphenylyl)carbazol-3-yl]-N-phenylamino}-9-(4-biphenylyl)carbazole.
Figure 55:
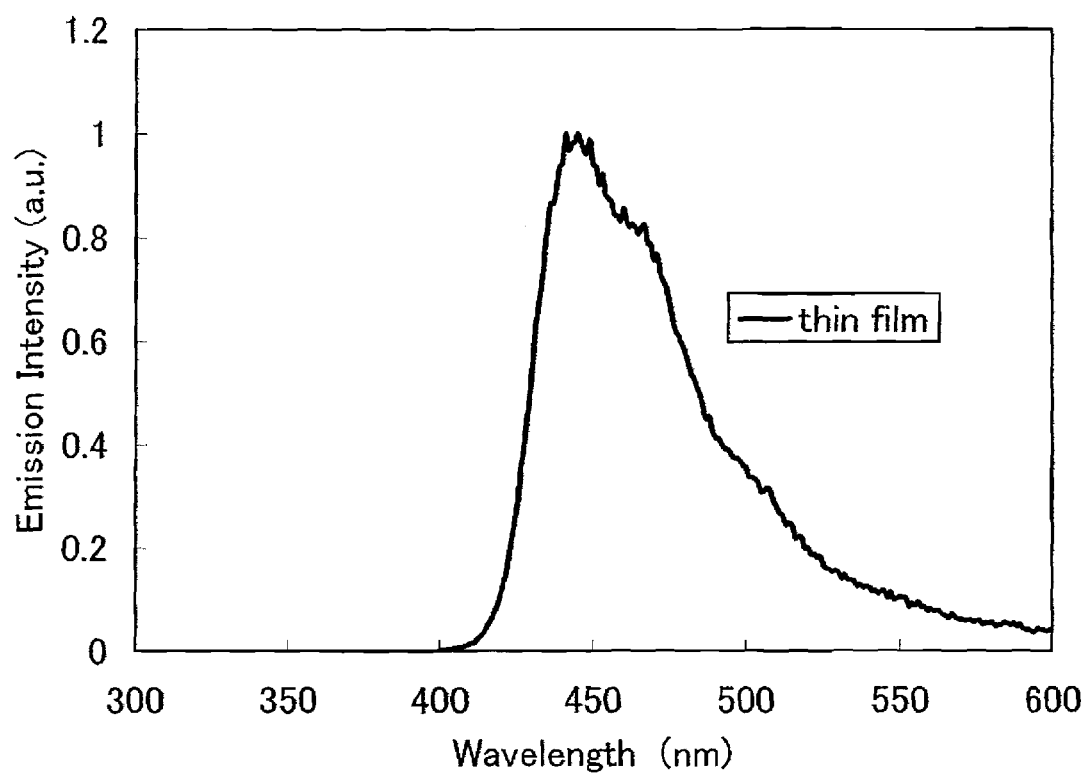
FIG. 55 is a diagram showing the emission spectrum for a thin film of 3-{N-[9-(4-biphenylyl)carbazol-3-yl]-N-phenylamino}-9-(4-biphenylyl)carbazole.

FIG. 54 shows the absorption spectrum for a thin film of BCzBCA1. An ultraviolet-visible spectrophotometer (V-550, by JASCO Corporation) was used for the measurement. The thin film was evaporated over a quartz substrate as a sample, and the absorption spectrum thereof, from which the absorption spectrum of quartz was subtracted, is shown in FIG. 54. In FIG. 54, the horizontal axis indicates the wavelength (nm) and the vertical axis indicates the absorption intensity (arbitrary unit). The maximum absorption wavelength was 318 nm in the case of the thin film. FIG. 55 shows the emission spectrum for the thin film of BCzBCA1. In FIG. 55, the horizontal axis indicates the wavelength (nm) and the vertical axis indicates the emission intensity (arbitrary unit). The maximum emission wavelength was 445 nm (the excitation wavelength: 318 nm) in the case of the thin film.

The HOMO level and the LUMO level of BCzBCA1 in a thin-film state were measured. The value of the HOMO level was obtained by converting the ionization potential measured by using a photoelectron spectrometer (AC-2, by Riken Keiki Co., Ltd.) to a negative value. Furthermore, the value of the LUMO level was obtained by setting the absorption edge of the thin film in FIG. 54 as an energy gap and adding the value of the absorption edge to the value of the HOMO level. As a result, the HOMO level was −5.14 eV, and the LUMO level was −2.04 eV.

Embodiment 14

As an example of the carbazole derivative used in the present invention, a synthesis method of 3,6-bis[N-(1-naphthyl)-N-(9-phenylcarbazol-3-yl)amino]-9-(4-biphenylyl) carbazole (abbreviation: BCzPCN2) represented by the structural formula (71) will be explained.

(71)

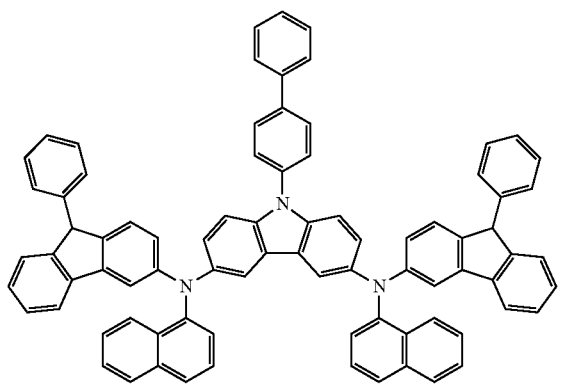

[Step 1]

First, a synthesis method of 3,6-dibromo-9-(4-biphenylyl) carbazole will be explained. (C-1) shows a synthesis scheme of 3,6-dibromo-9-(4-biphenylyl)carbazole.

(C-1)

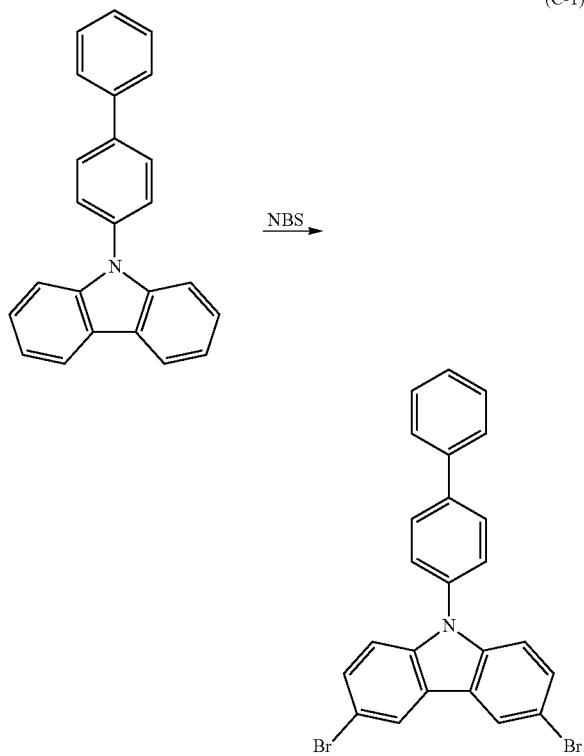

Figure 56A:
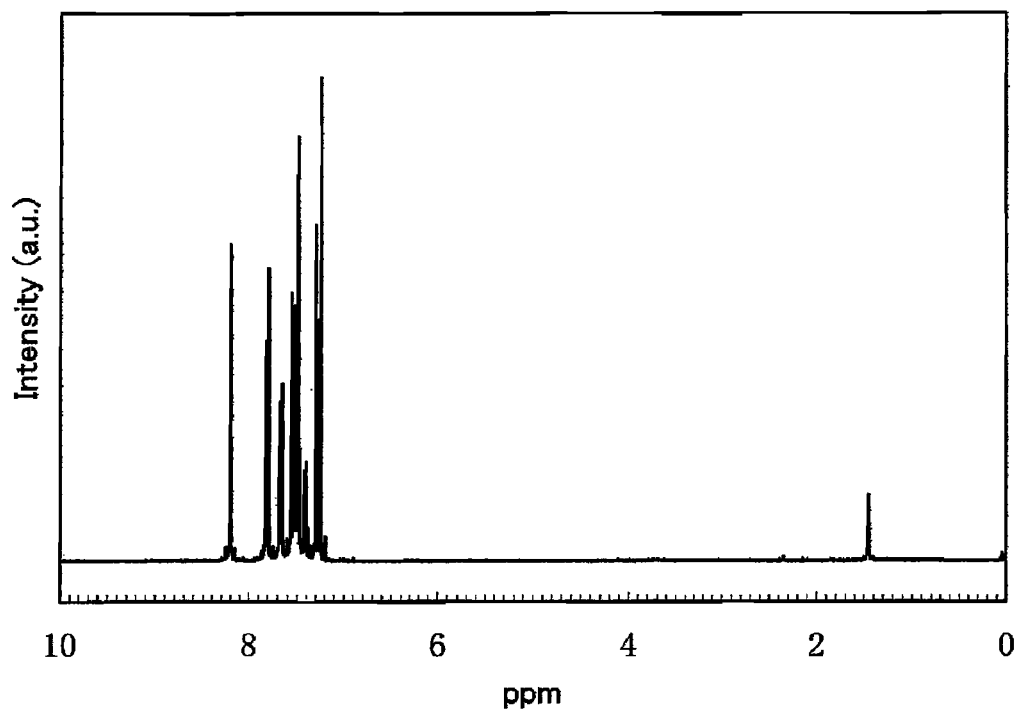
FIGS. 56A and 56B are diagrams each showing an $^1$H-NMR chart of 3,6-dibromo-9-(4-biphenylyl)carbazole.
Figure 56B:
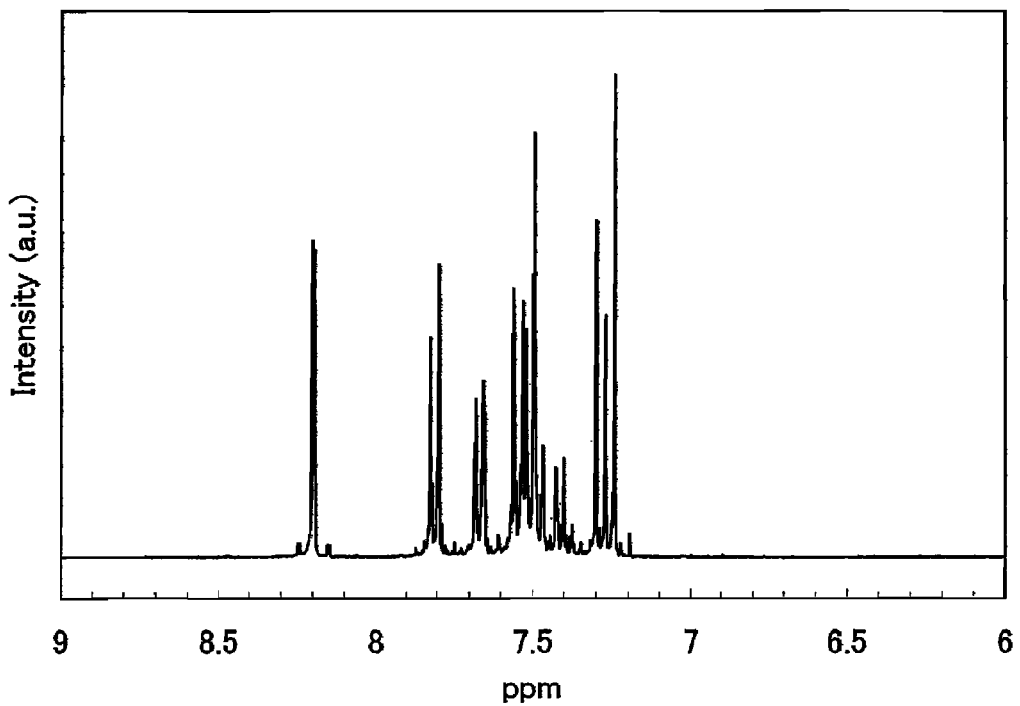
Figure 57A:
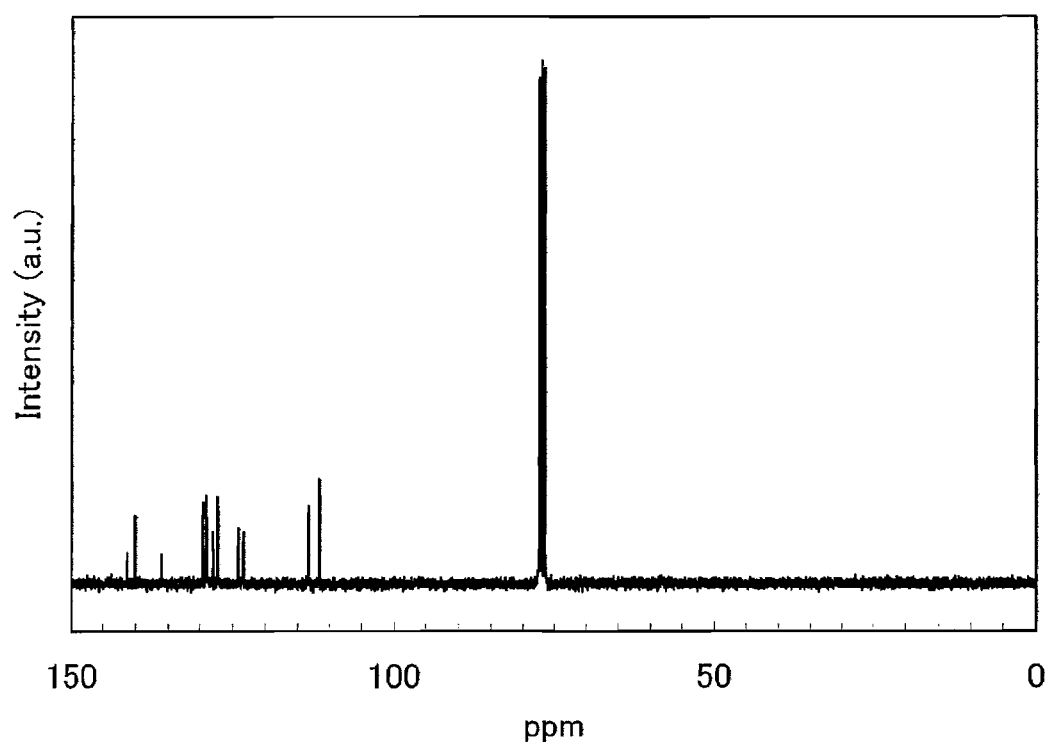
FIGS. 57A and 57B are diagrams each showing a $^{13}$C-NMR chart of 3,6-dibromo-9-(4-biphenylyl)carbazole.
Figure 57B:
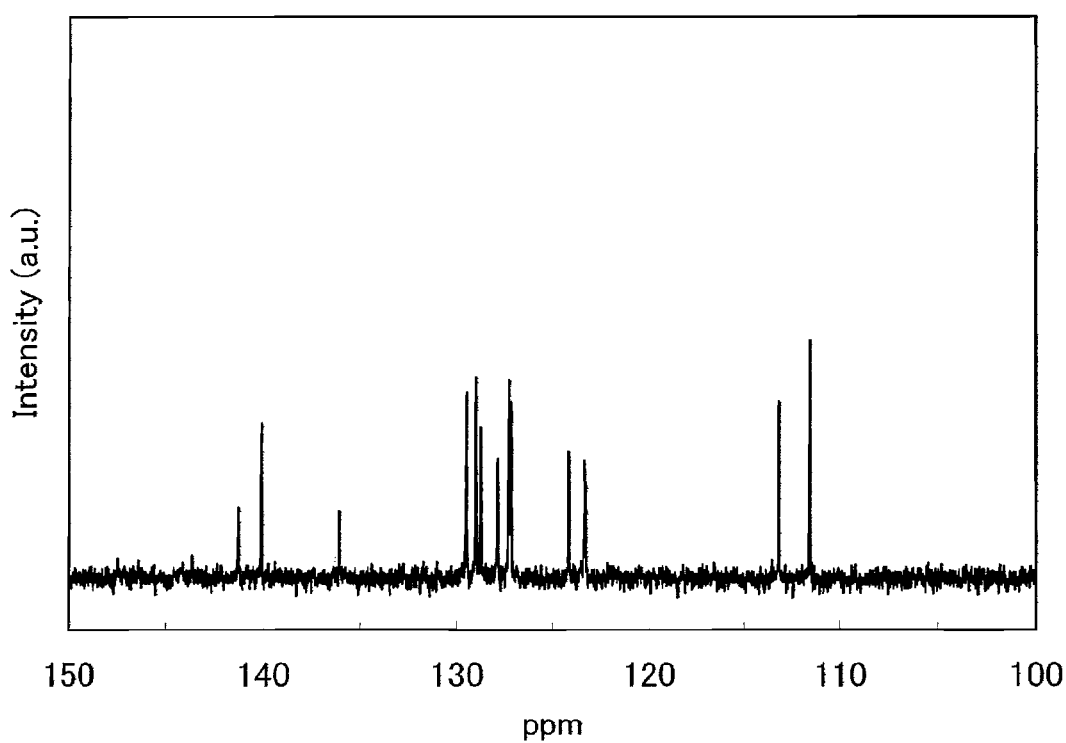

9.6 g (30 mmol) of 9-(4-biphenylyl)carbazole was dissolved in a mixed solution of 250 mL of toluene, 250 mL of ethyl acetate, and 50 mL of glacial acetic acid, and 13 g (75 mmol) of N-bromosuccinimide was slowly added therein. This mixture was stirred for 5 days (approximately 100 hours), washed with water and a sodium thiosulfate aqueous solution, neutralized with a sodium hydroxide aqueous solution, and washed with water again. Magnesium sulfate was added therein to remove moisture, and filtration was performed to obtain the filtrate. The filtrate was concentrated, collected, and dried; thus, 15 g of a beige powder of 3,6-dibromo-9-(4-biphenylyl)carbazole was obtained (yield: 100%). The following shows NMR data. $^1$H-NMR (300 MHz, CDCl$_3$-d): δ=7.29 (d, J=8.7, 2H), 7.40 (t, J=7.5, 1H), 7.47-7.56 (m, 6H), 7.67 (d, J=7.5, 2H), 7.81 (d, J=8.4, 2H), 8.20 (d, J=2.1, 2H). In addition, FIGS. 56A and 56B each show an $^1$H-NMR chart, and a portion of 6.0 to 9.0 ppm in FIG. 56A is enlarged and shown in FIG. 56B. Further, the following shows $^{13}$C-NMR data. $^{13}$C-NMR: (75.5 MHz, CDCl$_3$-d): δ=111.6, 113.3, 123.3, 123.3, 124.2, 127.2, 127.3, 127.9, 128.8, 129.0, 129.5, 136.1, 140.1, 141.3. In addition, FIGS. 57A and 57B each show a $^{13}$C-NMR chart, and a portion of 100 to 150 ppm in FIG. 57A is enlarged and shown in FIG. 57B.

[Step 2]

Next, a synthesis method of 3,6-bis[N-(1-naphthyl)-N-(9-phenylcarbazol-3-yl)amino]-9-(4-biphenylyl)carbazole (abbreviation: BCzPCN2) will be explained. (C-2) shows a synthesis scheme of BCzPCN2.

(C-2)

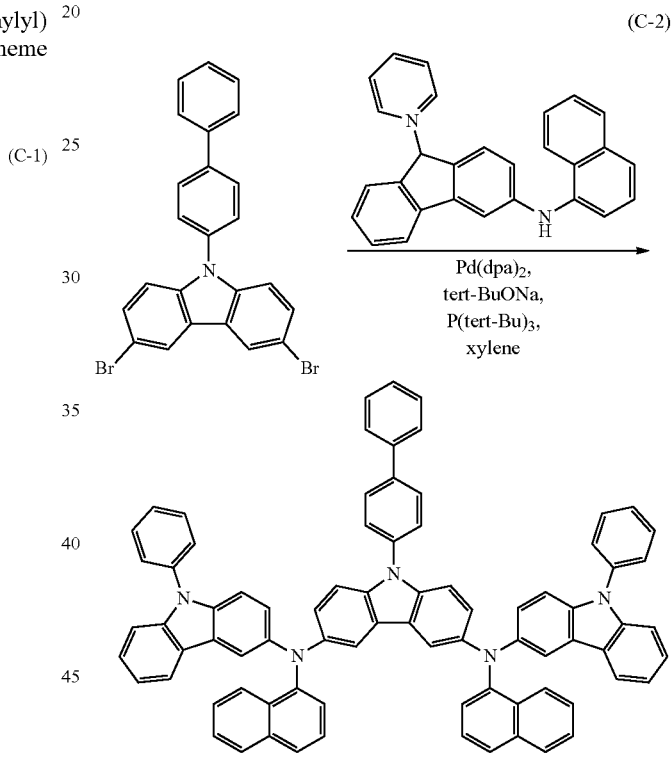

Figure 58A:
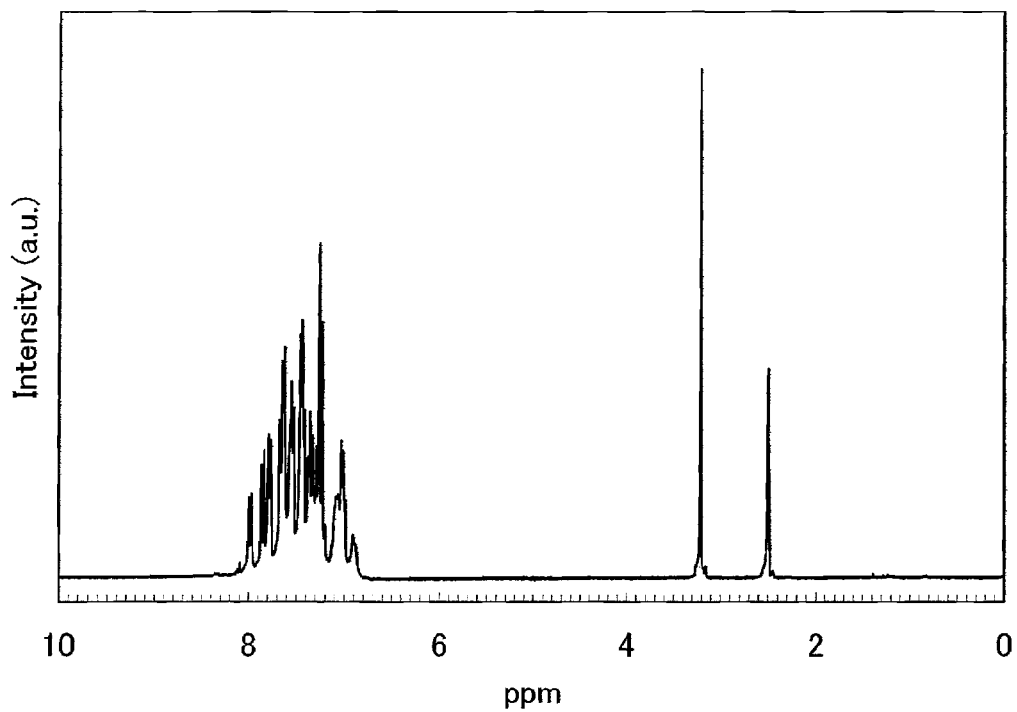
FIGS. 58A and 58B are diagrams each showing an $^1$H-NMR chart of 3,6-bis[N-(1-naphthyl)-N-(9-phenylcarbazol-3-yl)amino]-9-(4-biphenylyl)carbazole.
Figure 58B:
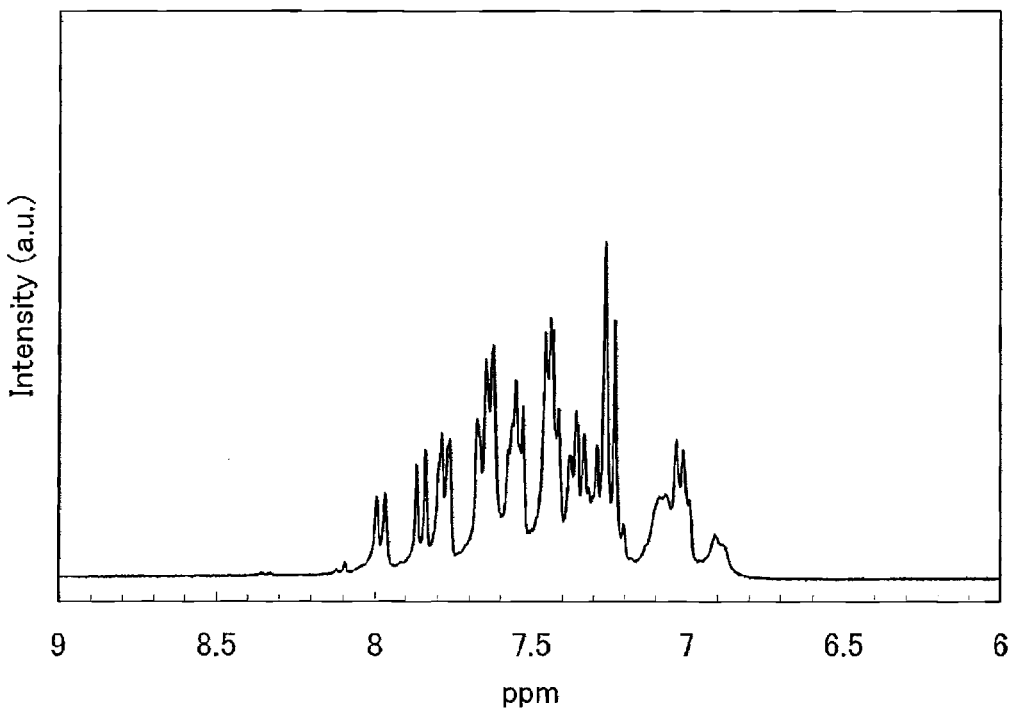
Figure 59A:
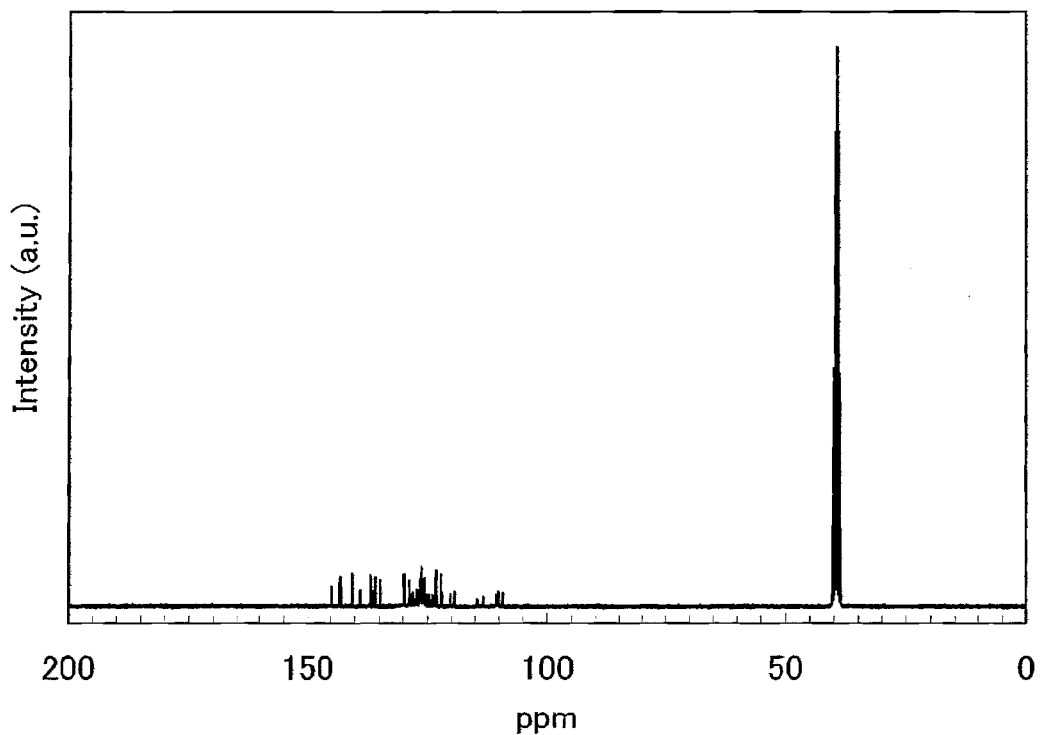
FIGS. 59A and 59B are diagrams each showing a $^{13}$C-NMR chart of 3,6-bis[N-(1-naphthyl)-N-(9-phenylcarbazol-3-yl)amino]-9-(4-biphenylyl)carbazole.
Figure 59B:
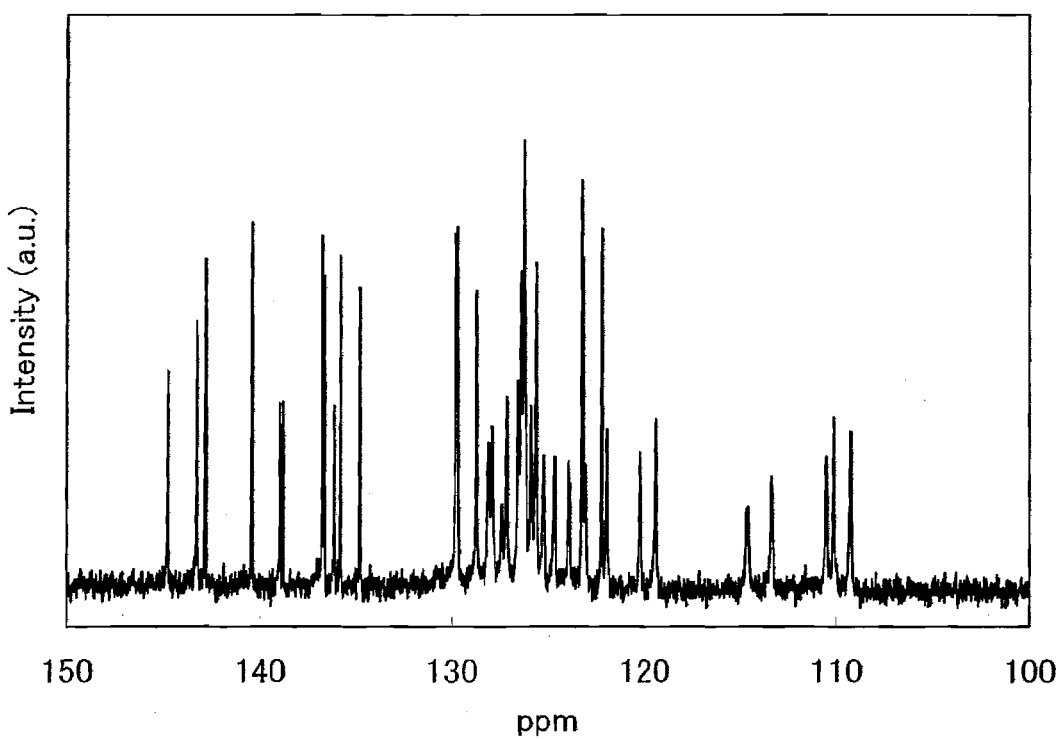

2.4 g (5.0 mmol) of 3,6-dibromo-9-(4-biphenylyl)carbazole, 3.8 g (10 mmol) of PCN, 580 mg (1.0 mmol) of bis(dibenzylideneacetone)palladium(0), 6.0 mL (3 mmol) of a 10 wt % hexane solution of tri-tert-butylphosphine, and 3.0 g (30 mmol) of sodium-tert-butoxide were put in a three-neck flask, and nitrogen was substituted for air in the flask. 10 mL of dehydrated xylene was added therein, and the flask was deaerated. In a nitrogen atmosphere, the mixture was heated and stirred at 130° C. for 12 hours. After the reaction was terminated, approximately 550 mL of warm toluene was added to the suspension, and the suspension was filtered through Florisil, alumina, and Celite. The obtained filtrate was concentrated and sorted by silica gel column chromatography (toluene:hexane=2:1). Sorted solvent was concentrated and precipitated by adding hexane and by irradiation with ultrasonic waves; thus, 2.7 g of a lemon-colored powder of 3,6-bis[N-(1-naphthyl)-N-(9-phenylcarbazol-3-yl)amino]-9-(4-biphenylyl)carbazole (abbreviation: BCzPCN2) was obtained (yield: 51%). The following shows NMR data. $^1$H-NMR (300 MHz, DMSO-d): δ=6.88-7.67 (m, 45H), 7.76-7.79 (d, J=7.8, 4H), 7.84-7.86 (d, J=7.8, 2H), 7.97-7.99 (d, J=7.8, 2H). In addition, FIGS. 58A and 58B each show an $^1$H-NMR chart, and a portion of 6.0 to 9.0 ppm in FIG. 58A is enlarged and shown in FIG. 58B. Further, the following shows $^{13}$C-NMR data. $^{13}$C-NMR: (75.5 MHz, DMSO-d): δ=109.3, 110.1, 110.5, 113.3, 113.3, 114.5, 114.6, 119.4, 120.2, 122.0, 122.2, 123.1, 123.2, 123.3, 124.0, 124.7, 125.2, 125.6, 125.9, 126.2, 126.4, 126.5, 127.1, 127.4, 127.9, 128.1, 128.7, 129.7, 129.8, 134.8, 135.8, 136.1, 136.7, 136.8, 138.8, 139.0, 140.4, 142.9, 143.3, 144.8. In addition, FIGS. 59A and 59B each show a $^{13}$C-NMR chart, and a portion of 100 to 150 ppm in FIG. 59A is enlarged and shown in FIG. 59B.

Thermogravimetry-Differential Thermal Analysis (TG-DTA) of the obtained BCzPCN2 was performed similarly to Embodiments 1 to 3. A thermogravimetric/differential thermal analyzer (TG/DTA-320, by Seiko Instruments Inc.) was used for the measurement, which evaluated thermophysical properties in a nitrogen atmosphere at heating rate of 10° C./min. As a result, from the relationship between the weight and the temperature (thermogravimetry), the temperature at which the weight is less than or equal to 95% with respect to the weight at the onset of measurement at normal pressure was greater than or equal to 500° C.

Figure 60:
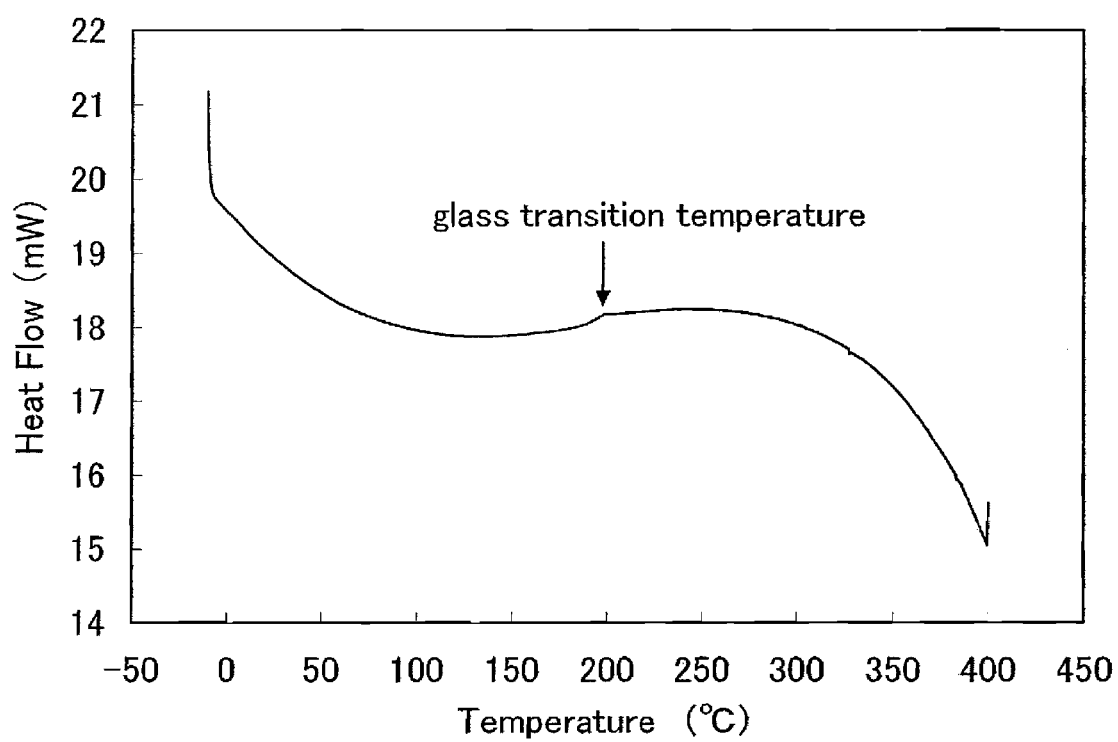
FIG. 60 is a diagram showing a result of Thermogravimetry-Differential Thermal Analysis of 3,6-bis[N-(1-naphthyl)-N-(9-phenylcarbazol-3-yl)amino]-9-(4-biphenylyl)carbazole.

Furthermore, the glass transition temperature (Tg) was measured using a differential scanning calorimeter (Pyris 1 DSC, by PerkinElmer, Inc.). First, the sample was heated from −10° C. to 400° C. at 40° C./min, and then cooled to −10° C. at 40° C./min. Thereafter, the sample was heated to 400° C. at 10° C./min, whereby a DSC chart of FIG. 60 was obtained. A temperature is shown in an X axis and a heat flow is shown in a Y axis, respectively. An upwardness in the heat flow shows endotherm. According to this chart, it was found that the glass transition temperature (Tg) of BCzPCN2 is 185° C. Thus, it was found that BCzPCN2 has a high glass transition temperature. It is to be noted that an endothermic peak showing a melting point was not observed in this measurement.

Figure 61:
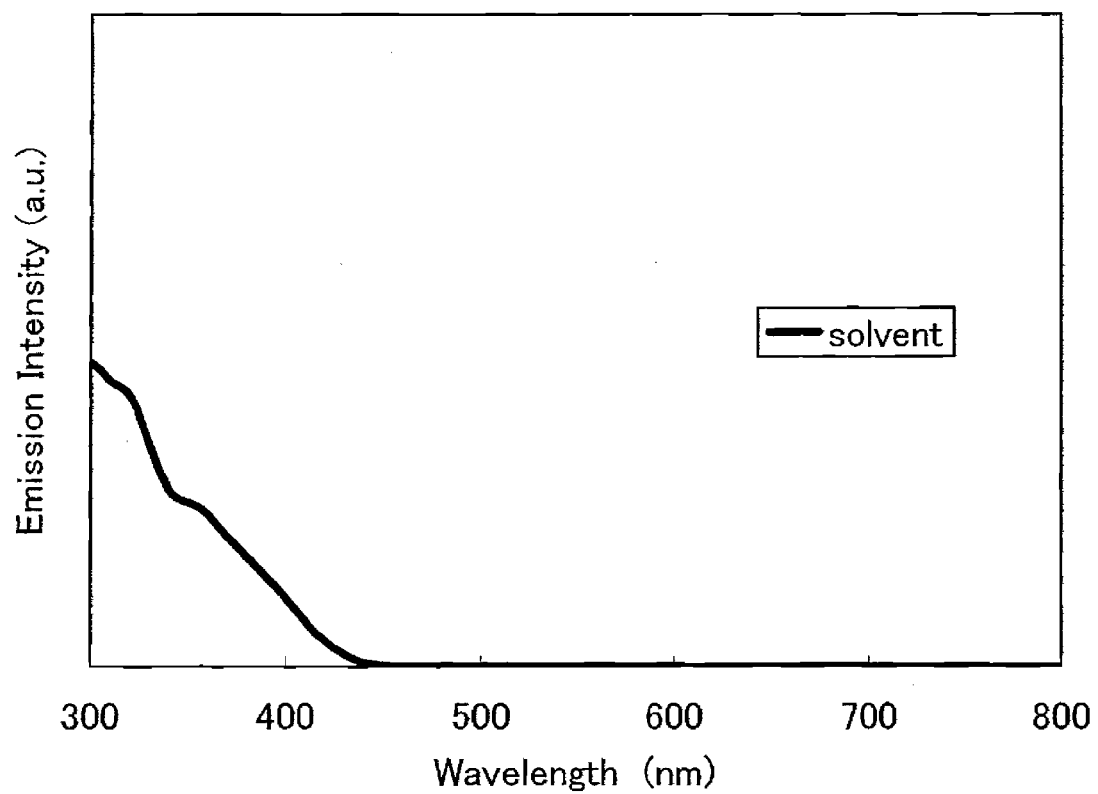
FIG. 61 is a diagram showing the absorption spectrum of 3,6-bis[N-(1-naphthyl)-N-(9-phenylcarbazol-3-yl)amino]-9-(4-biphenylyl)carbazole.
Figure 62:
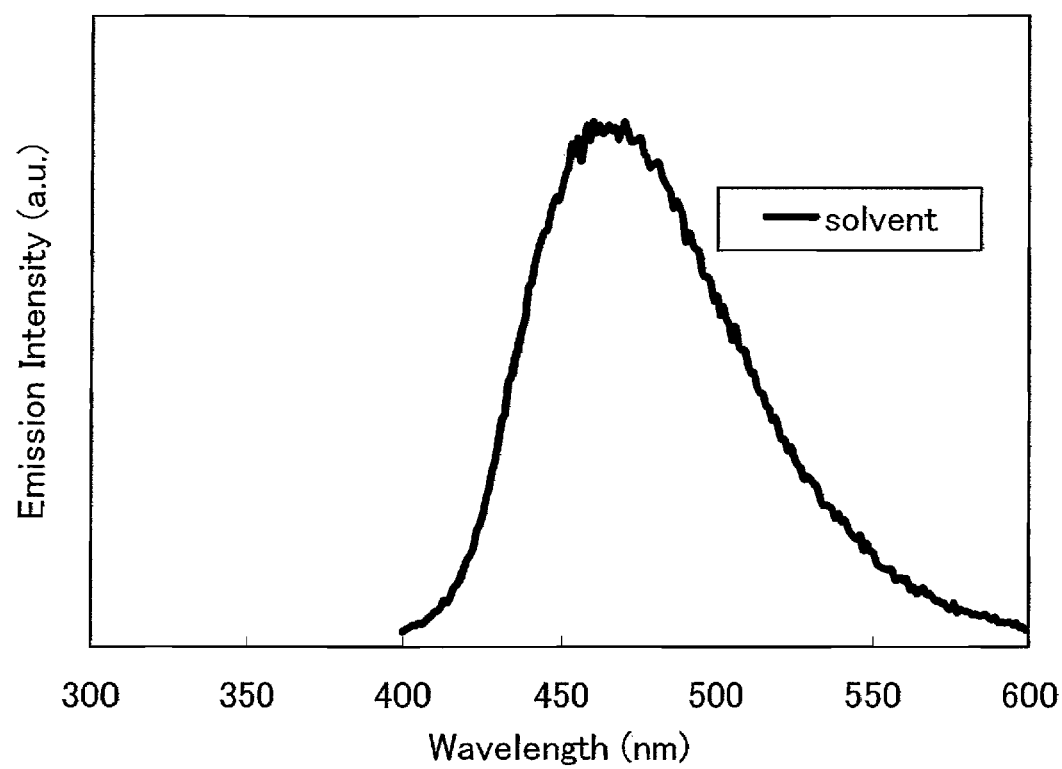
FIG. 62 is a diagram showing the emission spectrum of 3,6-bis[N-(1-naphthyl)-N-(9-phenylcarbazol-3-yl)amino]-9-(4-biphenylyl)carbazole.

FIG. 61 shows the absorption spectrum for a toluene solution of BCzPCN2. An ultraviolet-visible spectrophotometer (V-550, by JASCO Corporation) was used for the measurement. The solution was put in a quartz cell as a sample, and the absorption spectrum thereof, from which the absorption spectrum of quartz was subtracted, is shown in FIG. 61. In FIG. 61, the horizontal axis indicates the wavelength (nm) and the vertical axis indicates the emission intensity (arbitrary unit). The maximum absorption wavelength was 370 nm in the case of the toluene solution. FIG. 62 shows the emission spectrum for the toluene solution of BCzBCA2. In FIG. 62, the horizontal axis indicates the wavelength (nm) and the vertical axis indicates the emission intensity (arbitrary unit). The maximum emission wavelength was 465 nm (the excitation wavelength: 320 nm) in the case of the toluene solution.

This application is based on Japanese Patent Application serial No. 2006-017431 filed in Japan Patent Office on Jan. 26, 2006, the entire contents of which are hereby incorporated by reference.

EXPLANATION OF REFERENCE

11: semiconductor layer, 12: insulating layer, 13: composite layer, 14: second layer, 15: gate electrode, 16: substrate, 17: conductive layer, 18: source electrode and drain electrode, 19: buffer layer, 501: element substrate, 502: counter substrate, 503: pixel portion, 504: external connection portion, 521: substrate, 522: gate electrode, 523: gate insulating layer, 524: semiconductor layer, 525: conductive layer, 526: conductive layer, 527: transistor, 528: insulating layer, 529: pixel electrode, 530: alignment film, 531: counter substrate, 532: counter electrode, 533: alignment film, 534: liquid crystal layer, 535: spacer, 540: composite layer, 541: composite layer, 551: substrate, 552: gate electrode, 553: gate insulating layer, 554: conductive layer, 555: conductive layer, 556: semiconductor layer, 557: transistor, 558a: insulating layer, 558b: insulating layer, 550: pixel electrode, 560: alignment film, 561: counter substrate, 562: counter electrode, 563: alignment film, 564: liquid crystal layer, 545: spacer, 570: composite layer, 571: composite layer, 600: substrate, 601: gate electrode, 602: gate insulating film, 603: semiconductor layer, 604: composite layer, 605: composite layer, 606: conductive layer, 607: conductive layer, 608: interlayer insulating film, 609: pixel electrode, 610: insulating layer, 611: common electrode, 612: passivation film, 613: space, 614: counter substrate, 615: organic field effect transistor, 616: light emitting layer, 617: light emitting element, 619: gate electrode, 620: substrate, 621: semiconductor layer, 622: gate insulating film, 623: conductive layer, 624: conductive layer, 625: composite layer, 626: composite layer, 628: first interlayer insulating film, 629: second interlayer insulating film, 630: pixel electrode, 631: insulating layer, 632: common electrode, 634: space, 635: counter substrate, 636: organic field effect transistor, 637: light emitting element, 638: light emitting layer, 1610: main body, 1611: pixel portion, 1612: driver IC, 1613: receiver device, 1614: film battery, 5531: display portion, 5532: housing, 5533: speaker, 5541: supporting body, 5542: display portion, 5543: integrated circuit chip, 5544: integrated circuit, 5545: integrated circuit, 5551: display portion, 5552: main body, 5553: antenna, 5554: audio output portion, 5555: audio input portion, 5556: operation switch, 5557: operation switch

What is claimed is:

1. An electronic book comprising:

a main body; and a pixel portion; the pixel portion comprising an organic field effect transistor, the organic field effect transistor comprising:

a semiconductor layer containing an organic semiconductor material; and a source electrode and a drain electrode in a same layer;

a gate electrode; and a gate insulating film interposed between the gate electrode and one of the source electrode and the drain electrode, wherein at least one of the source electrode and the drain electrode comprises a composite layer comprising an organic compound and an inorganic compound;

wherein the main body is selected from the group of a plastic and a film;

wherein the organic compound is a carbazole derivative represented by a general formula (1);

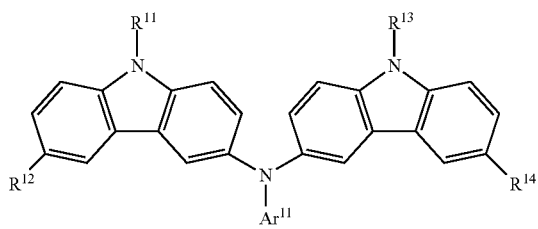

(1)

wherein each of $R^{11}$ and $R^{13}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{11}$ represents an aryl group having 6 to 25 carbon atoms or a heteroaryl group having 5 to 9 carbon atoms; $R^{12}$ represents hydrogen, an alkyl group having 1 to 6 carbon atoms, or an aryl group having 6 to 12 carbon atoms; $R^{14}$ represents hydrogen, an alkyl group having 1 to 6 carbon atoms, an aryl group having 6 to 12 carbon atoms, or a substituent represented by a general formula (2); and wherein in the substituent represented by the general formula (2), $R^{15}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{12}$ represents an aryl group having 6 to 25 carbon atoms or a heteroaryl group having 5 to 9 carbon atoms; and $R^{16}$ represents hydrogen, an alkyl group having 1 to 6 carbon atoms, or an aryl group having 6 to 12 carbon atoms

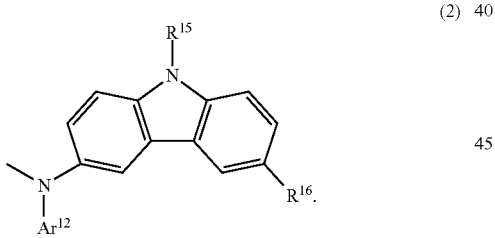

(2)

2. The electronic book according to claim 1, wherein any one of $R^{11}$ and $R^{13}$ is an aryl group having 6 to 25 carbon atoms or a heteroaryl group having 5 to 9 carbon atoms.

3. The electronic book according to claim 1, wherein any one of $R^{11}$ and $R^{13}$ is a phenyl group.

4. The electronic book according to claim 1, wherein each of $R^{11}$ and $R^{13}$ is an aryl group having 6 to 25 carbon atoms or a heteroaryl group having 5 to 9 carbon atoms.

5. The electronic book according to claim 1, wherein each of $R^{11}$ and $R^{13}$ is a phenyl group.

6. The electronic book according to claim 1, wherein $R^{12}$ is hydrogen, a tert-butyl group, a phenyl group, or a biphenyl group.

7. The electronic book according to claim 1, wherein $R^{14}$ is hydrogen, a tert-butyl group, a phenyl group, or a biphenyl group.

8. The electronic book according to claim 1, wherein $R^{14}$ is a substituent represented by the general formula (2).

9. The electronic book according to claim 8, wherein $R^{15}$ is an aryl group having 6 to 25 carbon atoms or a heteroaryl group having 5 to 9 carbon atoms.

10. The electronic book according to claim 8, wherein $R^{16}$ is hydrogen, a tert-butyl group, a phenyl group, or a biphenyl group.

11. The electronic book according to claim 1, wherein the inorganic compound is transition metal oxide.

12. The electronic book according to claim 1, wherein the inorganic compound is titanium oxide, zirconium oxide, hafnium oxide, vanadium oxide, niobium oxide, tantalum oxide, chromium oxide, molybdenum oxide, tungsten oxide, rhenium oxide, or ruthenium oxide.

13. An electronic book comprising:
a main body; and
a pixel portion; the pixel portion comprising an organic field effect transistor,
the organic field effect transistor comprising:
  a semiconductor layer comprising an organic semiconductor material;
  composite layers comprising an organic compound and an inorganic compound so as to be in a same layer and be in contact with the semiconductor layer as electrodes;
  a gate electrode; and
  a gate insulating film interposed between the gate electrode and the composite layers,
wherein the main body is selected from the group of a plastic and a film;
wherein the organic compound is a carbazole derivative represented by a general formula (3); and

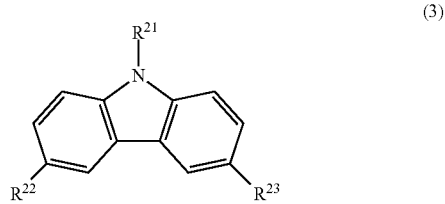

(3)

wherein $R^{21}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $R^{22}$ represents hydrogen, an alkyl group having 1 to 6 carbon atoms, or an aryl group having 6 to 12 carbon atoms; and $R^{23}$ represents a substituent represented by a general formula (4); and in the substituent represented by the general formula (4), $R^{24}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{21}$ represents an aryl group having 6 to 25 carbon atoms or a heteroaryl group having 5 to 9 carbon atoms; and $R^{25}$ represents hydrogen, an alkyl group having 1 to 6 carbon atoms, or an aryl group having 6 to 12 carbon atoms

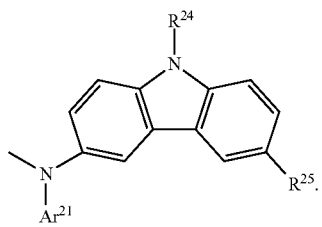

(4)

14. The electronic book according to claim 13, wherein $R^{22}$ is hydrogen, a tert-butyl group, a phenyl group, or a biphenyl group.

15. The electronic book according to claim 13, wherein $R^{24}$ is an aryl group having 6 to 25 carbon atoms or a heteroaryl group having 5 to 9 carbon atoms.

16. The electronic book according to claim 13, wherein $R^{24}$ is a phenyl group.

17. The electronic book according to claim 13, wherein $R^{21}$ is an aryl group having 6 to 25 carbon atoms or a heteroaryl group having 5 to 9 carbon atoms.

18. The electronic book according to claim 13, wherein $R^{21}$ is a phenyl group.

19. The electronic book according to claim 13, wherein the inorganic compound is transition metal oxide.

20. The electronic book according to claim 13, wherein the inorganic compound is titanium oxide, zirconium oxide, hafnium oxide, vanadium oxide, niobium oxide, tantalum oxide, chromium oxide, molybdenum oxide, tungsten oxide, rhenium oxide, or ruthenium oxide.

21. An electronic book comprising:
a main body; and
a pixel portion; the pixel portion comprising an organic field effect transistor,
the organic field effect transistor comprising:
a semiconductor layer comprising an organic semiconductor material;
composite layers comprising an organic compound and an inorganic compound so as to be in a same layer and be in contact with the semiconductor layer as electrodes;
a gate electrode; and
a gate insulating film interposed between the gate electrode and the composite layers;
wherein the main body is selected from the group of a plastic and a film;
wherein the organic compound is a carbazole derivative represented by a general formula (5); and

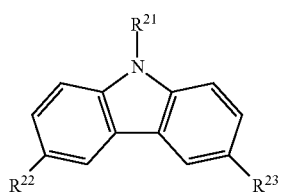

(5)

wherein $R^{21}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; each of $R^{22}$ and $R^{23}$ has a substituent represented by a general formula (6); and in the substituent represented by the general formula (6), $R^{24}$ represents hydrogen, an alkyl group having 1 to 6 carbon atoms, an aryl group having 6 to 25 carbon atoms, a heteroaryl group having 5 to 9 carbon atoms, an arylalkyl group, or an acyl group having 1 to 7 carbon atoms; $Ar^{21}$ represents an aryl group having 6 to 25 carbon atoms or a heteroaryl group having 5 to 9 carbon atoms; and $R^{25}$ represents hydrogen, an alkyl group having 1 to 6 carbon atoms, or an aryl group having 6 to 12 carbon atoms

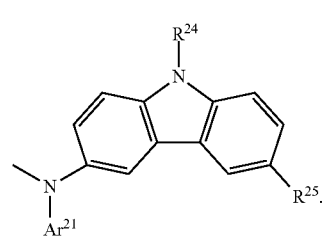

(6)

22. The electronic book according to claim 21, wherein $R^{25}$ is hydrogen, a tert-butyl group, a phenyl group, or a biphenyl group.

23. The electronic book according to claim 21, wherein $R^{24}$ is an aryl group having 6 to 25 carbon atoms or a heteroaryl group having 5 to 9 carbon atoms.

24. The electronic book according to claim 21, wherein $R^{24}$ is a phenyl group.

25. The electronic book according to claim 21, wherein $R^{21}$ is an aryl group having 6 to 25 carbon atoms or a heteroaryl group having 5 to 9 carbon atoms.

26. The electronic book according to claim 21, wherein $R^{21}$ is a phenyl group.

27. The electronic book according to claim 21, wherein the inorganic compound is transition metal oxide.

28. The electronic book according to claim 21, wherein the inorganic compound is titanium oxide, zirconium oxide, hafnium oxide, vanadium oxide, niobium oxide, tantalum oxide, chromium oxide, molybdenum oxide, tungsten oxide, rhenium oxide, or ruthenium oxide.

29. An electronic book comprising:
a main body; and
a pixel portion; the pixel portion comprising an organic field effect transistor,
the organic field effect transistor comprising:
a semiconductor layer comprising an organic semiconductor material;
composite layers comprising an organic compound and an inorganic compound so as to be in a same layer and be in contact with the semiconductor layer as electrodes;
a gate electrode; and
a gate insulating film interposed between the gate electrode and the composite layers,
wherein the main body is selected from the group of a plastic and a film;
wherein the organic compound is a carbazole derivative represented by a general formula (7); and

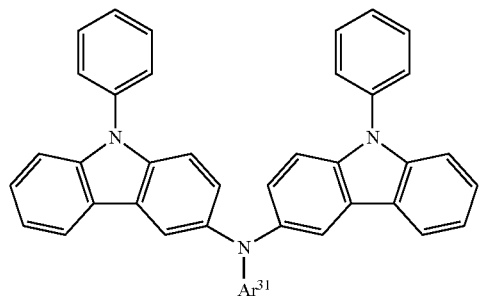

(7)

wherein Ar$^{31}$ represents a phenyl group or a naphthyl group.

30. The electronic book according to claim 29, wherein the inorganic compound is transition metal oxide.

31. The electronic book according to claim 29, wherein the inorganic compound is titanium oxide, zirconium oxide, hafnium oxide, vanadium oxide, niobium oxide, tantalum oxide, chromium oxide, molybdenum oxide, tungsten oxide, rhenium oxide, or ruthenium oxide.

32. An electronic book comprising:
 a main body; and
 a pixel portion; the pixel portion comprising an organic field effect transistor,
 the organic field effect transistor comprising:
  a semiconductor layer comprising an organic semiconductor material;
  composite layers comprising an organic compound and an inorganic compound so as to be in a same layer and be in contact with the semiconductor layer as electrodes;
  a gate electrode; and
  a gate insulating film interposed between the gate electrode and the composite layers,
 wherein the main body is selected from the group of a plastic and a film;
 wherein the organic compound is a carbazole derivative represented by a general formula (8); and

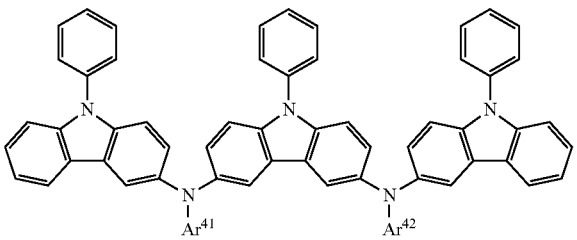

(8)

wherein each of Ar$^{41}$ and Ar$^{42}$ represents a phenyl group or a naphthyl group.

33. The electronic book according to claim 32, wherein the inorganic compound is transition metal oxide.

34. The electronic book according to claim 32, wherein the inorganic compound is titanium oxide, zirconium oxide, hafnium oxide, vanadium oxide, niobium oxide, tantalum oxide, chromium oxide, molybdenum oxide, tungsten oxide, rhenium oxide, or ruthenium oxide.

* * * * *

UNITED STATES PATENT AND TRADEMARK OFFICE
CERTIFICATE OF CORRECTION

PATENT NO. : 8,362,474 B2
APPLICATION NO. : 13/280596
DATED : January 29, 2013
INVENTOR(S) : Shinobu Furukawa et al.

It is certified that error appears in the above-identified patent and that said Letters Patent is hereby corrected as shown below:

In the Specification

At column 3, line 42 "$Ar^{12}$ an" should be -- $Ar^{12}$ represents an --;

At column 41, line 9 "(p-tent-butylphenyl)" should be -- "(p-tert-butylphenyl) --;

At column 41, lines 10-11 "(4-tent-butylphenyl)" should be -- "(4-tert-butylphenyl) --;

At column 44, line 46 "feinted" should be -- formed --;

At column 62, line 12 "(mu)" should be -- (nm) --;

At column 62, line 44 "(P'1'E" should be -- (PTE --;

At column 72, line 26 "sodium-tent-butoxide" should be -- sodium-tert-butoxide --.

Signed and Sealed this
Nineteenth Day of November, 2013

Teresa Stanek Rea
*Deputy Director of the United States Patent and Trademark Office*